US012479923B2

(12) United States Patent
Chen et al.

(10) Patent No.: US 12,479,923 B2
(45) Date of Patent: Nov. 25, 2025

(54) CHIMERIC ANTIGEN RECEPTORS AND RELATED METHODS AND COMPOSITIONS FOR THE TREATMENT OF CANCER

(71) Applicant: THE REGENTS OF THE UNIVERSITY OF CALIFORNIA, Oakland, CA (US)

(72) Inventors: Yvonne Yu-Hsuan Chen, Los Angeles, CA (US); Ximin Chen, Los Angeles, CA (US); Laurence Chen, Walnut, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 18/915,927

(22) Filed: Oct. 15, 2024

(65) Prior Publication Data

US 2025/0109213 A1 Apr. 3, 2025

Related U.S. Application Data

(63) Continuation of application No. 17/908,703, filed as application No. PCT/US2021/020511 on Mar. 2, 2021.

(60) Provisional application No. 63/084,138, filed on Sep. 28, 2020, provisional application No. 62/984,139, filed on Mar. 2, 2020.

(51) Int. Cl.

| | |
|---|---|
| ***C07K 16/28*** | (2006.01) |
| ***A61K 40/11*** | (2025.01) |
| ***A61K 40/31*** | (2025.01) |
| ***A61K 40/42*** | (2025.01) |
| ***C07K 14/705*** | (2006.01) |
| ***C07K 14/725*** | (2006.01) |

(52) U.S. Cl.

CPC .......... *C07K 16/2887* (2013.01); *A61K 40/11* (2025.01); *A61K 40/31* (2025.01); *A61K 40/4211* (2025.01); *A61K 40/4221* (2025.01); *A61K 40/4258* (2025.01); *C07K 14/7051* (2013.01); *C07K 14/70521* (2013.01); *A61K 2239/31* (2023.05); *A61K 2239/38* (2023.05); *A61K 2239/47* (2023.05); *A61K 2239/48* (2023.05); *C07K 2317/24* (2013.01); *C07K 2317/31* (2013.01); *C07K 2317/565* (2013.01); *C07K 2317/622* (2013.01)

(58) Field of Classification Search

CPC ............ C07K 16/2887; C07K 14/7051; C07K 14/70521; C07K 2317/24; C07K 2317/31; C07K 2317/565; C07K 2317/622; A61K 40/11; A61K 40/31; A61K 40/4211; A61K 40/4221; A61K 40/4258; A61K 2239/31; A61K 2239/38; A61K 2239/47; A61K 2239/48

See application file for complete search history.

(56) References Cited

U.S. PATENT DOCUMENTS

| | | | |
|---|---|---|---|
| 2005/0037420 | A1 | 2/2005 | Zhang et al. |
| 2019/0106501 | A1 | 4/2019 | Press et al. |

FOREIGN PATENT DOCUMENTS

| | | | |
|---|---|---|---|
| CN | 1835977 | A | 9/2006 |
| CN | 110741016 | A | 1/2020 |
| JP | S2019-510498 | | 4/2019 |
| JP | S2019-515652 | | 6/2019 |
| JP | S2019-534246 | | 11/2019 |
| JP | S2019-535244 | | 12/2019 |
| WO | WO 2017/172981 | | 10/2017 |
| WO | WO 2018/045325 | | 3/2018 |
| WO | WO 2018/075807 | | 4/2018 |
| WO | WO 2019/014456 | | 1/2019 |
| WO | WO 2019/067805 | | 4/2019 |
| WO | WO 2020/181164 | | 9/2020 |
| WO | WO 2022/178367 | | 8/2022 |

OTHER PUBLICATIONS

Rafiq, S., Hackett, C.S. & Brentjens, R.J. Engineering strategies to overcome the current roadblocks in CAR T cell therapy. Nat Rev Clin Oncol 17, 147-167 (2020). (Year: 2020).*

Ajina, A. et al., "Strategies to Address Chimeric Antigen Receptor Tonic Signaling", *Molecular Cancer Therapeutics*, 17(9); pp. 1795-1815, 2018.

Constantinescu et al., "The Erythropoietin Receptor Cytosolic Juxtamembrane Domain Contains an Essential, Precisely Oriented, Hydrophobic Motif" Molecular Cell 2001. 7:377-385.

Frigault et al., "Identification of Chimeric Antigen Receptors That Mediate Constitutive or Inducible Proliferation of T Cells" Cancer Immunology Research, 2015. 3(4):356-367.

(Continued)

*Primary Examiner* — Julie Wu

*Assistant Examiner* — Amber K Faust

(74) *Attorney, Agent, or Firm* — Norton Rose Fulbright US LLP

(57) ABSTRACT

Aspects of the disclosure relate to novel scFv molecules that are useful for incorporation into novel chimeric antigen receptors with enhance anti-tumor activity. Further aspects relate to a polypeptide comprising a CAR comprising, in order from amino proximal to carboxy proximal end, a scFv, a transmembrane domain, a torsional linker, and a cytoplasmic region comprising a primary intracellular signaling domain, wherein the torsional linker comprises 1-12 alanine residues. Also described are nucleic acids comprising a sequence encoding a polypeptide of the disclosure, vectors, such as lentiviral vectors comprising the nucleic acids of the disclosure, cells comprising and/or expressing nucleic acids and/or polypeptides of the disclosure, and populations of cells comprising the cell embodiments of the disclosure. Also provided are methods of making cells that express a polypeptide and methods of treating patients with the polypeptides and cell compositions of the disclosure.

18 Claims, 80 Drawing Sheets

Specification includes a Sequence Listing.

(56) References Cited

OTHER PUBLICATIONS

Gomes-Silva et al., "Tonic 4-1BB Costimulation in Chimeric Antigen Receptors Impedes T Cell Survival and Is Vector-Dependent" Cell Reports, 2017. 21:17-26.
Guedan, S. et al., "Engineering and Design of Chimeric Antigen Receptors", *Molecular Therapy—Methods & Clinical Development*, 12; pp. 145-156, 2019.
International Search Report and Written Opinion issued in Corresponding PCT Application No. PCT/US2021/020511, dated Aug. 31, 2021.
Liu et al., "Construction of a fluorescein-responsive chimeric receptor with strict ligand dependency" Biotechnology and Bioengineering 2008, 101(5):975-984.
Long et al., "4-1BB costimulation ameliorates T cell exhaustion induced by tonic signaling of chimeric antigen receptors" Nature Medicine 2015, 21(6):581-590.
Supplemental Search Report issued in corresponding European Application No. 21764636, dated Apr. 8, 2024.
Till et al., "Adoptive immunotherapy for indolent non-Hodgkin lymphoma and mantle cell lymphoma using genetically modified autologous CD20-specific T cells" Blood 2008; 112(6):2261-2271.
Till et al., "CD20-specific adoptive immunotherapy for lymphoma using a chimeric antigen receptor with both CD28 and 4-1BB domains: pilot clinical trial results" Blood 2012; 199(17):3940-3950.
Wang et al., "Effective response and delayed toxicities of refractory advanced diffuse large B-cell lymphoma treated by CD20-directed chimeric antigen receptor-modified T cells" Clinical Immunology 2014; 155:160-175.
Watanabe et al., "Fine-tuning the CAR spacer improves T-cell potency" Oncoimmunology, 2016. 5(12):e1253656, 15 pages.
Ximin, C. et al., "Rational Tuning of CAR Tonic Signaling Yields Superior T-Cell Therapy for Cancer", *bioRxiv*, 2020. (doi: https://doi.org/10.1101/2020.10.01.322990).
Office Action issued in corresponding Japanese Patent Application No. 2022-552528, dated Mar. 3, 2025.
Office Action issued in corresponding Chinese Application No. 202180032322.2, dated Jul. 31, 2025. (English Translation Provided).

* cited by examiner

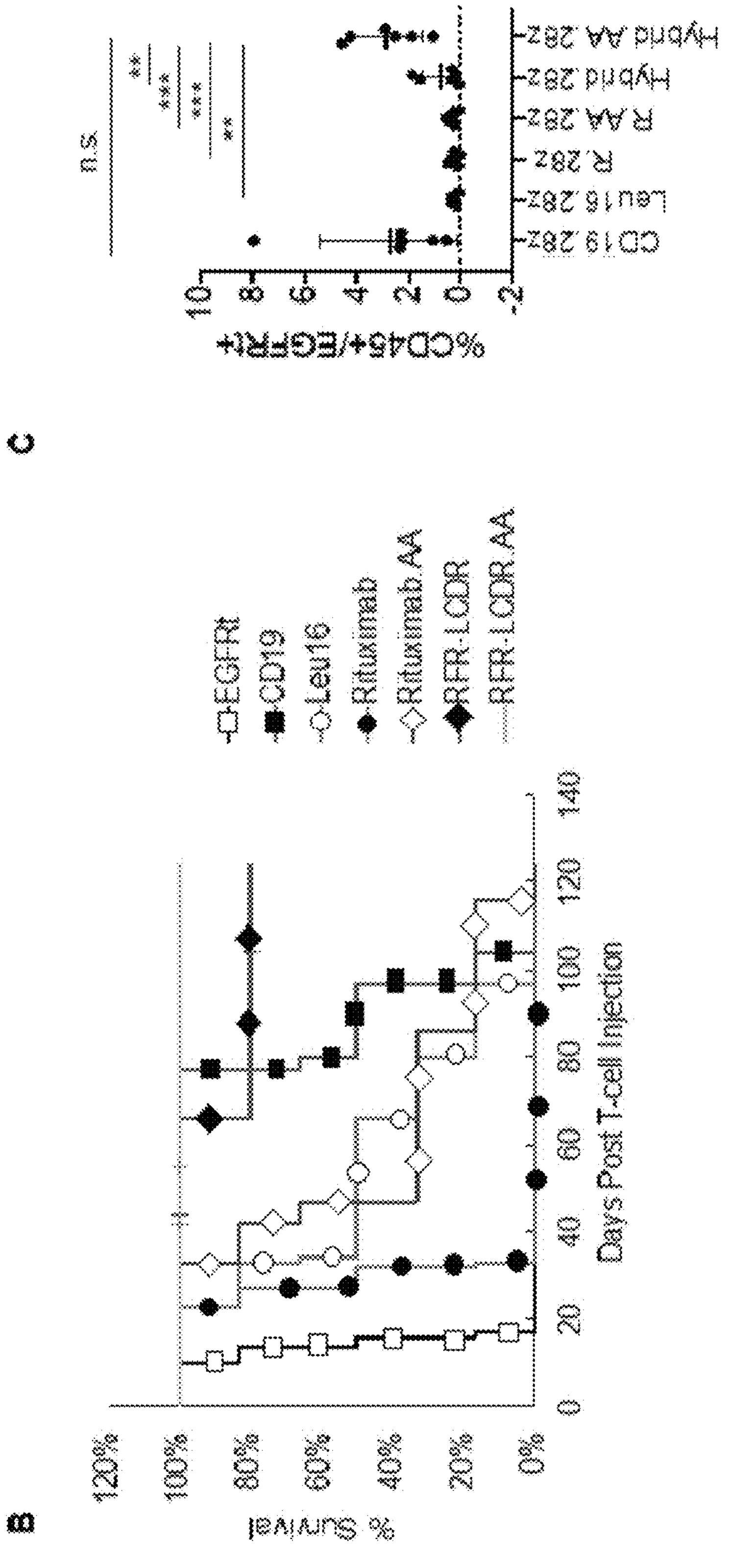
FIG. 9B-C

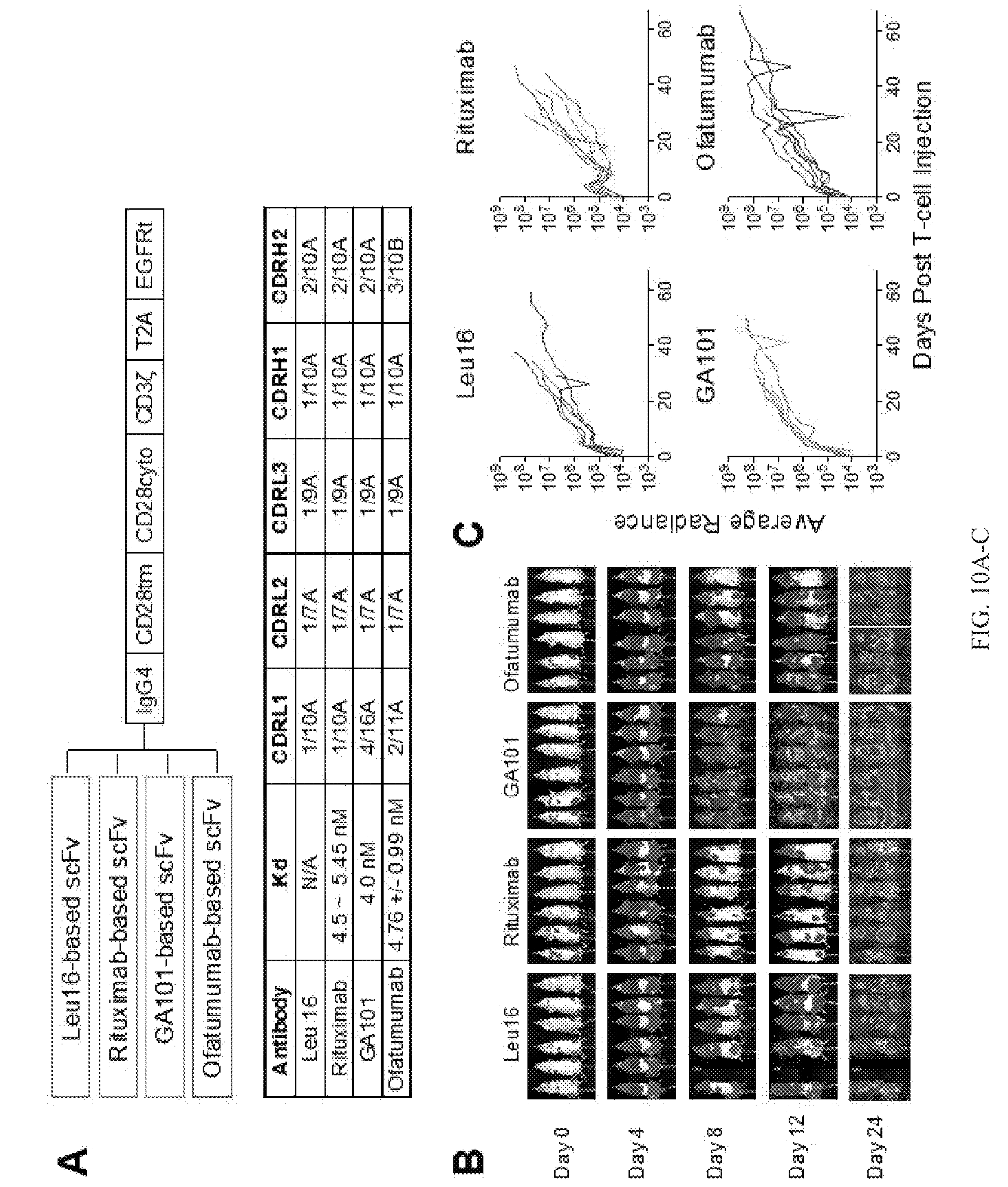
| Antibody | Kd | CDRL1 | CDRL2 | CDRL3 | CDRH1 | CDRH2 |
|---|---|---|---|---|---|---|
| Leu 16 | N/A | 1/10A | 1/7A | 1/9A | 1/10A | 2/10A |
| Rituximab | 4.5 ~ 5.45 nM | 1/10A | 1/7A | 1/9A | 1/10A | 2/10A |
| GA101 | 4.0 nM | 4/16A | 1/7A | 1/9A | 1/10A | 2/10A |
| Ofatumumab | 4.76 +/- 0.99 nM | 2/11A | 1/7A | 1/9A | 1/10A | 3/10B |
FIG. 10A-C

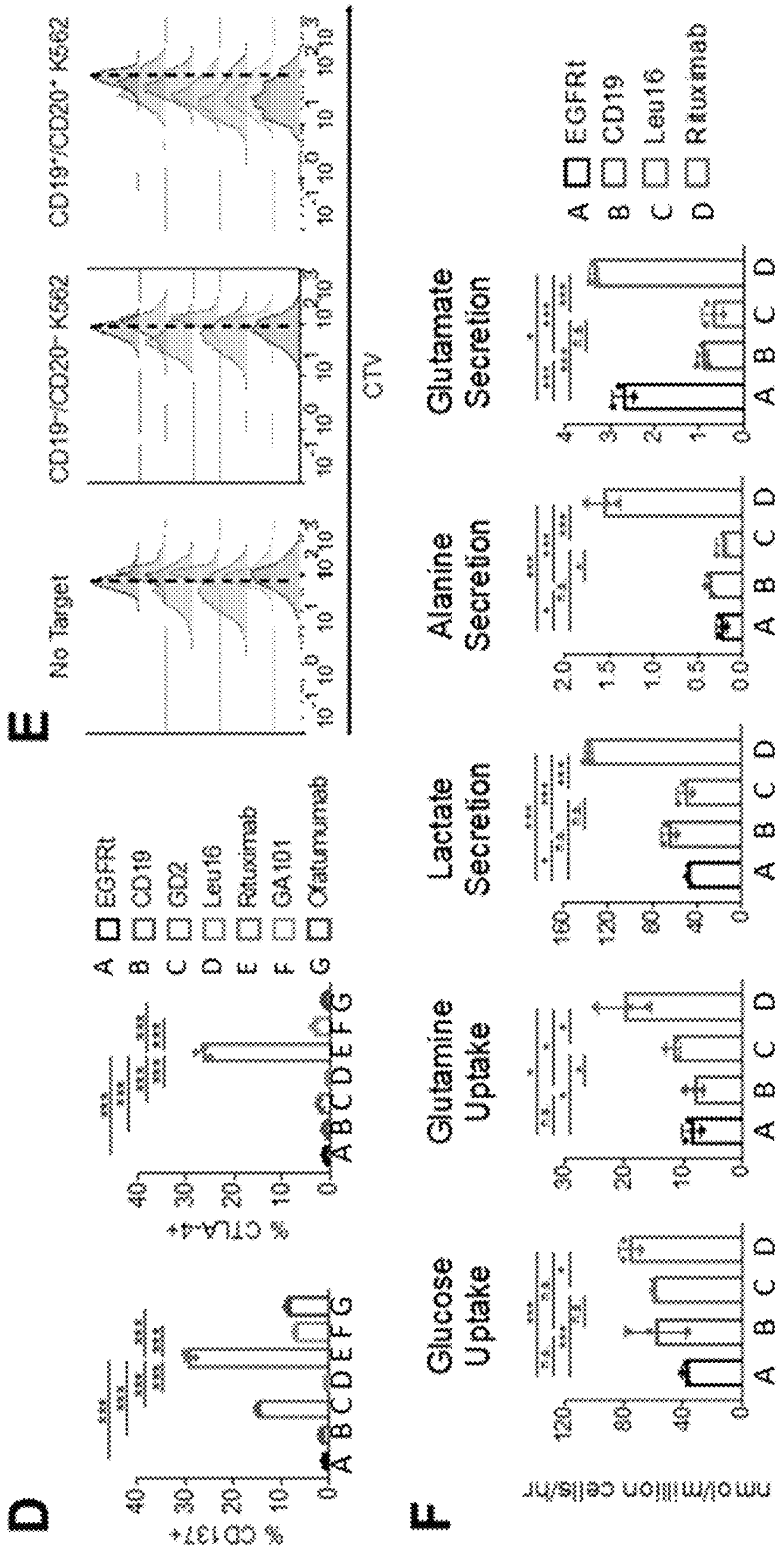
FIG. 10D-F

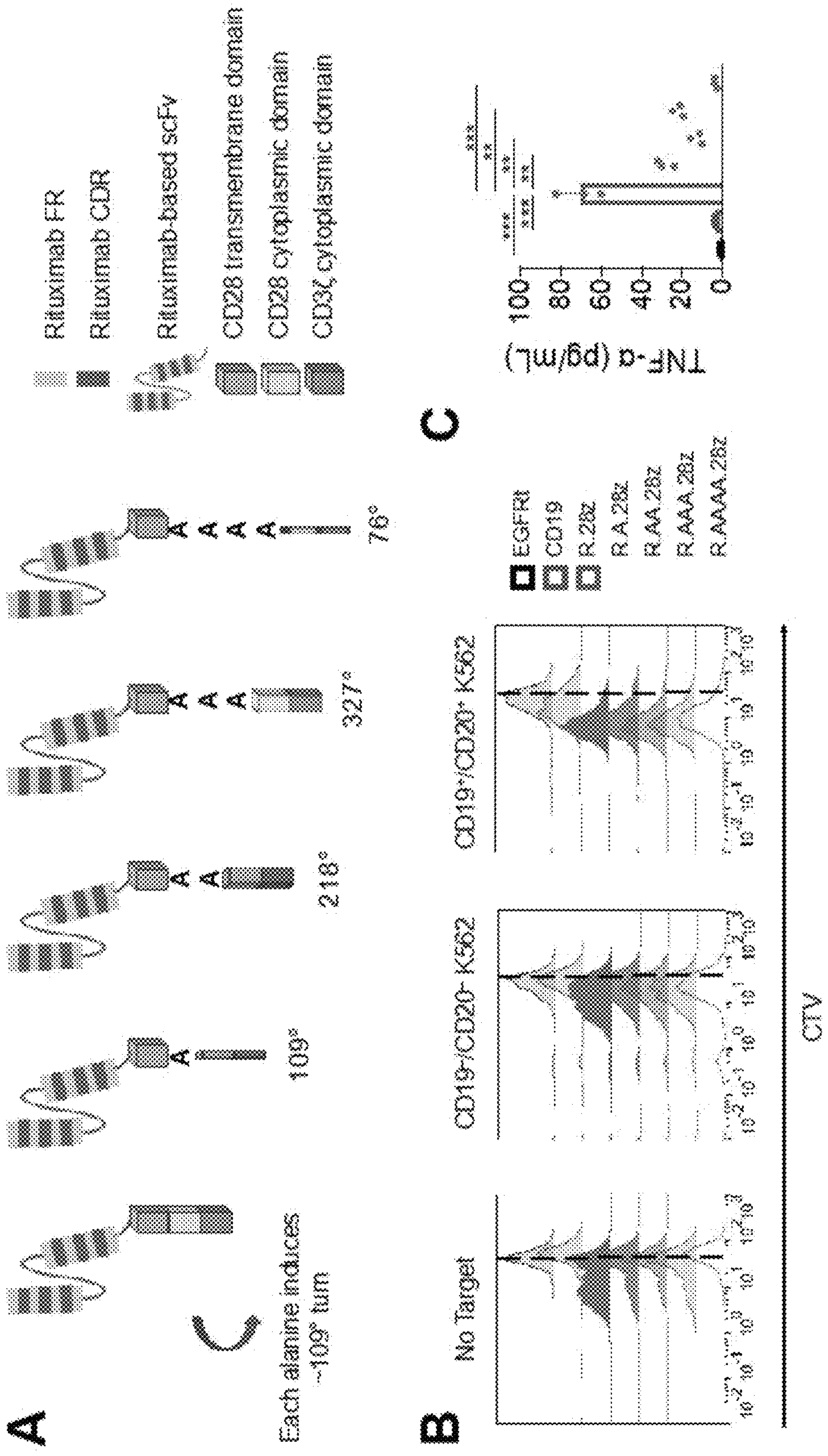
FIG. 11A-C

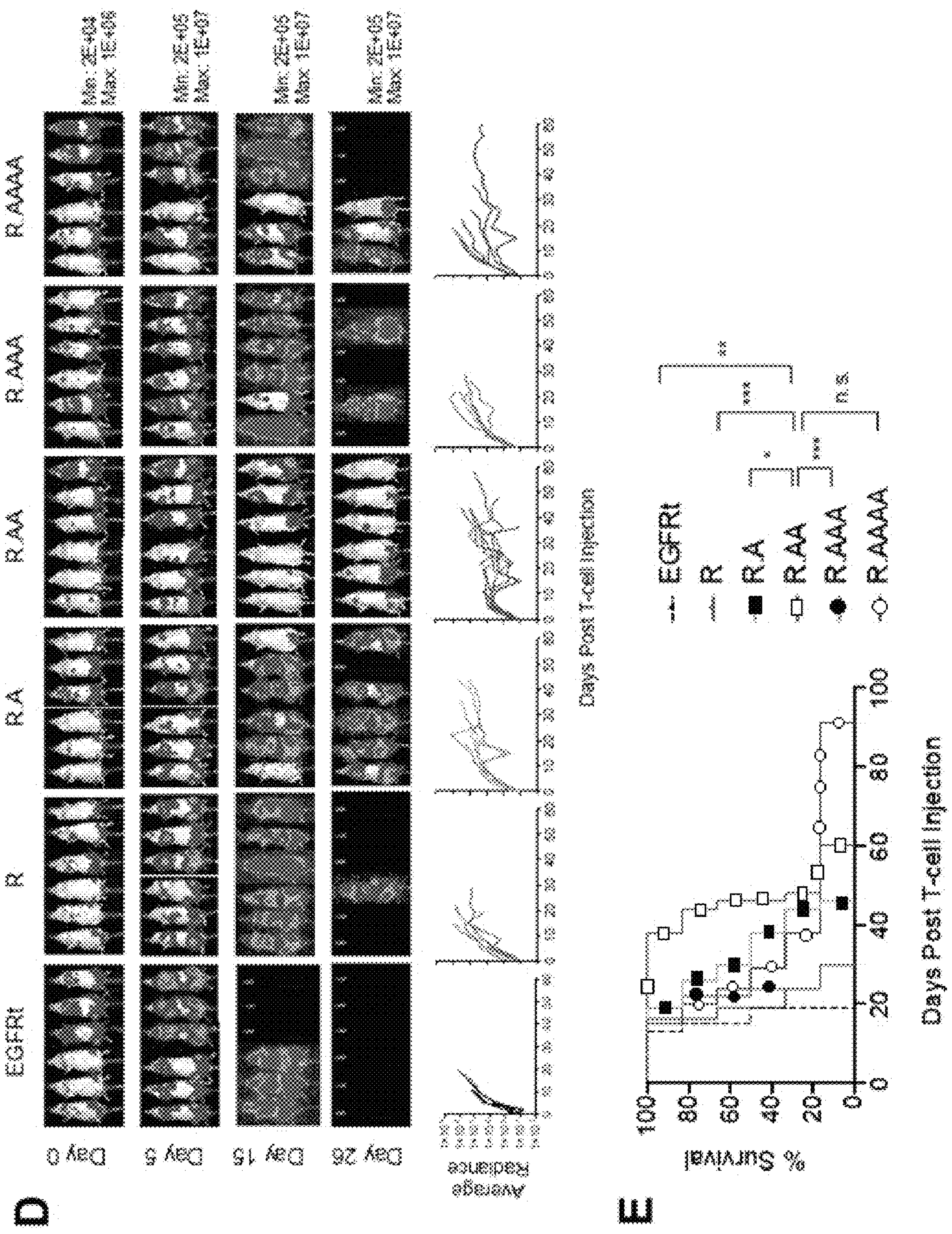
FIG. 11D-E

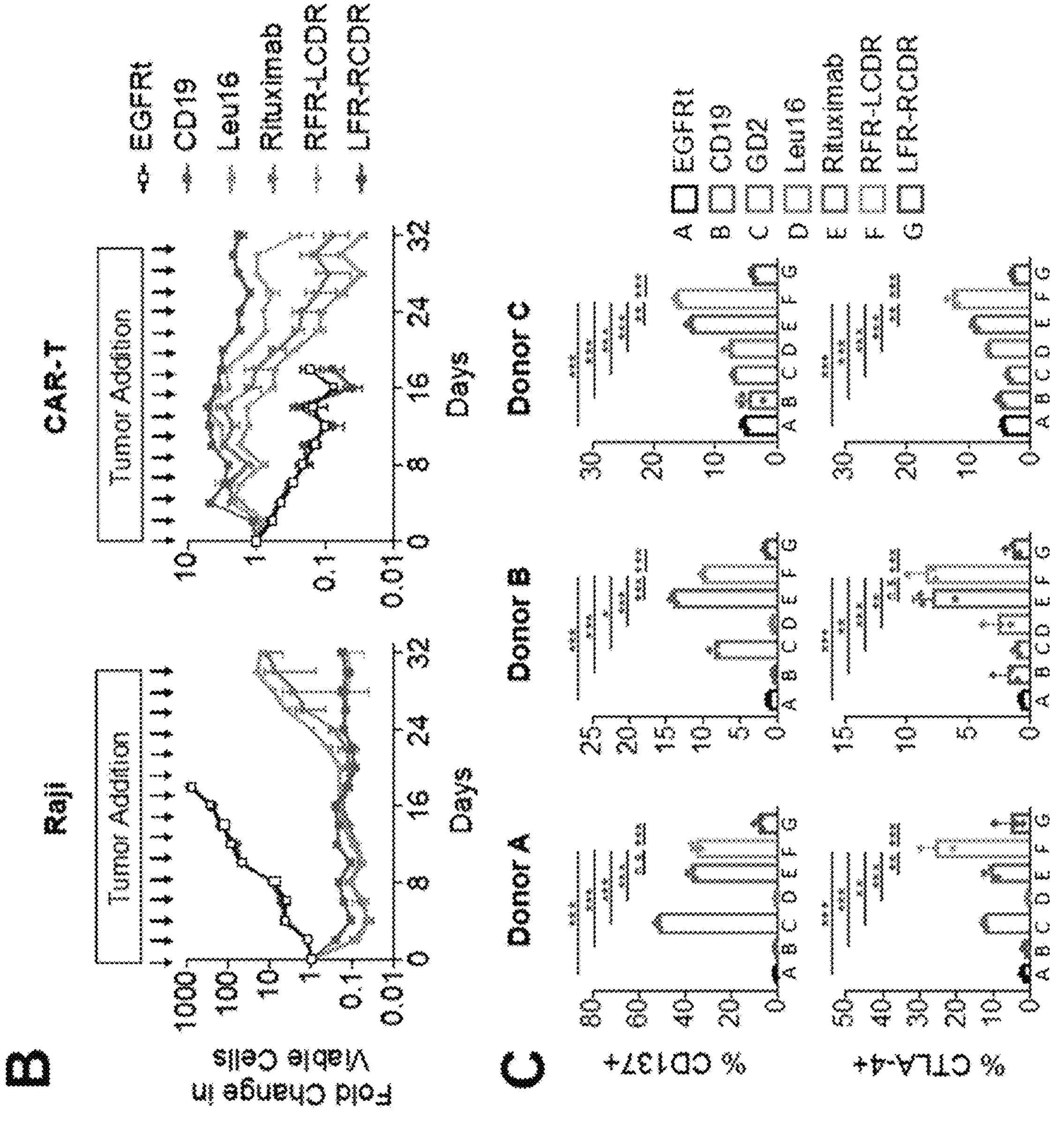
FIG. 12B-C

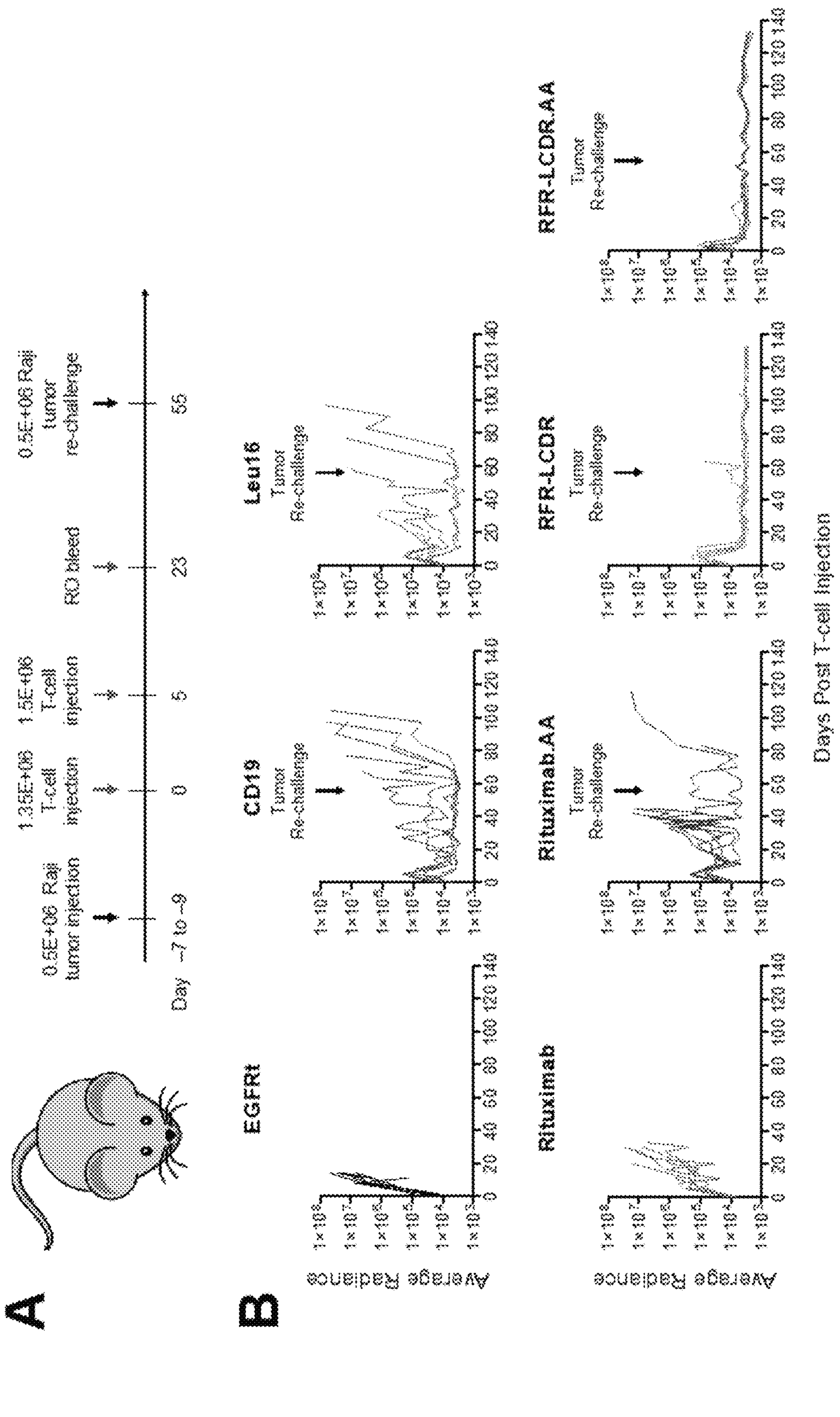
FIG. 13A-B

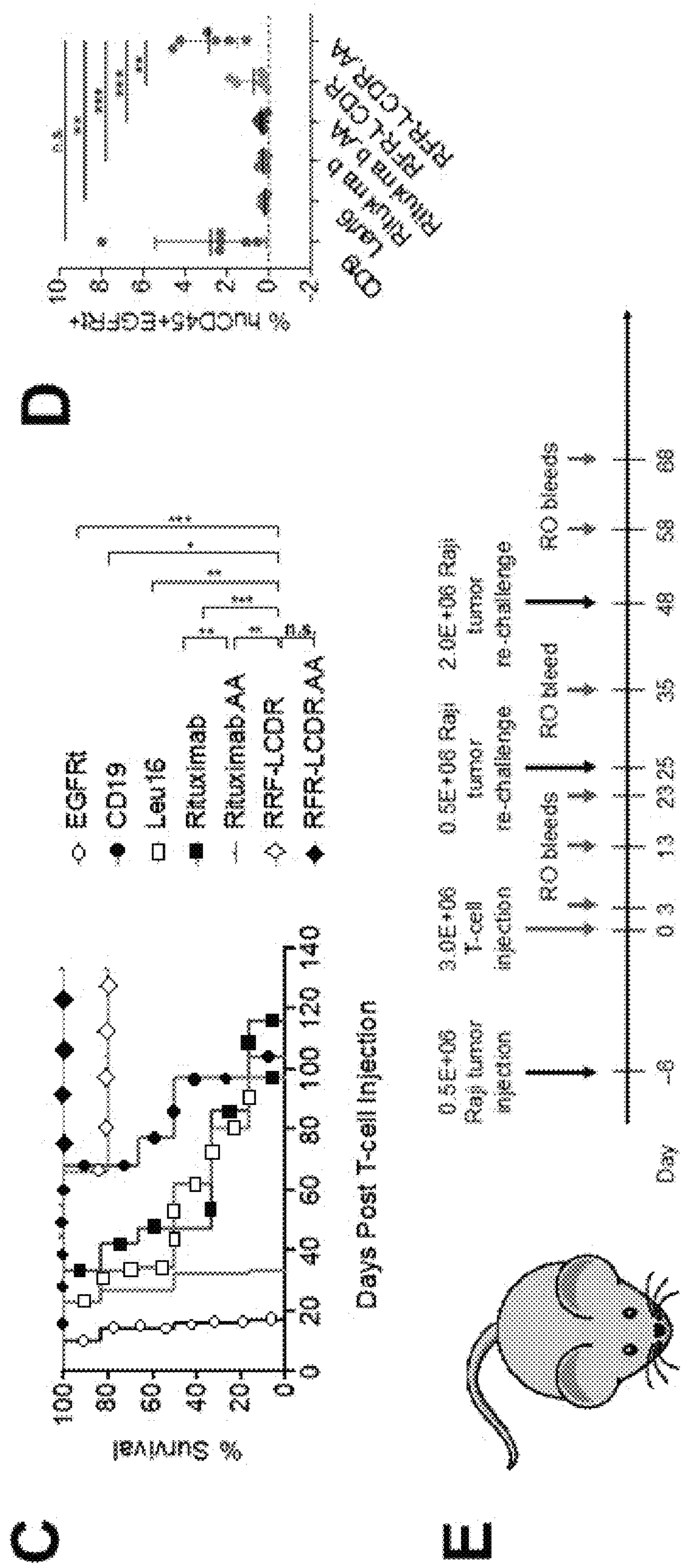
FIG. 13C-E

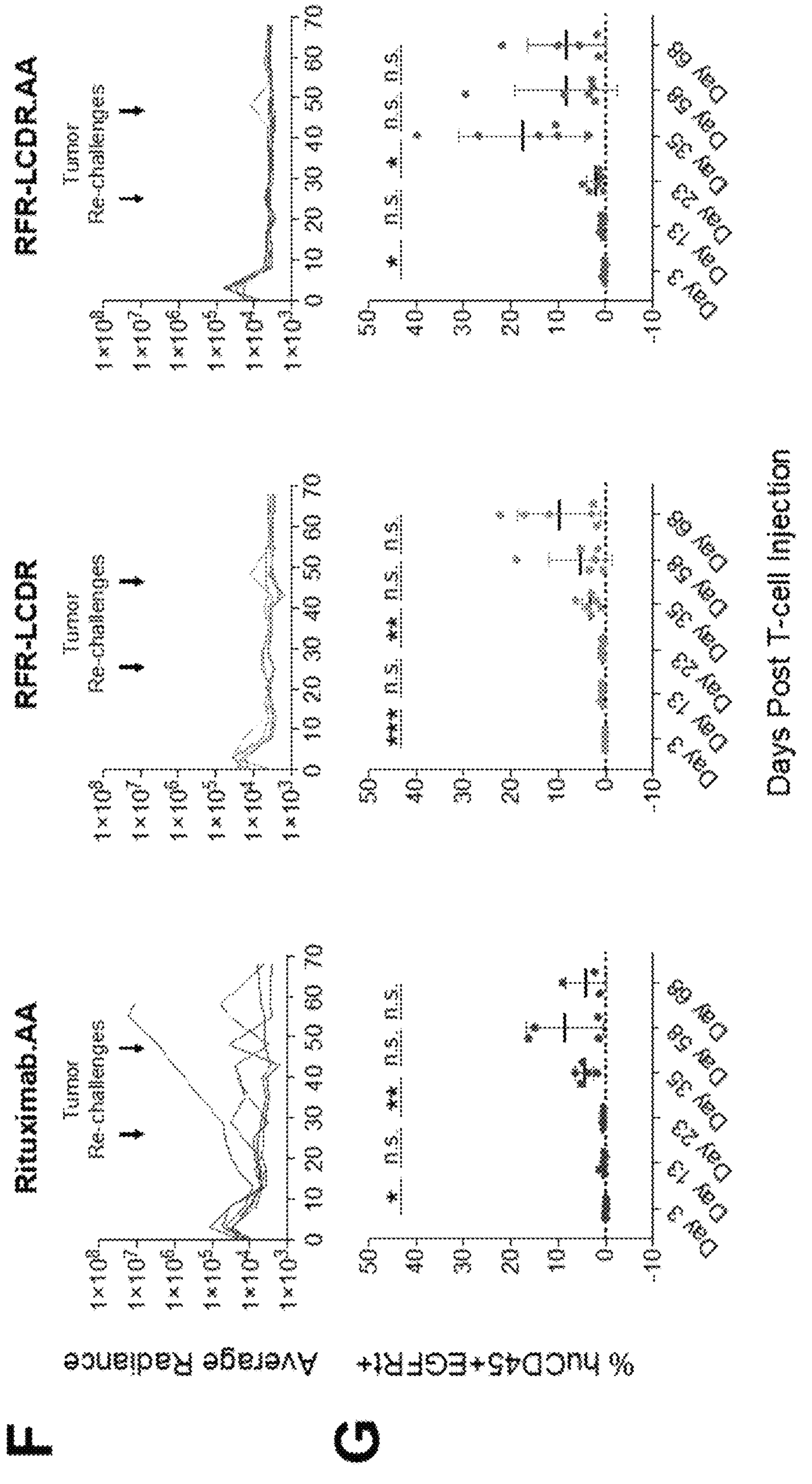
FIG. 13F-G

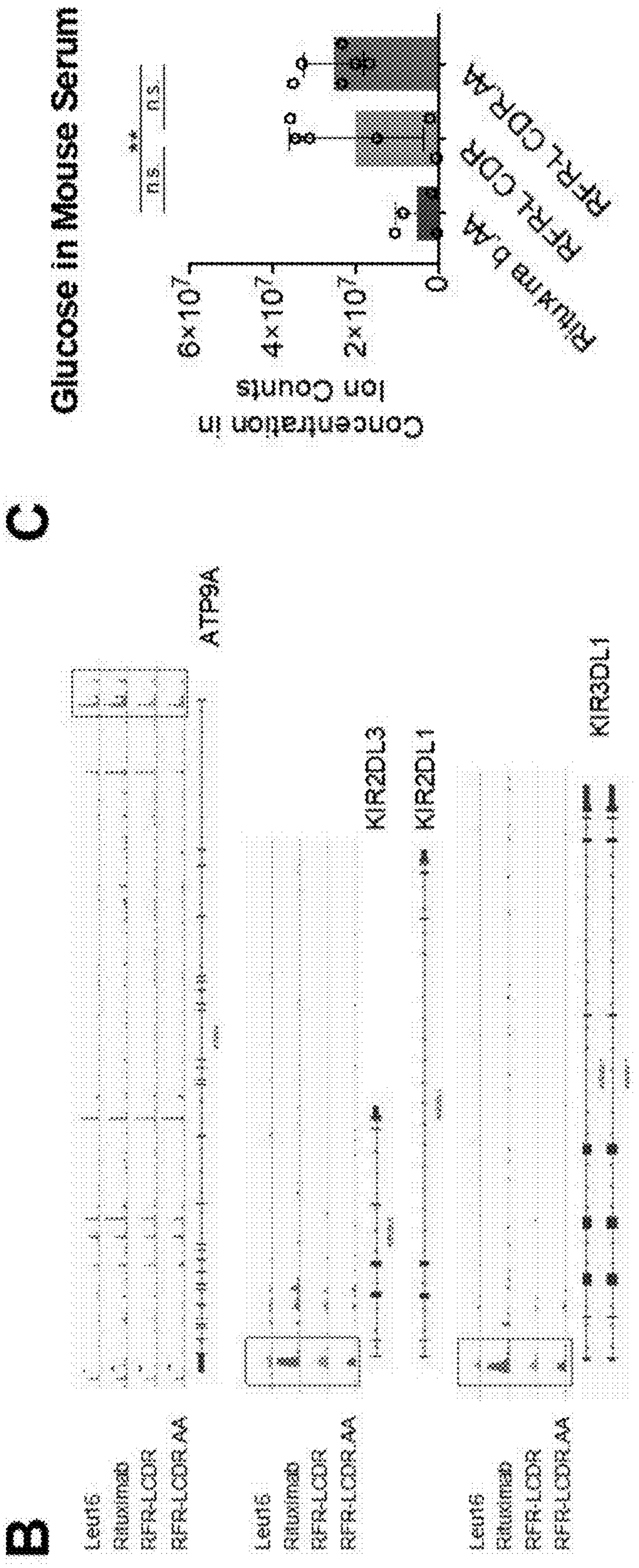
FIG. 14B-C

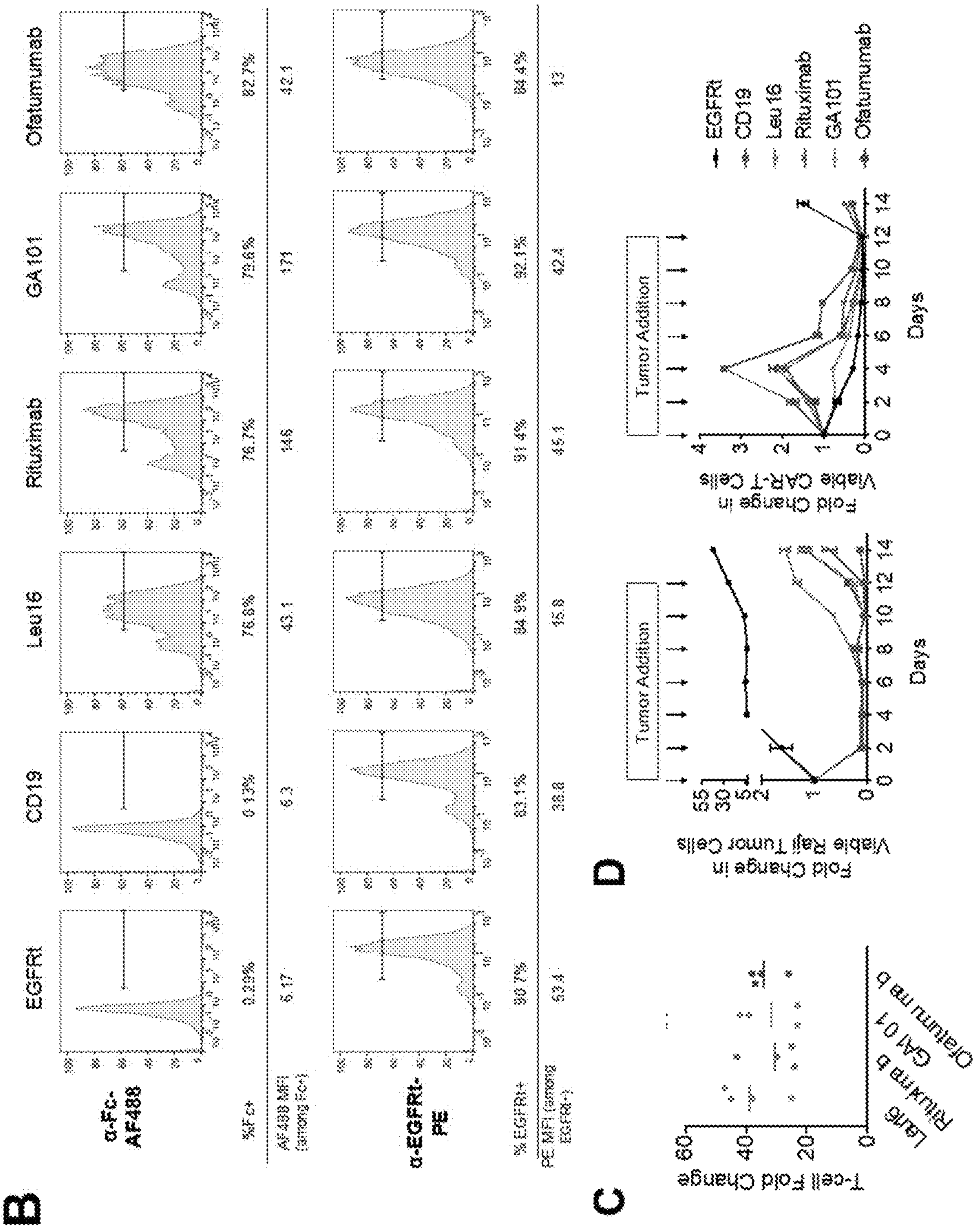
FIG. 16B-D

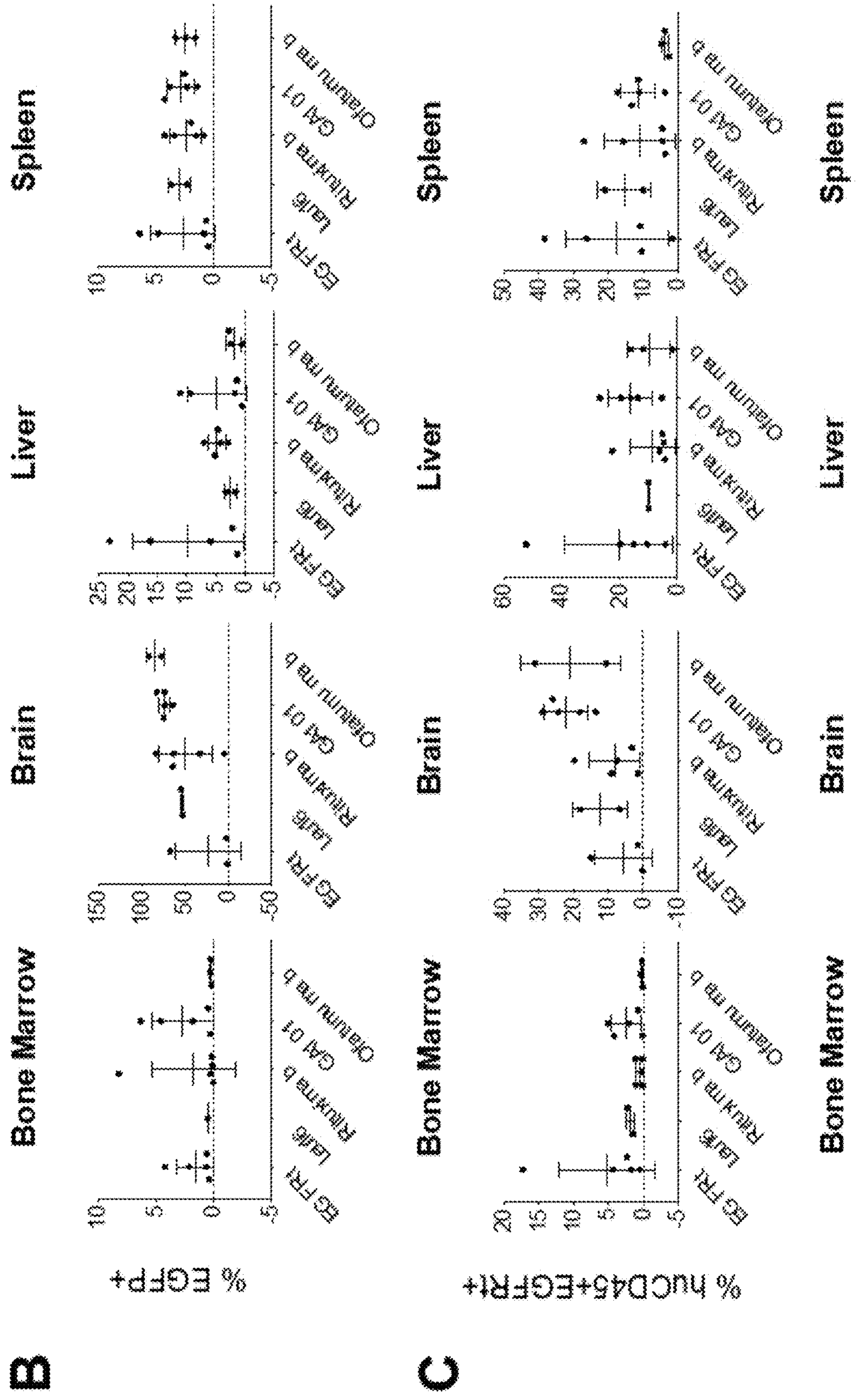
FIG. 17B-C

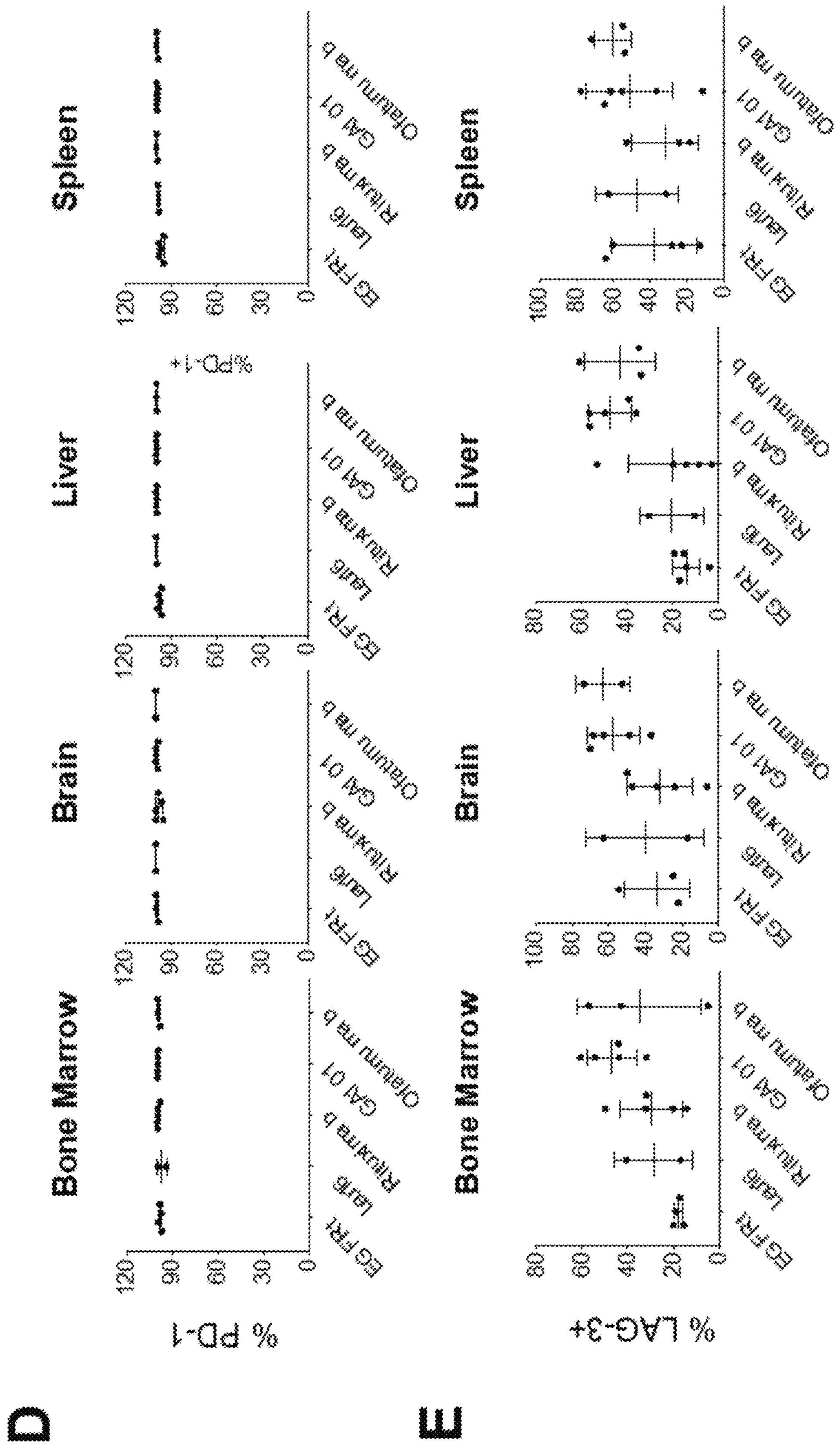
FIG. 17D-E

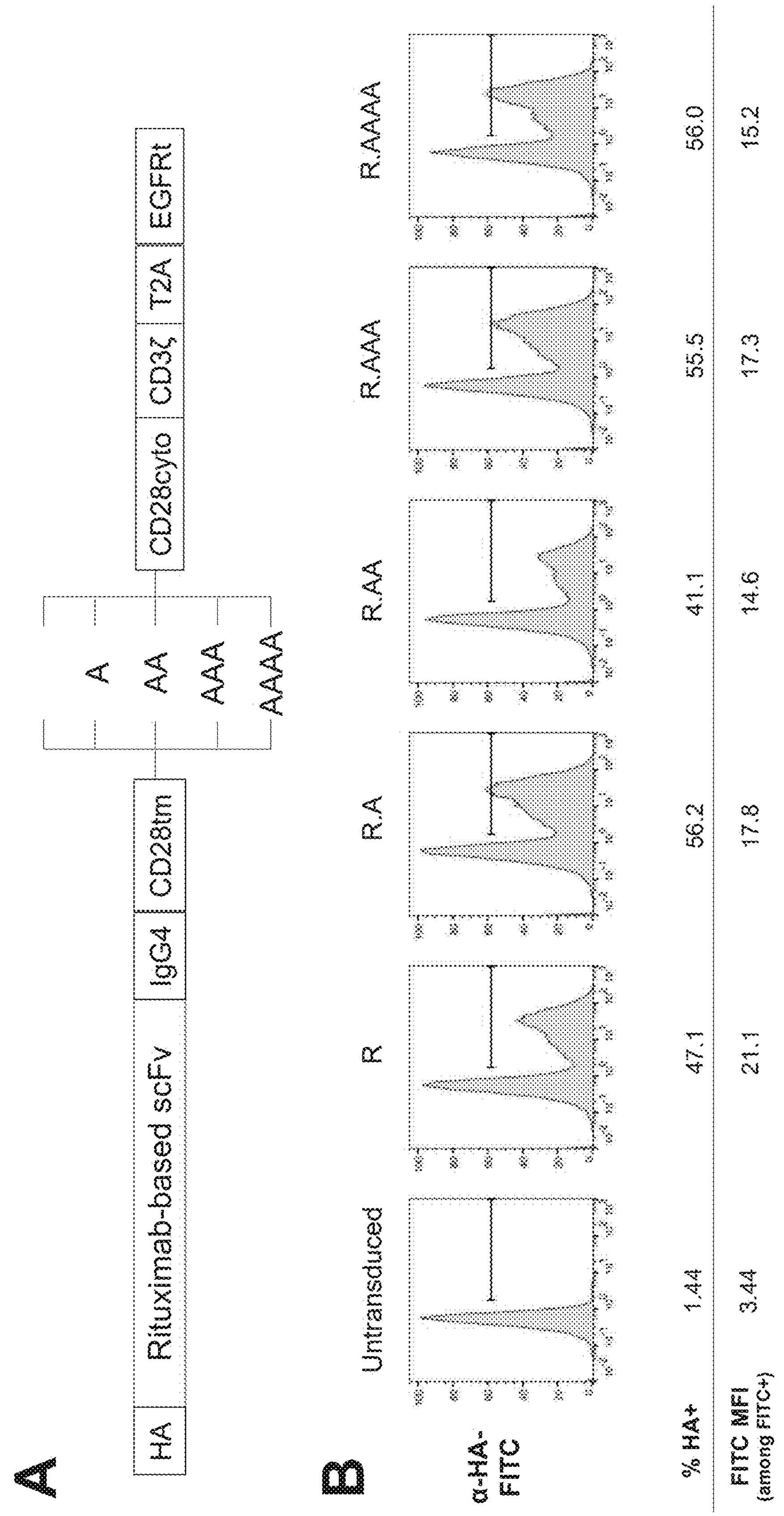
FIG. 20A-B

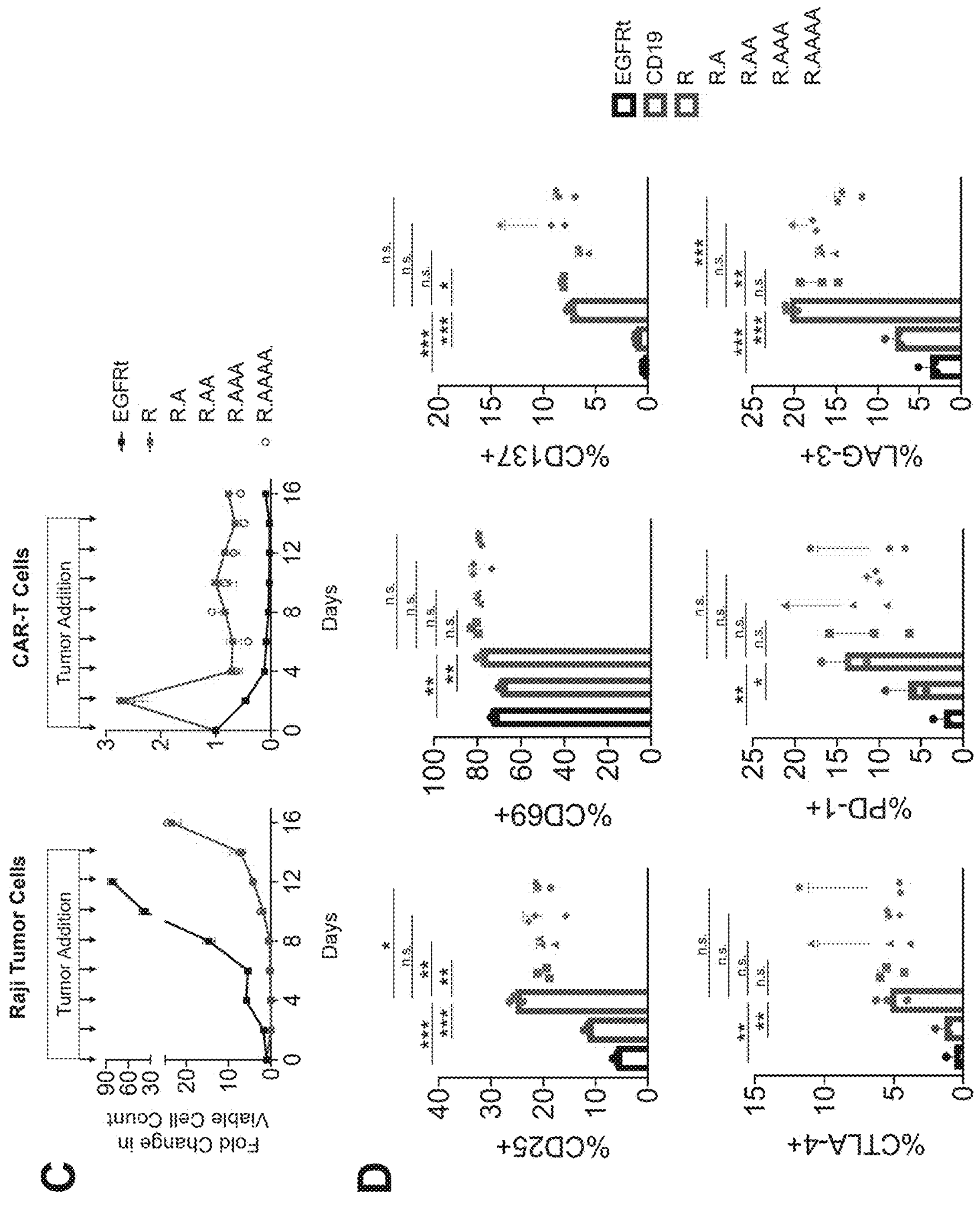
FIG. 20C-D

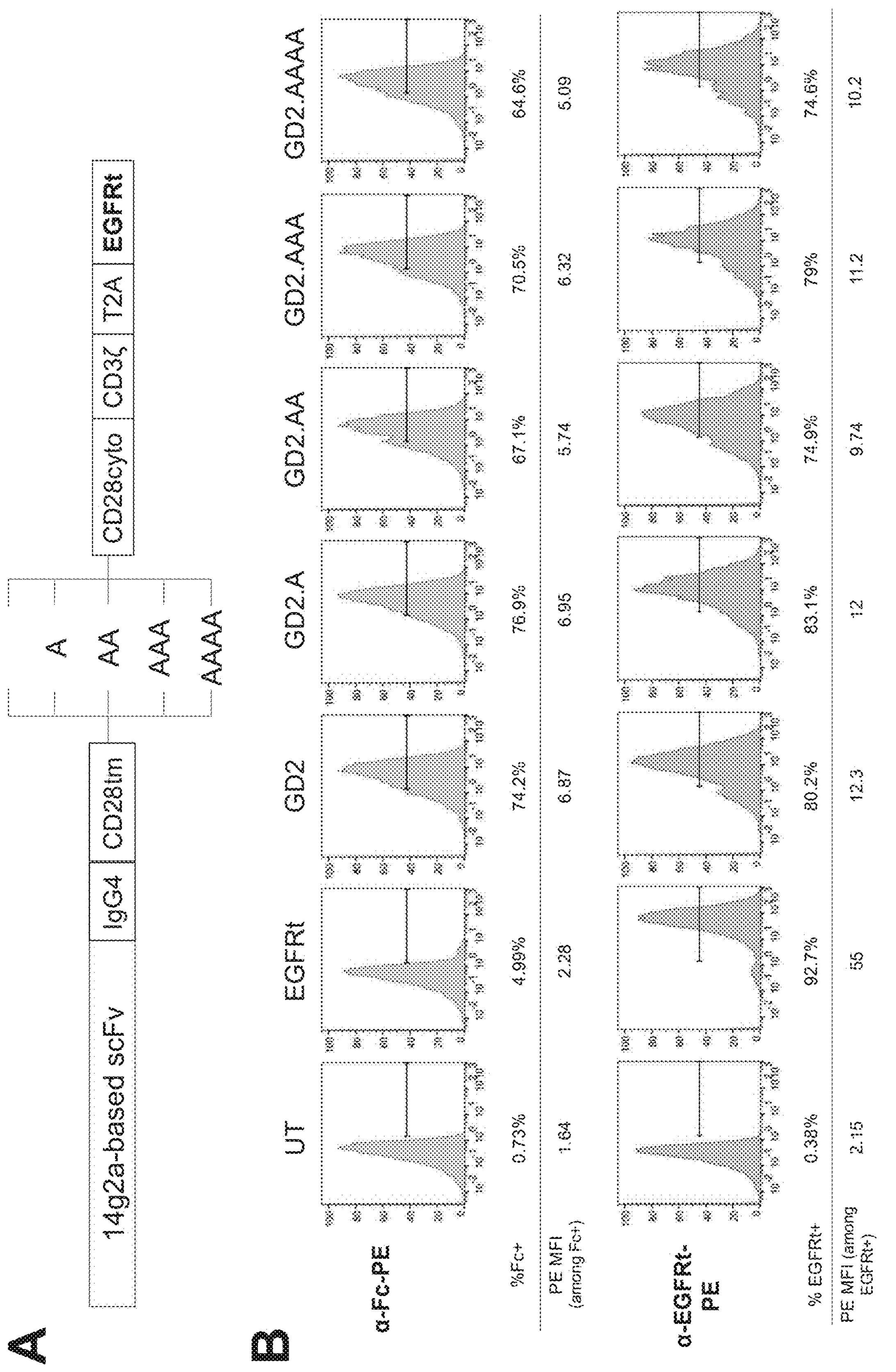
FIG. 21A-B

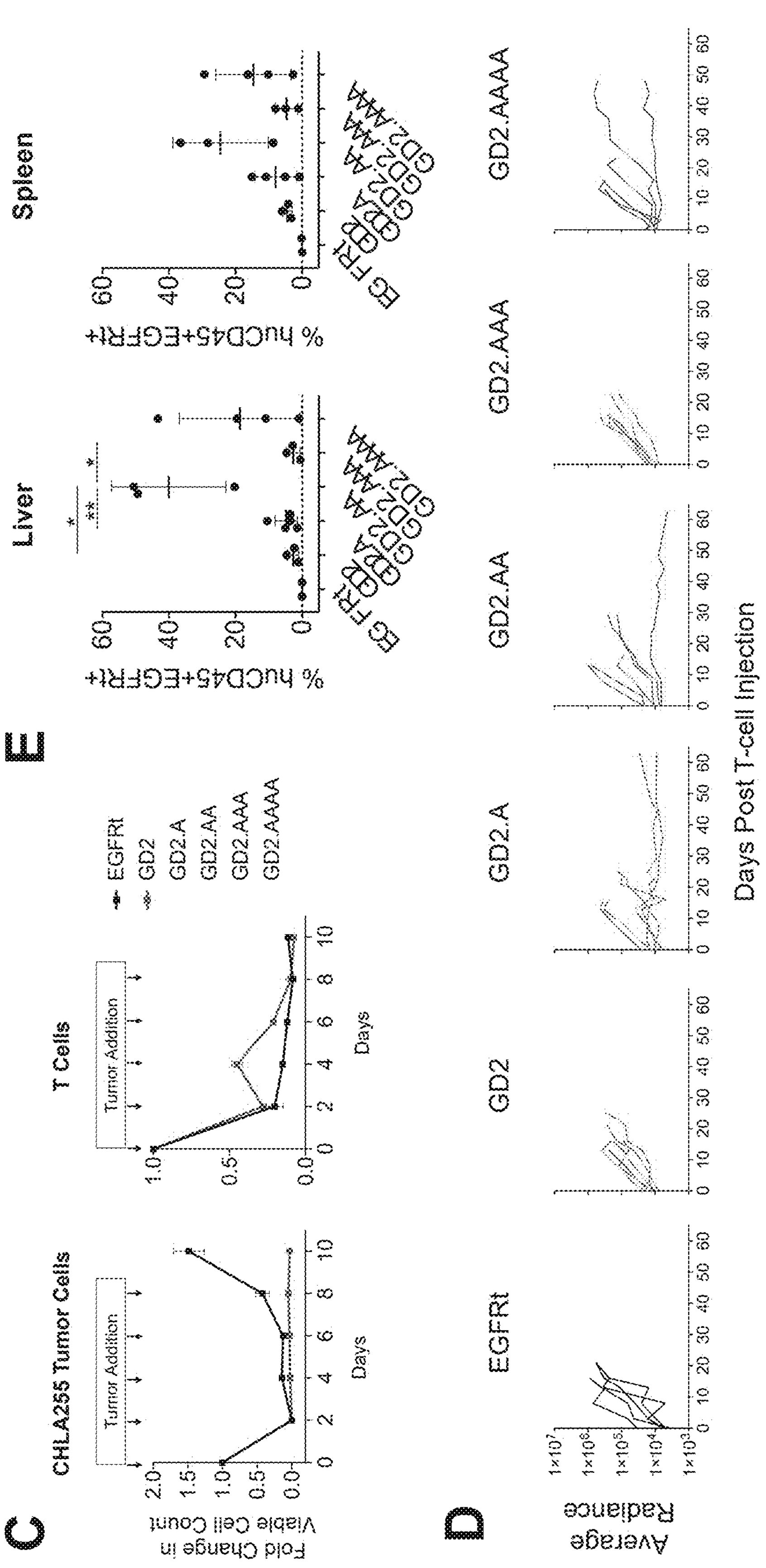
FIG. 21C-E

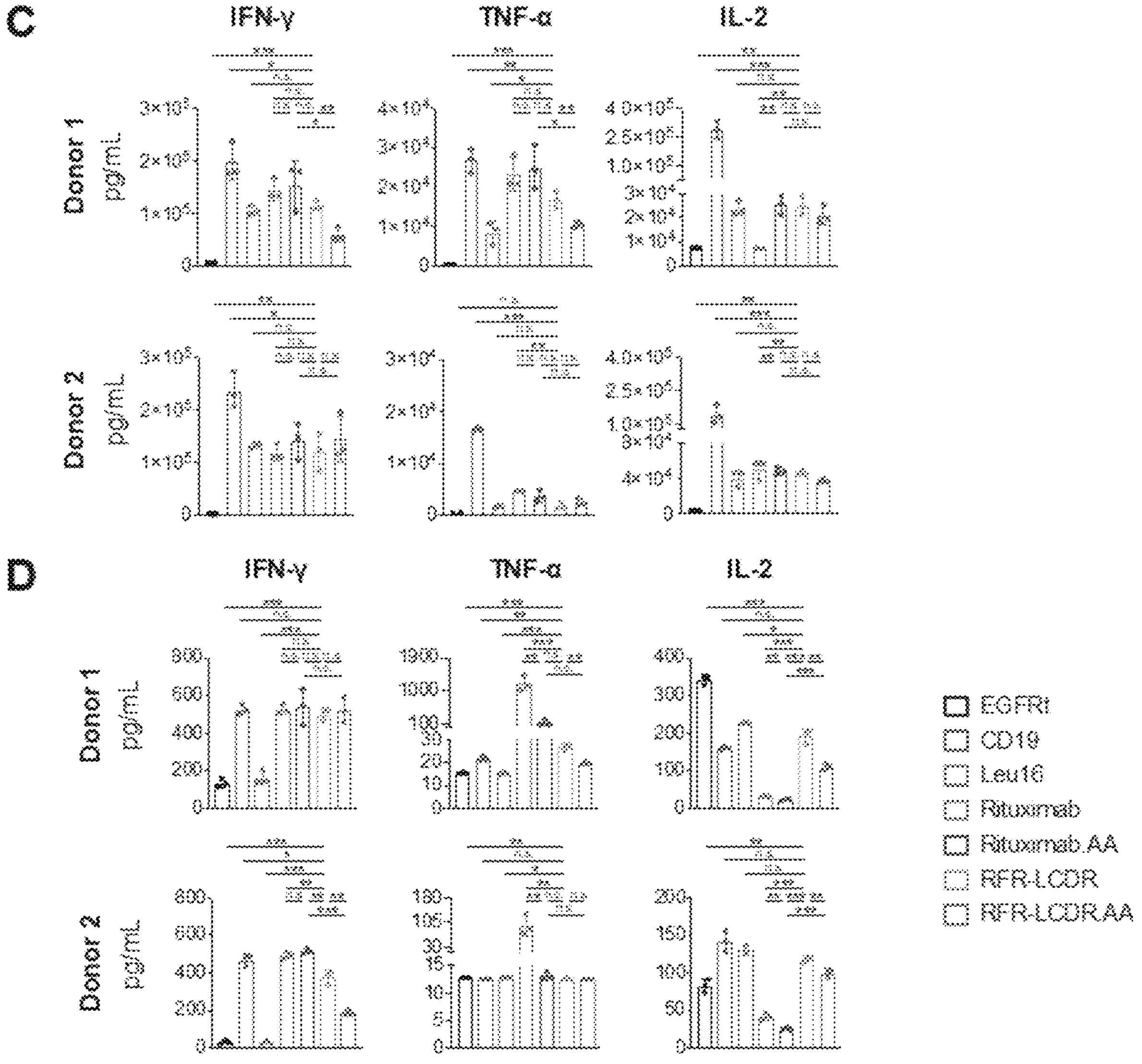
FIG. 22C-D

FIG. 24A-B

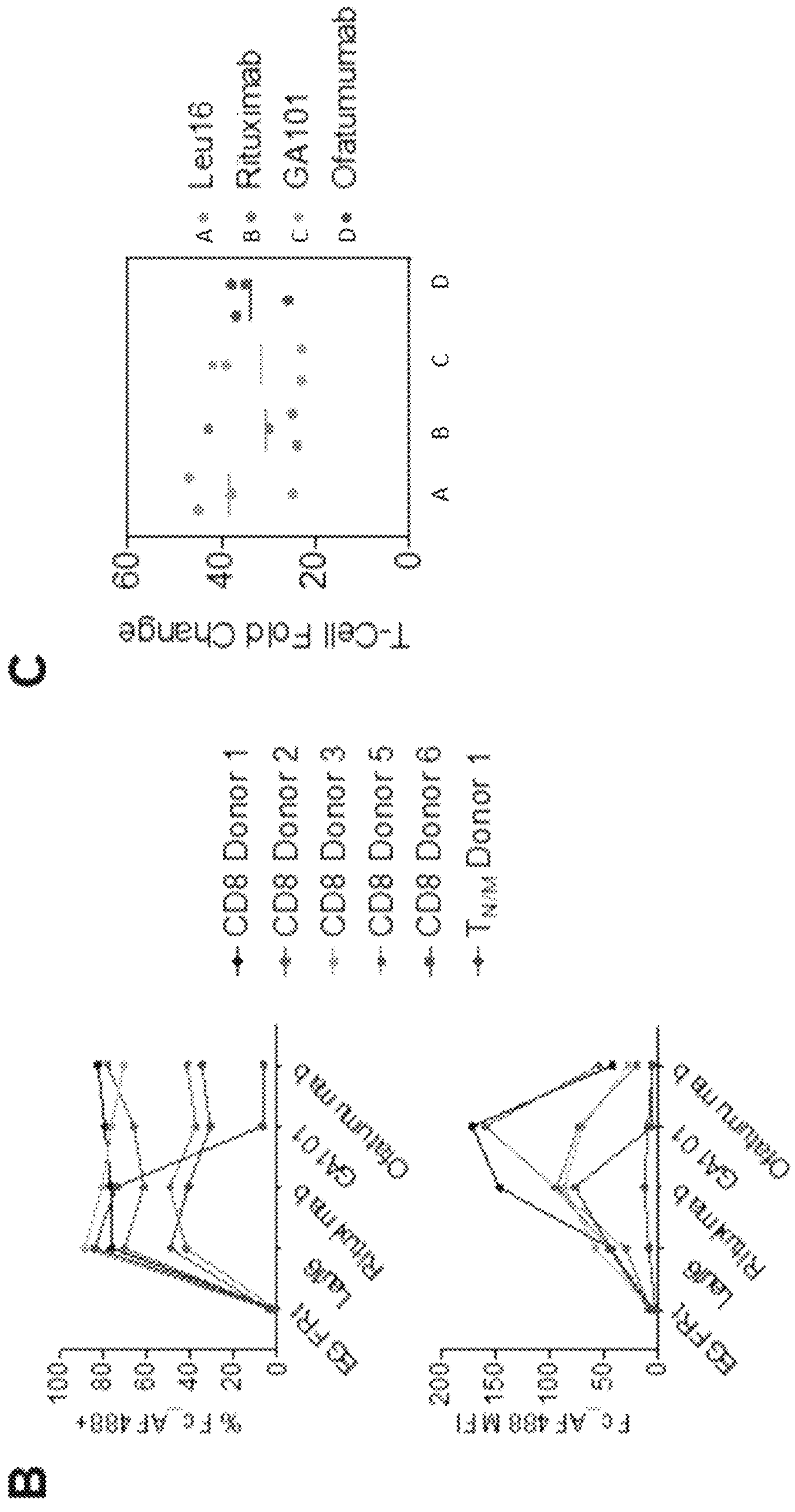
FIG. 27B-C

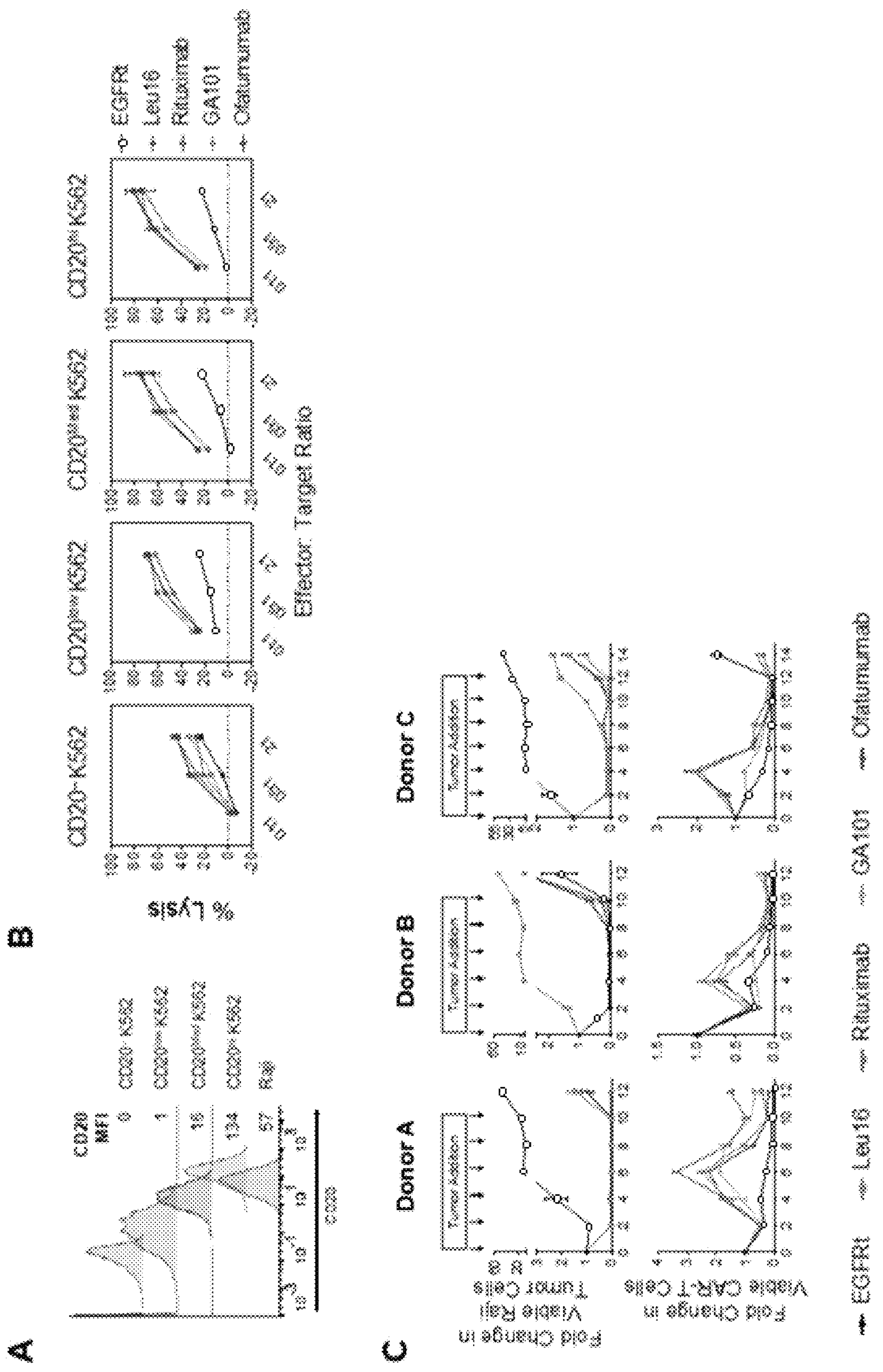
FIG. 28A-C

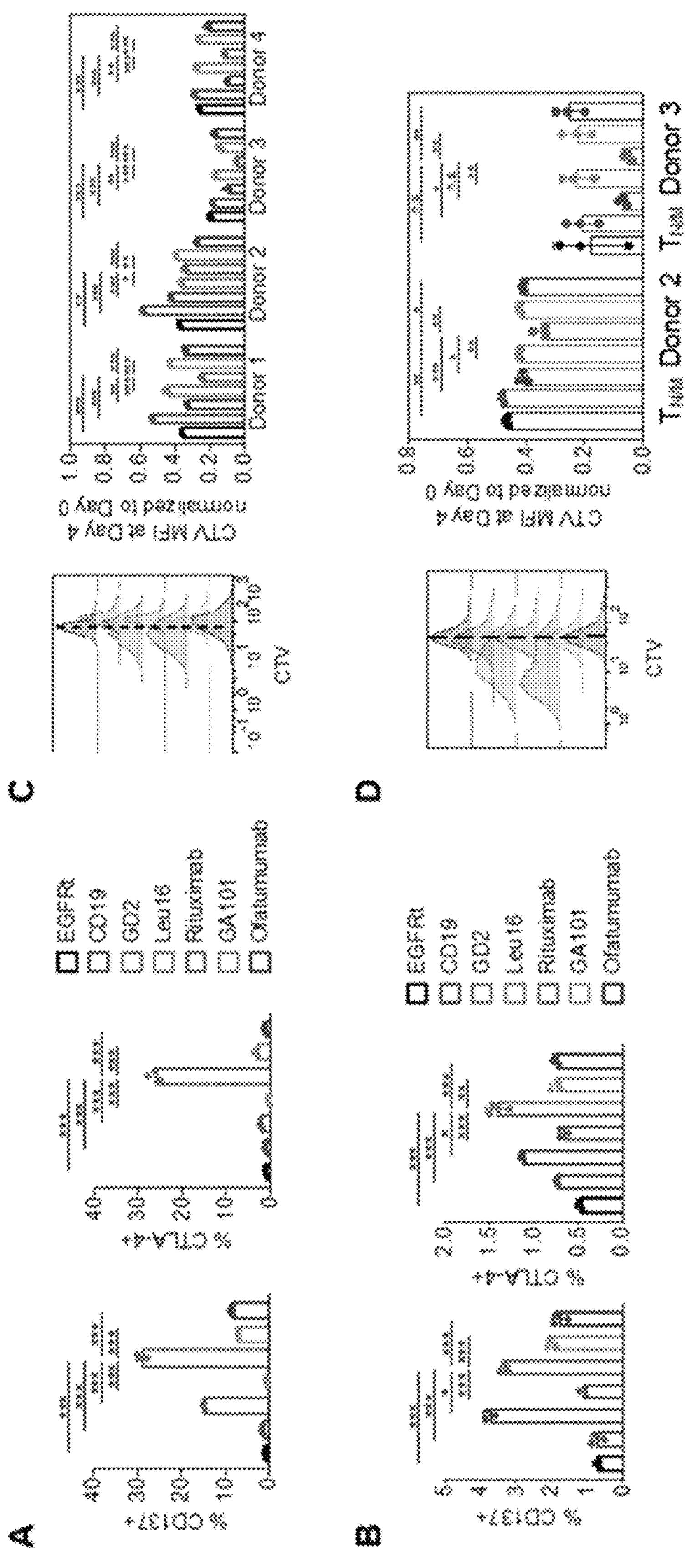
FIG. 29A-D

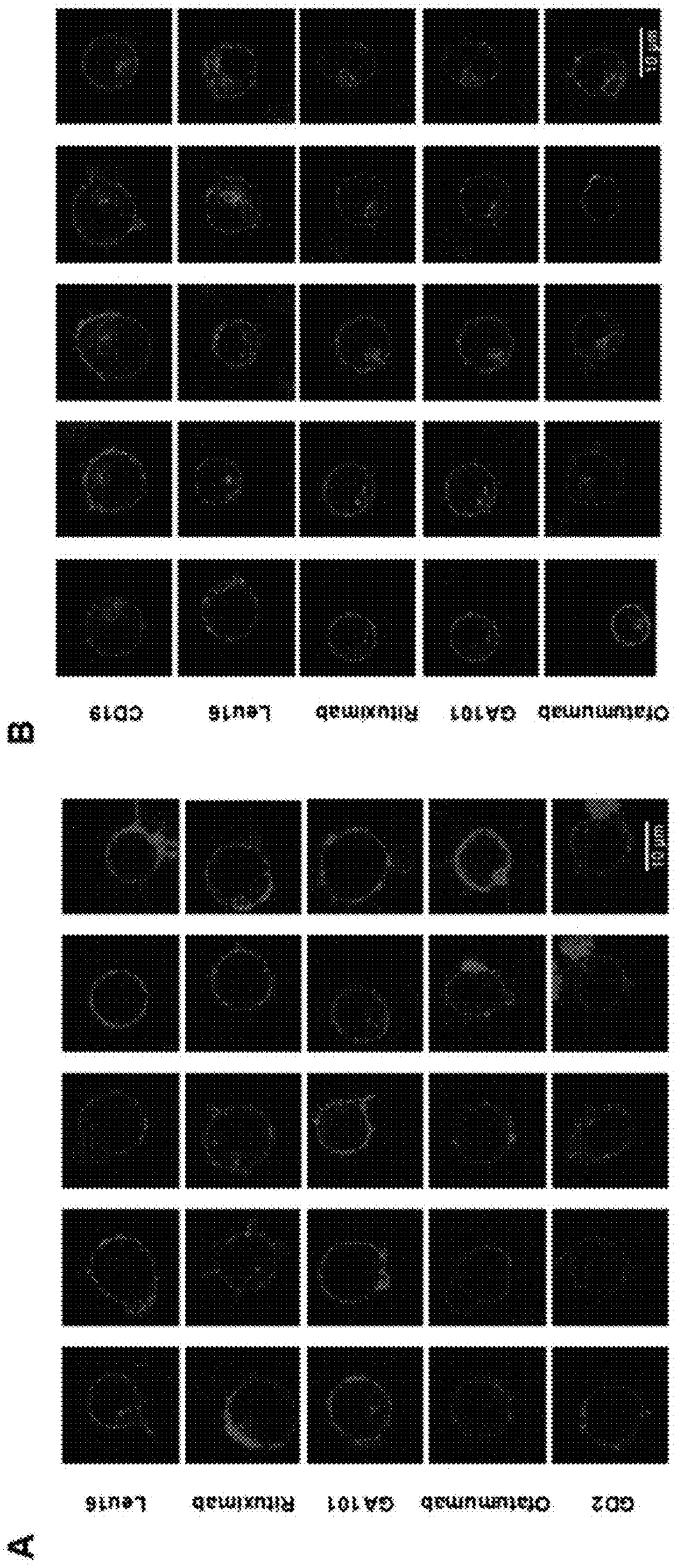
FIG. 31A-B

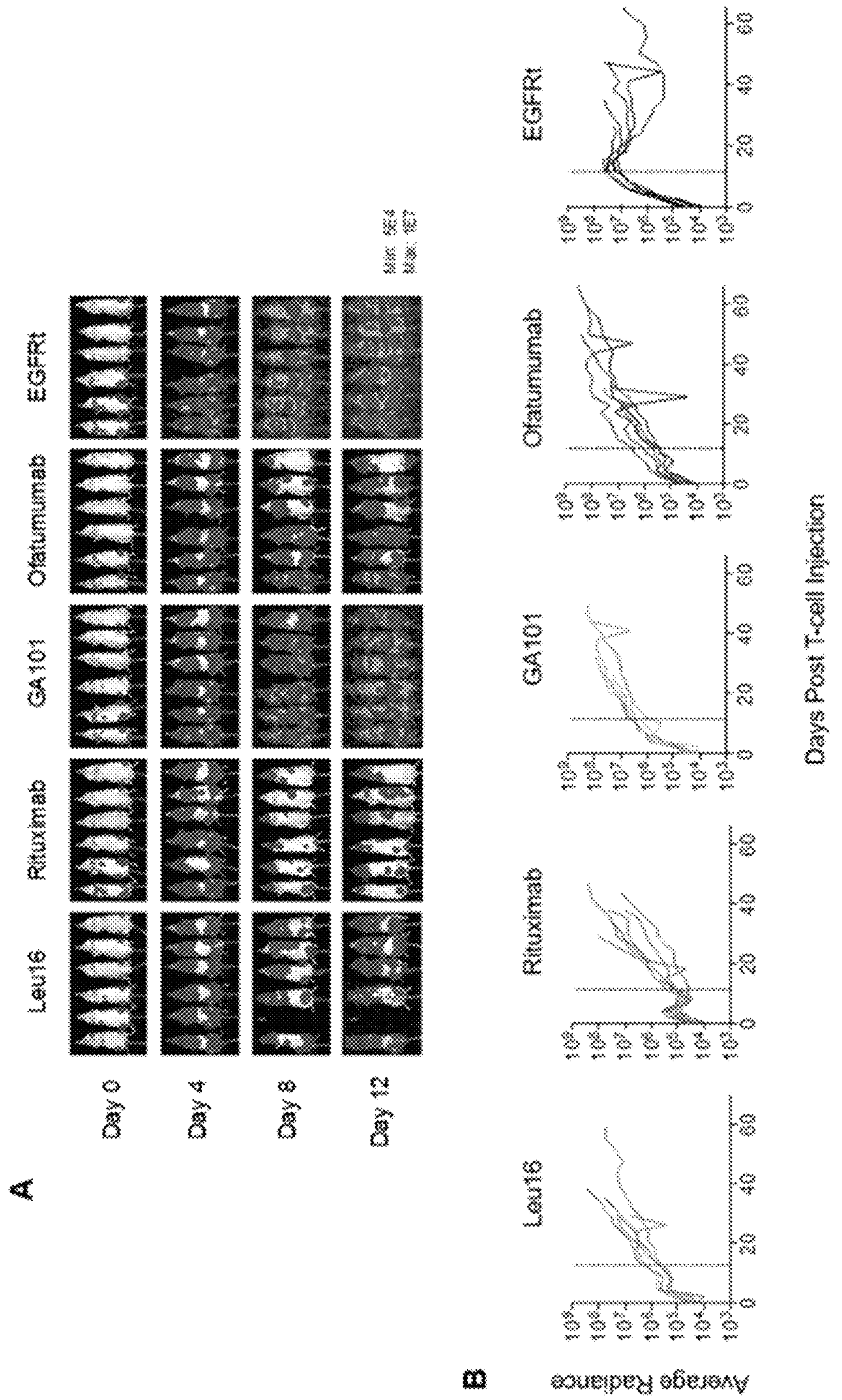
FIG. 32A-B

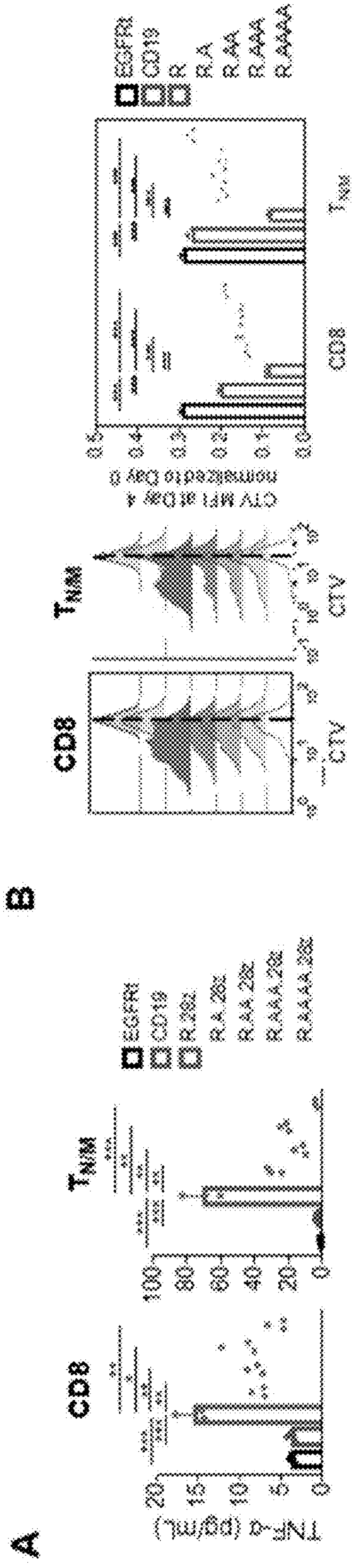
FIG. 34A-B

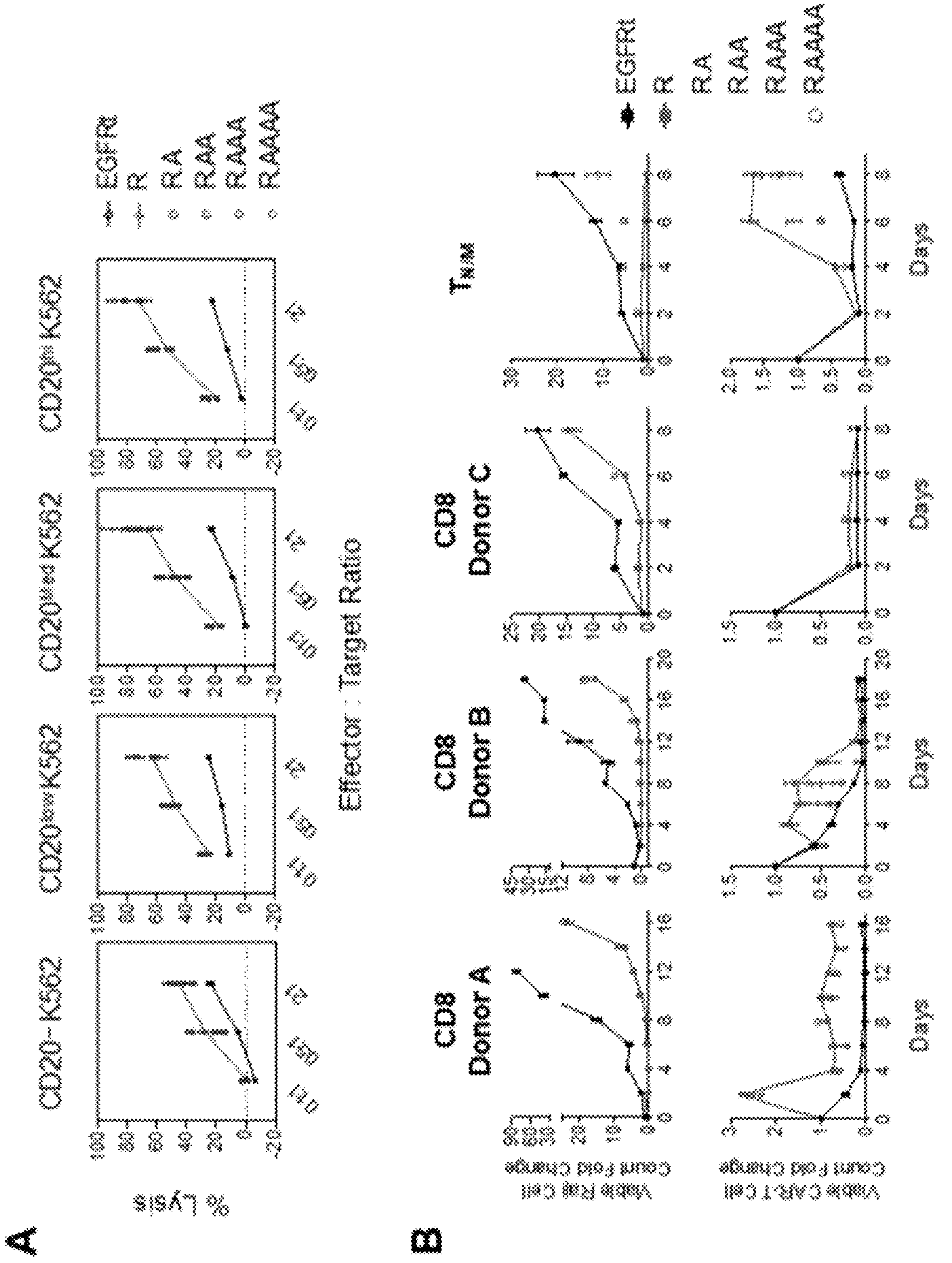
FIG. 35A-B

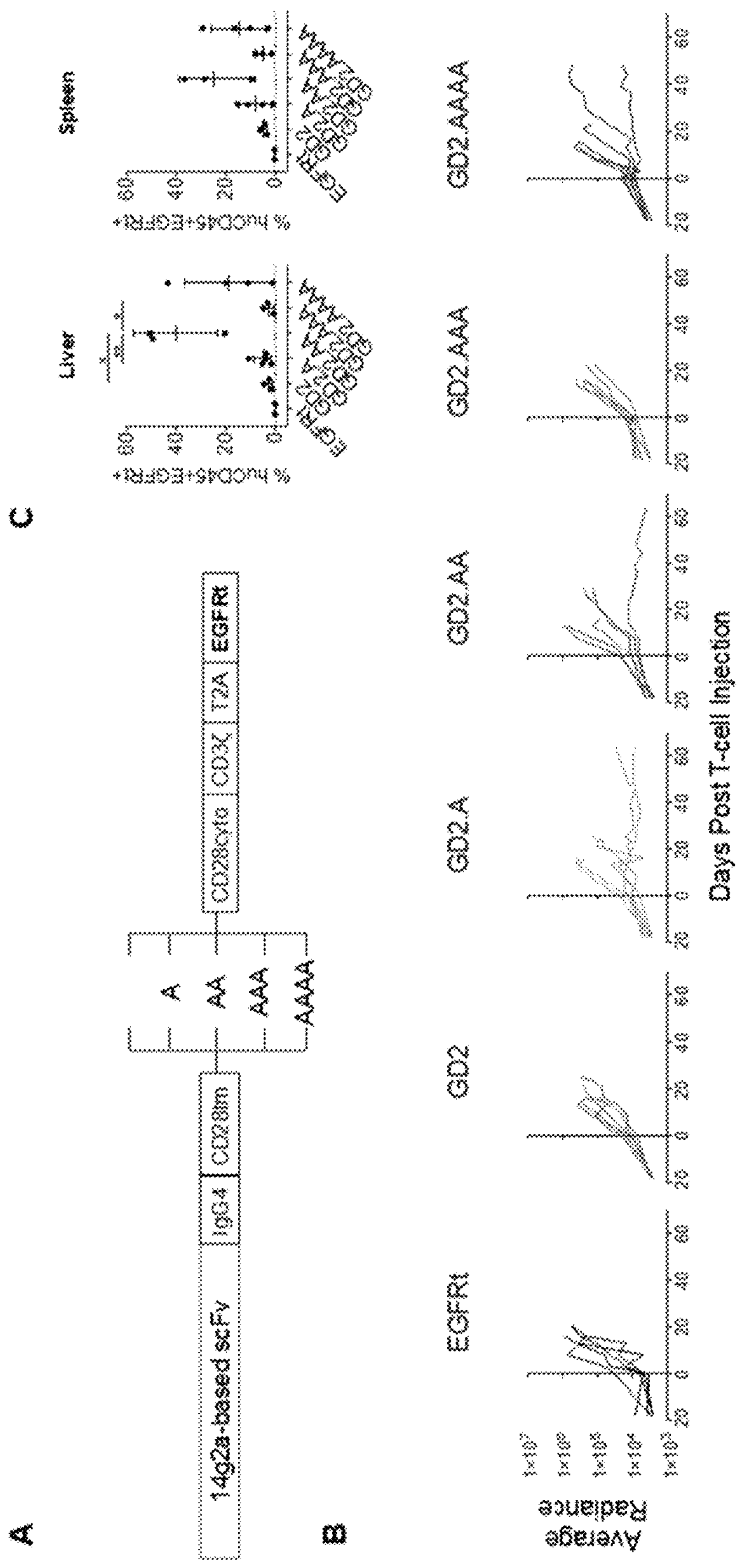
FIG. 36A-C

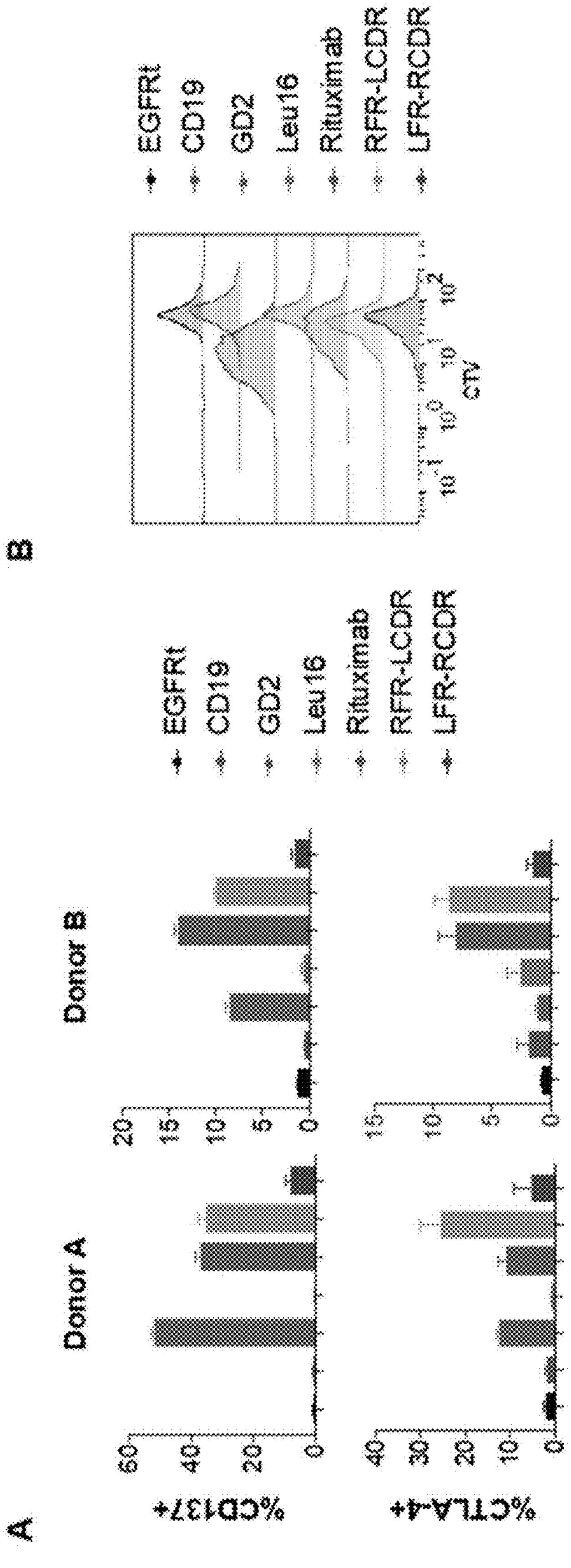
FIG. 38A-B

| KD (M) | Leu16 | Rituximab | Hybrid |
|---|---|---|---|
| Run 1 | 1.57E-07 | 1.10E-07 | 7.55E-08 |
| Run 2 | 1.27E-07 | 1.23E-07 | 9.55E-08 |
| Run 3 | 1.31E-07 | 1.22E-07 | 8.22E-08 |
| Avg | 1.38E-07 | 1.19E-07 | 8.44E-08 |
| SD | 1.63E-08 | 7.13E-09 | 1.02E-08 |

$p = 0.131$ $p = 0.009$ $p = 0.008$

| ka (1/Ms) | Leu16 | Rituximab | Hybrid |
|---|---|---|---|
| Run 1 | 3.99E+03 | 5.76E+03 | 9.22E+03 |
| Run 2 | 5.41E+03 | 6.50E+03 | 7.36E+03 |
| Run 3 | 3.87E+03 | 5.02E+03 | 8.73E+03 |
| Avg | 4.42E+03 | 5.76E+03 | 8.44E+03 |
| SD | 8.56E+02 | 7.39E+02 | 9.65E+02 |

$p = 0.110$ $p = 0.019$ $p = 0.006$

| kdis (1/s) | Leu16 | Rituximab | Hybrid |
|---|---|---|---|
| Run 1 | 6.26E-04 | 6.35E-04 | 6.96E-04 |
| Run 2 | 6.85E-04 | 7.99E-04 | 7.03E-04 |
| Run 3 | 5.06E-04 | 6.15E-04 | 7.17E-04 |
| Avg | 6.05E-04 | 6.83E-04 | 7.05E-04 |
| SD | 9.08E-05 | 1.01E-04 | 1.09E-05 |

$p = 0.380$ $p = 0.720$ $p = 0.131$

FIG. 39

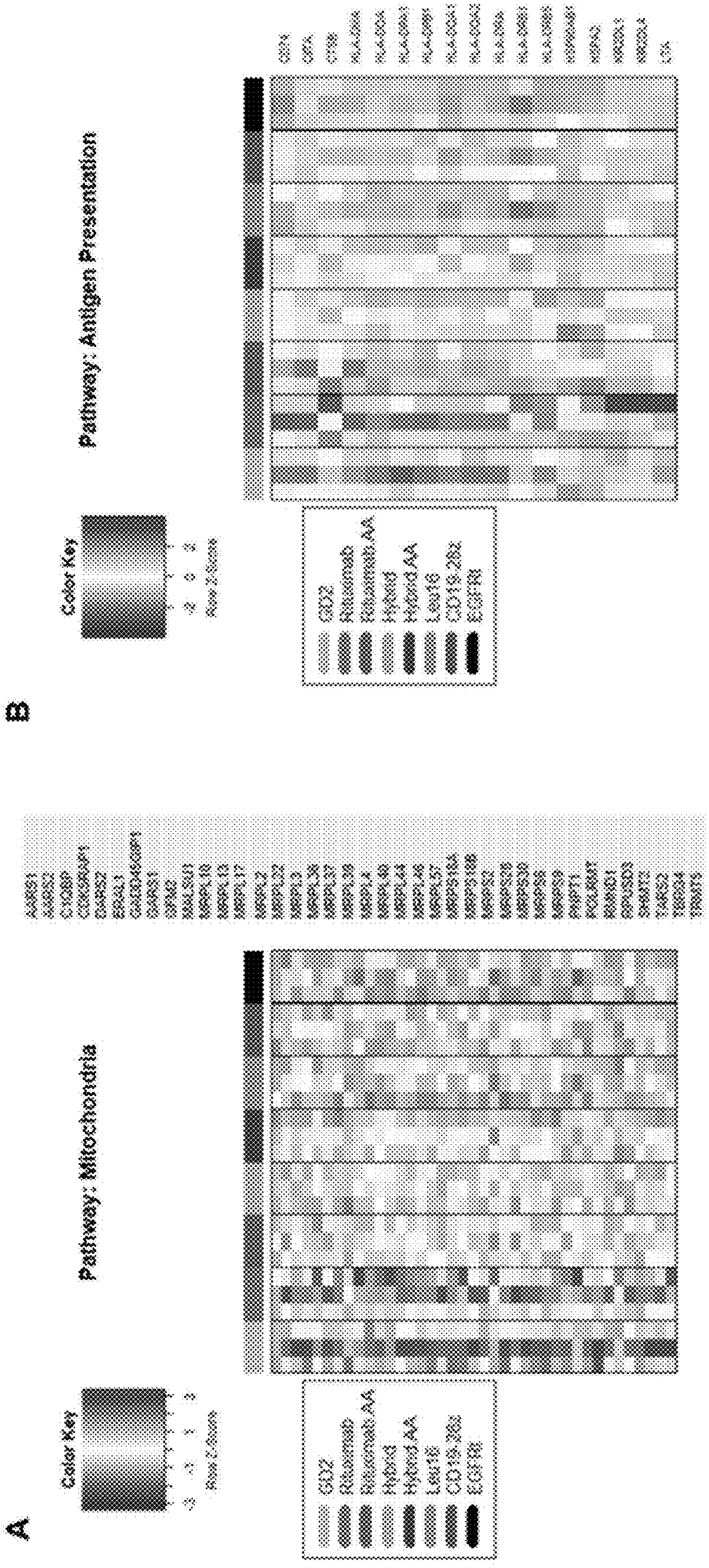
FIG. 43A-B

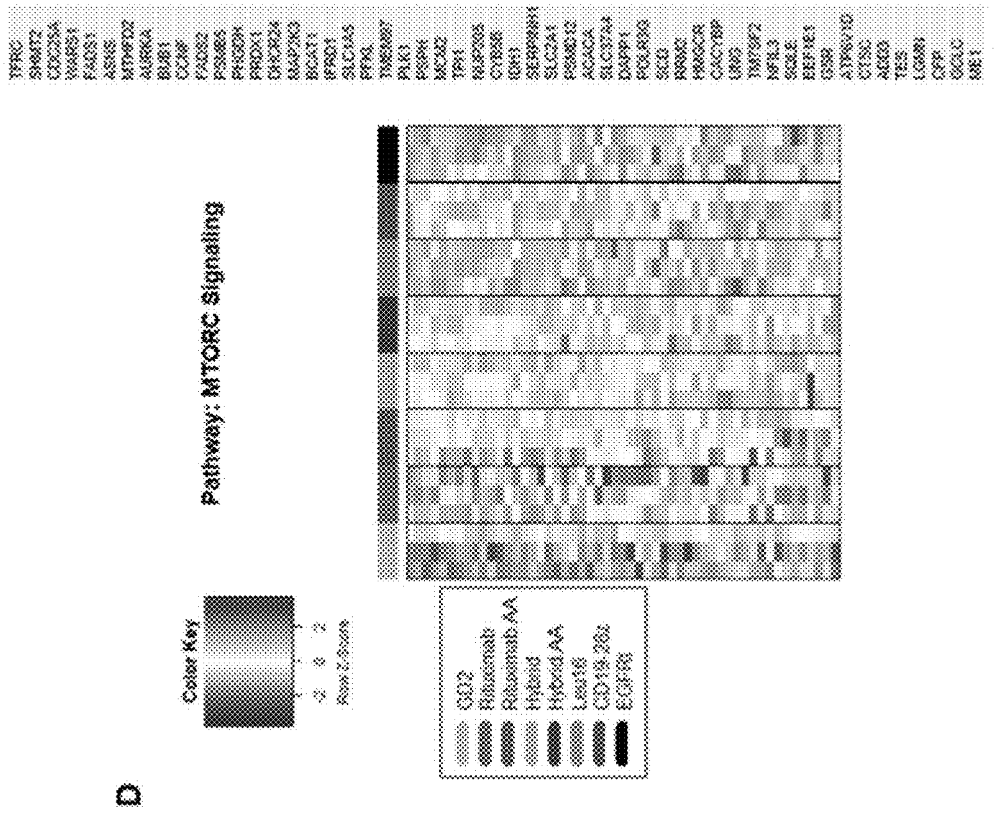
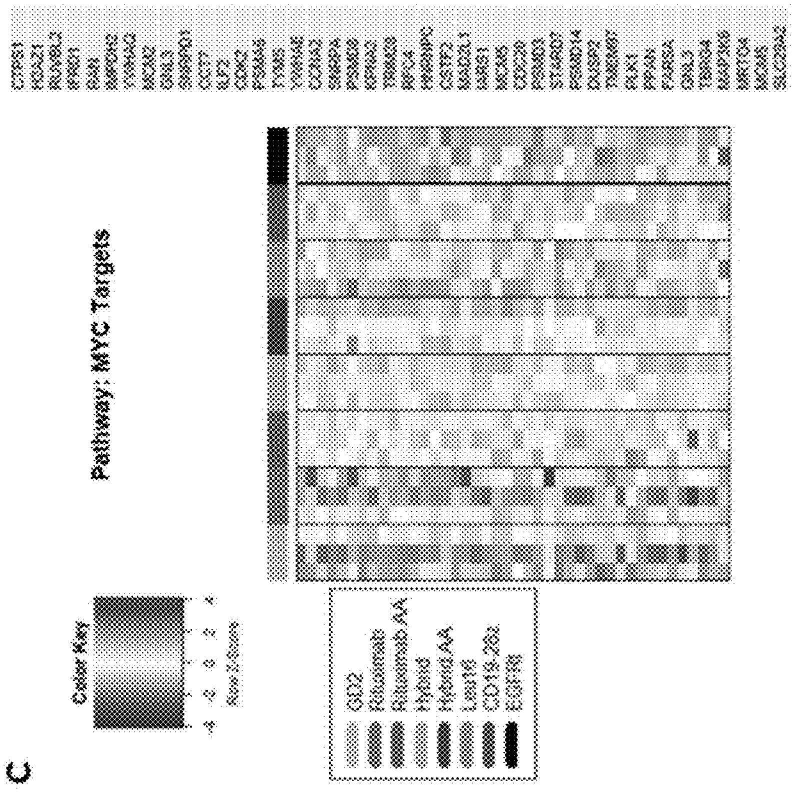
FIG. 43C-D

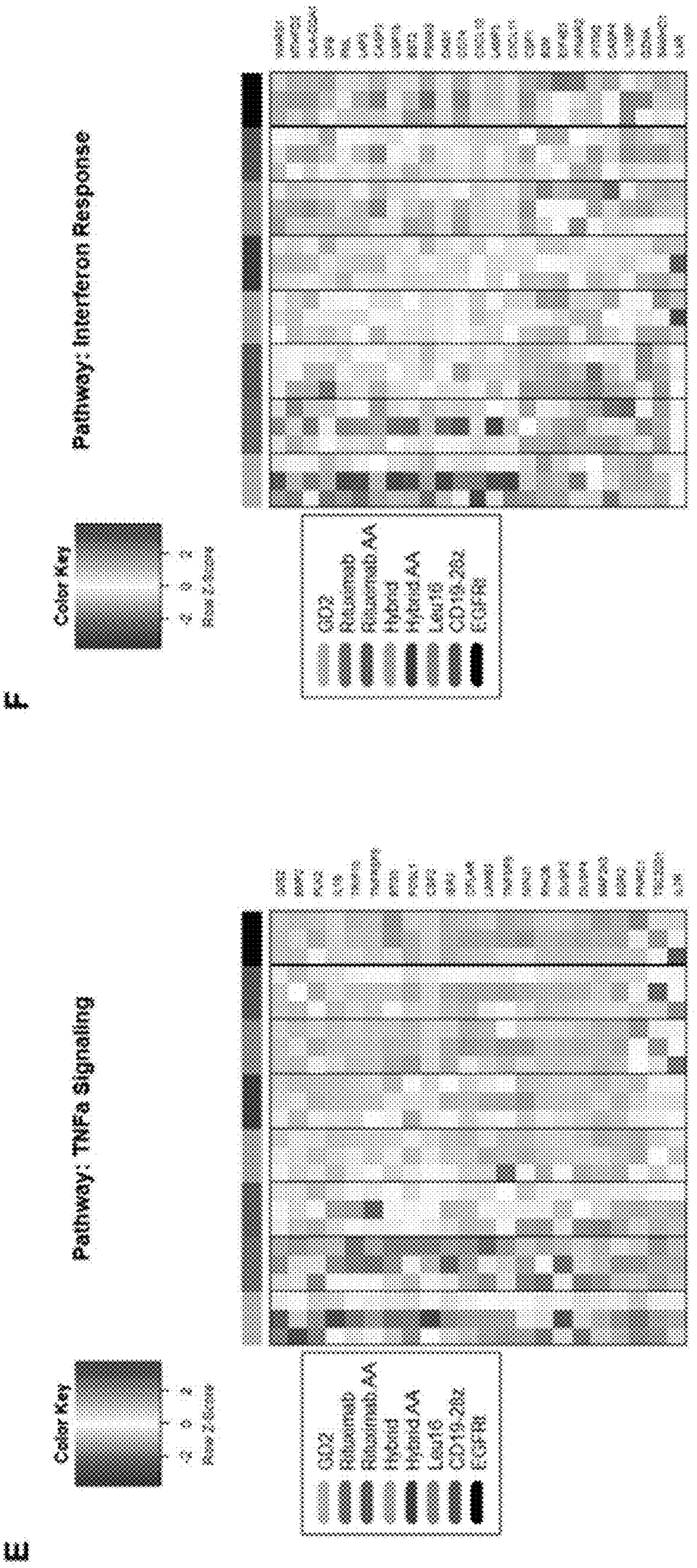
FIG. 43E-F

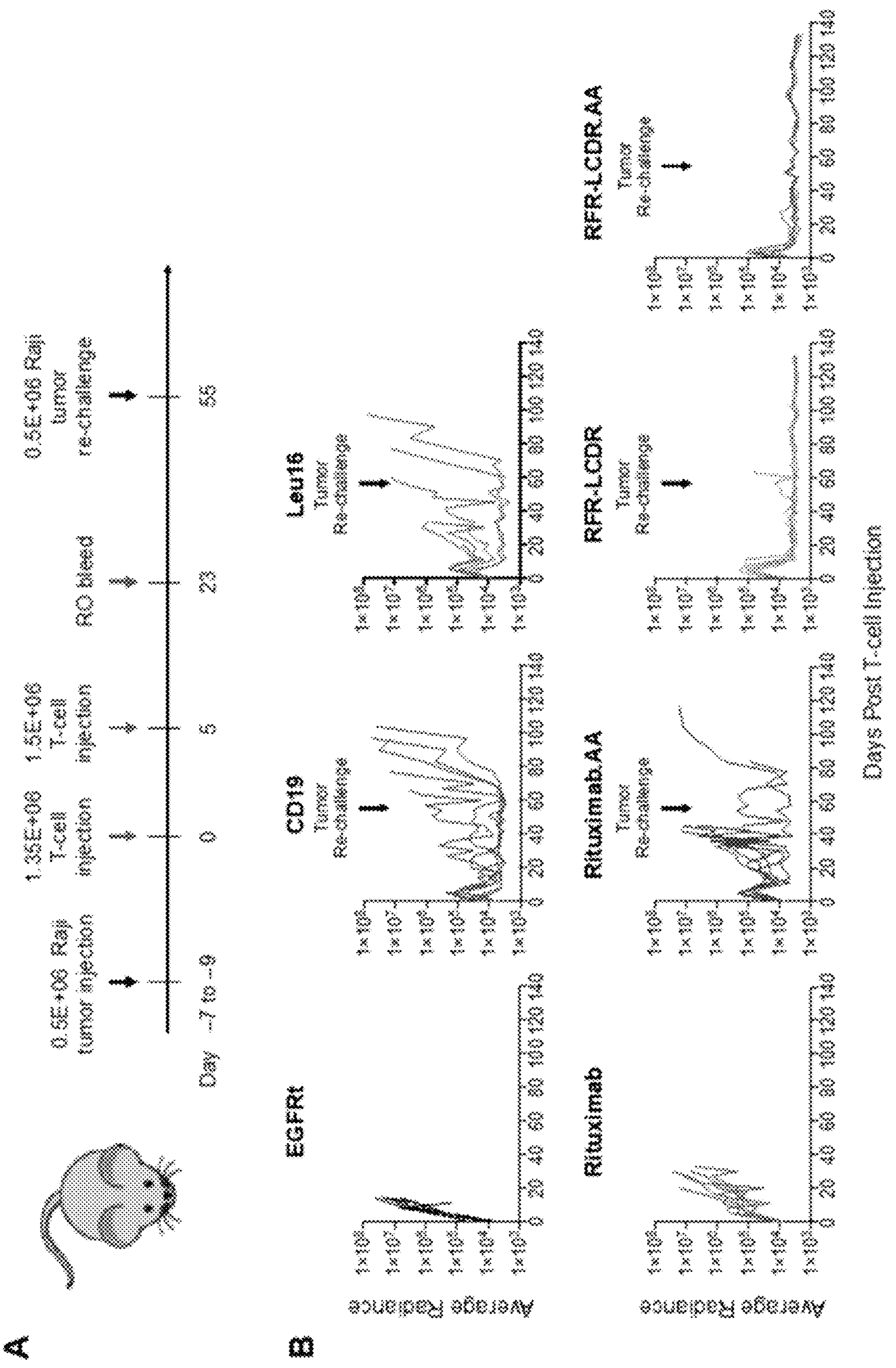
FIG. 44A-B

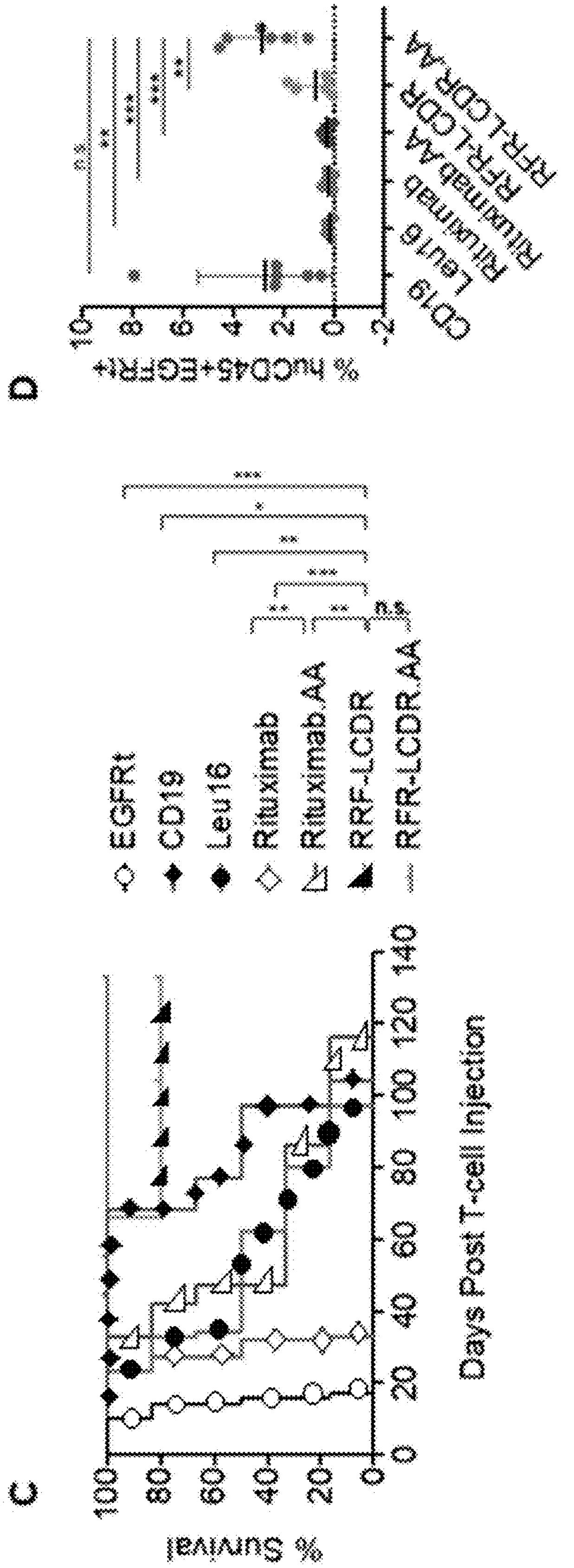
FIG. 44C-D

SEQUENCE LISTING

```
Sequence total quantity: 160
SEQ ID NO: 1            moltype = AA  length = 106
FEATURE                 Location/Qualifiers
source                  1..106
                        mol_type = protein
                        organism = synthetic construct
SEQUENCE: 1
DIVLTQSPAI LSASPGEKVT MTCRASSSVN YMDWYQKKPG SSPKPWIYAT SNLASGVPAR  60
FSGSGSGTSY SLTISRVEAE DAATYYCQQW SFNPPTFGGG TKLEIK                 106

SEQ ID NO: 2            moltype = AA  length = 122
FEATURE                 Location/Qualifiers
source                  1..122
                        mol_type = protein
                        organism = synthetic construct
SEQUENCE: 2
EVQLQQSGAE LVKPGASVKM SCKASGYTFT SYNMHWVKQT PGQGLEWIGA IYPGNGDTSY  60
NQKFKGKATL TADKSSSTAY MQLSSLTSED SADYYCARSN YYGSSYWFFD VWGAGTTVTV  120
SS                                                                 122

SEQ ID NO: 3            moltype = AA  length = 106
```

```
FEATURE                 Location/Qualifiers
source                  1..106
                        mol_type = protein
                        organism = synthetic construct
SEQUENCE: 3
QIVLSQSPAI LSASPGEKVT MTCRASSSVS YIHWFQQKPG SSPKPWIYAT SNLASGVPVR  60
FSGSGSGTSY SLTISRVEAE DAATYYCQQW TSNPPTFGGG TKLEIK                106

SEQ ID NO: 4            moltype = AA  length = 121
FEATURE                 Location/Qualifiers
source                  1..121
                        mol_type = protein
                        organism = synthetic construct
SEQUENCE: 4
QVQLQQPGAE LVKPGASVKM SCKASGYTFT SYNMHWVKQT PGRGLEWIGA IYPGNGDTSY  60
NQKFKGKATL TADKSSSTAY MQLSSLTSED SAVYYCARST YYGGDWYFNV WGAGTTVTVS  120
S                                                                  121

SEQ ID NO: 5            moltype = AA  length = 106
FEATURE                 Location/Qualifiers
source                  1..106
                        mol_type = protein
                        organism = synthetic construct
SEQUENCE: 5
QIVLSQSPAI LSASPGEKVT MTCRASSSVN YMDWFQQKPG SSPKPWIYAT SNLASGVPVR  60
FSGSGSGTSY SLTISRVEAE DAATYYCQQW SFNPPTFGGG TKLEIK                106

SEQ ID NO: 6            moltype = AA  length = 122
FEATURE                 Location/Qualifiers
source                  1..122
                        mol_type = protein
                        organism = synthetic construct
SEQUENCE: 6
QVQLQQPGAE LVKPGASVKM SCKASGYTFT SYNMHWVKQT PGRGLEWIGA IYPGNGDTSY  60
NQKFKGKATL TADKSSSTAY MQLSSLTSED SAVYYCARSN YYGSSYWFFD VWGAGTTVTV  120
SS                                                                 122

SEQ ID NO: 7            moltype = AA  length = 106
FEATURE                 Location/Qualifiers
source                  1..106
                        mol_type = protein
                        organism = synthetic construct
SEQUENCE: 7
DIVLTQSPAI LSASPGEKVT MTCRASSSVS YIHWYQKKPG SSPKPWIYAT SNLASGVPAR  60
FSGSGSGTSY SLTISRVEAE DAATYYCQQW TSNPPTFGGG TKLEIK                106

SEQ ID NO: 8            moltype = AA  length = 121
FEATURE                 Location/Qualifiers
source                  1..121
                        mol_type = protein
                        organism = synthetic construct
SEQUENCE: 8
EVQLQQSGAE LVKPGASVKM SCKASGYTFT SYNMHWVKQT PGQGLEWIGA IYPGNGDTSY  60
NQKFKGKATL TADKSSSTAY MQLSSLTSED SADYYCARST YYGGDWYFNV WGAGTTVTVS  120
S                                                                  121

SEQ ID NO: 9            moltype = AA  length = 5
FEATURE                 Location/Qualifiers
source                  1..5
                        mol_type = protein
                        organism = synthetic construct
SEQUENCE: 9
SYNMH                                                              5

SEQ ID NO: 10           moltype = AA  length = 17
FEATURE                 Location/Qualifiers
source                  1..17
                        mol_type = protein
                        organism = synthetic construct
SEQUENCE: 10
AIYPGNGDTS YNQKFKG                                                 17

SEQ ID NO: 11           moltype = AA  length = 13
FEATURE                 Location/Qualifiers
source                  1..13
                        mol_type = protein
                        organism = synthetic construct
SEQUENCE: 11
SNYYGSSYWF FDV                                                     13
```

```
SEQ ID NO: 12          moltype = AA  length = 10
FEATURE                Location/Qualifiers
source                 1..10
                       mol_type = protein
                       organism = synthetic construct
SEQUENCE: 12
RASSSVNYMD                                                  10

SEQ ID NO: 13          moltype = AA  length = 7
FEATURE                Location/Qualifiers
source                 1..7
                       mol_type = protein
                       organism = synthetic construct
SEQUENCE: 13
ATSNLAS                                                     7

SEQ ID NO: 14          moltype = AA  length = 9
FEATURE                Location/Qualifiers
source                 1..9
                       mol_type = protein
                       organism = synthetic construct
SEQUENCE: 14
QQWSFNPPT                                                   9

SEQ ID NO: 15          moltype = AA  length = 30
FEATURE                Location/Qualifiers
source                 1..30
                       mol_type = protein
                       organism = synthetic construct
SEQUENCE: 15
EVQLQQSGAE LVKPGASVKM SCKASGYTFT                            30

SEQ ID NO: 16          moltype = AA  length = 14
FEATURE                Location/Qualifiers
source                 1..14
                       mol_type = protein
                       organism = synthetic construct
SEQUENCE: 16
WVKQTPGQGL EWIG                                             14

SEQ ID NO: 17          moltype = AA  length = 32
FEATURE                Location/Qualifiers
source                 1..32
                       mol_type = protein
                       organism = synthetic construct
SEQUENCE: 17
KATLTADKSS STAYMQLSSL TSEDSADYYC AR                         32

SEQ ID NO: 18          moltype = AA  length = 11
FEATURE                Location/Qualifiers
source                 1..11
                       mol_type = protein
                       organism = synthetic construct
SEQUENCE: 18
WGAGTTVTVS S                                                11

SEQ ID NO: 19          moltype = AA  length = 23
FEATURE                Location/Qualifiers
source                 1..23
                       mol_type = protein
                       organism = synthetic construct
SEQUENCE: 19
DIVLTQSPAI LSASPGEKVT MTC                                   23

SEQ ID NO: 20          moltype = AA  length = 15
FEATURE                Location/Qualifiers
source                 1..15
                       mol_type = protein
                       organism = synthetic construct
SEQUENCE: 20
WYQKKPGSSP KPWIY                                            15

SEQ ID NO: 21          moltype = AA  length = 32
FEATURE                Location/Qualifiers
source                 1..32
                       mol_type = protein
                       organism = synthetic construct
SEQUENCE: 21
```

```
GVPARFSGSG SGTSYSLTIS RVEAEDAATY YC                        32

SEQ ID NO: 22          moltype = AA  length = 10
FEATURE                Location/Qualifiers
source                 1..10
                       mol_type = protein
                       organism = synthetic construct
SEQUENCE: 22
FGGGTKLEIK                                                 10

SEQ ID NO: 23          moltype = AA  length = 12
FEATURE                Location/Qualifiers
source                 1..12
                       mol_type = protein
                       organism = synthetic construct
SEQUENCE: 23
STYYGGDWYF NV                                              12

SEQ ID NO: 24          moltype = AA  length = 10
FEATURE                Location/Qualifiers
source                 1..10
                       mol_type = protein
                       organism = synthetic construct
SEQUENCE: 24
RASSSVSYIH                                                 10

SEQ ID NO: 25          moltype = AA  length = 9
FEATURE                Location/Qualifiers
source                 1..9
                       mol_type = protein
                       organism = synthetic construct
SEQUENCE: 25
QQWTSNPPT                                                  9

SEQ ID NO: 26          moltype = AA  length = 30
FEATURE                Location/Qualifiers
source                 1..30
                       mol_type = protein
                       organism = synthetic construct
SEQUENCE: 26
QVQLQQPGAE LVKPGASVKM SCKASGYTFT                           30

SEQ ID NO: 27          moltype = AA  length = 14
FEATURE                Location/Qualifiers
source                 1..14
                       mol_type = protein
                       organism = synthetic construct
SEQUENCE: 27
WVKQTPGRGL EWIG                                            14

SEQ ID NO: 28          moltype = AA  length = 32
FEATURE                Location/Qualifiers
source                 1..32
                       mol_type = protein
                       organism = synthetic construct
SEQUENCE: 28
KATLTADKSS STAYMQLSSL TSEDSAVYYC AR                        32

SEQ ID NO: 29          moltype = AA  length = 23
FEATURE                Location/Qualifiers
source                 1..23
                       mol_type = protein
                       organism = synthetic construct
SEQUENCE: 29
QIVLSQSPAI LSASPGEKVT MTC                                  23

SEQ ID NO: 30          moltype = AA  length = 15
FEATURE                Location/Qualifiers
source                 1..15
                       mol_type = protein
                       organism = synthetic construct
SEQUENCE: 30
WFQQKPGSSP KPWIY                                           15

SEQ ID NO: 31          moltype = AA  length = 32
FEATURE                Location/Qualifiers
source                 1..32
                       mol_type = protein
                       organism = synthetic construct
```

```
SEQUENCE: 31
GVPVRFSGSG SGTSYSLTIS RVEAEDAATY YC                              32

SEQ ID NO: 32          moltype = AA  length = 18
FEATURE                Location/Qualifiers
source                 1..18
                       mol_type = protein
                       organism = synthetic construct
SEQUENCE: 32
GSTSGGGSGG GSGGGGSS                                              18

SEQ ID NO: 33          moltype = AA  length = 1060
FEATURE                Location/Qualifiers
source                 1..1060
                       mol_type = protein
                       organism = synthetic construct
SEQUENCE: 33
METDTLLLWV LLLWVPGSTG QIVLSQSPAI LSASPGEKVT MTCRASSSVN YMDWFQQKPG  60
SSPKPWIYAT SNLASGVPVR FSGSGSGTSY SLTISRVEAE DAATYYCQQW SFNPPTFGGG  120
TKLEIKGSTS GGGSGGGSGG GGSSQVQLQQ PGAELVKPGA SVKMSCKASG YTFTSYNMHW  180
VKQTPGRGLE WIGAIYPGNG DTSYNQKFKG KATLTADKSS STAYMQLSSL TSEDSAVYYC  240
ARSNYYGSSY WFFDVWGAGT TVTVSSESKY GPPCPPCPAP EFEGGPSVFL FPPKPKDTLM  300
ISRTPEVTCV VVDVSQEDPE VQFNWYVDGV EVHNAKTKPR EEQFQSTYRV VSVLTVLHQD  360
WLNGKEYKCK VSNKGLPSSI EKTISKAKGQ PREPQVYTLP PSQEEMTKNQ VSLTCLVKGF  420
YPSDIAVEWE SNGQPENNYK TTPPVLDSDG SFFLYSRLTV DKSRWQEGNV FSCSVMHEAL  480
HNHYTQKSLS LSLGKMFWVL VVVGGVLACY SLLVTVAFII FWVRSKRSRG GHSDYMNMTP  540
RRPGPTRKHY QPYAPPRDFA AYRSGGGRVK FSRSADAPAY QQGQNQLYNE LNLGRREEYD  600
VLDKRRGRDP EMGGKPRRKN PQEGLYNELQ KDKMAEAYSE IGMKGERRRG KGHDGLYQGL  660
STATKDTYDA LHMQALPPRL EGGGEGRGSL LTCGDVEENP GPRMLLLVTS LLLCELPHPA  720
FLLIPRKVCN GIGIGEFKDS LSINATNIKH FKNCTSISGD LHILPVAFRG DSFTHTPPLD  780
PQELDILKTV KEITGFLLIQ AWPENRTDLH AFENLEIIRG RTKQHGQFSL AVVSLNITSL  840
GLRSLKEISD GDVIISGNKN LCYANTINWK KLFGTSGQKT KIISNRGENS CKATGQVCHA  900
LCSPEGCWGP EPRDCVSCRN VSRGRECVDK CNLLEGEPRE FVENSECIQC HPECLPQAMN  960
ITCTGRGPDN CIQCAHYIDG PHCVKTCPAG VMGENNTLVW KYADAGHVCH LCHPNCTYGC  1020
TGPGLEGCPT NGPKIPSIAT GMVGALLLLL VVALGIGLFM                      1060

SEQ ID NO: 34          moltype = AA  length = 1059
FEATURE                Location/Qualifiers
source                 1..1059
                       mol_type = protein
                       organism = synthetic construct
SEQUENCE: 34
METDTLLLWV LLLWVPGSTG DIVLTQSPAI LSASPGEKVT MTCRASSSVS YIHWYQKKPG  60
SSPKPWIYAT SNLASGVPAR FSGSGSGTSY SLTISRVEAE DAATYYCQQW TSNPPTFGGG  120
TKLEIKGSTS GGGSGGGSGG GGSSEVQLQQ SGAELVKPGA SVKMSCKASG YTFTSYNMHW  180
VKQTPGQGLE WIGAIYPGNG DTSYNQKFKG KATLTADKSS STAYMQLSSL TSEDSADYYC  240
ARSTYYGGDW YFNVWGAGTT VTVSSESKYG PPCPPCPAPE FEGGPSVFLF PPKPKDTLMI  300
SRTPEVTCVV VDVSQEDPEV QFNWYVDGVE VHNAKTKPRE EQFQSTYRVV SVLTVLHQDW  360
LNGKEYKCKV SNKGLPSSIE KTISKAKGQP REPQVYTLPP SQEEMTKNQV SLTCLVKGFY  420
PSDIAVEWES NGQPENNYKT TPPVLDSDGS FFLYSRLTVD KSRWQEGNVF SCSVMHEALH  480
NHYTQKSLSL SLGKMFWVLV VVGGVLACYS LLVTVAFIIF WVRSKRSRGG HSDYMNMTPR  540
RPGPTRKHYQ PYAPPRDFAA YRSGGGRVKF SRSADAPAYQ QGQNQLYNEL NLGRREEYDV  600
LDKRRGRDPE MGGKPRRKNP QEGLYNELQK DKMAEAYSEI GMKGERRRGK GHDGLYQGLS  660
TATKDTYDAL HMQALPPRLE GGGEGRGSLL TCGDVEENPG PRMLLLVTSL LLCELPHPAF  720
LLIPRKVCNG IGIGEFKDSL SINATNIKHF KNCTSISGDL HILPVAFRGD SFTHTPPLDP  780
QELDILKTVK EITGFLLIQA WPENRTDLHA FENLEIIRGR TKQHGQFSLA VVSLNITSLG  840
LRSLKEISDG DVIISGNKNL CYANTINWKK LFGTSGQKTK IISNRGENSC KATGQVCHAL  900
CSPEGCWGPE PRDCVSCRNV SRGRECVDKC NLLEGEPREF VENSECIQCH PECLPQAMNI  960
TCTGRGPDNC IQCAHYIDGP HCVKTCPAGV MGENNTLVWK YADAGHVCHL CHPNCTYGCT  1020
GPGLEGCPTN GPKIPSIATG MVGALLLLLV VALGIGLFM                       1059

SEQ ID NO: 35          moltype = AA  length = 20
FEATURE                Location/Qualifiers
source                 1..20
                       mol_type = protein
                       organism = synthetic construct
SEQUENCE: 35
METDTLLLWV LLLWVPGSTG                                            20

SEQ ID NO: 36          moltype = AA  length = 229
FEATURE                Location/Qualifiers
source                 1..229
                       mol_type = protein
                       organism = synthetic construct
SEQUENCE: 36
ESKYGPPCPP CPAPEFEGGP SVFLFPPKPK DTLMISRTPE VTCVVVDVSQ EDPEVQFNWY  60
VDGVEVHNAK TKPREEQFQS TYRVVSVLTV LHQDWLNGKE YKCKVSNKGL PSSIEKTISK  120
AKGQPREPQV YTLPPSQEEM TKNQVSLTCL VKGFYPSDIA VEWESNGQPE NNYKTTPPVL  180
DSDGSFFLYS RLTVDKSRWQ EGNVFSCSVM HEALHNHYTQ KSLSLSLGK             229
```

```
SEQ ID NO: 37           moltype = AA  length = 28
FEATURE                 Location/Qualifiers
source                  1..28
                        mol_type = protein
                        organism = synthetic construct
SEQUENCE: 37
MFWVLVVVGG VLACYSLLVT VAFIIFWV                                    28

SEQ ID NO: 38           moltype = AA  length = 41
FEATURE                 Location/Qualifiers
source                  1..41
                        mol_type = protein
                        organism = synthetic construct
SEQUENCE: 38
RSKRSRGGHS DYMNMTPRRP GPTRKHYQPY APPRDFAAYR S                     41

SEQ ID NO: 39           moltype = AA  length = 112
FEATURE                 Location/Qualifiers
source                  1..112
                        mol_type = protein
                        organism = synthetic construct
SEQUENCE: 39
RVKFSRSADA PAYQQGQNQL YNELNLGRRE EYDVLDKRRG RDPEMGGKPR RKNPQEGLYN  60
ELQKDKMAEA YSEIGMKGER RRGKGHDGLY QGLSTATKDT YDALHMQALP PR          112

SEQ ID NO: 40           moltype = AA  length = 24
FEATURE                 Location/Qualifiers
source                  1..24
                        mol_type = protein
                        organism = synthetic construct
SEQUENCE: 40
LEGGGEGRGS LLTCGDVEEN PGPR                                        24

SEQ ID NO: 41           moltype = AA  length = 357
FEATURE                 Location/Qualifiers
source                  1..357
                        mol_type = protein
                        organism = synthetic construct
SEQUENCE: 41
MLLLVTSLLL CELPHPAFLL IPRKVCNGIG IGEFKDSLSI NATNIKHFKN CTSISGDLHI  60
LPVAFRGDSF THTPPLDPQE LDILKTVKEI TGFLLIQAWP ENRTDLHAFE NLEIIRGRTK  120
QHGQFSLAVV SLNITSLGLR SLKEISDGDV IISGNKNLCY ANTINWKKLF GTSGQKTKII  180
SNRGENSCKA TGQVCHALCS PEGCWGPEPR DCVSCRNVSR GRECVDKCNL LEGEPREFVE  240
NSECIQCHPE CLPQAMNITC TGRGPDNCIQ CAHYIDGPHC VKTCPAGVMG ENNTLVWKYA  300
DAGHVCHLCH PNCTYGCTGP GLEGCPTNGP KIPSIATGMV GALLLLLVVA LGIGLFM     357

SEQ ID NO: 42           moltype = AA  length = 1040
FEATURE                 Location/Qualifiers
source                  1..1040
                        mol_type = protein
                        organism = synthetic construct
SEQUENCE: 42
QIVLSQSPAI LSASPGEKVT MTCRASSSVN YMDWFQQKPG SSPKPWIYAT SNLASGVPVR  60
FSGSGSGTSY SLTISRVEAE DAATYYCQQW SFNPPTFGGG TKLEIKGSTS GGGSGGGSGG  120
GGSSQVQLQQ PGAELVKPGA SVKMSCKASG YTFTSYNMHW VKQTPGRGLE WIGAIYPGNG  180
DTSYNQKFKG KATLTADKSS STAYMQLSSL TSEDSAVYYC ARSNYYGSSY WFFDVWGAGT  240
TVTVSSESKY GPPCPPCPAP EFEGGPSVFL FPPKPKDTLM ISRTPEVTCV VVDVSQEDPE  300
VQFNWYVDGV EVHNAKTKPR EEQFQSTYRV VSVLTVLHQD WLNGKEYKCK VSNKGLPSSI  360
EKTISKAKGQ PREPQVYTLP PSQEEMTKNQ VSLTCLVKGF YPSDIAVEWE SNGQPENNYK  420
TTPPVLDSDG SFFLYSRLTV DKSRWQEGNV FSCSVMHEAL HNHYTQKSLS LSLGKMFWVL  480
VVVGGVLACY SLLVTVAFII FWVRSKRSRG GHSDYMNMTP RRPGPTRKHY QPYAPPRDFA  540
AYRSGGGRVK FSRSADAPAY QQGQNQLYNE LNLGRREEYD VLDKRRGRDP EMGGKPRRKN  600
PQEGLYNELQ KDKMAEAYSE IGMKGERRRG KGHDGLYQGL STATKDTYDA LHMQALPPRL  660
EGGGEGRGSL LTCGDVEENP GPRMLLLVTS LLLCELPHPA FLLIPRKVCN GIGIGEFKDS  720
LSINATNIKH FKNCTSISGD LHILPVAFRG DSFTHTPPLD PQELDILKTV KEITGFLLIQ  780
AWPENRTDLH AFENLEIIRG RTKQHGQFSL AVVSLNITSL GLRSLKEISD GDVIISGNKN  840
LCYANTINWK KLFGTSGQKT KIISNRGENS CKATGQVCHA LCSPEGCWGP EPRDCVSCRN  900
VSRGRECVDK CNLLEGEPRE FVENSECIQC HPECLPQAMN ITCTGRGPDN CIQCAHYIDG  960
PHCVKTCPAG VMGENNTLVW KYADAGHVCH LCHPNCTYGC TGPGLEGCPT NGPKIPSIAT  1020
GMVGALLLLL VVALGIGLFM                                              1040

SEQ ID NO: 43           moltype = AA  length = 1039
FEATURE                 Location/Qualifiers
source                  1..1039
                        mol_type = protein
                        organism = synthetic construct
SEQUENCE: 43
DIVLTQSPAI LSASPGEKVT MTCRASSSVS YIHWYQKKPG SSPKPWIYAT SNLASGVPAR  60
```

```
FSGSGSGTSY SLTISRVEAE DAATYYCQQW TSNPPTFGGG TKLEIKGSTS GGGSGGGSGG  120
GGSSEVQLQQ SGAELVKPGA SVKMSCKASG YTFTSYNMHW VKQTPGQGLE WIGAIYPGNG  180
DTSYNQKFKG KATLTADKSS STAYMQLSSL TSEDSADYYC ARSTYYGGDW YFNVWGAGTT  240
VTVSSESKYG PPCPPCPAPE FEGGPSVFLF PPKPKDTLMI SRTPEVTCVV VDVSQEDPEV  300
QFNWYVDGVE VHNAKTKPRE EQFQSTYRVV SVLTVLHQDW LNGKEYKCKV SNKGLPSSIE  360
KTISKAKGQP REPQVYTLPP SQEEMTKNQV SLTCLVKGFY PSDIAVEWES NGQPENNYKT  420
TPPVLDSDGS FFLYSRLTVD KSRWQEGNVF SCSVMHEALH NHYTQKSLSL SLGKMFWVLV  480
VVGGVLACYS LLVTVAFIIF WVRSKRSRGG HSDYMNMTPR RPGPTRKHYQ PYAPPRDFAA  540
YRSGGGRVKF SRSADAPAYQ QGQNQLYNEL NLGRREEYDV LDKRRGRDPE MGGKPRRKNP  600
QEGLYNELQK DKMAEAYSEI GMKGERRRGK GHDGLYQGLS TATKDTYDAL HMQALPPRLE  660
GGGEGRGSLL TCGDVEENPG PRMLLLVTSL LLCELPHPAF LLIPRKVCNG IGIGEFKDSL  720
SINATNIKHF KNCTSISGDL HILPVAFRGD SFTHTPPLDP QELDILKTVK EITGFLLIQA  780
WPENRTDLHA FENLEIIRGR TKQHGQFSLA VVSLNITSLG LRSLKEISDG DVIISGNKNL  840
CYANTINWKK LFGTSGQKTK IISNRGENSC KATGQVCHAL CSPEGCWGPE PRDCVSCRNV  900
SRGRECVDKC NLLEGEPREF VENSECIQCH PECLPQAMNI TCTGRGPDNC IQCAHYIDGP  960
HCVKTCPAGV MGENNTLVWK YADAGHVCHL CHPNCTYGCT GPGLEGCPTN GPKIPSIATG  1020
MVGALLLLLV VALGIGLFM                                              1039

SEQ ID NO: 44          moltype = AA  length = 15
FEATURE                Location/Qualifiers
source                 1..15
                       mol_type = protein
                       organism = synthetic construct
SEQUENCE: 44
CPEPKSCDTP PPCPR                                                  15

SEQ ID NO: 45          moltype = AA  length = 12
FEATURE                Location/Qualifiers
source                 1..12
                       mol_type = protein
                       organism = synthetic construct
SEQUENCE: 45
ELKTPLGDTT HT                                                     12

SEQ ID NO: 46          moltype = AA  length = 10
FEATURE                Location/Qualifiers
source                 1..10
                       mol_type = protein
                       organism = synthetic construct
SEQUENCE: 46
KSCDKTHTCP                                                        10

SEQ ID NO: 47          moltype = AA  length = 7
FEATURE                Location/Qualifiers
source                 1..7
                       mol_type = protein
                       organism = synthetic construct
SEQUENCE: 47
KCCVDCP                                                           7

SEQ ID NO: 48          moltype = AA  length = 7
FEATURE                Location/Qualifiers
source                 1..7
                       mol_type = protein
                       organism = synthetic construct
SEQUENCE: 48
KYGPPCP                                                           7

SEQ ID NO: 49          moltype = AA  length = 15
FEATURE                Location/Qualifiers
source                 1..15
                       mol_type = protein
                       organism = synthetic construct
SEQUENCE: 49
EPKSCDKTHT CPPCP                                                  15

SEQ ID NO: 50          moltype = AA  length = 17
FEATURE                Location/Qualifiers
source                 1..17
                       mol_type = protein
                       organism = synthetic construct
SEQUENCE: 50
ELKTPLGDTT HTCPRCP                                                17

SEQ ID NO: 51          moltype = AA  length = 12
FEATURE                Location/Qualifiers
source                 1..12
                       mol_type = protein
                       organism = synthetic construct
```

```
SEQUENCE: 51
SPNMVPHAHH AQ                                                    12

SEQ ID NO: 52           moltype = AA  length = 12
FEATURE                 Location/Qualifiers
source                  1..12
                        mol_type = protein
                        organism = synthetic construct
SEQUENCE: 52
ESKYGPPCPP CP                                                    12

SEQ ID NO: 53           moltype = AA  length = 15
FEATURE                 Location/Qualifiers
source                  1..15
                        mol_type = protein
                        organism = synthetic construct
SEQUENCE: 53
EPKSCDKTYT CPPCP                                                 15

SEQ ID NO: 54           moltype = AA  length = 45
FEATURE                 Location/Qualifiers
source                  1..45
                        mol_type = protein
                        organism = synthetic construct
SEQUENCE: 54
TTTPAPRPPT PAPTIASQPL SLRPEACRPA AGGAVHTRGL DFACD                45

SEQ ID NO: 55           moltype = AA  length = 110
FEATURE                 Location/Qualifiers
source                  1..110
                        mol_type = protein
                        organism = synthetic construct
SEQUENCE: 55
APEFEGGPSV FLFPPKPKDT LMISRTPEVT CVVVDVSQED PEVQFNWYVD GVEVHNAKTK  60
PREEQFQSTY RVVSVLTVLH QDWLNGKEYK CKVSNKGLPS SIEKTISKAK            110

SEQ ID NO: 56           moltype = AA  length = 107
FEATURE                 Location/Qualifiers
source                  1..107
                        mol_type = protein
                        organism = synthetic construct
SEQUENCE: 56
GQPREPQVYT LPPSQEEMTK NQVSLTCLVK GFYPSDIAVE WESNGQPENN YKTTPPVLDS  60
DGSFFLYSRL TVDKSRWQEG NVFSCSVMHE ALHNHYTQKS LSLSLGK               107

SEQ ID NO: 57           moltype = AA  length = 27
FEATURE                 Location/Qualifiers
source                  1..27
                        mol_type = protein
                        organism = synthetic construct
SEQUENCE: 57
FWVLVVVGGV LACYSLLVTV AFIIFWV                                    27

SEQ ID NO: 58           moltype = AA  length = 23
FEATURE                 Location/Qualifiers
source                  1..23
                        mol_type = protein
                        organism = synthetic construct
SEQUENCE: 58
LGLLVAGVLV LLVSLGVAIH LCC                                        23

SEQ ID NO: 59           moltype = AA  length = 25
FEATURE                 Location/Qualifiers
source                  1..25
                        mol_type = protein
                        organism = synthetic construct
SEQUENCE: 59
ALIVLGGVAG LLLFIGLGIF FCVRC                                      25

SEQ ID NO: 60           moltype = AA  length = 23
FEATURE                 Location/Qualifiers
source                  1..23
                        mol_type = protein
                        organism = synthetic construct
SEQUENCE: 60
LCYLLDGILF IYGVILTALF LRV                                        23

SEQ ID NO: 61           moltype = AA  length = 26
FEATURE                 Location/Qualifiers
```

```
source                  1..26
                        mol_type = protein
                        organism = synthetic construct
SEQUENCE: 61
WVLVVVGGVL ACYSLLVTVA FIIFWV                                        26

SEQ ID NO: 62           moltype = AA  length = 26
FEATURE                 Location/Qualifiers
source                  1..26
                        mol_type = protein
                        organism = synthetic construct
SEQUENCE: 62
VAAILGLGLV LGLLGPLAIL LALYLL                                        26

SEQ ID NO: 63           moltype = AA  length = 24
FEATURE                 Location/Qualifiers
source                  1..24
                        mol_type = protein
                        organism = synthetic construct
SEQUENCE: 63
ALPAALAVIS FLLGLGLGVA CVLA                                          24

SEQ ID NO: 64           moltype = AA  length = 113
FEATURE                 Location/Qualifiers
source                  1..113
                        mol_type = protein
                        organism = synthetic construct
SEQUENCE: 64
MGGLEPCSRL LLLPLLLAVS GLRPVQAQAQ SDCSCSTVSP GVLAGIVMGD LVLTVLIALA  60
VYFLGRLVPR GRGAAEAATR KQRITETESP YQELQGQRSD VYSDLNTQRP YYK         113

SEQ ID NO: 65           moltype = AA  length = 112
FEATURE                 Location/Qualifiers
source                  1..112
                        mol_type = protein
                        organism = synthetic construct
SEQUENCE: 65
MGGLEPCSRL LLLPLLLAVS GLRPVQAQAQ SDCSCSTVSP GVLAGIVMGD LVLTVLIALA  60
VYFLGRLVPR GRGAAEATRK QRITETESPY QELQGQRSDV YSDLNTQRPY YK          112

SEQ ID NO: 66           moltype = AA  length = 102
FEATURE                 Location/Qualifiers
source                  1..102
                        mol_type = protein
                        organism = synthetic construct
SEQUENCE: 66
MGGLEPCSRL LLLPLLLAVS DCSCSTVSPG VLAGIVMGDL VLTVLIALAV YFLGRLVPRG  60
RGAAEAATRK QRITETESPY QELQGQRSDV YSDLNTQRPY YK                      102

SEQ ID NO: 67           moltype = AA  length = 101
FEATURE                 Location/Qualifiers
source                  1..101
                        mol_type = protein
                        organism = synthetic construct
SEQUENCE: 67
MGGLEPCSRL LLLPLLLAVS DCSCSTVSPG VLAGIVMGDL VLTVLIALAV YFLGRLVPRG  60
RGAAEATRKQ RITETESPYQ ELQGQRSDVY SDLNTQRPYY K                       101

SEQ ID NO: 68           moltype = AA  length = 86
FEATURE                 Location/Qualifiers
source                  1..86
                        mol_type = protein
                        organism = synthetic construct
SEQUENCE: 68
MIPAVVLLLL LLVEQAAALG EPQLCYILDA ILFLYGIVLT LLYCRLKIQV RKAAITSYEK  60
SDGVYTGLST RNQETYETLK HEKPPQ                                        86

SEQ ID NO: 69           moltype = AA  length = 21
FEATURE                 Location/Qualifiers
source                  1..21
                        mol_type = protein
                        organism = synthetic construct
SEQUENCE: 69
DGVYTGLSTR NQETYETLKH E                                             21

SEQ ID NO: 70           moltype = AA  length = 171
FEATURE                 Location/Qualifiers
source                  1..171
                        mol_type = protein
```

```
                        organism = synthetic construct
SEQUENCE: 70
MEHSTFLSGL VLATLLSQVS PFKIPIEELE DRVFVNCNTS ITWVEGTVGT LLSDITRLDL  60
GKRILDPRGI YRCNGTDIYK DKESTVQVHY RMCQSCVELD PATVAGIIVT DVIATLLLAL  120
GVFCFAGHET GRLSGAADTQ ALLRNDQVYQ PLRDRDDAQY SHLGGNWARN K           171

SEQ ID NO: 71           moltype = AA  length = 127
FEATURE                 Location/Qualifiers
source                  1..127
                        mol_type = protein
                        organism = synthetic construct
SEQUENCE: 71
MEHSTFLSGL VLATLLSQVS PFKIPIEELE DRVFVNCNTS ITWVEGTVGT LLSDITRLDL  60
GKRILDPRGI YRCNGTDIYK DKESTVQVHY RTADTQALLR NDQVYQPLRD RDDAQYSHLG  120
GNWARNK                                                             127

SEQ ID NO: 72           moltype = AA  length = 21
FEATURE                 Location/Qualifiers
source                  1..21
                        mol_type = protein
                        organism = synthetic construct
SEQUENCE: 72
DQVYQPLRDR DDAQYSHLGG N                                            21

SEQ ID NO: 73           moltype = AA  length = 207
FEATURE                 Location/Qualifiers
source                  1..207
                        mol_type = protein
                        organism = synthetic construct
SEQUENCE: 73
MQSGTHWRVL GLCLLSVGVW GQDGNEEMGG ITQTPYKVSI SGTTVILTCP QYPGSEILWQ  60
HNDKNIGGDE DDKNIGSDED HLSLKEFSEL EQSGYYVCYP RGSKPEDANF YLYLRARVCE  120
NCMEMDVMSV ATIVIVDICI TGGLLLLVYY WSKNRKAKAK PVTRGAGAGG RQRGQNKERP  180
PPVPNPDYEP IRKGQRDLYS GLNQRRI                                       207

SEQ ID NO: 74           moltype = AA  length = 21
FEATURE                 Location/Qualifiers
source                  1..21
                        mol_type = protein
                        organism = synthetic construct
SEQUENCE: 74
NPDYEPIRKG QRDLYSGLNQ R                                            21

SEQ ID NO: 75           moltype = AA  length = 182
FEATURE                 Location/Qualifiers
source                  1..182
                        mol_type = protein
                        organism = synthetic construct
SEQUENCE: 75
MEQGKGLAVL ILAIILLQGT LAQSIKGNHL VKVYDYQEDG SVLLTCDAEA KNITWFKDGK  60
MIGFLTEDKK KWNLGSNAKD PRGMYQCKGS QNKSKPLQVY YRMCQNCIEL NAATISGFLF  120
AEIVSIFVLA VGVYFIAGQD GVRQSRASDK QTLLPNDQLY QPLKDREDDQ YSHLQGNQLR  180
RN                                                                  182

SEQ ID NO: 76           moltype = AA  length = 21
FEATURE                 Location/Qualifiers
source                  1..21
                        mol_type = protein
                        organism = synthetic construct
SEQUENCE: 76
DQLYQPLKDR EDDQYSHLQG N                                            21

SEQ ID NO: 77           moltype = AA  length = 163
FEATURE                 Location/Qualifiers
source                  1..163
                        mol_type = protein
                        organism = synthetic construct
SEQUENCE: 77
MKWKALFTAA ILQAQLPITE AQSFGLLDPK LCYLLDGILF IYGVILTALF LRVKFSRSAD  60
APAYQQGQNQ LYNELNLGRR EEYDVLDKRR GRDPEMGGKP RRKNPQEGLY NELQKDKMAE  120
AYSEIGMKGE RRRGKGHDGL YQGLSTATKD TYDALHMQAL PPR                     163

SEQ ID NO: 78           moltype = AA  length = 164
FEATURE                 Location/Qualifiers
source                  1..164
                        mol_type = protein
                        organism = synthetic construct
SEQUENCE: 78
MKWKALFTAA ILQAQLPITE AQSFGLLDPK LCYLLDGILF IYGVILTALF LRVKFSRSAD  60
```

```
APAYQQGQNQ LYNELNLGRR EEYDVLDKRR GRDPEMGGKP QRRKNPQEGL YNELQKDKMA  120
EAYSEIGMKG ERRRGKGHDG LYQGLSTATK DTYDALHMQA LPPR                   164

SEQ ID NO: 79          moltype = AA  length = 21
FEATURE                Location/Qualifiers
source                 1..21
                       mol_type = protein
                       organism = synthetic construct
SEQUENCE: 79
NQLYNELNLG RREEYDVLDK R                                            21

SEQ ID NO: 80          moltype = AA  length = 22
FEATURE                Location/Qualifiers
source                 1..22
                       mol_type = protein
                       organism = synthetic construct
SEQUENCE: 80
EGLYNELQKD KMAEAYSEIG MK                                           22

SEQ ID NO: 81          moltype = AA  length = 21
FEATURE                Location/Qualifiers
source                 1..21
                       mol_type = protein
                       organism = synthetic construct
SEQUENCE: 81
DGLYQGLSTA TKDTYDALHM Q                                            21

SEQ ID NO: 82          moltype = AA  length = 226
FEATURE                Location/Qualifiers
source                 1..226
                       mol_type = protein
                       organism = synthetic construct
SEQUENCE: 82
MPGGPGVLQA LPATIFLLFL LSAVYLGPGC QALWMHKVPA SLMVSLGEDA HFQCPHNSSN  60
NANVTWWRVL HGNYTWPPEF LGPGEDPNGT LIIQNVNKSH GGIYVCRVQE GNESYQQSCG  120
TYLRVRQPPP RPFLDMGEGT KNRIITAEGI ILLFCAVVPG TLLLFRKRWQ NEKLGLDAGD  180
EYEDENLYEG LNLDDCSMYE DISRGLQGTY QDVGSLNIGD VQLEKP                 226

SEQ ID NO: 83          moltype = AA  length = 188
FEATURE                Location/Qualifiers
source                 1..188
                       mol_type = protein
                       organism = synthetic construct
SEQUENCE: 83
MPGGPGVLQA LPATIFLLFL LSAVYLGPGC QALWMHKVPA SLMVSLGEDA HFQCPHNSSN  60
NANVTWWRVL HGNYTWPPEF LGPGEDPNEP PPRPFLDMGE GTKNRIITAE GIILLFCAVV  120
PGTLLLFRKR WQNEKLGLDA GDEYEDENLY EGLNLDDCSM YEDISRGLQG TYQDVGSLNI  180
GDVQLEKP                                                           188

SEQ ID NO: 84          moltype = AA  length = 21
FEATURE                Location/Qualifiers
source                 1..21
                       mol_type = protein
                       organism = synthetic construct
SEQUENCE: 84
ENLYEGLNLD DCSMYEDISR G                                            21

SEQ ID NO: 85          moltype = AA  length = 68
FEATURE                Location/Qualifiers
source                 1..68
                       mol_type = protein
                       organism = synthetic construct
SEQUENCE: 85
FWVLVVVGGV LACYSLLVTV AFIIFWVRSK RSRLLHSDYM NMTPRRPGPT RKHYQPYAPP  60
RDFAAYRS                                                           68

SEQ ID NO: 86          moltype = AA  length = 68
FEATURE                Location/Qualifiers
source                 1..68
                       mol_type = protein
                       organism = synthetic construct
SEQUENCE: 86
FWVLVVVGGV LACYSLLVTV AFIIFWVRSK RSRLLHSDYM NMTPRRPGPT RKHYQPYAPP  60
RDFAAYRS                                                           68

SEQ ID NO: 87          moltype = AA  length = 42
FEATURE                Location/Qualifiers
source                 1..42
                       mol_type = protein
```

```
                        organism = synthetic construct
SEQUENCE: 87
KRGRKKLLYI FKQPFMRPVQ TTQEEDGCSC RFPEEEEGGC EL                  42

SEQ ID NO: 88           moltype = AA  length = 44
FEATURE                 Location/Qualifiers
source                  1..44
                        mol_type = protein
                        organism = synthetic construct
SEQUENCE: 88
FWVRSKRSRL LHSDYMNMTP RRPGPTRKHY QPYAPPRDFA AYRS                44

SEQ ID NO: 89           moltype = AA  length = 35
FEATURE                 Location/Qualifiers
source                  1..35
                        mol_type = protein
                        organism = synthetic construct
SEQUENCE: 89
TKKKYSSSVH DPNGEYMFMR AVNTAKKSRL TDVTL                          35

SEQ ID NO: 90           moltype = AA  length = 37
FEATURE                 Location/Qualifiers
source                  1..37
                        mol_type = protein
                        organism = synthetic construct
SEQUENCE: 90
RRDQRLPPDA HKPPGGGSFR TPIQEEQADA HSTLAKI                        37

SEQ ID NO: 91           moltype = AA  length = 114
FEATURE                 Location/Qualifiers
source                  1..114
                        mol_type = protein
                        organism = synthetic construct
SEQUENCE: 91
CCLRRHQGKQ NELSDTAGRE INLVDAHLKS EQTEASTRQN SQVLLSETGI YDNDPDLCFR  60
MQEGSEVYSN PCLEENKPGI VYASLNHSVI GPNSRLARNV KEAPTEYASI CVRS       114

SEQ ID NO: 92           moltype = AA  length = 49
FEATURE                 Location/Qualifiers
source                  1..49
                        mol_type = protein
                        organism = synthetic construct
SEQUENCE: 92
HQRRKYRSNK GESPVEPAEP CRYSCPREEE GSTIPIQEDY RKPEPACSP           49

SEQ ID NO: 93           moltype = AA  length = 187
FEATURE                 Location/Qualifiers
source                  1..187
                        mol_type = protein
                        organism = synthetic construct
SEQUENCE: 93
RRACRKRIRQ KLHLCYPVQT SQPKLELVDS RPRRSSTQLR SGASVTEPVA EERGLMSQPL  60
METCHSVGAA YLESLPLQDA SPAGGPSSPR DLPEPRVSTE HTNNKIEKIY IMKADTVIVG  120
TVKAELPEGR GLAGPAEPEL EEELEADHTP HYPEQETEPP LGSCSDVMLS VEEEGKEDPL  180
PTAASGK                                                         187

SEQ ID NO: 94           moltype = AA  length = 54
FEATURE                 Location/Qualifiers
source                  1..54
                        mol_type = protein
                        organism = synthetic construct
SEQUENCE: 94
HIWQLRSQCM WPRETQLLLE VPPSTEDARS CQFPEEERGE RSAEEKGRLG DLWV      54

SEQ ID NO: 95           moltype = AA  length = 60
FEATURE                 Location/Qualifiers
source                  1..60
                        mol_type = protein
                        organism = synthetic construct
SEQUENCE: 95
CVKRRKPRGD VVKVIVSVQR KRQEAEGEAT VIEALQAPPD VTTVAVEETI PSFTGRSPNH  60

SEQ ID NO: 96           moltype = AA  length = 9
FEATURE                 Location/Qualifiers
source                  1..9
                        mol_type = protein
                        organism = synthetic construct
SEQUENCE: 96
YPYDVPDYA                                                       9
```

```
SEQ ID NO: 97           moltype = AA  length = 8
FEATURE                 Location/Qualifiers
source                  1..8
                        mol_type = protein
                        organism = synthetic construct
SEQUENCE: 97
DYKDDDDK                                                                    8

SEQ ID NO: 98           moltype = AA  length = 10
FEATURE                 Location/Qualifiers
source                  1..10
                        mol_type = protein
                        organism = synthetic construct
SEQUENCE: 98
EQKLISEEDL                                                                  10

SEQ ID NO: 99           moltype = AA  length = 5
FEATURE                 Location/Qualifiers
source                  1..5
                        mol_type = protein
                        organism = synthetic construct
SEQUENCE: 99
GSGGS                                                                       5

SEQ ID NO: 100          moltype = AA  length = 4
FEATURE                 Location/Qualifiers
source                  1..4
                        mol_type = protein
                        organism = synthetic construct
SEQUENCE: 100
GGGS                                                                        4

SEQ ID NO: 101          moltype = AA  length = 4
FEATURE                 Location/Qualifiers
source                  1..4
                        mol_type = protein
                        organism = synthetic construct
SEQUENCE: 101
GGSG                                                                        4

SEQ ID NO: 102          moltype = AA  length = 5
FEATURE                 Location/Qualifiers
source                  1..5
                        mol_type = protein
                        organism = synthetic construct
SEQUENCE: 102
GGSGG                                                                       5

SEQ ID NO: 103          moltype = AA  length = 5
FEATURE                 Location/Qualifiers
source                  1..5
                        mol_type = protein
                        organism = synthetic construct
SEQUENCE: 103
GSGSG                                                                       5

SEQ ID NO: 104          moltype = AA  length = 5
FEATURE                 Location/Qualifiers
source                  1..5
                        mol_type = protein
                        organism = synthetic construct
SEQUENCE: 104
GSGGG                                                                       5

SEQ ID NO: 105          moltype = AA  length = 5
FEATURE                 Location/Qualifiers
source                  1..5
                        mol_type = protein
                        organism = synthetic construct
SEQUENCE: 105
GGGSG                                                                       5

SEQ ID NO: 106          moltype = AA  length = 5
FEATURE                 Location/Qualifiers
source                  1..5
                        mol_type = protein
                        organism = synthetic construct
SEQUENCE: 106
```

```
GSSSG                                                      5

SEQ ID NO: 107          moltype = AA  length = 5
FEATURE                 Location/Qualifiers
source                  1..5
                        mol_type = protein
                        organism = synthetic construct
SEQUENCE: 107
EAAAK                                                      5

SEQ ID NO: 108          moltype = AA  length = 118
FEATURE                 Location/Qualifiers
source                  1..118
                        mol_type = protein
                        organism = synthetic construct
SEQUENCE: 108
QVQLQESGPG LVKPSQTLSI TCTVSGFSLA SYNIHWVRQP PGKGLEWLGV IWAGGSTNYN  60
SALMSRLTIS KDNSKNQVFL KMSSLTAADT AVYYCAKRSD DYSWFAYWGQ GTLVTVSS    118

SEQ ID NO: 109          moltype = AA  length = 108
FEATURE                 Location/Qualifiers
source                  1..108
                        mol_type = protein
                        organism = synthetic construct
SEQUENCE: 109
ENQMTQSPSS LSASVGDRVT MTCRASSSVS SSYLHWYQQK SGKAPKVWIY STSNLASGVP  60
SRFSGSGSGT DYTLTISSLQ PEDFATYYCQ QYSGYPITFG QGTKVEIK              108

SEQ ID NO: 110          moltype = AA  length = 5
FEATURE                 Location/Qualifiers
source                  1..5
                        mol_type = protein
                        organism = synthetic construct
SEQUENCE: 110
SYNIH                                                      5

SEQ ID NO: 111          moltype = AA  length = 16
FEATURE                 Location/Qualifiers
source                  1..16
                        mol_type = protein
                        organism = synthetic construct
SEQUENCE: 111
VIWAGGSTNY NSALMS                                          16

SEQ ID NO: 112          moltype = AA  length = 10
FEATURE                 Location/Qualifiers
source                  1..10
                        mol_type = protein
                        organism = synthetic construct
SEQUENCE: 112
RSDDYSWFAY                                                 10

SEQ ID NO: 113          moltype = AA  length = 12
FEATURE                 Location/Qualifiers
source                  1..12
                        mol_type = protein
                        organism = synthetic construct
SEQUENCE: 113
RASSSVSSSY LH                                              12

SEQ ID NO: 114          moltype = AA  length = 7
FEATURE                 Location/Qualifiers
source                  1..7
                        mol_type = protein
                        organism = synthetic construct
SEQUENCE: 114
STSNLAS                                                    7

SEQ ID NO: 115          moltype = AA  length = 9
FEATURE                 Location/Qualifiers
source                  1..9
                        mol_type = protein
                        organism = synthetic construct
SEQUENCE: 115
QQYSGYPIT                                                  9

SEQ ID NO: 116          moltype = AA  length = 30
FEATURE                 Location/Qualifiers
source                  1..30
```

```
                        mol_type = protein
                        organism = synthetic construct
SEQUENCE: 116
QVQLQESGPG LVKPSQTLSI TCTVSGFSLA                                      30

SEQ ID NO: 117          moltype = AA  length = 14
FEATURE                 Location/Qualifiers
source                  1..14
                        mol_type = protein
                        organism = synthetic construct
SEQUENCE: 117
WVRQPPGKGL EWLG                                                       14

SEQ ID NO: 118          moltype = AA  length = 32
FEATURE                 Location/Qualifiers
source                  1..32
                        mol_type = protein
                        organism = synthetic construct
SEQUENCE: 118
RLTISKDNSK NQVFLKMSSL TAADTAVYYC AK                                   32

SEQ ID NO: 119          moltype = AA  length = 11
FEATURE                 Location/Qualifiers
source                  1..11
                        mol_type = protein
                        organism = synthetic construct
SEQUENCE: 119
WGQGTLVTVS S                                                          11

SEQ ID NO: 120          moltype = AA  length = 23
FEATURE                 Location/Qualifiers
source                  1..23
                        mol_type = protein
                        organism = synthetic construct
SEQUENCE: 120
ENQMTQSPSS LSASVGDRVT MTC                                             23

SEQ ID NO: 121          moltype = AA  length = 15
FEATURE                 Location/Qualifiers
source                  1..15
                        mol_type = protein
                        organism = synthetic construct
SEQUENCE: 121
WYQQKSGKAP KVWIY                                                      15

SEQ ID NO: 122          moltype = AA  length = 32
FEATURE                 Location/Qualifiers
source                  1..32
                        mol_type = protein
                        organism = synthetic construct
SEQUENCE: 122
GVPSRFSGSG SGTDYTLTIS SLQPEDFATY YC                                   32

SEQ ID NO: 123          moltype = AA  length = 10
FEATURE                 Location/Qualifiers
source                  1..10
                        mol_type = protein
                        organism = synthetic construct
SEQUENCE: 123
FGQGTKVEIK                                                            10

SEQ ID NO: 124          moltype = AA  length = 113
FEATURE                 Location/Qualifiers
source                  1..113
                        mol_type = protein
                        organism = synthetic construct
SEQUENCE: 124
EVQLLQSGPE LEKPGASVMI SCKASGSSFT GYNMNWVRQN IGKSLEWIGA IDPYYGGTSY  60
NQKFKGRATL TVDKSSSTAY MHLKSLTSED SAVYYCVSGM EYWGQGTSVT VSS         113

SEQ ID NO: 125          moltype = AA  length = 115
FEATURE                 Location/Qualifiers
source                  1..115
                        mol_type = protein
                        organism = synthetic construct
SEQUENCE: 125
DVVMTQTPLS LPVSLGDQAS ISCRSSQSLV HRNGNTYLHW YLQKPGQSPK LLIHKVSNRF  60
SGVPDRFSGS GSGTDFTLKI SRVEAEDLGV YFCSQSTHVP PLTFGAGTKL ELKRA       115
```

```
SEQ ID NO: 126          moltype = AA  length = 5
FEATURE                 Location/Qualifiers
source                  1..5
                        mol_type = protein
                        organism = synthetic construct
SEQUENCE: 126
GYNMN                                                             5

SEQ ID NO: 127          moltype = AA  length = 17
FEATURE                 Location/Qualifiers
source                  1..17
                        mol_type = protein
                        organism = synthetic construct
SEQUENCE: 127
AIDPYYGGTS YNQKFKG                                                17

SEQ ID NO: 128          moltype = AA  length = 4
FEATURE                 Location/Qualifiers
source                  1..4
                        mol_type = protein
                        organism = synthetic construct
SEQUENCE: 128
GMEY                                                              4

SEQ ID NO: 129          moltype = AA  length = 16
FEATURE                 Location/Qualifiers
source                  1..16
                        mol_type = protein
                        organism = synthetic construct
SEQUENCE: 129
RSSQSLVHRN GNTYLH                                                 16

SEQ ID NO: 130          moltype = AA  length = 7
FEATURE                 Location/Qualifiers
source                  1..7
                        mol_type = protein
                        organism = synthetic construct
SEQUENCE: 130
KVSNRFS                                                           7

SEQ ID NO: 131          moltype = AA  length = 10
FEATURE                 Location/Qualifiers
source                  1..10
                        mol_type = protein
                        organism = synthetic construct
SEQUENCE: 131
SQSTHVPPLT                                                        10

SEQ ID NO: 132          moltype = AA  length = 30
FEATURE                 Location/Qualifiers
source                  1..30
                        mol_type = protein
                        organism = synthetic construct
SEQUENCE: 132
EVQLLQSGPE LEKPGASVMI SCKASGSSFT                                  30

SEQ ID NO: 133          moltype = AA  length = 14
FEATURE                 Location/Qualifiers
source                  1..14
                        mol_type = protein
                        organism = synthetic construct
SEQUENCE: 133
WVRQNIGKSL EWIG                                                   14

SEQ ID NO: 134          moltype = AA  length = 32
FEATURE                 Location/Qualifiers
source                  1..32
                        mol_type = protein
                        organism = synthetic construct
SEQUENCE: 134
RATLTVDKSS STAYMHLKSL TSEDSAVYYC VS                               32

SEQ ID NO: 135          moltype = AA  length = 11
FEATURE                 Location/Qualifiers
source                  1..11
                        mol_type = protein
                        organism = synthetic construct
SEQUENCE: 135
WGQGTSVTVS S                                                      11
```

```
SEQ ID NO: 136          moltype = AA  length = 23
FEATURE                 Location/Qualifiers
source                  1..23
                        mol_type = protein
                        organism = synthetic construct
SEQUENCE: 136
DVVMTQTPLS LPVSLGDQAS ISC                                          23

SEQ ID NO: 137          moltype = AA  length = 15
FEATURE                 Location/Qualifiers
source                  1..15
                        mol_type = protein
                        organism = synthetic construct
SEQUENCE: 137
WYLQKPGQSP KLLIH                                                   15

SEQ ID NO: 138          moltype = AA  length = 32
FEATURE                 Location/Qualifiers
source                  1..32
                        mol_type = protein
                        organism = synthetic construct
SEQUENCE: 138
GVPDRFSGSG SGTDFTLKIS RVEAEDLGVY FC                                32

SEQ ID NO: 139          moltype = AA  length = 12
FEATURE                 Location/Qualifiers
source                  1..12
                        mol_type = protein
                        organism = synthetic construct
SEQUENCE: 139
FGAGTKLELK RA                                                      12

SEQ ID NO: 140          moltype = AA  length = 118
FEATURE                 Location/Qualifiers
source                  1..118
                        mol_type = protein
                        organism = synthetic construct
SEQUENCE: 140
EVQLLQSGPE LEKPGASVMI SCKASGSSFT SYNIHWVRQN IGKSLEWIGV IWAGGSTNYN  60
SALMSRATLT VDKSSSTAYM HLKSLTSEDS AVYYCVSRSD DYSWFAYWGQ GTSVTVSS    118

SEQ ID NO: 141          moltype = AA  length = 110
FEATURE                 Location/Qualifiers
source                  1..110
                        mol_type = protein
                        organism = synthetic construct
SEQUENCE: 141
DVVMTQTPLS LPVSLGDQAS ISCRASSSVS SSYLHWYLQK PGQSPKLLIH STSNLASGVP  60
DRFSGSGSGT DFTLKISRVE AEDLGVYFCQ QYSGYPITFG AGTKLELKRA             110

SEQ ID NO: 142          moltype = AA  length = 5
FEATURE                 Location/Qualifiers
source                  1..5
                        mol_type = protein
                        organism = synthetic construct
SEQUENCE: 142
DKTHT                                                              5

SEQ ID NO: 143          moltype = AA  length = 113
FEATURE                 Location/Qualifiers
source                  1..113
                        mol_type = protein
                        organism = synthetic construct
SEQUENCE: 143
QVQLQESGPG LVKPSQTLSI TCTVSGFSLA GYNMNWVRQP PGKGLEWLGA IDPYYGGTSY  60
NQKFKGRLTI SKDNSKNQVF LKMSSLTAAD TAVYYCAKGM EYWGQGTLVT VSS         113

SEQ ID NO: 144          moltype = AA  length = 113
FEATURE                 Location/Qualifiers
source                  1..113
                        mol_type = protein
                        organism = synthetic construct
SEQUENCE: 144
ENQMTQSPSS LSASVGDRVT MTCRSSQSLV HRNGNTYLHW YQQKSGKAPK VWIYKVSNRF  60
SGVPSRFSGS GSGTDYTLTI SSLQPEDFAT YYCSQSTHVP PLTFGQGTKV EIK         113

SEQ ID NO: 145          moltype = AA  length = 4
FEATURE                 Location/Qualifiers
```

```
source                  1..4
                        mol_type = protein
                        organism = synthetic construct
SEQUENCE: 145
CPPC                                                                     4

SEQ ID NO: 146          moltype = AA  length = 12
FEATURE                 Location/Qualifiers
source                  1..12
                        mol_type = protein
                        organism = synthetic construct
VARIANT                 1..12
                        note = This sequence may encompass 1-12 residues
SEQUENCE: 146
AAAAAAAAAA AA                                                            12

SEQ ID NO: 147          moltype = AA  length = 50
FEATURE                 Location/Qualifiers
VARIANT                 1..50
                        note = This sequence may encompass 1-10 "Gly Gly Gly Gly
                         Ser" repeating units
source                  1..50
                        mol_type = protein
                        organism = synthetic construct
SEQUENCE: 147
GGGGSGGGGS GGGGSGGGGS GGGGSGGGGS GGGGSGGGGS GGGGSGGGGS            50

SEQ ID NO: 148          moltype = AA  length = 50
FEATURE                 Location/Qualifiers
VARIANT                 1..50
                        note = This sequence may encompass 1-10 "Glu Ala Ala Ala
                         Lys" repeating units
source                  1..50
                        mol_type = protein
                        organism = synthetic construct
SEQUENCE: 148
EAAAKEAAAK EAAAKEAAAK EAAAKEAAAK EAAAKEAAAK EAAAKEAAAK            50

SEQ ID NO: 149          moltype = AA  length = 5
FEATURE                 Location/Qualifiers
source                  1..5
                        mol_type = protein
                        organism = synthetic construct
SEQUENCE: 149
GGGGS                                                                    5

SEQ ID NO: 150          moltype = AA  length = 20
FEATURE                 Location/Qualifiers
source                  1..20
                        mol_type = protein
                        organism = synthetic construct
SEQUENCE: 150
GGGGSGGGGS GGGGSGGGGS                                                    20

SEQ ID NO: 151          moltype = AA  length = 10
FEATURE                 Location/Qualifiers
VARIANT                 1..10
                        note = This sequence may encompass 1-10 residues
source                  1..10
                        mol_type = protein
                        organism = synthetic construct
SEQUENCE: 151
AAAAAAAAAA                                                               10

SEQ ID NO: 152          moltype = AA  length = 4
FEATURE                 Location/Qualifiers
source                  1..4
                        mol_type = protein
                        organism = synthetic construct
SEQUENCE: 152
AAAA                                                                     4

SEQ ID NO: 153          moltype = AA  length = 122
FEATURE                 Location/Qualifiers
source                  1..122
                        mol_type = protein
                        organism = synthetic construct
SEQUENCE: 153
EVQLVESGGG LVQPGRSLRL SCAASGFTFN DYAMHWVRQA PGKGLEWVST ISWNSGSIGY  60
```

-continued

```
ADSVKGRFTI SRDNAKKSLY LQMNSLRAED TALYYCAKDI QYGNYYYGMD VWGQGTTVTV  120
SS                                                                 122

SEQ ID NO: 154          moltype = AA  length = 5
FEATURE                 Location/Qualifiers
source                  1..5
                        mol_type = protein
                        organism = synthetic construct
SEQUENCE: 154
GGGGS                                                              5

SEQ ID NO: 155          moltype = AA  length = 9
FEATURE                 Location/Qualifiers
source                  1..9
                        mol_type = protein
                        organism = unidentified
SEQUENCE: 155
LAGLIDADG                                                          9

SEQ ID NO: 156          moltype = AA  length = 30
FEATURE                 Location/Qualifiers
VARIANT                 1..30
                        note = This sequence may encompass 1-6 "Gly Gly Gly Gly
                         Ser" repeating units
source                  1..30
                        mol_type = protein
                        organism = synthetic construct
SEQUENCE: 156
GGGGSGGGGS GGGGSGGGGS GGGGSGGGGS                                   30

SEQ ID NO: 157          moltype = AA  length = 30
FEATURE                 Location/Qualifiers
VARIANT                 1..30
                        note = This sequence may encompass 1-6 "Glu Ala Ala Ala
                         Lys" repeating units
source                  1..30
                        mol_type = protein
                        organism = synthetic construct
SEQUENCE: 157
EAAAKEAAAK EAAAKEAAAK EAAAKEAAAK                                   30

SEQ ID NO: 158          moltype = AA  length = 112
FEATURE                 Location/Qualifiers
source                  1..112
                        mol_type = protein
                        organism = synthetic construct
SEQUENCE: 158
DIVMTQTPLS LPVTPGEPAS ISCRSSKSLL HSNGITYLYW YLQKPGQSPQ LLIYQMSNLV  60
SGVPDRFSGS GSGTDFTLKI SRVEAEDVGV YYCAQNLELP YTFGGGTKVE IK          112

SEQ ID NO: 159          moltype = AA  length = 107
FEATURE                 Location/Qualifiers
source                  1..107
                        mol_type = protein
                        organism = synthetic construct
SEQUENCE: 159
EIVLTQSPAT LSLSPGERAT LSCRASQSVS SYLAWYQQKP GQAPRLLIYD ASNRATGIPA  60
RFSGSGSGTD FTLTISSLEP EDFAVYYCQQ RSNWPITFGQ GTRLEIK                107

SEQ ID NO: 160          moltype = AA  length = 119
FEATURE                 Location/Qualifiers
source                  1..119
                        mol_type = protein
                        organism = synthetic construct
SEQUENCE: 160
QVQLVQSGAE VKKPGSSVKV SCKASGYAFS YSWMNWVRQA PGQGLEWMGR IFPGDGDTDY  60
NGKFKGRVTI TADKSTSTAY MELSSLRSED TAVYYCARNV FDGYWLVYWG QGTLVTVSS   119
```

CHIMERIC ANTIGEN RECEPTORS AND RELATED METHODS AND COMPOSITIONS FOR THE TREATMENT OF CANCER

This application is a continuation of U.S. patent application Ser. No. 17/908,703, filed Sep. 1, 2022, which is a national phase application under 35 U.S.C. § 371 of International Application No. PCT/US2021/020511, filed Mar. 2, 2021, which claims benefit of priority of U.S. Provisional Application No. 62/984,139, filed Mar. 2, 2020, and U.S. Provisional Application No. 63/084,138, filed Sep. 28, 2020, all of which are hereby incorporated by reference in their entirety.

The application contains a Sequence Listing in compliance with ST.26 format and is hereby incorporated by reference in its entirety. Said Sequence Listing, created on Dec. 17, 2024, is named UCLAP0112USC1_SUB.xml and is 152,536 bytes in size.

BACKGROUND

I. Field of the Invention

This invention relates generally to the fields of molecular biology and immunotherapy.

II. Background

CD20 is a clinically validated target for B-cell malignancies. Chimeric antigen receptor (CAR)-T cells targeting CD20 have been tested clinically and shown to be safe, but not as efficacious as CD19 CAR-T cell therapy against B-cell lymphoma. Several previous publications stipulated that a major reason for the unique efficacy of the CD19 CAR is its lack of tonic signaling. Specifically, it has been argued that most CARs exhibit basal signaling even in the absence of antigen stimulation, that this "tonic signaling" behavior triggers premature T-cell dysfunction, and that the CD19 CAR is uniquely efficacious because it does not tonically signal and thus does not induce premature T-cell dysfunction. It has further been proposed that CAR tonic signaling is a result of antigen-independent clustering of CAR molecules on the T-cell surface, and that this clustering behavior is a result of the specific sequence of the scFv domain of the CAR. There is a need for improved CARs that support robust T-cell mediated anti-tumor function, potentially by modulating the tonic signaling behavior of the CARs.

SUMMARY OF THE DISCLOSURE

Embodiments concern compositions comprising chimeric antigen receptors, nucleic acids encoding chimeric antigen receptors, and cells able to express chimeric antigen receptors, as well as methods of engineering and/or producing chimeric antigen receptors and methods of using these compositions. Accordingly, the compositions and methods of the disclosure provide a process for redesigning a CAR with increased in vivo efficacy and the resulting CAR, which can be used in additional methods of the disclosure.

Aspects of the disclosure relate to a polypeptide comprising an anti-CD20 single chain variable fragment (scFv) comprising: a light chain variable region (VL) comprising in order from amino-proximal to carboxy-proximal end of the light chain variable region: light chain framework region 1 (LFR1), light chain complementarity-determining region 1 (LCDR1), light chain framework region 2 (LFR2), light chain complementarity-determining region 2 (LCDR2), light chain framework region 3 (LFR3), light chain complementarity-determining region 3 (LCDR3), and light chain framework region 4 (LFR4); and a heavy chain variable region (VH) comprising in order from amino-proximal to carboxy-proximal end of the heavy chain variable region: heavy chain framework region 1 (HFR1), heavy chain complementarity-determining region 1 (HCDR1), heavy chain framework region 2 (HFR2), heavy chain complementarity-determining region 2 (HCDR2), heavy chain framework region 3 (HFR3), heavy chain complementarity-determining region 3 (HCDR3), and heavy chain framework region 4 (HFR4); wherein LFR1, LFR2, LFR3, LFR4, LCDR1, LCDR2, and LCDR3 comprise an amino acid sequence with at least 90% sequence identity to SEQ ID NOS:29, 30, 31, 22, 12, 13, and 14, respectively; and wherein HFR1, HFR2, HFR3, HFR4, HCDR1, HCDR2, and HCDR3 comprise an amino acid sequence with at least 90% sequence identity to SEQ ID NOS:26, 27, 28, 18, 9, 10, and 11, respectively.

Further aspects relate to a polypeptide comprising an anti-CD20 scFv comprising: a light chain variable region comprising in order from amino-proximal to carboxy-proximal end of the light chain variable region: LFR1, LCDR1, LFR2, LCDR2, LFR3, LCDR3, and LFR4; and a heavy chain variable region comprising in order from amino-proximal to carboxy-proximal end of the heavy chain variable region: HFR1, HCDR1, HFR2, HCDR2, HFR3, HCDR3, and HFR4; wherein LFR1, LFR2, LFR3, LFR4, LCDR1, LCDR2, and LCDR3 comprise an amino acid sequence with at least 90% sequence identity to SEQ ID NOS:19, 20, 21, 22, 24, 13, and 25, respectively; and wherein HFR1, HFR2, HFR3, HFR4, HCDR1, HCDR2, and HCDR3 comprise an amino acid sequence with at least 90% sequence identity to SEQ ID NOS:15, 16, 17, 18, 9, 10, and 23, respectively.

Further aspects relate to A polypeptide comprising an anti-CD20 single chain variable fragment (scFv) comprising: a light chain variable region (VL) comprising in order from amino-proximal to carboxy-proximal end of the light chain variable region: light chain framework region 1 (LFR1), light chain complementarity-determining region 1 (LCDR1), light chain framework region 2 (LFR2), light chain complementarity-determining region 2 (LCDR2), light chain framework region 3 (LFR3), light chain complementarity-determining region 3 (LCDR3), and light chain framework region 4 (LFR4); and a heavy chain variable region (VH) comprising in order from amino-proximal to carboxy-proximal end of the heavy chain variable region: heavy chain framework region 1 (HFR1), heavy chain complementarity-determining region 1 (HCDR1), heavy chain framework region 2 (HFR2), heavy chain complementarity-determining region 2 (HCDR2), heavy chain framework region 3 (HFR3), heavy chain complementarity-determining region 3 (HCDR3), and heavy chain framework region 4 (HFR4); wherein LFR1, LFR2, LFR3, LFR4, LCDR1, LCDR2, and LCDR3 comprise an amino acid sequence with at least 90% sequence identity to the LFR1, LFR2, LFR3, LFR4, LCDR1, LCDR2, and LCDR3, respectively, of the variable region of SEQ ID NO:5; and wherein HFR1, HFR2, HFR3, HFR4, HCDR1, HCDR2, and HCDR3 comprise an amino acid sequence with at least 90% sequence identity to the HFR1, HFR2, HFR3, HFR4, HCDR1, HCDR2, and HCDR3, respectively, of the variable region of SEQ ID NO:6.

Also described is a polypeptide comprising an anti-CD20 single chain variable fragment (scFv) comprising: a light chain variable region (VL) comprising in order from amino-proximal to carboxy-proximal end of the light chain variable region: light chain framework region 1 (LFR1), light chain complementarity-determining region 1 (LCDR1), light chain framework region 2 (LFR2), light chain complementarity-determining region 2 (LCDR2), light chain framework region 3 (LFR3), light chain complementarity-determining region 3 (LCDR3), and light chain framework region 4 (LFR4); and a heavy chain variable region (VH) comprising in order from amino-proximal to carboxy-proximal end of the heavy chain variable region: heavy chain framework region 1 (HFR1), heavy chain complementarity-determining region 1 (HCDR1), heavy chain framework region 2 (HFR2), heavy chain complementarity-determining region 2 (HCDR2), heavy chain framework region 3 (HFR3), heavy chain complementarity-determining region 3 (HCDR3), and heavy chain framework region 4 (HFR4); wherein LFR1, LFR2, LFR3, LFR4, LCDR1, LCDR2, and LCDR3 comprise an amino acid sequence with at least 90% sequence identity to the LFR1, LFR2, LFR3, LFR4, LCDR1, LCDR2, and LCDR3, respectively, of the variable region of SEQ ID NO:7; and wherein HFR1, HFR2, HFR3, HFR4, HCDR1, HCDR2, and HCDR3 comprise an amino acid sequence with at least 90% sequence identity to the HFR1, HFR2, HFR3, HFR4, HCDR1, HCDR2, and HCDR3, respectively, of the variable region of SEQ ID NO:8.

Further aspects relate to a polypeptide comprising an anti-GD2 single chain variable fragment (scFv) comprising: a light chain variable region (VL) comprising in order from amino-proximal to carboxy-proximal end of the light chain variable region: light chain framework region 1 (LFR1), light chain complementarity-determining region 1 (LCDR1), light chain framework region 2 (LFR2), light chain complementarity-determining region 2 (LCDR2), light chain framework region 3 (LFR3), light chain complementarity-determining region 3 (LCDR3), and light chain framework region 4 (LFR4); and a heavy chain variable region (VH) comprising in order from amino-proximal to carboxy-proximal end of the heavy chain variable region: heavy chain framework region 1 (HFR1), heavy chain complementarity-determining region 1 (HCDR1), heavy chain framework region 2 (HFR2), heavy chain complementarity-determining region 2 (HCDR2), heavy chain framework region 3 (HFR3), heavy chain complementarity-determining region 3 (HCDR3), and heavy chain framework region 4 (HFR4); wherein LFR1, LFR2, LFR3, LFR4, LCDR1, LCDR2, and LCDR3 comprise an amino acid sequence with at least 90% sequence identity to SEQ ID NOS:136, 137, 138, 139, 113, 114, and 115, respectively; and wherein HFR1, HFR2, HFR3, HFR4, HCDR1, HCDR2, and HCDR3 comprise an amino acid sequence with at least 90% sequence identity to SEQ ID NOS:132, 133, 134, 135, 110, 111, and 112, respectively.

Also described is a polypeptide comprising an anti-GD2 single chain variable fragment (scFv) comprising: a light chain variable region (VL) comprising in order from amino-proximal to carboxy-proximal end of the light chain variable region: light chain framework region 1 (LFR1), light chain complementarity-determining region 1 (LCDR1), light chain framework region 2 (LFR2), light chain complementarity-determining region 2 (LCDR2), light chain framework region 3 (LFR3), light chain complementarity-determining region 3 (LCDR3), and light chain framework region 4 (LFR4); and a heavy chain variable region (VH) comprising in order from amino-proximal to carboxy-proximal end of the heavy chain variable region: heavy chain framework region 1 (HFR1), heavy chain complementarity-determining region 1 (HCDR1), heavy chain framework region 2 (HFR2), heavy chain complementarity-determining region 2 (HCDR2), heavy chain framework region 3 (HFR3), heavy chain complementarity-determining region 3 (HCDR3), and heavy chain framework region 4 (HFR4); wherein LFR1, LFR2, LFR3, LFR4, LCDR1, LCDR2, and LCDR3 comprise an amino acid sequence with at least 90% sequence identity to the LFR1, LFR2, LFR3, LFR4, LCDR1, LCDR2, and LCDR3, respectively, of the variable region of SEQ ID NO:141; and wherein HFR1, HFR2, HFR3, HFR4, HCDR1, HCDR2, and HCDR3 comprise an amino acid sequence with at least 90% sequence identity to the HFR1, HFR2, HFR3, HFR4, HCDR1, HCDR2, and HCDR3, respectively, of the variable region of SEQ ID NO:140.

Further aspects relate to a polypeptide comprising an anti-GD2 single chain variable fragment (scFv) comprising: a light chain variable region (VL) comprising in order from amino-proximal to carboxy-proximal end of the light chain variable region: light chain framework region 1 (LFR1), light chain complementarity-determining region 1 (LCDR1), light chain framework region 2 (LFR2), light chain complementarity-determining region 2 (LCDR2), light chain framework region 3 (LFR3), light chain complementarity-determining region 3 (LCDR3), and light chain framework region 4 (LFR4); and a heavy chain variable region (VH) comprising in order from amino-proximal to carboxy-proximal end of the heavy chain variable region: heavy chain framework region 1 (HFR1), heavy chain complementarity-determining region 1 (HCDR1), heavy chain framework region 2 (HFR2), heavy chain complementarity-determining region 2 (HCDR2), heavy chain framework region 3 (HFR3), heavy chain complementarity-determining region 3 (HCDR3), and heavy chain framework region 4 (HFR4); wherein LFR1, LFR2, LFR3, LFR4, LCDR1, LCDR2, and LCDR3 comprise an amino acid sequence with at least 90% sequence identity to SEQ ID NOS:120, 121, 122, 123, 129, 130, and 131, respectively; and wherein HFR1, HFR2, HFR3, HFR4, HCDR1, HCDR2, and HCDR3 comprise an amino acid sequence with at least 90% sequence identity to SEQ ID NOS:116, 117, 118, 119, 126, 127, and 128, respectively.

Also described is a polypeptide comprising an anti-GD2 single chain variable fragment (scFv) comprising: a light chain variable region (VL) comprising in order from amino-proximal to carboxy-proximal end of the light chain variable region: light chain framework region 1 (LFR1), light chain complementarity-determining region 1 (LCDR1), light chain framework region 2 (LFR2), light chain complementarity-determining region 2 (LCDR2), light chain framework region 3 (LFR3), light chain complementarity-determining region 3 (LCDR3), and light chain framework region 4 (LFR4); and a heavy chain variable region (VH) comprising in order from amino-proximal to carboxy-proximal end of the heavy chain variable region: heavy chain framework region 1 (HFR1), heavy chain complementarity-determining region 1 (HCDR1), heavy chain framework region 2 (HFR2), heavy chain complementarity-determining region 2 (HCDR2), heavy chain framework region 3 (HFR3), heavy chain complementarity-determining region 3 (HCDR3), and heavy chain framework region 4 (HFR4); wherein LFR1, LFR2, LFR3, LFR4, LCDR1, LCDR2, and LCDR3 comprise an amino acid sequence with at least 90% sequence identity to the LFR1, LFR2, LFR3, LFR4, LCDR1, LCDR2, and LCDR3, respectively, of the variable region of SEQ ID NO:144; and wherein HFR1, HFR2, HFR3, HFR4, HCDR1, HCDR2, and HCDR3 comprise an amino acid sequence with at least 90% sequence identity to the HFR1, HFR2, HFR3, HFR4, HCDR1, HCDR2, and HCDR3, respectively, of the variable region of SEQ ID NO:143.

Aspects of the disclosure also relate to a polypeptide comprising a CAR comprising, in order from amino proximal to carboxy proximal end, a scFv comprising a variable heavy (VH) and a variable light (VL) region, a transmembrane domain, and a cytoplasmic region comprising a primary intracellular signaling domain; wherein the scFv is a hybrid scFv comprising framework regions (FRs) and complementarity-determining regions (CDRs) that are derived from different antigen binding regions or antibodies that bind the same antigen.

Further aspects relate to a polypeptide comprising a CAR comprising, in order from amino proximal to carboxy proximal end, a scFv, a transmembrane domain, a torsional linker, and a cytoplasmic region comprising a primary intracellular signaling domain, wherein the torsional linker comprises 1-12 alanine residues.

Aspects of the disclosure relate to a method of making a CAR comprising introducing a torsional linker into a CAR between the transmembrane domain and the cytoplasmic domain; wherein the torsional linker comprises 1-12 alanine residues. Also described is a method of making a CAR with a hybrid scFv, a transmembrane domain and a cytoplasmic region comprising a primary intracellular signaling domain comprising combining CDRs derived from a first antigen binding region or antibody with FRs derived from a second antigen binding region or antibody, wherein the first and second antigen binding region or antibody bind to the same antigen. Methods of producing these CARs may comprise or further comprise reproducing cells comprising nucleic acids encoding one or more of these designed CARs. In some embodiments, the CAR comprises an FR and CDRs from antibodies or antigen binding regions that differ in their tonic signaling intensities.

Also described are nucleic acids comprising a sequence encoding a polypeptide of the disclosure, vectors, such as lentiviral vectors comprising the nucleic acids of the disclosure, cells comprising and/or expressing nucleic acids and/or polypeptides of the disclosure, and populations of cells comprising the cell embodiments of the disclosure. Further embodiments relate to compositions and pharmaceutically acceptable formulations comprising the polypeptides, nucleic acids, cells, and populations of cells of the disclosure. Also provided are methods of making cells that express a polypeptide, the method comprising introducing into a cell a nucleic acid of the disclosure. Also described are cells, polypeptides, and CARs made by the methods of the disclosure. Yet further aspects relate to a method of treating a patient with cancer comprising administering to the patient an effective amount of a composition of the disclosure.

Further aspects relate to a method for screening a CAR comprising: providing a CAR with a hybrid scFv, a transmembrane domain and a cytoplasmic region comprising a primary intracellular signaling domain comprising combining CDRs derived from a first antigen binding region or antibody with FRs derived from a second antigen binding region or antibody, wherein the first and second antigen binding region or antibody bind to the same antigen; and evaluating, determining, or measuring the function of the CAR.

In some embodiments, evaluating, determining, or measuring the function of the CAR comprises evaluating the tonic signaling intensity of the CAR. In some embodiments, evaluating, determining, or measuring the tonic signaling intensity comprises a CDV dilution assay and/or expression evaluation by antibody staining for activation markers. In some embodiments, evaluating, determining, or measuring the function of the CAR comprises determining one or more of tumor killing efficacy, tumor clearance efficacy, in vivo survival, in vivo tumor clearance, in vivo reduction of tumor burden. In some embodiments, the method may comprise or further comprise making a CAR with a hybrid scFv comprising combining CDRs derived from a first antigen binding region or antibody with FRs derived from a second antigen binding region or antibody, wherein the first and second antigen binding region or antibody bind to the same antigen.

In some embodiments, LFR1, LFR2, LFR3, LFR4, LCDR1, LCDR2, and LCDR3 comprise an amino acid sequence with at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to the LFR1, LFR2, LFR3, LFR4, LCDR1, LCDR2, and LCDR3, respectively, of the variable region of SEQ ID NO:141; and wherein HFR1, HFR2, HFR3, HFR4, HCDR1, HCDR2, and HCDR3 comprise an amino acid sequence with at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to the HFR1, HFR2, HFR3, HFR4, HCDR1, HCDR2, and HCDR3, respectively, of the variable region of SEQ ID NO:140.

In some embodiments, LFR1, LFR2, LFR3, LFR4, LCDR1, LCDR2, and LCDR3 comprise an amino acid sequence with at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to the LFR1, LFR2, LFR3, LFR4, LCDR1, LCDR2, and LCDR3, respectively, of the variable region of SEQ ID NO:144; and wherein HFR1, HFR2, HFR3, HFR4, HCDR1, HCDR2, and HCDR3 comprise an amino acid sequence with at least 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 10000 (or any derivable range therein) sequence identity to the HFR1, HFR2, HFR3, HFR4, HCDR1, HCDR2, and HCDR3, respectively, of the variable region of SEQ ID NO:143.

"Single-chain Fv" or "scFv" antibody fragments comprise at least a portion of the VH and VL domains of an antibody, such as the CDRs of each, wherein these domains are present in a single polypeptide chain. It is contemplated that an scFv includes a CDR1, CDR2, and/or CDR3 of a heavy chain variable region and a CDR1, CDR2, and/or CDR3 of a light chain variable region in some embodiments. It is further contemplated that a CDR1, CDR2, or CDR3 may comprise or consist of a sequence set forth in a SEQ ID NO provided herein as CDR1, CDR2, or CDR3, respectively. A CDR may also comprise 1, 2, 3, 4, 5, 6, 7, 8, 9, 10, 11, 12, 13, 14, 15, 16, 16, 18, 19, 20, 21, 22, 23, or more contiguous amino acid residues (or any range derivable therein) flanking one or both sides of a particular CDR sequence; therefore, there may be one or more additional amino acids at the N-terminal or C-terminal end of a particular CDR sequence, such as those shown in SEQ ID NOS:9-14, 23, 24, 25, 110-115, and 126-131. It is further contemplated that an scFv includes a HFR1, HFR2, HFR3, and/or HFR4 of a heavy chain variable region and a LFR1, LFR2, LFR3, and/or LFR4 of a light chain variable region in some embodiments. The FR are the regions flanking the CDRs. For example, the scFv may comprise a heavy chain variable region comprising, from amino to carboxy end, HFR1, HCDR1, HFR2, HCDR2, HFR3, HCDR3, and HFR4. Similarly, the scFv may comprise a light chain variable region comprising, from amino to carboxy end, LFR1, LCDR1, LFR2, LCDR2, LFR3, LCDR3, and LFR4. It is further contemplated that a HFR1, HFR2, HFR3, HFR4, LFR1, LFR2, LFR2, or LFR4 may comprise or consist of a sequence set forth in a SEQ ID NO provided herein as HFR1, HFR2, HFR3, HFR4, LFR1, LFR2, LFR2, or LFR4, respectively. A FR may also comprise 1, 2, 3, 4, 5, 6, 7, 8, 9, 10, 11, 12, 13, 14, 15, 16, 16, 18, 19, 20, 21, 22, 23, 24, 25, 26, 27, 28, 29, 30, or more contiguous amino acid residues (or any range derivable therein) flanking one or both sides of a particular FR sequence; therefore, there may be one or more additional amino acids at the N-terminal or C-terminal end of a particular FR sequence, such as those shown in SEQ ID NOS:15-22, 26-31, 116-123, and 132-139.

In some embodiments, LFR1 comprises an amino acid sequence with, with at least, at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:29. In some embodiments, LFR2 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:30. In some embodiments, LFR3 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:31. In some embodiments, LFR4 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:22. In some embodiments, LCDR1 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:12. In some embodiments, LCDR2 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:13. In some embodiments, LCDR3 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:14. In some embodiments, HFR1 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:26. In some embodiments, HFR2 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:27. In some embodiments, HFR3 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:28. In some embodiments, HFR4 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:18. In some embodiments, HCDR1 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:9. In some embodiments, HCDR2 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:10. In some embodiments, HCDR3 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:11.

In some embodiments, LFR1, LFR2, LFR3, LFR4, LCDR1, LCDR2, and/or LCDR3 comprise the amino acid sequence of SEQ ID NOS:29, 30, 31, 22, 12, 13, and 14, respectively and HFR1, HFR2, HFR3, HFR4, HCDR1, HCDR2, and/or HCDR3 comprise the amino acid sequence of SEQ ID NOS:26, 27, 28, 18, 9, 10, and 11, respectively. In some embodiments, LFR1, LFR2, LFR3, LFR4, LCDR1, LCDR2, and/or LCDR3 comprise the amino acid sequence of SEQ ID NOS:19, 20, 21, 22, 24, 13, and 25, respectively; and HFR1, HFR2, HFR3, HFR4, HCDR1, HCDR2, and/or HCDR3 comprise the amino acid sequence of SEQ ID NOS:15, 16, 17, 18, 9, 10, and 23, respectively. In some embodiments, VL comprises the amino acid sequence of SEQ ID NO:5 and VH comprises the amino acid sequence of SEQ ID NO:6. In further embodiments, VL comprises the amino acid sequence of SEQ ID NO:7 and VH comprises the amino acid sequence of SEQ ID NO:8.

In some embodiments, LFR1 comprises an amino acid sequence with at least, at most, exactly, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100/o (or any derivable range therein) sequence identity to SEQ ID NO:19. In some embodiments, LFR2 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:20. In some embodiments, LFR3 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:21. In some embodiments, LFR4 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:22. In some embodiments, LCDR1 comprises an amino acid sequence with, with at least, or with at most 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:24. In some embodiments, LCDR2 comprises an amino acid sequence with, with at least, with at most or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:13. In some embodiments, LCDR3 comprises an amino acid sequence with, with at least, with at most or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:25. In some embodiments, HFR1 comprises an amino acid sequence with at least, at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:15. In some embodiments, HFR2 comprises an amino acid sequence with, with at least, with at most or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:16. In some embodiments, HFR3 comprises an amino acid sequence with, with at least, or with at most 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100/o (or any derivable range therein) sequence identity to SEQ ID NO:17. In some embodiments, HFR4 comprises an amino acid sequence with, with at least, or with at most 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:18. In some embodiments, HCDR1 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:9. In some embodiments, HCDR2 comprises an amino acid sequence with, with at least, or with at most or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:10. In some embodiments, HCDR3 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:23.

In some embodiments, the light chain variable region comprises an amino acid sequence with at least 90% sequence identity to SEQ ID NO:5 and a heavy chain variable region comprising an amino acid sequence with at least 90% sequence identity to SEQ ID NO:6. In some embodiments, the light chain variable region comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:5 and a heavy chain variable region comprising an amino acid sequence with, with at least, or with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:6.

In some embodiments, the light chain variable region comprises an amino acid sequence with at least 90% sequence identity to SEQ ID NO:7 and a heavy chain variable region comprising an amino acid sequence with at least 90% sequence identity to SEQ ID NO:8. In some embodiments, the light chain variable region comprises an amino acid sequence with at least, at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:7 and a heavy chain variable region comprising an amino acid sequence with, with at least, or with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:8.

In some embodiments, LFR1 comprises an amino acid sequence with, with at least, at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:136. In some embodiments, LFR2 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:137. In some embodiments, LFR3 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:138. In some embodiments, LFR4 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:139. In some embodiments, LCDR1 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO: 113. In some embodiments, LCDR2 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:114. In some embodiments, LCDR3 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:115. In some embodiments, HFR1 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:132. In some embodiments, HFR2 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:133. In some embodiments, HFR3 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:134. In some embodiments, HFR4 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:135. In some embodiments, HCDR1 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:110. In some embodiments, HCDR2 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:111. In some embodiments, HCDR3 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:112.

In some embodiments, LFR1 comprises an amino acid sequence with, with at least, at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:120. In some embodiments, LFR2 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:121. In some embodiments, LFR3 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:122. In some embodiments, LFR4 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:123. In some embodiments, LCDR1 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO: 129. In some embodiments, LCDR2 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:130. In some embodiments, LCDR3 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:131. In some embodiments, HFR1 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:116. In some embodiments, HFR2 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:117. In some embodiments, HFR3 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:118. In some embodiments, HFR4 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:119. In some embodiments, HCDR1 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:126. In some embodiments, HCDR2 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:127. In some embodiments, HCDR3 comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:128.

In some embodiments, LFR1, LFR2, LFR3, LFR4, LCDR1, LCDR2, and/or LCDR3 comprise the amino acid sequence of SEQ ID NOS:136, 137, 138, 139, 113, 114, and 115, respectively and HFR1, HFR2, HFR3, HFR4, HCDR1, HCDR2, and/or HCDR3 comprise the amino acid sequence of SEQ ID NOS:132, 133, 134, 135, 110, 111, and 112, respectively. In some embodiments, LFR1, LFR2, LFR3, LFR4, LCDR1, LCDR2, and/or LCDR3 comprise the amino acid sequence of SEQ ID NOS: 120, 121, 122, 123, 129, 130, and 131, respectively; and HFR1, HFR2, HFR3, HFR4, HCDR1, HCDR2, and/or HCDR3 comprise the amino acid sequence of SEQ ID NOS:116, 117, 118, 119, 126, 127, and 128, respectively. In some embodiments, VL comprises the amino acid sequence of SEQ ID NO:141 and VH comprises the amino acid sequence of SEQ ID NO:140. In further embodiments, VL comprises the amino acid sequence of SEQ ID NO:144 and VH comprises the amino acid sequence of SEQ ID NO: 143.

In some embodiments, the light chain variable region comprises an amino acid sequence with at least 90% sequence identity to SEQ ID NO:141 and a heavy chain variable region comprising an amino acid sequence with at least 90% sequence identity to SEQ ID NO:140. In some embodiments, the light chain variable region comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:141 and a heavy chain variable region comprising an amino acid sequence with, with at least, or with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:140.

In some embodiments, the light chain variable region comprises an amino acid sequence with at least 90% sequence identity to SEQ ID NO:144 and a heavy chain variable region comprising an amino acid sequence with at least 90% sequence identity to SEQ ID NO:143. In some embodiments, the light chain variable region comprises an amino acid sequence with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:144 and a heavy chain variable region comprising an amino acid sequence with, with at least, or with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% (or any derivable range therein) sequence identity to SEQ ID NO:143.

In some embodiments, LFR1, LFR2, LFR3, LFR4, LCDR1, LCDR2, and/or LCDR3 comprise the amino acid sequence of the LFR1, LFR2, LFR3, LFR4, LCDR1, LCDR2, and/or LCDR3 from the variable region of SEQ ID NO:5 and/or wherein HFR1, HFR2, HFR3, HFR4, HCDR1, HCDR2, and/or HCDR3 comprise the amino acid sequence of the HFR1, HFR2, HFR3, HFR4, HCDR1, HCDR2, and/or HCDR3 from the variable region of SEQ ID NO:5.

In some embodiments, LFR1, LFR2, LFR3, LFR4, LCDR1, LCDR2, and/or LCDR3 comprise the amino acid sequence of the LFR1, LFR2, LFR3, LFR4, LCDR1, LCDR2, and/or LCDR3 from the variable region of SEQ ID NO:7 and/or wherein HFR1, HFR2, HFR3, HFR4, HCDR1, HCDR2, and/or HCDR3 comprise the amino acid sequence of the HFR1, HFR2, HFR3, HFR4, HCDR1, HCDR2, and/or HCDR3 from the variable region of SEQ ID NO:8.

In some embodiments, LFR1, LFR2, LFR3, LFR4, LCDR1, LCDR2, and/or LCDR3 comprise the amino acid sequence of the LFR1, LFR2, LFR3, LFR4, LCDR1, LCDR2, and/or LCDR3 from the variable region of SEQ ID NO:141 and/or wherein HFR1, HFR2, HFR3, HFR4, HCDR1, HCDR2, and/or HCDR3 comprise the amino acid sequence of the HFR1, HFR2, HFR3, HFR4, HCDR1, HCDR2, and/or HCDR3 from the variable region of SEQ ID NO:140.

In some embodiments, LFR1, LFR2, LFR3, LFR4, LCDR1, LCDR2, and/or LCDR3 comprise the amino acid sequence of the LFR1, LFR2, LFR3, LFR4, LCDR1, LCDR2, and/or LCDR3 from the variable region of SEQ ID NO:144 and/or wherein HFR1, HFR2, HFR3, HFR4, HCDR1, HCDR2, and/or HCDR3 comprise the amino acid sequence of the HFR1, HFR2, HFR3, HFR4, HCDR1, HCDR2, and/or HCDR3 from the variable region of SEQ ID NO:143.

The scFv of the disclosure may be a hybrid scFv. The term hybrid refers to a scFv that has the LFR1, LFR2, LFR3, LFR4, HFR1, HFR2, HFR3, and HFR4 from one antigen binding region or antibody, such as a antigen binding region of a scFv, antibody, single-domain antibody, or other antibody-derived antigen-binding fragment and has the LCDR1, LCDR2, LCDR3, HCDR1, HCDR2, and HCDR3 from a different antigen binding region or antibody, such as an antigen binding region of a scFv, antibody, single-domain antibody, or other antibody-derived antigen-binding fragment. In the hybrid scFvs, the LFR1, LFR2, LFR3, LFR4, HFR1, HFR2, HFR3, and HFR4 from a first antigen binding region and the LCDR1, LCDR2, LCDR3, HCDR1, HCDR2, and HCDR3 are from a second antigen binding region. Accordingly, the CDR regions of one antigen binding molecule are grafted, in their corresponding order, onto the FR of another antigen binding molecule. This is further exemplified by the embodiments herein that demonstrate the combining of the FR of the VH and VL regions of one antibody with the CDRs of the VH and VL regions of another antibody. The CDRs and FRs need not be derived directly from an antibody, but can be derived from any antigen-binding fragment comprising a VH and VL region, such as another scFv, a single-domain antibody, a TCR, and other antigen binding regions known in the art and described herein. The hybrid may further comprise, comprise at most, or comprise at least 1, 2, 3, 4, 5, 6, 7, 8, 9, 10, 11, 12, 13, 14, 15, 16, or 17 substitutions (or any range derivable therein) in the FR or CDRs of the hybrid CAR. The hybrid scFvs of the disclosure are hybrids of two different antigen binding regions or antibodies that bind to the same antigen. In some embodiments, the two different antigen binding regions or antibodies bind to a different epitope on the same antigen. In some embodiments, the two different antigen binding regions or antibodies bind to overlapping epitopes on the same antigen. In some embodiments, two different antigen binding regions or antibodies bind to the same epitope on the antigen. The hybrid scFv may be a hybrid of two different antigen binding regions or antibodies from the same species. In some embodiments, the CDRs are derived from an antigen binding region or antibody that is from a human antibody and the FRs are derived from an antigen binding region or antibody that is also from a human antibody. In some embodiments, the CDRs are derived from an antigen binding region or antibody that is from a non-human antibody and the FRs are derived from an antigen binding region or antibody that is also from a non-human antibody. In some embodiments, the CDRs are derived from an antigen binding region or antibody that is from a mouse antibody and the FRs are derived from an antigen binding region or antibody that is also from a mouse antibody. In one embodiment, the CDRs are derived from an antigen binding region or antibody that is from a human or humanized antibody or antigen binding region and the FRs are derived from an antigen binding region or antibody that is of non-human origin, such as a mouse. In some embodiments, the hybrid scFv is derived from antigen binding regions or antibodies that have been determined to have reduced, low, or non-significant immunogenicity. In some embodiments, the hybrid scFv is derived from antigen binding regions or antibodies that have been approved for human use. In some embodiments, hybrid scFvs of the disclosure exclude humanized scFvs. Other suitable sources of the antigen binding regions or antibodies include goat, rat, horse, rabbit, mammalian, and non-human primates. In some embodiments, the CDRs and/or FRs are non-immunogenic or are reduced in immunogenicity in humans. In some embodiments, the immunogenic potential in humans of the hybrid scFv and/or polypeptide comprising the hybrid scFv is not statistically different than the non-hybrid scFv and/or polypeptide comprising the non-hybrid scFv. The non-hybrid scFv may be the scFv or antigen binding region that serves as the source of CDRs in the hybrid scFv or the non-hybrid scFv may be the scFv or antigen binding region that serves as the source of FRs in the hybrid scFv. The CDRs of the hybrid scFv may comprise, comprise at least, or comprise at most 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 (or any derivable range therein) substitutions, deletions, or additions relative to the CDRs of the antibody or antigen binding region from which the CDRs are derived from. The FRs of the hybrid scFv may comprise, comprise at least, or comprise at most 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 (or any derivable range therein) substitutions, deletions, or additions relative to the FRs of the antibody or antigen binding region from which the FRs are derived from.

In some embodiments, there are polypeptides comprised of an FR from one antibody or antigen binding region and CDRs from a different antibody or antigen binding region, where the difference is because of sequence and not because they recognize/bind to different epitopes and/or antigen. The FRs and CDRs may be derived from antigen binding regions or antibodies of different tonic signaling intensities. In some embodiments, the FRs are derived from an antigen binding region or antibody of higher tonic signaling intensity than the antigen binding region or antibody in which the CDRs are derived from. In some embodiments, the CDRs are derived from an antigen binding region or antibody of higher tonic signaling intensity than the antigen binding region or antibody in which the FRs are derived from. The term “tonic signaling intensity” or “tonic signaling” when used herein refers to the level of stimulation of CAR signaling in the absence of antigen stimulation. Tonic signaling can be determined by a CTV dilution assay (described in example 3) and/or by antigen-independent activation-marker expression evaluation by antibody staining for activation markers, such as CD137 and/or CTLA-4 (described in Example 3). In some embodiments, the medium fluorescence intensity (MFI) in a CTV dilution assay is at least 1.5, 2, 2.5, 3, 3.5, 4, or 5 fold (or any derivable range therein) higher in cells with a non-hybrid scFv derived from the same antigen binding region or antibody as the FRs or CDRs of the hybrid scFv as compared to the hybrid scFv. In some embodiments, the CD137+ expression is at least 2, 5, 10, 15, 20, 25, 30, 35, 40, 45, or 50 fold (or any derivable range therein) higher in cells with a hybrid scFv compared to a non-hybrid scFv derived from the same antigen binding region or antibody as the FRs or CDRs. In some embodiments, the CTLA-4+ expression is at least 2, 5, 10, 15, 20, 25, 30, 35, 40, 45, or 50 fold (or any derivable range therein) higher in cells with a hybrid scFv compared to a non-hybrid scFv derived from the same antigen binding region or antibody as the FRs or CDRs. Furthermore, the hybrid scFvs may comprise CDRs and FRs of different tonic signaling intensities. For example, the CDRs may be derived from a CAR that exhibits at least 1.5, 2, 2.5, 3, 3.5, 4, or 5 fold (or any derivable range therein) MFI in a CTV dilution assay compared to the CAR from which the FRs are derived. In some embodiments, the CDRs may be derived from a CAR that exhibits at least 1.5, 2, 2.5, 3, 3.5, 4, or 5 fold (or any derivable range therein) MFI in a CTV dilution assay compared to the CAR from which the CDRs are derived. In some embodiments, the CDRs may be derived from a CAR that exhibits at least 2, 5, 10, 15, 20, 25, 30, 35, 40, 45, or 50 fold (or any derivable range therein) higher CD137+ expression compared to the CAR from which the CDRs are derived. In some embodiments, the FRs may be derived from a CAR that exhibits at least 2, 5, 10, 15, 20, 25, 30, 35, 40, 45, or 50 fold (or any derivable range therein) higher CD137+ expression compared to the CAR from which the FRs are derived. In some embodiments, the CDRs may be derived from a CAR that exhibits at least 2, 5, 10, 15, 20, 25, 30, 35, 40, 45, or 50 fold (or any derivable range therein) higher CTLA4+ expression compared to the CAR from which the CDRs are derived. In some embodiments, the FRs may be derived from a CAR that exhibits at least 2, 5, 10, 15, 20, 25, 30, 35, 40, 45, or 50 fold (or any derivable range therein) higher CTLA4+ expression compared to the CAR from which the FRs are derived. In some embodiments, the CDRs may be derived from a CAR that exhibits at least 2, 5, 10, 15, 20, 25, 30, 35, 40, 45, or 50 fold (or any derivable range therein) higher activation marker expression compared to the CAR from which the CDRs are derived. In some embodiments, the FRs may be derived from a CAR that exhibits at least 2, 5, 10, 15, 20, 25, 30, 35, 40, 45, or 50 fold (or any derivable range therein) higher activation marker expression compared to the CAR from which the FRs are derived. The polypeptide may be one that is further defined has having increased tumor killing activity compared to a CAR with a non-hybrid scFv, wherein the non-hybrid scFv is derived from the same antigen binding region or antibody as the hybrid scFv FRs and/or wherein the polypeptide has increased tumor killing activity compared to a CAR with a non-hybrid scFv, wherein the non-hybrid scFv is derived from the same antigen binding region or antibody as the hybrid scFv CDRs. For example, CAR T cells comprising the hybrid scFv may show a target cell fold change that is at least significantly less than or at least 2, 3, 4, or 5 fold less than a non-hybrid scFv derived from the same antigen binding region or antibody as the FRs or CDRs after at least 10, 11, 12, 13, 14, 15, 16, 17, 18, 19, 20, 21, 22, 23, 24, 25, 26, 27, 28, 29, or 30 days in co-culture. In some embodiments, the polypeptide has increased tumor cell clearance activity compared to a CAR with a non-hybrid scFv, wherein the non-hybrid scFv is derived from the same antigen binding region or antibody s of the hybrid scFv FRs and/or wherein the polypeptide has increased tumor killing activity compared to a CAR with a non-hybrid scFv, wherein the non-hybrid scFv is derived from the same antigen binding region or antibody as the hybrid scFv CDRs. For example, CAR T cells comprising the hybrid scFv may show a tumor cell clearance fold change that is at least significantly more (as shown by a decrease in the average radiance of marked cells) than or at least 2, 3, 4, 5, 10, 20, 50, 100, 500, or 1000 fold more than a non-hybrid scFv derived from the same antigen binding region or antibody as the FRs or CDRs after at least 20, 40, 60, 80, 100, 120, 140, 160, or 180 days post T-cell injection. In some embodiments, the CDRs or FRs of the hybrid CAR are from a non-hybrid scFv of CAR that has been demonstrated to not have any significant tumor killing activity, tumor cell clearance, or in vivo efficacy as seen by in vivo tumor clearance or increase in survival over a negative control.

In some embodiments, the polypeptide comprises a linker between the VH and VL. In some embodiments, the linker is 4-40 amino acids in length. In some embodiments, the linker is, is at least, is at most, or is about 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (or any derivable range therein) amino acid residues in length. In some embodiments, the linker comprises at least 4 glycine and/or serine residues. In some embodiments, the linker comprises at least 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 (or any derivable range therein) glycine and/or serine residues. In some embodiments, the linker comprises $(GGGGS)_n$, wherein n is 1, 2, 3, 4, 5, 6, 7, 8, 9, or 10 (or any derivable range therein). In some embodiments, the linker comprises GSTSGGGSGGGSGGGGSS (SEQ ID NO:32) or a linker with at least 80, 81, 82, 83, 84, 85, 86, 87, 88, 89, 90, 91, 92, 93, 94, 95, 96, 97, 98, 99, or 100% (or any derivable range therein) sequence identity to SEQ ID NO:32. In some embodiments, the linker comprises, or consists of, the amino acid sequence: $(EAAAK)_n$, wherein n is 1, 2, 3, 4, 5, 6, 7, 8, 9, or 10 (or any derivable range therein). In some embodiments, the linker comprises GGGGS. In some embodiments, the linker is $(GGGGS)_4$.

In some embodiments, the VH is amino proximal to the VL. In some embodiments, the VH is carboxy proximal to the VL. A first region is carboxy proximal to a second region when the first region is attached to the carboxy terminus of the second region. There may be further intervening amino acid residues between the first and second regions. Thus, the regions need not be immediately adjacent, unless specifically specified as not having intervening amino acid residues. The term "amino-proximal" is similarly defined in that a first region is amino-proximal to a second region when the first region is attached to the amino terminus of the second region. Similarly, there may be further intervening amino acid residues between the first and second regions unless stated otherwise.

In some embodiments, the polypeptide comprises a chimeric antigen receptor (CAR) comprising the scFv, a transmembrane domain and a cytoplasmic region comprising a primary intracellular signaling domain. In some embodiments, the CAR molecules discussed herein have the three main regions of a CAR molecule, which are an extracellular domain that binds to one or more target molecule(s), a cytoplasmic region that contains a primary intracellular signaling domain, and a transmembrane region between the extracellular domain and the cytoplasmic domain. Some CAR molecules have a spacer that is between the extracellular domain and the transmembrane domain. Furthermore, one or more linkers may be included in CAR molecules between or within one or more regions, such as between different binding regions within the extracellular domain or within a binding region, such as between the variable region of a light chain (VH) and the variable region of a heavy chain (VL). Any embodiment regarding a specific region may be implemented with respect to any other specific region disclosed herein. Any of these regions may be immediately adjacent either on the N-terminal side or the C-terminal side of another region depending on its function but it is also contemplated that there may have, have at least, or have at most at least or at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, or 99 amino acids intervening between contiguous regions (or any range derivable therein). In some embodiments, the polypeptide comprises a single transmembrane domain and/or a single cytoplasmic region comprising a primary intracellular signaling domain. In some embodiments, the polypeptide comprises, in order from amino proximal end to carboxy proximal end, the scFv, the transmembrane domain, and the cytoplasmic region comprising a primary intracellular signaling domain. In some embodiments, the CAR is monospecific. In some embodiments, the CAR is bispecific. In some embodiments, the CAR further comprises an extracellular spacer between the transmembrane domain and the scFv. In some embodiments, the extracellular spacer is between 8 and 1000 amino acids in length. In some embodiments, the extracellular spacer is between 8 and 500 amino acids in length. In some embodiments, the extracellular spacer is between 100-300 amino acids in length. In some embodiments, the extracellular spacer has fewer than 100 amino acids. In some embodiments, the extracellular spacer is at least, at most, exactly, or about 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327,328, 329, 330, 331,332, 333, 334, 335, 336, 337,338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, or 500 amino acids (or any derivable range therein). In some embodiments, the extracellular spacer is or comprises an IgG4 hinge, a CD8α hinge, an IgG1 hinge, a CD34 hinge, or fragments thereof. In some embodiments, the extracellular spacer comprises a IgG4 hinge or fragment thereof. In some embodiments, the extracellular spacer comprises or further comprises a CH1, CH2, and/or a CH3 region. In some embodiments, the spacer comprises or consists of an IgG4 hinge polypeptide, CH2 region, and CH3 region. In some embodiments, the CH2 region comprises L235E and/or N297Q substitutions. In some embodiments, the spacer comprises a polypeptide with at least 80% sequence identity to SEQ ID NO:36, or a fragment thereof. In some embodiments, the spacer comprises a polypeptide with, with at least, with at most, or about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% sequence identity (or any derivable range therein) to SEQ ID NO:36, or a fragment thereof.

In some embodiments, the transmembrane domain is an alpha or beta chain of the T cell receptor, CD28, CD3ε (epsilon), CD45, CD4, CD5, CD8, CD9, CD16, CD22, CD33, CD37, CD64, CD80, CD86, CD123, CD134, CD137 or CD154 transmembrane domain. In some embodiments, the transmembrane domain comprises or is a CD28 transmembrane domain or is derived from a CD28 transmembrane domain. In some embodiments, the transmembrane domain comprises a polypeptide with at least 80% sequence identity to SEQ ID NO:37, or a fragment thereof. In some embodiments, the transmembrane domain comprises a polypeptide with, with at least, with at most, or with about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% sequence identity (or any derivable range therein) to SEQ ID NO:37, or a fragment thereof.

In some embodiments, the primary intracellular signaling domain is or comprises CD3-zeta or is derived from the intracellular signaling domain of CD3-zeta. In some embodiments, the primary intracellular signaling domain comprises a polypeptide with at least 80% sequence identity to SEQ ID NO:39, or a fragment thereof. In some embodiments, the primary intracellular signaling domain comprises a polypeptide with, with at least, with at most, or with about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% sequence identity (or any derivable range therein) to SEQ ID NO:39, or a fragment thereof.

In some embodiments, the cytoplasmic region further comprises one or more costimulatory domains. In some embodiments, the cytoplasmic region comprises two costimulatory domains. In some embodiments, the one or more costimulatory domain(s) comprise a costimulatory domain from one or more of 4-1BB (CD137), CD28, IL-15Rα, OX40, CD2, CD27, CDS, ICAM-1, LFA-1 (CD11a/CD18), and/or ICOS (CD278). In some embodiments, the one or more costimulatory domains comprise a costimulatory domain from CD28 or a costimulatory domain derived from CD28. In some embodiments, the costimulatory domain comprises a polypeptide with at least 80% sequence identity to SEQ ID NO:38, or a fragment thereof. In some embodiments, the costimulatory domain comprises a polypeptide with, with at least, with at most, or with about 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% sequence identity (or any derivable range therein) to SEQ ID NO:38, or a fragment thereof.

In some embodiments, the polypeptide further comprises a torsional linker between the transmembrane domain and the cytoplasmic region. In some embodiments, the torsional linker comprises or consists of 1, 2, 3, 4, 5, 6, 7, 8, 9, or 10 amino acid residues (or any derivable range therein). In some embodiments, the amino acid residues comprise or consist of alanine residues. In some embodiments, the torsional linker comprises at least, at most, or exactly 1, 2, 3, 4, 5, 6, 7, 8, 9, or 10 (or any derivable range therein) alanine residues. In some embodiments, the torsional linker comprises at least, at most, or exactly 1, 2, 3, 4, 5, 6, 7, 8, 9, or 10 (or any derivable range therein) contiguous alanine residues. In some embodiments, the torsional linker consists of 2 or 4 alanine residues. In some embodiments, the torsional linker comprises 2 alanine residues. In some embodiments, the torsional linker comprises 3 alanine residues. In some embodiments, the torsional linker comprises 4 alanine residues. In some embodiments, the torsional linker comprises at least, at most, or exactly 1, 2, 3, 4, 5, 6, 7, 8, 9, or 10 (or any derivable range therein) contiguous alanine residues. In some embodiments, the torsional linker consists of 2 alanine residues.

In some embodiments, the scFv comprises an anti-CD20 scFv. In some embodiments, the scFv comprises an anti-GD2 scFv. In some embodiments, the scFv comprises an anti-BCMA, anti-CD123, anti-CD138, anti-CD19, anti-CD20, antiCD22, anti-CD38, anti-CD5, anti-Ig kappa chain, anti-LeY, anti-NKG2D, anti-ROR1, anti-WT1, anti-C-Met, anti-CAIX, anti-CD133, anti-CD171, anti-CD70, anti-CEA, anti-EGFR, anti-EGFRvIII, anti-Ep-CAM, anti-EphA2, anti-FAP, anti-GD2, anti-GPC3, anti-Her2, anti-HPV16-E6, anti-IL13Ra2, anti-MAGEA3, anti-MAGEA4, anti-MART1, anti-Mesothlin, anti-MUC1, anti-MUC6, anti-NY-ESO-1, anti-PD-L1, anti-PSCA, anti-PSMA, anti-ROR1, or anti-VEGFR2 scFv.

Nucleic acids comprising a sequence that encodes the polypeptides disclosed herein, and portions thereof, are provided in embodiments. A nucleic acid may comprise RNA or DNA. In certain embodiments, the nucleic acid is an expression construct. In some embodiments, the expression construct is a vector. In certain embodiments, the vector is a viral vector. The viral vector is a retroviral vector or derived from a retrovirus in particular embodiments. In some embodiments, the retroviral vector comprises a lentiviral vector or is derived from a lentivirus. It is noted that a viral vector is an integrating nucleic acid in certain embodiments. Additionally, a nucleic acid may be a molecule involved in gene editing such that a nucleic acid (such as a guide RNA) encoding a CAR is used to incorporate a CAR-coding sequence into a particular locus of the genome, such as the TRAC gene. This involves a gene editing system such as CRISPR/Cas9 in some embodiments. A nucleic acid, polynucleotide, or polynucleotide region (or a polypeptide or polypeptide region) has a certain percentage (for example, 60%, 65%, 70%, 75%, 80%, 85%, 90%, 95%, 98% or 99%—or any range derivable therein) of "sequence identity" or "homology" to another sequence means that, when aligned, that percentage of bases (or amino acids) are the same in comparing the two sequences. This alignment and the percent homology or sequence identity can be determined using software programs known in the art, for example those described in Ausubel et al. eds. (2007) Current Protocols in Molecular Biology. It is contemplated that a nucleic acid may have such sequence identity or homology to any nucleic acid SEQ ID NO provided herein.

In other embodiments, there is a cell or a population of cells comprising a nucleic acid that encodes all or part of any polypeptide discussed herein. In certain embodiments, a cell or population of cells contains within its genome a sequence encoding any of the polypeptides described herein. This includes, but is not limited to, a lentivirus or retrovirus that has integrated into the cell's genome. In some embodiments, a cell or population of cells expresses all or part of any CAR discussed herein, including, but not limited to those with the amino acid sequence of any of SEQ ID NO:1-144. Progeny (F1, F2, and beyond) of cells in which a nucleic acid encoding a polypeptide was introduced are included in the cells or populations of cells disclosed herein. In some embodiments, a cell or population of cells is a T cell, a natural killer (NK) cell, a natural killer T cell (NKT), an invariant natural killer T cell (iNKT), stem cell, lymphoid progenitor cell, peripheral blood mononuclear cell (PBMC), hematopoietic stem and progenitor cell (HSPC), hematopoietic stem cell (HSC), CD34+ cell, peripheral blood stem cell (PBSC), bone marrow cell, fetal liver cell, embryonic stem cell, cord blood cell, induced pluripotent stem cell (iPS cell). Specific embodiments concern a cell that is a T cell or an NK cell. In some embodiments, T cell comprises a naïve memory T cell. In some embodiments, the naïve memory T cell comprises a CD4+ or CD8+ T cell. In some embodiments, the cells are a population of cells comprising both CD4+ and CD8+ T cells. In some embodiments, the cells are a population of cells comprising naïve memory T cells comprising CD4+ and CD8+ T cells. In some embodiments, the T cell comprises a T cell from a population of CD14 depleted, CD25 depleted, and/or CD62L enriched PBMCs.

In some aspects, the disclosure relates to a cell comprising one or more polypeptides described herein. In some embodiments, the cell is an immune cell. In some embodiments, the cell is a progenitor cell or stem cell. In some embodiments, the progenitor or stem cell is in vitro differentiated into an immune cell. In some embodiments, the cell is a T cell. In some embodiments, the cell is a CD4+ or CD8+ T cell. In some embodiments, the cell is a natural killer cell. In some embodiments, the cell is ex vivo. The term immune cells includes cells of the immune system that are involved in defending the body against both infectious disease and foreign materials. Immune cells may include, for example, neutrophils, eosinophils, basophils, natural killer cells, lymphocytes such as B cells and T cells, and monocytes. T cells may include, for example, CD4+, CD8+, T helper cells, cytotoxic T cells, γδ T cells, regulatory T cells, suppressor T cells, and natural killer T cells. In a specific embodiment, the T cell is a regulatory T cell.

In some embodiments, the population of cells comprise $10^3$-$10^8$ cells. In some embodiments, the population is about, is at least about, or is at most about $10^2$, $10^3$, $10^4$, $\mathbf{10^5}$, $\mathbf{10^6}$, $10^7$, $\mathbf{10^8}$, $\mathbf{10^9}$, $\mathbf{10^{10}}$, $10^{11}$, $10^{12}$ cells (or any range derivable therein). In certain embodiments, cells are autologous with respect to a patient who will receive them. In other embodiments, cells are not autologous and may be allogenic.

In some embodiments of the disclosure, method aspects relate to wherein the cell is infected with a virus encoding a polypeptide of the disclosure. In some embodiments, the virus comprises lentivirus or a lentiviral-derived virus or vector. In some embodiments, the cell is a T cell, a natural killer (NK) cell, a natural killer T cell (NKT), an invariant natural killer T cell (iNKT), stem cell, lymphoid progenitor cell, peripheral blood mononuclear cell (PBMC), bone marrow cell, fetal liver cell, embryonic stem cell, cord blood cell, induced pluripotent stem cell (iPS cell). In some embodiments, the cell is a T cell or an NK cell. In some embodiments, the T cell comprises a naïve memory T cell. In some embodiments, the naïve memory T cell comprises a CD4+ or CD8+ T cell. In some embodiments, the cell is not yet a T cell or NK cell, the method further comprising culturing the cell under conditions that promote the differentiation of the cell into a T cell or an NK cell.

In some embodiments, the methods further comprise culturing the cell under conditions to expand the cell before and or after introducing the nucleic acid into the cell. In some embodiments, the cell is cultured with serum-free medium.

Additional methods concern treating a patient with cancer comprising administering to the patient an effective amount of the composition comprising a cell population expressing a polypeptide of the disclosure. In some embodiments, a patient has relapsed or recurrent cancer. Further embodiments include a step of administering an additional therapy to the patient. In some embodiments, the patient has been previously treated to the cancer. In some embodiments, the patient has been determined to be resistant to the previous treatment. The previous treatment may be a cancer therapeutic described herein, such as those described as additional therapies. Further embodiments include a step of administering chemotherapy and/or radiation to the patient. In some embodiments, the additional therapy comprises an immunotherapy. In some embodiments, the additional therapy comprises an additional therapy described herein. In some embodiments, the immunotherapy comprises immune checkpoint inhibitor therapy. In some embodiments, the immunotherapy comprises an immunotherapy described herein. In some embodiments, the immune checkpoint inhibitor therapy comprises a PD-1 inhibitor and/or CTLA-4 inhibitor. In some embodiments, the immune checkpoint inhibitor therapy comprises one or more inhibitors of one or more immune checkpoint proteins described herein.

In some embodiments, the cancer comprises a CD20+ cancer, wherein a CD20+ cancer is one that comprises CD20+ cells or comprises at least 0.5, 1, 2, 3, 4, 5, 6, 7, 8, 9, 10, 11, 12, 13, 14, 15, 16, 17, 18, 19, 20, 25, 30, 35, 40, 45, 50, 55, 60, 65, 70, 75, 80, 85, or 90% CD20+ cancer cells in a population of tumor cells. In some embodiments, the cancer comprises melanoma. The CAR polypeptides of the current disclosure may have a region, domain, linker, spacer, or other portion thereof that comprises or consists of an amino acid sequence that is at least, at most, or exactly 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100% identical (or any range derivable therein) to all or a portion of the amino acid sequences described herein. In certain embodiments, a CAR polypeptide comprises or consists of an amino acid sequence that is, is at least, is at most, or exactly 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% identical (or any range derivable therein) to any one of SEQ ID NOS:1-144.

The cancer may lymphoma or neuroblastoma. In embodiments in which the CAR comprises a CD20 CAR, the targeted cancer may be lymphoma. In embodiments in which the CAR comprises a GD2 CAR, the targeted cancer may be neuroblastoma. Cancers that may be treated in the methods of the disclosure may also include cancers of the bladder, blood, bone, bone marrow, brain, breast, colon, esophagus, gastrointestine, gum, head, kidney, liver, lung, nasopharynx, neck, ovary, prostate, skin, stomach, testis, tongue, or uterus. In addition, the cancer may specifically be of the following histological type, though it is not limited to these: neoplasm, malignant; carcinoma; carcinoma, undifferentiated; giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; gastrinoma, malignant; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; carcinoid tumor, malignant; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; paget's disease, mammary; acinar cell carcinoma; adenosquamous carcinoma; adenocarcinoma w/squamous metaplasia; thymoma, malignant; ovarian stromal tumor, malignant; thecoma, malignant; granulosa cell tumor, malignant; androblastoma, malignant; sertoli cell carcinoma; leydig cell tumor, malignant; lipid cell tumor, malignant; paraganglioma, malignant; extra-mammary paraganglioma, malignant; pheochromocytoma; glomangiosarcoma; malignant melanoma; amelanotic melanoma; superficial spreading melanoma; malig melanoma in giant pigmented nevus; epithelioid cell melanoma; blue nevus, malignant; sarcoma; fibrosarcoma; fibrous histiocytoma, malignant; myxosarcoma; liposarcoma; leiomyosarcoma; rhabdomyosarcoma; embryonal rhabdomyosarcoma; alveolar rhabdomyosarcoma; stromal sarcoma; mixed tumor, malignant; mullerian mixed tumor; nephroblastoma; hepatoblastoma; carcinosarcoma; mesenchymoma, malignant; brenner tumor, malignant; phyllodes tumor, malignant; synovial sarcoma; mesothelioma, malignant; dysgerminoma; embryonal carcinoma; teratoma, malignant; struma ovarii, malignant; choriocarcinoma; mesonephroma, malignant; hemangiosarcoma; hemangioendothelioma, malignant; kaposi's sarcoma; hemangiopericytoma, malignant; lymphangiosarcoma; osteosarcoma; juxtacortical osteosarcoma; chondrosarcoma; chondroblastoma, malignant; mesenchymal chondrosarcoma; giant cell tumor of bone; ewing's sarcoma; odontogenic tumor, malignant; ameloblastic odontosarcoma; ameloblastoma, malignant; ameloblastic fibrosarcoma; pinealoma, malignant; chordoma; glioma, malignant; ependymoma; astrocytoma; protoplasmic astrocytoma; fibrillary astrocytoma; astroblastoma; glioblastoma; oligodendroglioma; oligodendroblastoma; primitive neuroectodermal; cerebellar sarcoma; ganglioneuroblastoma; neuroblastoma; retinoblastoma; olfactory neurogenic tumor; meningioma, malignant; neurofibrosarcoma; neurilemmoma, malignant; granular cell tumor, malignant; malignant lymphoma; Hodgkin's disease; Hodgkin's lymphoma; paragranuloma; malignant lymphoma, small lymphocytic; malignant lymphoma, large cell, diffuse; malignant lymphoma, follicular; mycosis fungoides; other specified non-Hodgkin's lymphomas; malignant histiocytosis; multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; and hairy cell leukemia.

In certain embodiments, polypeptides described throughout this disclosure are isolated, meaning they are not found in the cellular milieu. In some cases, they are purified, which means it is mostly if not completely separated from polypeptides having a different amino acid sequence and/or chemical formula.

The present disclosure provides, in some embodiments, a method for treating a subject with cancer comprising administering to the subject an effective amount of a population of cells or pharmaceutical composition comprising a chimeric polypeptide or nucleic acid encoding a chimeric polypeptide.

Use of the one or more sequences or compositions may be employed based on any of the methods described herein. Other embodiments are discussed throughout this application. Any embodiment discussed with respect to one aspect of the disclosure applies to other aspects of the disclosure as well and vice versa. For example, any step in a method described herein can apply to any other method. Moreover, any method described herein may have an exclusion of any step or combination of steps. The embodiments in the Example section are understood to be embodiments that are applicable to all aspects of the technology described herein.

Throughout this application, the term "about" is used according to its plain and ordinary meaning in the area of cell and molecular biology to indicate that a value includes the standard deviation of error for the device or method being employed to determine the value.

The use of the word "a" or "an" when used in conjunction with the term "comprising" may mean "one," but it is also consistent with the meaning of "one or more," "at least one," and "one or more than one."

As used herein, the terms "or" and "and/or" are utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." It is specifically contemplated that x, y, or z may be specifically excluded from an embodiment.

The words "comprising" (and any form of comprising, such as "comprise" and "comprises"), "having" (and any form of having, such as "have" and "has"), "including" (and any form of including, such as "includes" and "include"), "characterized by" (and any form of including, such as "characterized as"), or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. The phrase "consisting of" excludes any element, step, or ingredient not specified. The phrase "consisting essentially of" limits the scope of described subject matter to the specified materials or steps and those that do not materially affect its basic and novel characteristics. It is contemplated that embodiments described in the context of the term "comprising" may also be implemented in the context of the term "consisting of" or "consisting essentially of."

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. Aspects of an embodiment set forth in the Examples are also embodiments that may be implemented in the context of embodiments discussed elsewhere in a different Example or elsewhere in the application, such as in the Summary of Invention, Detailed Description of the Embodiments, Claims, and description of Figure Legends.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 9A-C. The RFR-LCDR hybrid CD20 CAR shows superior tumor clearance in vivo. NSG mice were engrafted with 0.5 million firefly luciferase-expressing Raji lymphoma cells and treated with two doses of T cells described for FIG. 2. Animals were re-challenged with a second dose of tumor cells 55 days after the first T-cell treatment. (A) Tumor progression was monitored through bioluminescence imaging. (B) Survival curve is shown as Kaplan-Meier curve. Results indicate the hybrid CAR is superior to both parental CD20 CARs as well as the CD19 CAR in tumor clearance and long-term relapse prevention. (C) Frequency of CAR-expressing human T cells in peripheral blood 23 days post initial T-cell injection was measured by flow cytometry. The addition of two alanine residues into the CAR improved the rituximab-based receptor, corroborating previous data shown in FIG. 5. Combining the hybrid CAR with two alanine insertion further accelerated the rate of initial tumor clearance and led to significantly increased T-cell persistence compared to the hybrid CAR without alanine insertion, indicating that the scFv alteration and alanine insertion strategies can be combined to result in synergistic improvements in CAR function.

FIG. 10A-F. (A) Schematic of a panel of $2^{nd}$-generation anti-CD20 CARs composed of scFvs derived from four different monoclonal antibodies fused to an IgG4 spacer, CD28 transmembrane and cytoplasmic domains, and CD3ζ signaling domain. The CAR is further fused via a self-cleaving T2A peptide to a truncated EGFR (EGFRt), which was used as transduction marker (top). $K_D$ values and CDR structure-family designations of the four antibodies from which scFvs were derived (bottom). FR and CDR sequences and structure-family designations were determined as previously described (Chothia and Lesk, 1987; Chothia et al., 1989; Kabat and Wu, 1971; Martin and Thornton, 1996). (B-C) NSG mice were injected intravenously (i.v.) with $0.5\times10^6$ firefly-luciferase-expressing Raji cells 6 days prior to treatment with $5\times10^6$ CD20-targeting CAR-T cells delivered i.v. (B) Tumor progression was monitored by bioluminescence imaging (n=6 mice per group). Minimum and maximum values on the radiance-intensity scale are $5\times10^4$ and $1\times10^7$, respectively. (C) Average radiance (p/sec/cm2/sr) of individual animals for each test group. (D) Activation and exhaustion maker expression on $CAR^+$ T cells were evaluated 11 days post Dynabead removal, without CD20 antigen stimulation. Data bars indicate the means of technical triplicates±1 standard deviation (S.D.). Results are representative of three independent experiments using T-cells derived from three different healthy donors. Unless otherwise noted, p values were determined by unpaired, two-tailed, two-sample Student's t-test; *p<0.05, p<0.01, *p<0.001, n.s. not statistically significant. (E) A 4-day T-cell proliferation assay on $CAR^+$ T cells with CellTrace Violet (CTV) dye in the absence or presence of target cells (on-target, $CD19^+/CD20^+$ K562 cells; off-target, parental K562 cells) at 2:1 effector-to-target (E:T) ratio. Data shown are representative of five independent experiments from five different healthy donors. (F) Metabolic rates of CD20 CAR-T cells cultured for 24 hours in RPMI supplemented with 10% dFBS and exogenous IL-2 and IL-15, without CD20 antigen stimulation. Data bars indicate the means of technical triplicates±1 S.D. Results are representative of three independent experiments from three different healthy donors. *p<0.05, p<0.01, *p<0.001, n.s. not statistically significant.

FIG. 11A-E. Torsional reorientation of signaling domain tunes CAR-T cell activity. (A) Schematic of alanine incorporation into the Rituximab-based CAR. (B) A 4-day T-cell proliferation assay with CellTrace Violet (CTV) dye in the absence or presence of target cells at 2:1 E:T ratio. Data shown are representative of three independent experiments from three different healthy donors. (C) TNF-α production of CAR-T cells was measured 7 days post Dynabead removal, without CD20 antigen stimulation. Results are representative of three independent experiments from three different healthy donors. *p<0.05, p<0.01, *p<0.001, n.s. not statistically significant. (D,E) NSG mice were injected intravenously with $0.5\times10^6$ firefly-luciferase-expressing Raji cells followed by two doses of $CAR^+$ T cells 6 days ($1.35\times10^6$ cells) and 12 days ($1.5\times10^6$ cells) later; n=6 mice per group. (D) Tumor progression was monitored by bioluminescence imaging (top). Average radiance (p/sec/cm2/sr) of individual animals are shown for each group (bottom). (E) Kaplan-Meier survival curve. Statistical significance was determined by log-rank (Mantel-Cox) test. *p<0.05, p 0.01, *p<0.001, n.s. not statistically significant.

FIG. 12A-E. scFv sequence hybridization yields functionally superior CAR variant. (A) Schematic of scFv sequence hybridization in CAR molecules. The Framework regions (FR) and complementarity-determining regions (CDRs) of Leu16- and rituximab-derived scFvs were intermixed to yield two new CAR variants. (B) RFR-LCDR hybrid CAR-T cells show superior anti-tumor function and T-cell proliferation upon repeated antigen challenge. CAR-T cells were challenged with Raji cells ($CD19^+/CD20^+$) at a 2:1 E:T ratio every two days. T-cell and target-cell counts were quantified by flow cytometry. Data shown are the means of technical triplicates±1 S.D. Results are representative of three independent experiments from three different healthy donors. (C) Activation and exhaustion maker expression was evaluated 11 days post Dynabead removal, without CD20 antigen stimulation. Data bars indicate the means of technical triplicates±1 S.D. Results are representative of three independent experiments from three different healthy donors. *p<0.05, p<0.01, *p<0.001, n.s. not statistically significant. (D) A 4-day CAR-T cell proliferation assay with CellTrace Violet (CTV) dye in the absence or presence of target cells at 2:1 E:T ratio. (E) Metabolic analysis of CAR-T cells in culture in the absence of antigen stimulation. CAR-T cells were cultured for 72 hours in RPMI supplemented with 10% heat-inactivated, dialyzed fetal bovine serum (HI-dFBS), IL-2, and IL-15. Data bars indicate the means of technical triplicates±1 S.D. Data are representative of three independent experiments from three different healthy donors. *p<0.05, p<0.01, *p<0.001, n.s. not statistically significant.

FIG. 13A-G. scFv hybridization in combination with torsional reorientation in CAR protein further enhance CAR-T cell function in vivo. (A-D) NSG mice were injected intravenously with firefly-luciferase-expressing Raji cells followed by two doses of $CAR^+$ T cells, and one Raji tumor rechallenge. (A) Schematic of in vivo experiment (n=6 mice per group). (B) Tumor signal in individual animals quantified by bioluminescence imaging. (C) Kaplan-Meier survival curve. Log-rank (Mantel-Cox) test was performed for pair-wise comparisons. *p<0.05, p<0.01, *p<0.001, n.s. not statistically significant. (D) Frequency of human $CD45^+EGFRt^+$ cell in peripherical blood collected from mice at Day 23 after first dose of T-cell infusion. (E-G) NSG mice were injected intravenously with firefly-luciferase expressing Raji cells followed by a single dose of $CAR^+$ T cells. Mice were re-challenged twice with Raji cells, on Day 25 and Day 45 post T-cell injection. (E) Schematic of in vivo experiment (n=6 mice per group). (F) Tumor signal in individual animals quantified by bioluminescence imaging. (G) Frequency of human $CD45^+EGFRt^+$ cell in peripherical blood collected from mice overtime. *p<0.05, p<0.01, *p<0.001, n.s. not statistically significant.

FIG. 14A-C. Transcriptomic and epigenetic analyses reveal CAR-dependent variations in T-cell phenotypes. (A,B) NSG mice were injected i.v. with $0.5\times10^6$ firefly-luciferase-expressing Raji cells 6 days prior to treatment with $2.85\times10^6$ $CAR^+$ T cells delivered i.v. Liver, spleen, cardiac blood, and bone marrow were collected from tumor-bearing mice 9 days after T-cell injection (n=2 mice per group). $CAR^+$ T cells were obtained by enriching for $huCD45^+$ $EGFRt^+$ populations, and subsequently analyzed by RNA-seq and ATAC-seq. (A) Volcano plots of differentially expressed genes of Rituximab CAR-T cells versus Leu16 (left), RFR-LCDR (middle), or RFR-LCDR.AA (right) CAR-T cells based on RNA-seq. All differentially expressed genes are plotted in grey. Genes that have at least 2-fold upregulation or downregulation ($\log_2FC>1$ or $\log_2FC<-1$) with FDR<0.05 are shown as red dots. The names of genes that appear in all three sets of pair-wise comparisons with $\log_2FC>1$ and FDR<0.05 or $\log_2FC<-1$ and FDR<0.05 are labeled. (B) Genome browser files of differentially accessible regions in Leu16, Rituximab, RFR-LCDR, RFR-LCDR.AA CAR-T cells at the ATP9A, KIR2DL3, KIR2DL1, KIR3DL1 loci. (C) Animals treated with Rituximab-based CAR-T cells show reduced glucose levels in serum. Blood serum was collected from animals in the study shown in FIG. 13E-G on Day 58 post T-cell injection. Glucose concentration in serum was measured by LC-MS. Data bars indicate the means of biological replicates±1 S.D. (n=6 for both hybrid CAR-T cell groups; n=4 for Rituximab.AA CAR-T cell treatment group due to death caused by tumor burden prior to sample collection date). *p<0.05, p<0.01, *p<0.001, n.s. not statistically significant.

Figure 1:
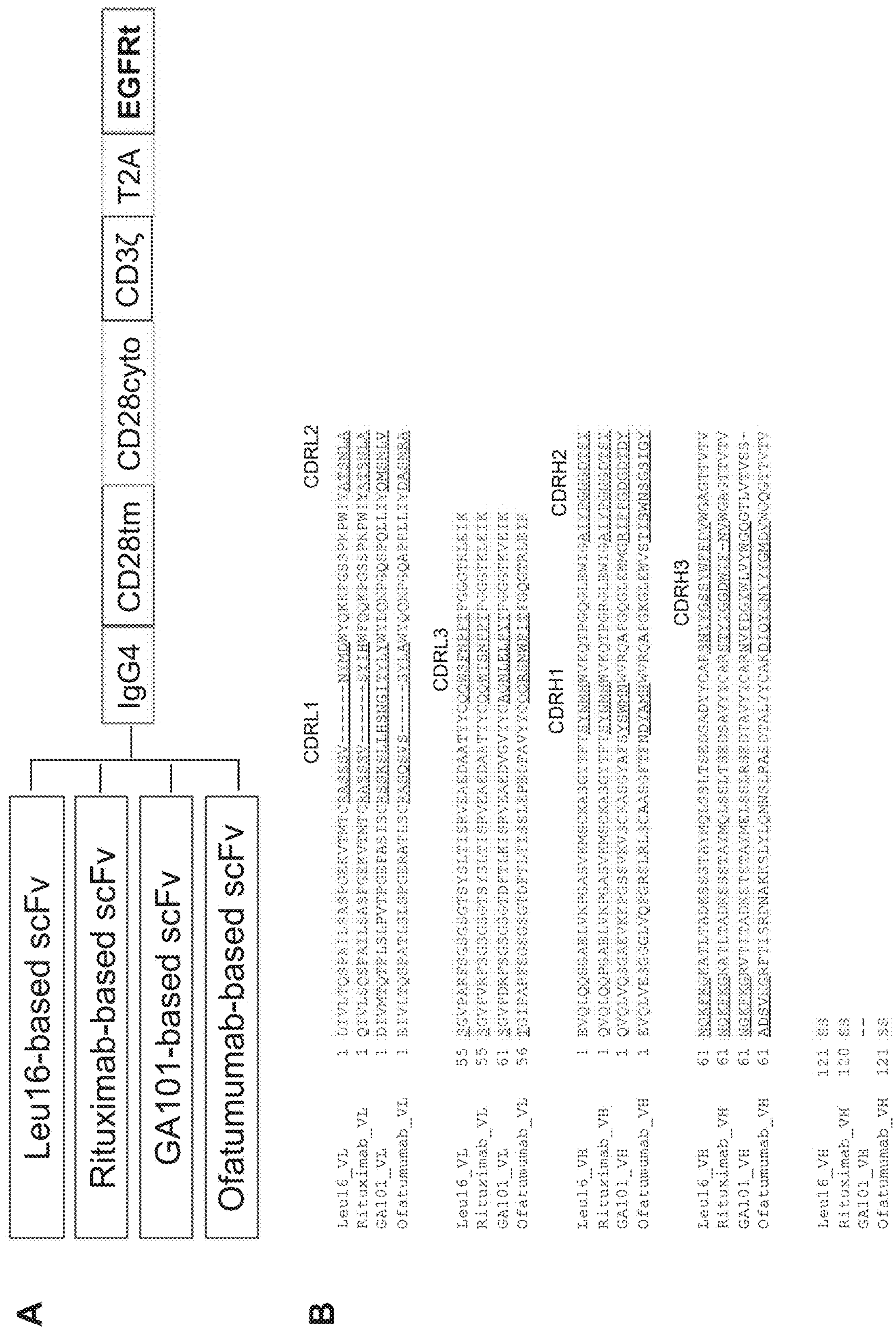
FIG. 1A-B. (A) Schematic of CD20 CARs constructed with scFv derived from various antibodies. All CARs were second generation receptors containing the CD28 co-stimulatory domain. (B) Sequence of scFv domains used in CD20 CAR construction. Leu16 VL (SEQ ID NO:1), Rituximab VL (SEQ ID NO:3), GA101 VL (SEQ ID NO:158), Ofatumumab VL (SEQ ID NO:159), Leu16 VH (SEQ ID NO:2), Rituximab VH (SEQ ID NO:4), GA101 VH (SEQ ID NO:160), Ofatumumab VH (SEQ ID NO:153).

FIG. 15A-D. RFR-LCDR.AA CAR-T cells show robust T-cell activation coupled with memory phenotype. (A) Gene Set Enrichment Analysis (GSEA) was performed on RNA-seq data obtained as described in FIG. 14A. A summary of results in pathways related to T-cell phenotype and function are shown in BubbleGUM map format (Spinelli et al., 2015). (B) Mountain plots of pathways related to T-cell subtype. (C) Mountain plots of pathways related to T-cell activation and interferon gamma signaling. (D) Mountain plots of pathways related to cell cycle, DNA replication, and cell metabolism.

FIG. 16A-D. Panel if CD20 CARs exhibit similar characteristics in vitro. (A) Alignment of leu16, rituximab, GA101 and ofatumumab scFv sequences using T-Coffee (Notredame et al., 2000). Leu16 VL (SEQ ID NO:1), Rituximab VL (SEQ ID NO:3), GA101 VL (SEQ ID NO:158), Ofatumumab VL (SEQ ID NO:159), Leu16 VH (SEQ ID NO:2), Rituximab VH (SEQ ID NO:4), GA101 VH (SEQ ID NO:160), Ofatumumab VH (SEQ ID NO:153). (B) CAR-T cell transduction efficiency as quantified by CAR surface expression (top) and transduction-marker expression (bottom), which were detected via antibody staining of the CAR's IgG4 extracellular spacer (Fc) and EGFRt, respectively. Median florescence intensity (MFI) and % positive of each antigen staining were noted below flow cytometry histograms. Results are representative of three independent experiments from three different healthy donors. (C) CD20 CAR-T cell proliferation during ex vivo culture with exogenous cytokine IL-2 and IL15. Fold change in total viable cell count between Day 2 and Day 14 are shown. Each data point represents one donor; data for 4 donors per construct are shown. No statistical difference between any of the donors was detected by unpaired, two-tailed, two-sample Student's t test. (D) CAR-T cell cytotoxicity and proliferation upon repeated antigen challenge. CD20 CAR-T cells were challenged with Raji tumor cells at a 2:1 effector-to-target (E:T) ratio every two days, and the number of viable Raji and CAR-T cell was quantified by flow cytometry. Data shown are the means of technical triplicates with error bars indicating±1 standard deviation (S.D.). Results are representative of three independent experiments from three different healthy donors.

FIG. 17A-E. Tumor progression and post-mortem CD20 CAR-T cell characterization in Raji xenograft model. (A) NSG mice were engrafted with firefly-luciferase-expressing Raji cells and treated with CD20 CAR-T cells as described in FIG. 10B. Tumor burden was measured by bioluminescence imaging, and the tumor growth rate between Day 12 post T-cell injection and the humane end point was quantified by fitting exponential regression curves to each individual animal's tumor progression data. The average doubling time ($T_{doubling}$) for tumor signal among the mice (n=6) in each group is shown above each plot. (B, C) Frequency of tumor cells (B) and human $CD45^{+}$EGFRt+ cell (B) in bone marrow, brain, liver, and spleen collected from mice at the time of euthanasia, as quantified by flow cytometry. (D,E) Frequency of PD-$1^{+}$ (D) and LAG-$3^{+}$ (E) cells among human $CD45^{+}$EGFRt+ cell in bone marrow, brain, liver, and spleen collected from mice at the time of euthanasia, as quantified by flow cytometry. No statistical difference between any of the donors was detected by unpaired, two-tailed, two-sample Student's t test for all data shown in panels (B) through (E).

Figure 18:
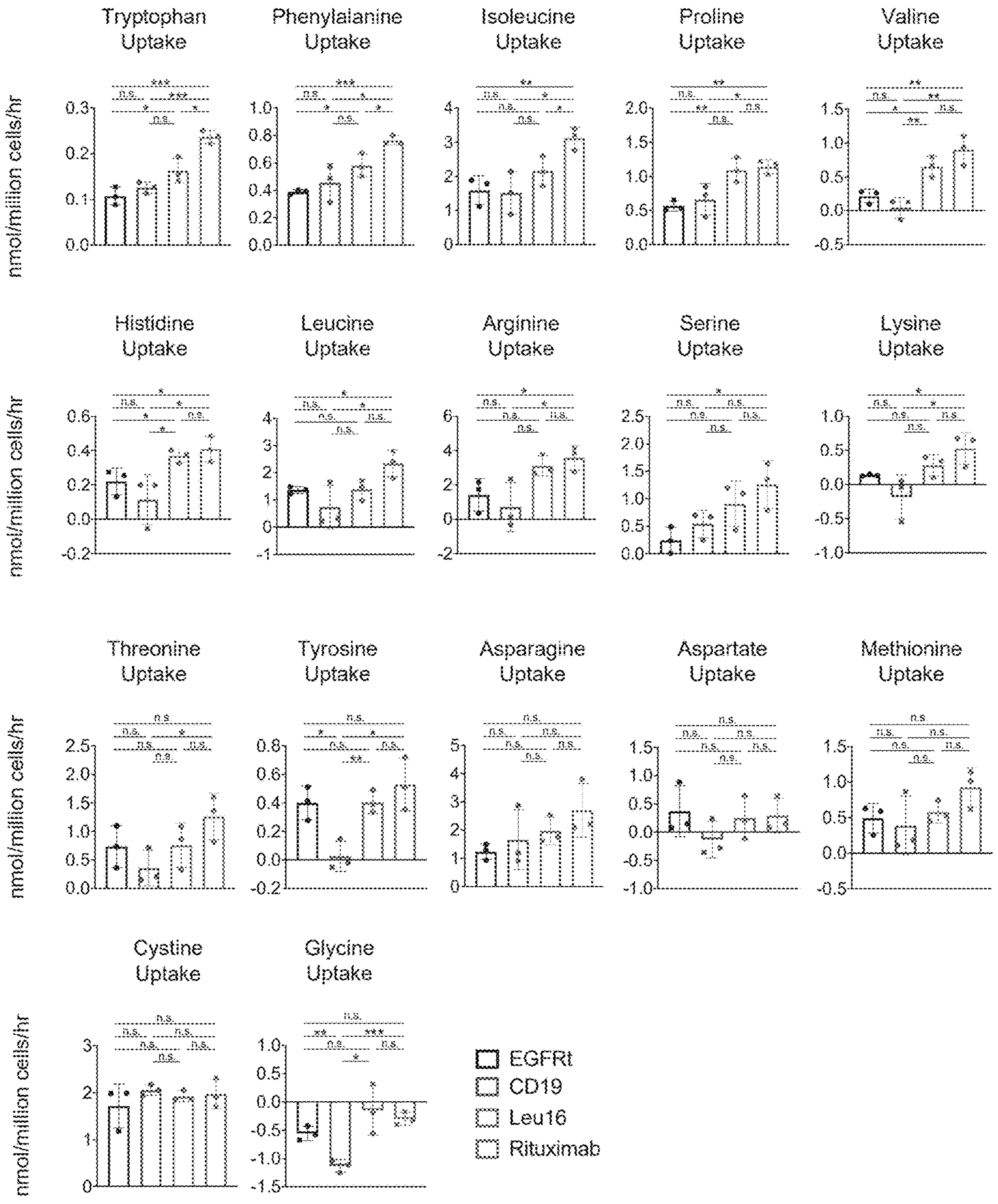

FIG. 18. Rituximab CAR-T cells are more metabolically activate than other CD20 CAR-T cells. Uptake of amino acids and other nutrients by CAR-T cells cultured for 24 hours in RPMI supplemented with 10% heat-inactivated dialyzed fetal bovine serum (HI-dFBS), IL-2, and IL-15. Data bars indicate the means of technical triplicates±1 S.D. Results are representative of three independent experiments from three different healthy donors. *p<0.05, p<0.01, *p<0.001, n.s. not statistically significant. Results in this figure are from the same experiment as in FIG. 10F. Each set of four bars represents, in order of left to right, data for EGFRt, CD19, Leu16, and Rituximab, respectively.

Figure 19:
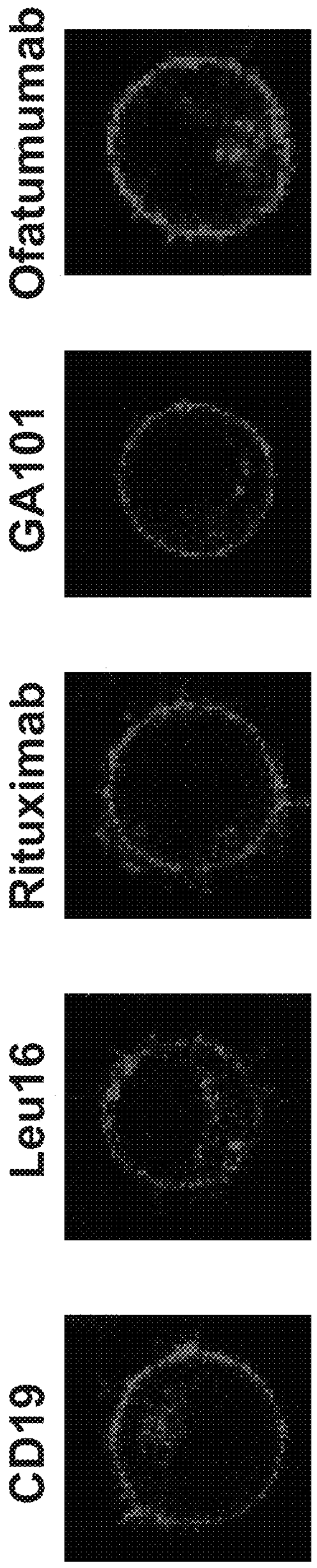

FIG. 19. CD20 CARs are uniformly distributed on T-cell surface in the absence of antigen engagement. Jurkat cells transduced with CAR-HaloTag fusion proteins were stained with the red fluorescent dye tetramethylrhodamine (TMR) and imaged by confocal microscopy. CAR molecules are uniformly distributed on cell surface in the absence of antigen stimulation.

FIG. 20A-D. Rituximab CAR-T cells with torsional reorientation exhibit similar in vitro cytotoxicity and antigen-independent activation-marker expression. (A) Schematic of rituximab-based CAR constructs with zero to four alanines inserted between the CD28 transmembrane and cytoplasmic domains. (B) CAR surface expression was quantified by antibody staining of HA tag fused to the N-terminus of each CAR. Data are representative of three independent experiments from three different healthy donors. (C) CAR-T cell cytotoxicity and proliferation upon repeated antigen challenge. CD20 CAR-T cells were challenged with Raji tumor cells at a 2:1 E:T ratio every two days, and the number of viable Raji and CAR-T cell was quantified by flow cytometry. Data shown are the means of technical triplicates with error bars indicating±1 standard deviation (S.D.). Results are representative of three independent experiments from three different healthy donors. (D) Activation- and exhaustion-maker expression were evaluated 11 days post Dynabead removal, without CD20 antigen stimulation. Data bars indicate the means of technical triplicates±1 S.D. Results are representative of three independent experiments from three different healthy donors. Unless otherwise noted, p values were determined by unpaired two-tailed Student's t test; *p<0.05, p<0.01, *p<0.001, n.s. not statistically significant.

FIG. 21A-E. GD2 CAR-T cells with torsional reorientation exhibit differential tumor control in vivo despite same in vitro performance. (A) Schematic of GD2 CAR constructs with zero to four alanines inserted between the CD28 transmembrane and cytoplasmic domains. (B) CAR surface expression (top) and transduction efficiency (bottom) were quantified by antibody staining of Fc and EGFRt. (C) CAR-T cell cytotoxicity and proliferation upon repeated antigen challenge. GD2 CAR-T cells were challenged with CHLA-255 tumor cells at a 2:1 E:T ratio every two days, and the number of viable Raji and CAR-T cell was quantified by flow cytometry. Data shown are the means of technical triplicates with error bars indicating±1 standard deviation (S.D.). (D,E) NSG mice were injected intravenously with $3.5\times10^{6}$ firefly-luciferase expressing CHLA-255 cells followed by $2\times10^{6}$ GD2 CAR-T cells 17 days later. (D) Tumor progression was monitored by bioluminescence imaging. (E) Frequency of human $CD45^{+}$EGFRt+ cell in liver and spleen collected from mice at the time of euthanasia was quantified by flow cytometry. *p<0.05, p<0.01, *p<0.001, n.s. not statistically significant.

FIG. 22A-D. In vitro characterization of hybrid CAR-T cells. (A) CAR surface expression (top) and transduction efficiency (bottom) were quantified by antibody staining of Fc and EGFRt. Results are representative of three independent experiments from three different healthy donors. (B) CAR molecules are uniformly distributed on T-cell surface in the absence of antigen stimulation. Jurkat cells transduced with CAR-HaloTag fusion protein were stained with TMR and imaged by confocal microscopy. (C,D) IFN-γ, TNF-α, IL-2 production in the presence (C) and absence (D) of $CD19^+/CD20^+$ K562 target cells. *$p<0.05$, $p<0.01$, *$p<0.001$, n.s. not statistically significant. For (C) and (D), each set of seven bars represents, in order of left to right, data for EGFRt, CD19, Leu16, Rituximab, Rituximab.AA, RFR-LCDR, and RFR-LCDR.AA, respectively.

Figure 23:
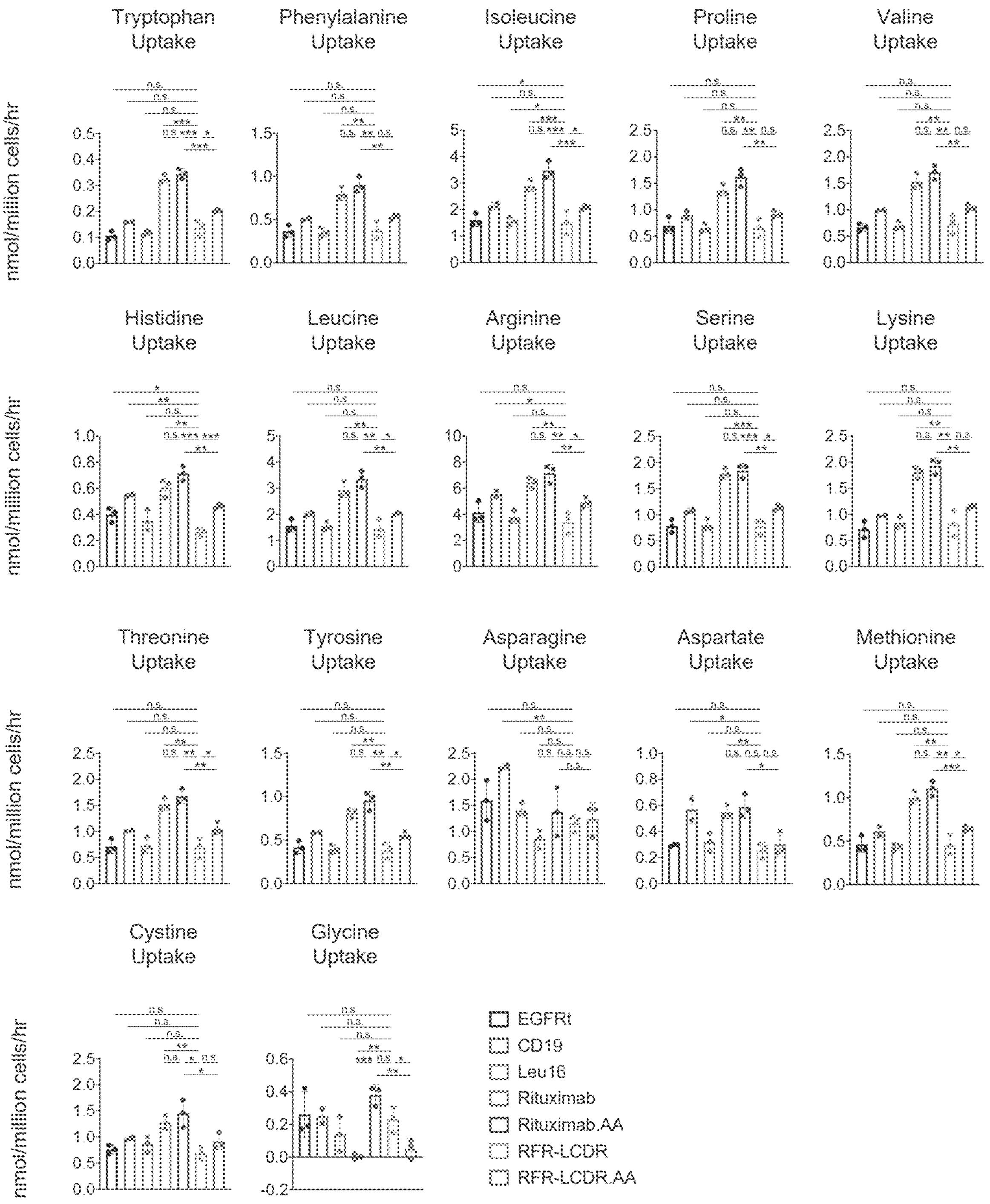

FIG. 23. Hybrid CAR-T cells exhibit reduced metabolic activities compared to rituximab CAR-T cells. Uptake of amino acids and other nutrients by CAR-T cells cultured for 72 hours in RPMI supplemented with 10% heat-inactivated dialyzed fetal bovine serum (HI-dFBS), IL-2, and IL-15. Data bars indicate the means of technical triplicates±1 S.D. Data are representative of three independent experiments from three different healthy donors. *$p<0.05$, $p<0.01$, *$p<0.001$, n.s. not statistically significant. Results in this figure are from the same experiment as in FIG. 12E. Each set of seven bars represents, in order of left to right, data for EGFRt, CD19, Leu16, Rituximab, Rituximab.AA, RFR-LCDR, and RFR-LCDR.AA, respectively.

Figure 24:
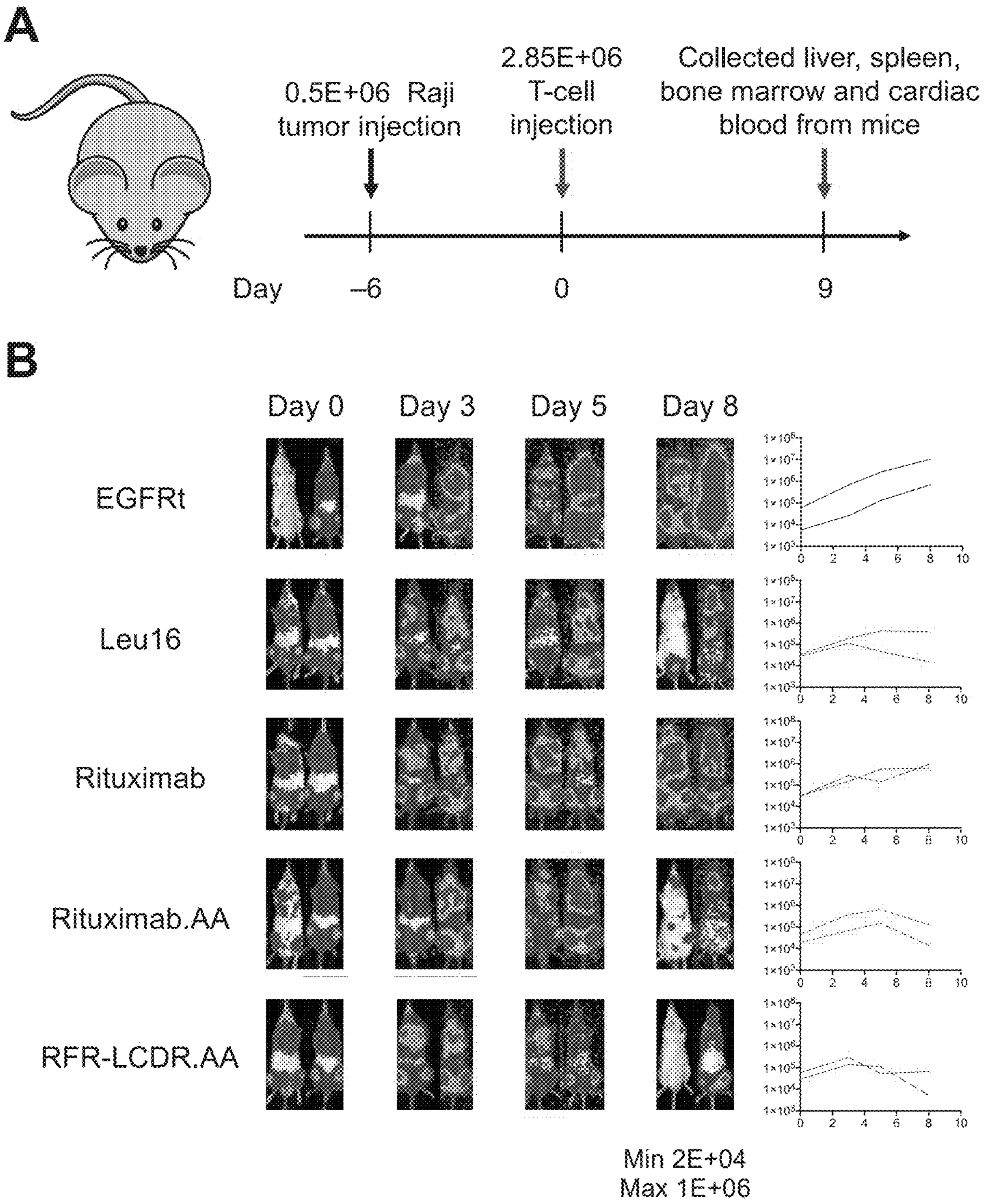

FIG. 24A-B. CAR-T cell harvest from tumor-bearing mice for transcriptomic and epigenetic profiling. NSG mice were injected intravenously with $0.5\times10^6$ firefly-luciferase expressing Raji cells followed by $2.85\times10^6$ of $CAR^+$ T cells 6 days later. $CAR^+$ T cells were collected from tumor-bearing mice 9 days after T-cell injection (n=2 mice per group). Only a small number of mock-transduced (EGFRt-only) T cells were recovered from mice, consistent with lack of T-cell expansion in the absence of antigen recognition. However, this poor cell recovery led to low read counts in RNA-seq and ATAC-seq that precluded reliable data analysis. As a result, these samples were excluded from the analyses shown in FIGS. 14, 14, and 25. (A) Schematic of in vivo experiment. (B) Tumor progression as monitored by bioluminescence imaging.

Figure 25:
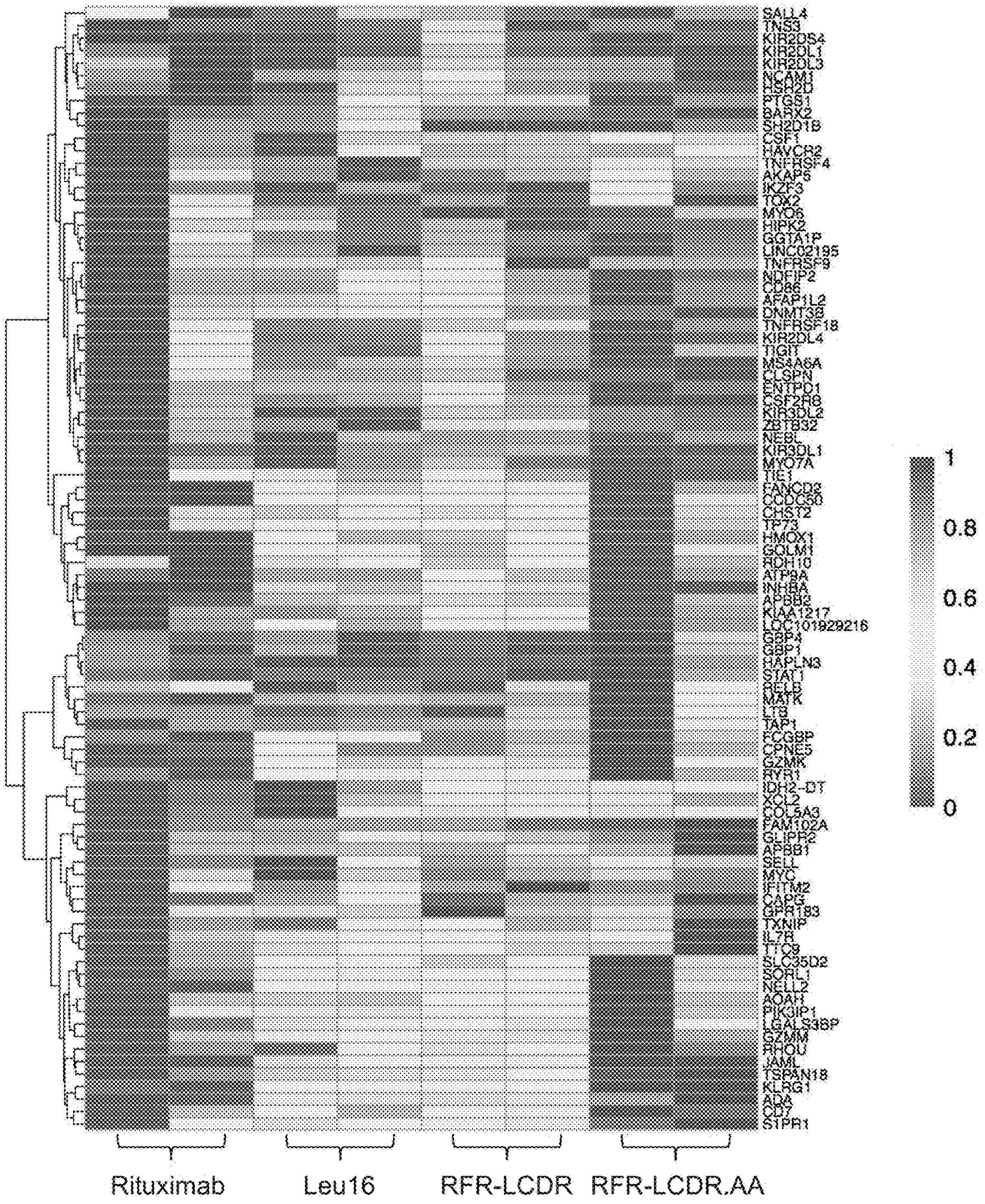

FIG. 25. RNA-seq reveals drastic transcriptomic differences across CD20 CAR-T cell variants recovered from tumor-bearing mice. Heatmap of differentially expressed genes (FDR<0.05) in ANOVA comparison of Leu16, Rituximab, RFR-LCDR, RFR-LCDR.AA CAR-T cells. Each column represents one mouse, and two biological replicates were analyzed for each treatment group. Each row is scaled to a maximum of 1 and minimum of 0 to highlight relative expression of each gene.

Figure 26:
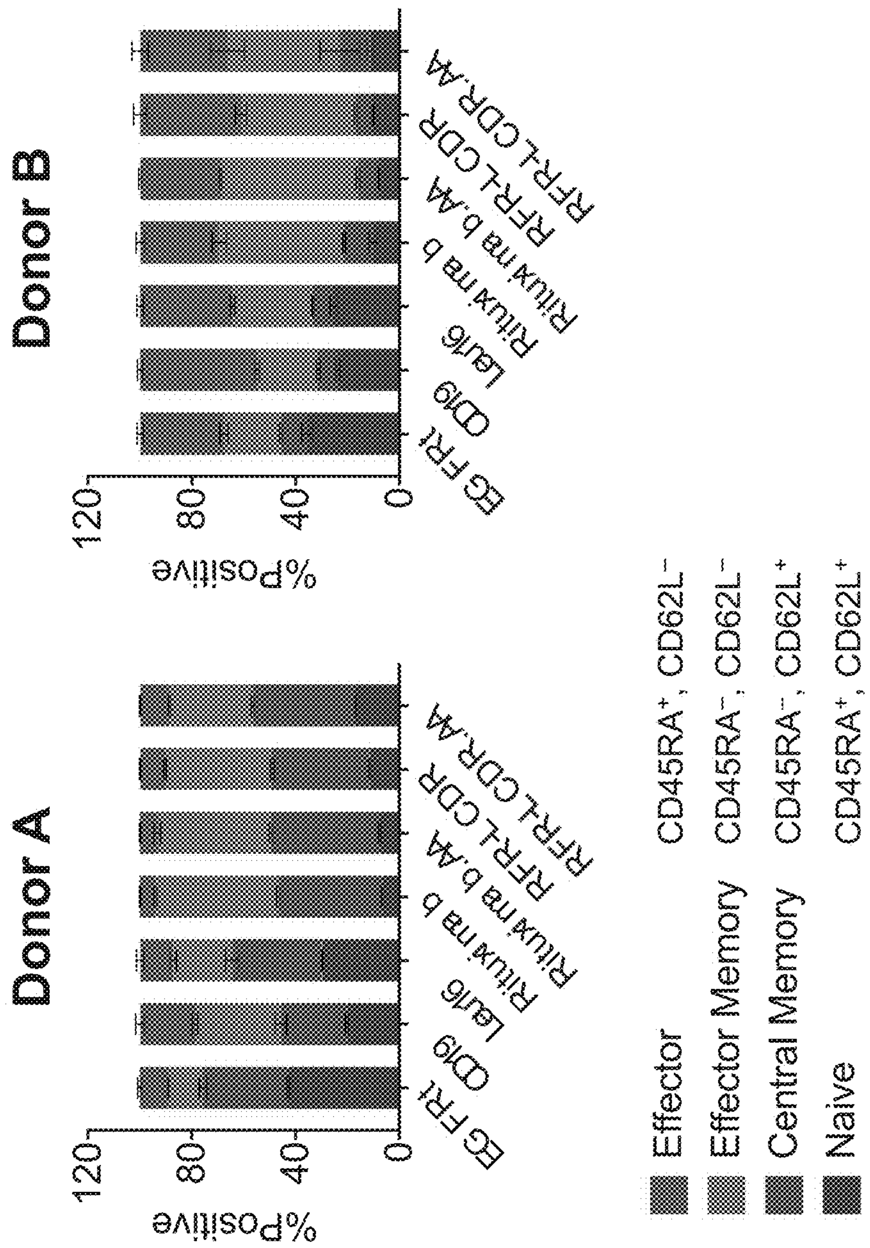

FIG. 26. T-cell subset distribution does not vary significantly among CAR-T cells in ex vivo culture. The subtype of CAR-T cells in ex vivo culture was determined by CD45RA and CD62L staining in the absence of antigen stimulation. $CD45RA^+CD62L^+$, $CD45RA^-$ $CD62L^+$, $CD45RA^-CD62L^-$, and $CD45RA^+CD62L^-$ indicate naïve, central memory, effector memory and effector cell types, respectively.

Figures 1, 27A:
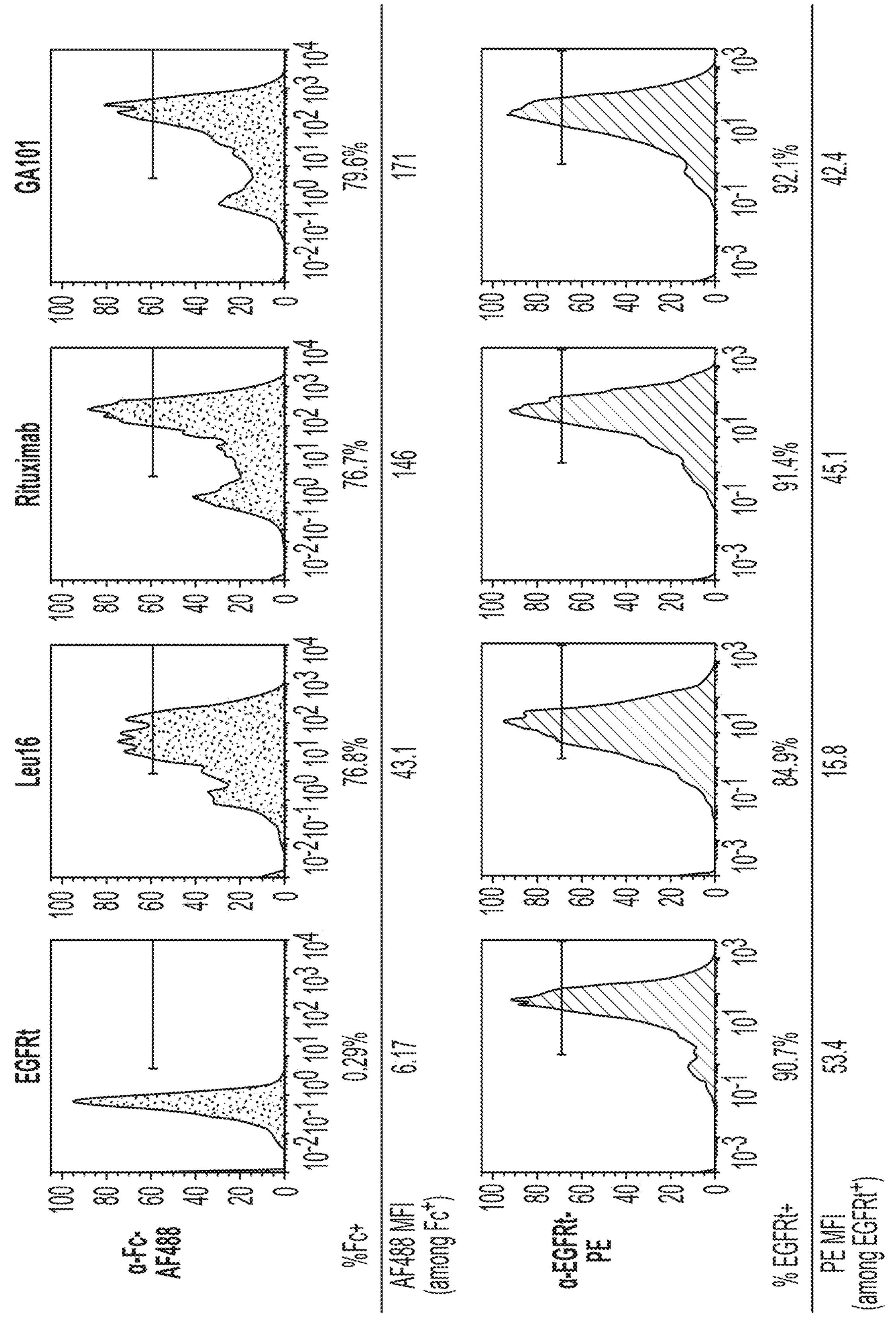
Figures 2, 27A:
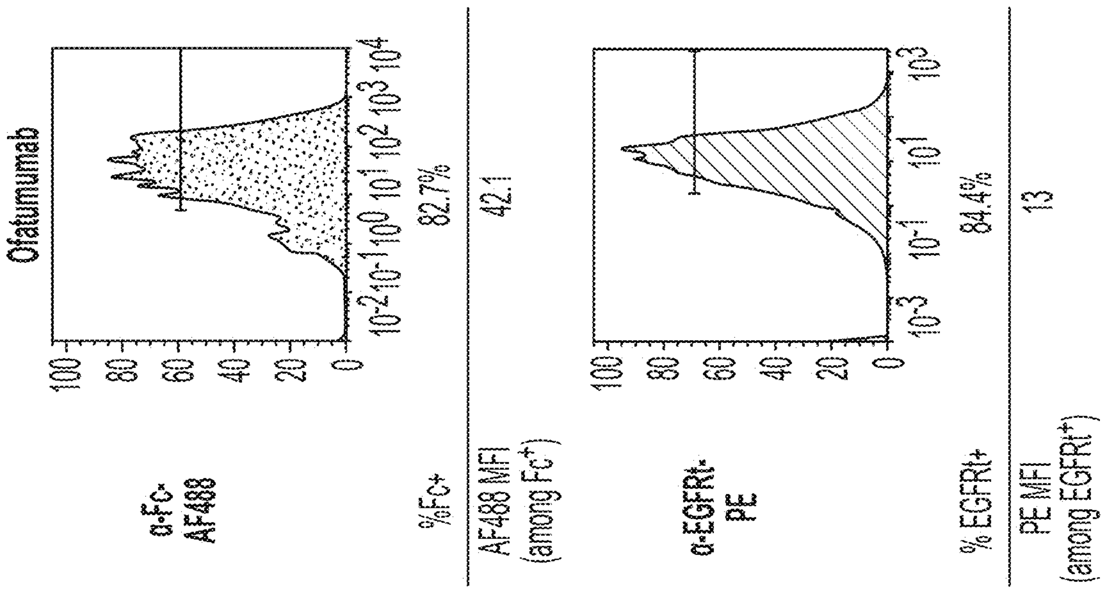

FIG. 27A-C. (A) CAR surface expression (top) and transduction-marker expression (bottom) detected via antibody staining of the CAR's IgG4 extracellular spacer (Fc) and EGFRt, respectively, from one donor. Percent positivity and median florescence intensity (MFI) of each sample are noted. (B) CAR surface staining data in % Fc+ and MFI for T cells generated from six different healthy donors are shown. (C) CD20 CAR CD8+ T-cell expansion during ex vivo culture with exogenous cytokine IL-2 and IL15. Fold change in total viable cell count between Day 2 and Day 14 are shown. Each data point represents one donor; data for 4 donors per construct are shown. No statistical difference between any of the donors was detected by unpaired, two-tailed, two-sample Student's t test.

FIG. 28A-C. (A) Flow cytometry analysis of CD20 expression levels on Raji and K562 cell lines. (B) A 24-hr lysis assay of CD20 CAR-TN/M cells against target cells with varying CD20 expression levels at three effector-to-target (E:T) ratios. Data bars indicate the means of technical triplicates±1 standard deviation (S.D.). No statistically significant difference was observed by unpaired, two-tailed, two-sample Student's t-test. (C) CAR CD8+ T-cell cytotoxicity and proliferation upon repeated antigen challenge with Raji tumor cells. CD20 CAR-T cells were challenged with Raji cells at a 2:1 E:T ratio every two days, and the number of viable Raji and CAR-T cell was quantified by flow cytometry. Data shown are the means of technical triplicates with error bars indicating±1 S.D. Results of three independent experiments from three different healthy donors are shown.

FIG. 29A-D. Antigen-independent CAR signaling or Rituximab-derived CD20 CAR, resulting in (A,B) upregulation of activation and exhaustion markers, and (C,D) T-cell proliferation in the absence of antigen stimulation. Tonic signaling in rituximab-based CAR-T cells was observed in both CD8+ (A,C) and naïve/memory T (TN/M) cells, which was sorted for CD14−/CD25−/CD62L+ phenotype. Each set of seven bars in A-D represents, in order from left to right, data for EGFRt, CD19, GD2, Leu16, Rituximab, GA101, and Ofatumumab, respectively.

Figure 30:
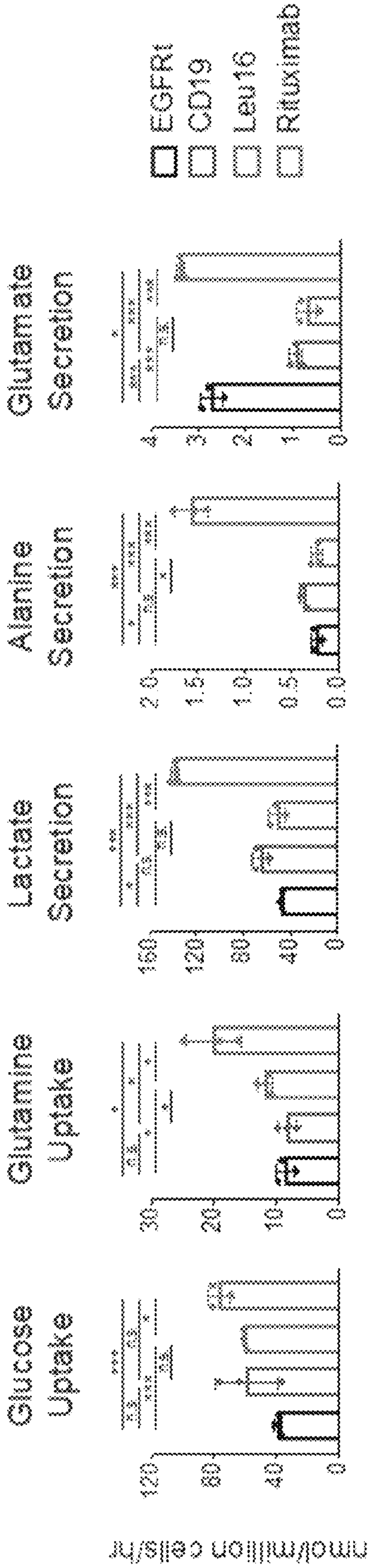

FIG. 30. Metabolic flux of Rituximab-derived CD20 CAR. Each set of four bars represents, in order from left to right, data for EGFRt, CD19, Leu16, and Rituximab, respectively.

FIG. 31A-B. (A) CAR expressing Jurkat cells were stained with anti-Fc antibodies conjugated to DyLight 405 and imaged by confocal microscope in the absence of antigen stimulation. (B) Jurkat cells transduced with CAR-HaloTag fusion proteins were stained with the red fluorescent dye tetramethylrhodamine (TMR) and imaged by confocal microscope in the absence of antigen stimulation.

FIG. 32A-B. (A) NSG mice were injected intravenously (i.v.) with $0.5\times10^6$ firefly-luciferase-expressing Raji cells 6 days prior to treatment with $5\times10^6$ $CD8^+$ CD20-targeting CAR-T cells delivered i.v. Tumor progression was monitored by bioluminescence imaging (n=6 mice per group). Minimum and maximum values on the radiance-intensity scale are $5\times10^4$ and $1\times10^7$, respectively. (B) Average radiance (p/sec/cm2/sr) of individual animals for each test group. Black dotted line denotes day 12 post T-cell injection, the time at which the rituximab CAR-T cell group began to rapidly lose tumor control. The end point of each trace indicates the humane end point of each animal.

Figure 33A:
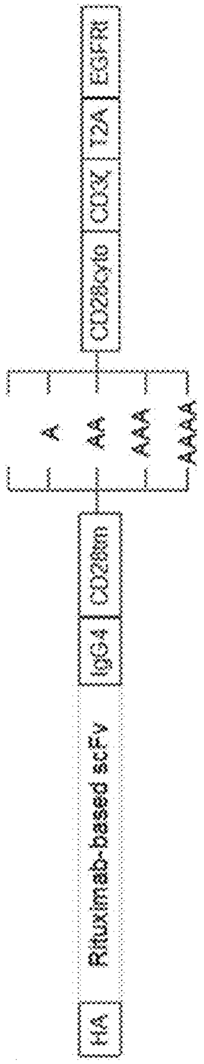
Figures 1, 33B:
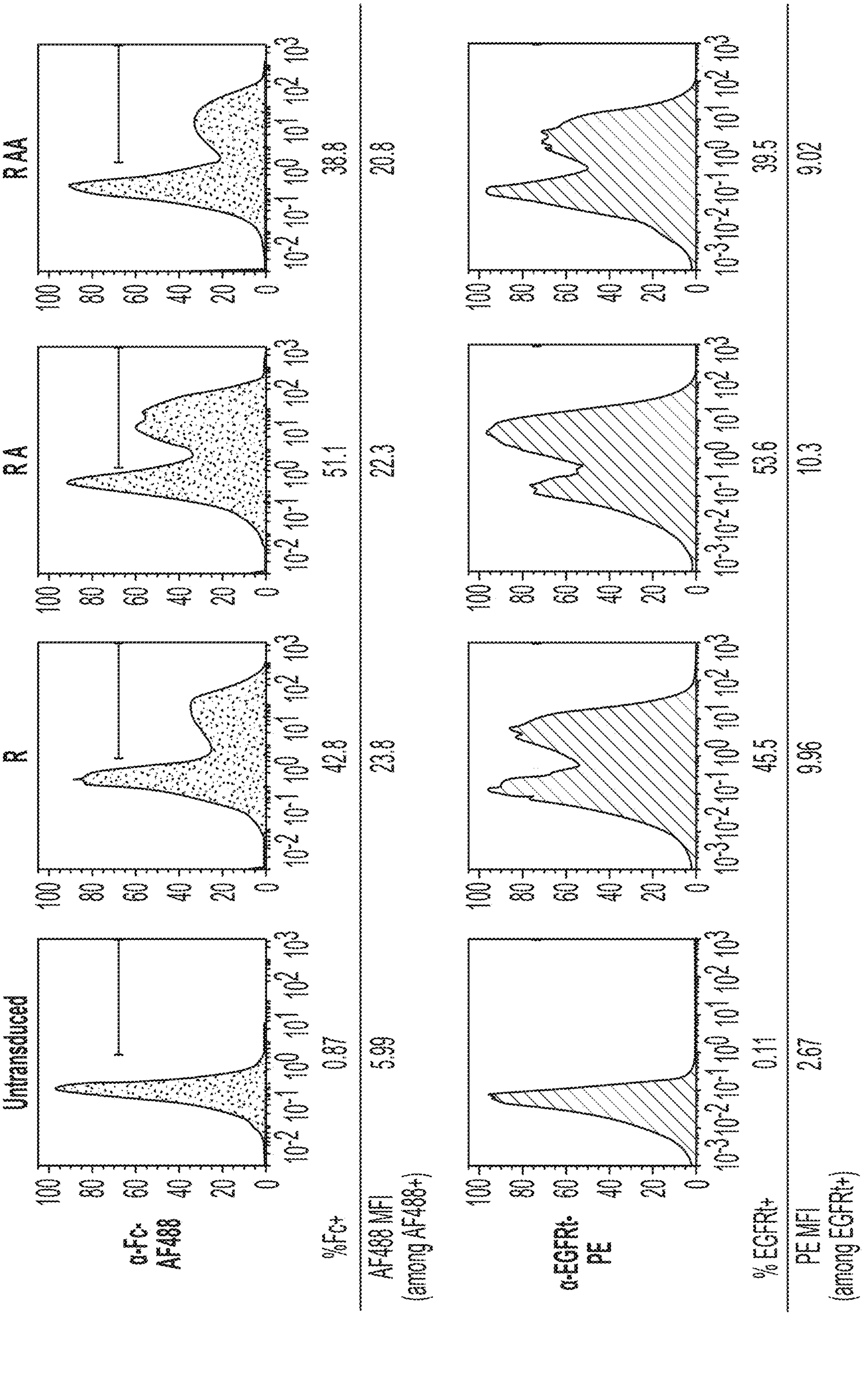
Figures 2, 33B:
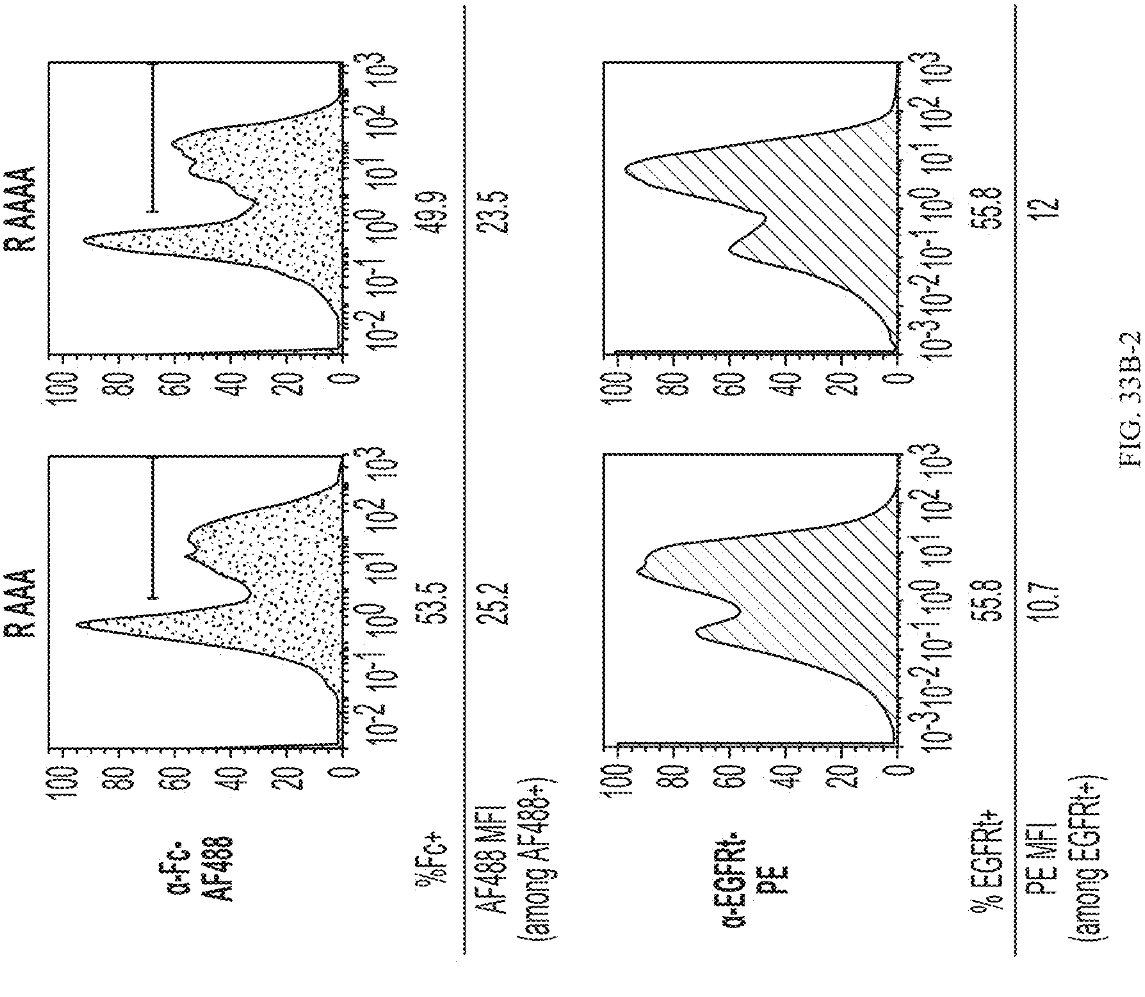
Figure 33C:
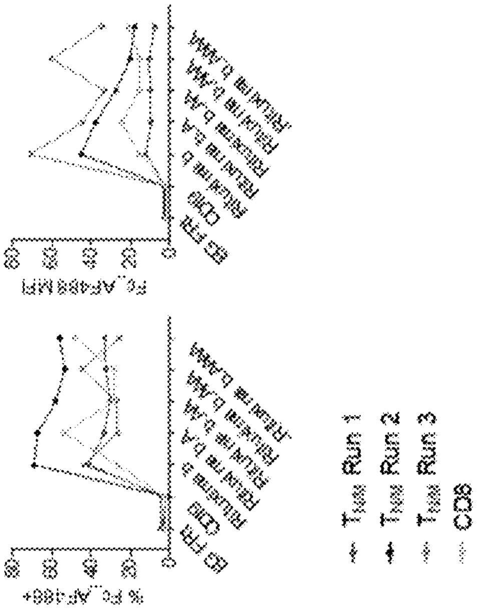

FIG. 33A-C. (A) Schematic of Alanine-insertion variants of rituximab-based CARs. (B) CAR surface expression (top) and transduction-marker expression (bottom) detected via antibody staining of the CAR's IgG4 extracellular spacer (Fc) and EGFRt, respectively, from one donor. Percent positivity and median florescence intensity (MFI) of each sample are noted. (C) CAR surface staining data in % Fc+ and MFI for T cells generated from four different T-cell manufacturing runs.

FIG. 34 A-B. (A) Tumor necrosis factor (TNF)-α production by CAR-T cells in the absence of antigen stimulation was measured 7 days post Dynabead removal. Results from one donor of bulk CD8 T cells and one donor of $T_{N/M}$ cells are shown. *p<0.05, p<0.01, *p<0.001, n.s. not statistically significant. (B) Proliferation of CAR CD8+ and $T_{N/M}$ cells stained with CTV dye was assayed after a 4-day culture in the absence of target cells or exogenous cytokines. Results from one donor of bulk CD8+ T cells and one donor of $T_{N/M}$ cells are shown. *p<0.05, p<0.01, *p<0.001, n.s. not statistically significant.

FIG. 35A-B. (A) A 24-hr lysis assay of rituximab CAR-TN/M cells against target cells with varying CD20 expression level at different E:T ratio. Data bars indicate the means of technical triplicates±1 S.D. No statistically significant difference was observed by unpaired, two-tailed, two-sample Student's t-test. (B) CAR-T cell cytotoxicity and proliferation upon repeated antigen challenge. CD20 CAR-T cells were challenged with Raji tumor cells at a 2:1 E:T ratio every two days, and the number of viable Raji and CAR-T cell was quantified by flow cytometry. Data shown are the means of technical triplicates with error bars indicating±1 S.D. Results from four independent experiments using T cells from four different healthy donors are shown.

FIG. 36A-C. (A) Schematic of GD2 CAR constructs with zero to four alanines inserted between the CD28 transmembrane and cytoplasmic domains. (B) NSG mice were injected intravenously with 3.5×106 firefly-luciferase expressing CHLA-255 cells followed by 2×106 GD2 CAR-T cells 17 days later. Tumor progression was monitored by bioluminescence imaging. (C) Frequency of human CD45+EGFRt+ cell in liver and spleen collected from mice at the time of euthanasia was quantified by flow cytometry. *p<0.05, p<0.01, *p<0.001, n.s. not statistically significant. The end point of each trace indicates the humane end point of each animal.

Figure 37A:
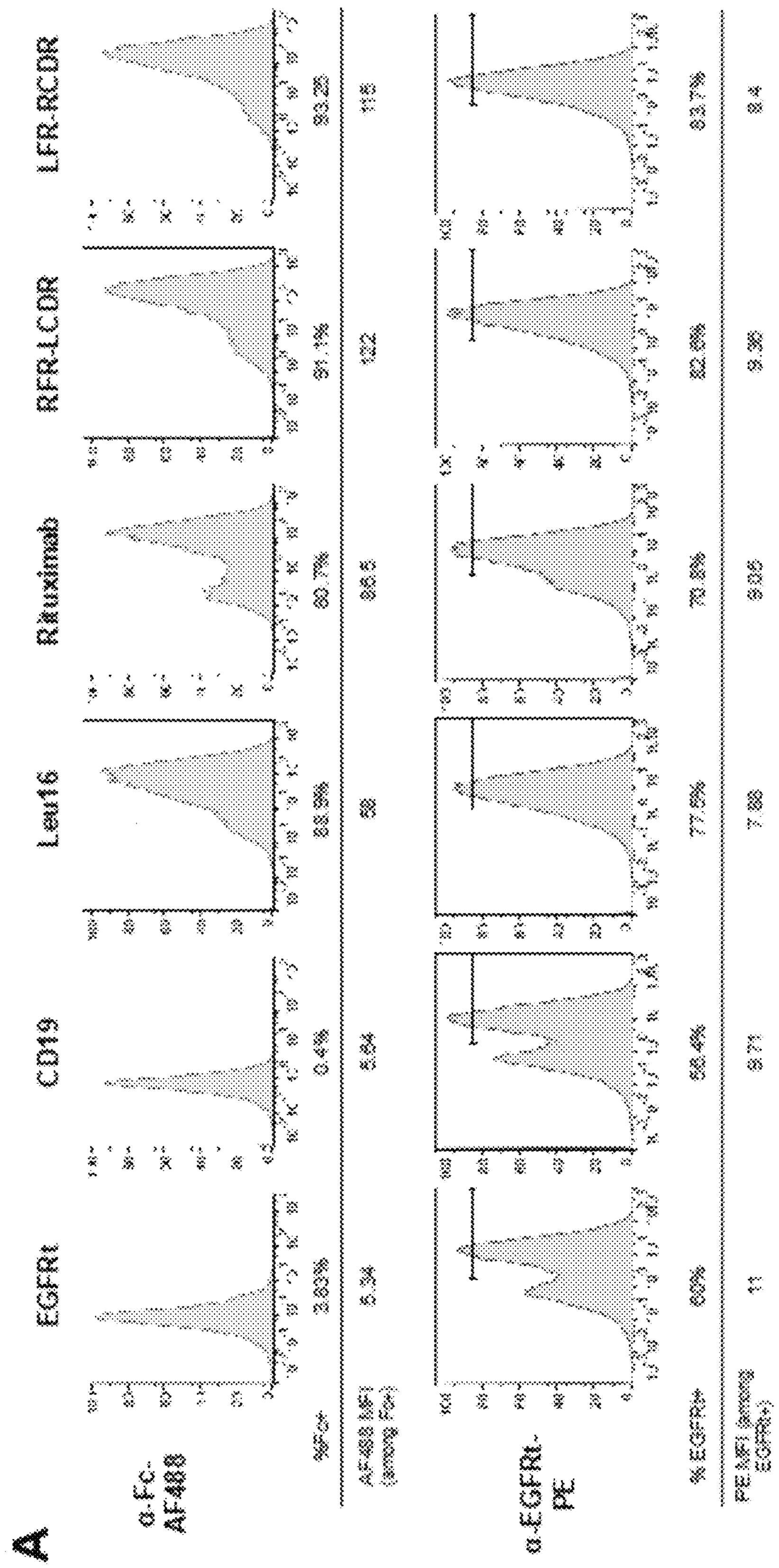
Figure 37B:
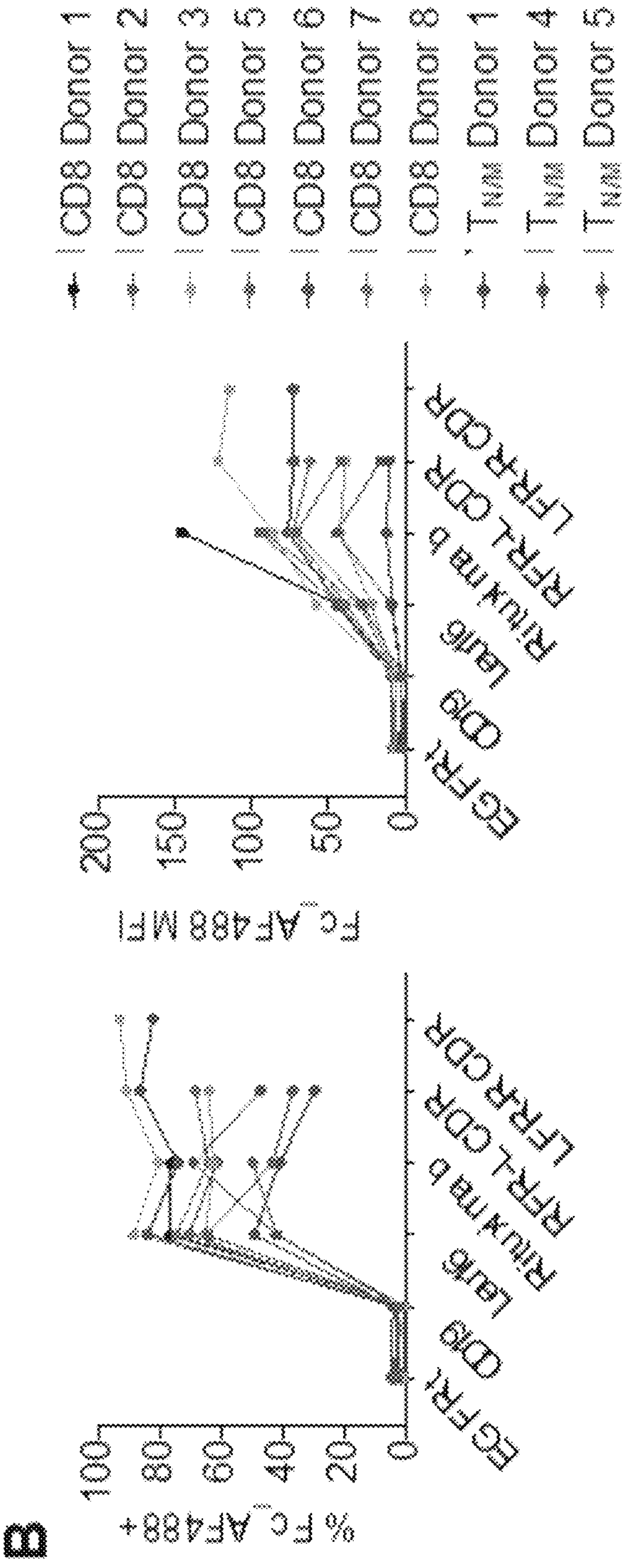

FIG. 37A-B. (A) CAR surface expression (top) and transduction efficiency (bottom) were quantified by antibody staining of Fc and EGFRt. (B) CAR surface staining data in % Fc+ and MFI for T cells generated from ten different healthy donors are shown.

FIG. 38A-B. The RFR-LCDR hybrid CD20 CAR shows antigen-independent CAR signaling, resulting in (A) upregulation of activation and exhaustion markers and (B) T-cell proliferation in the absence of antigen stimulation. The CD19 CAR and GD2 CAR were included as a negative and positive control, respectively, for tonic signaling. Each set of seven bars represents, in order of left to right, data for EGFRt, CD19, GD2, Leu16, Rituximab, RFR-LCDR, and LFR-RCDR, respectively.

FIG. 39. Binding kinetic parameters of Leu16, rituximab and RFR-LCDR scFvs were measured by bio-layer interferometry. KD: equilibrium dissociation constant; ka: association constant; kdis: dissociation constant; Avg: average of 3 runs; SD: standard deviation of 3 runs. Two-tailed Student's t test was used to calculate p values shown.

FIG. 40A-B. (A) RFR-LCDR.AA is a CAR construct that contains the RFR-LCDR scFv and two alanines inserted between the CD28 transmembrane and cytoplasmic domains. This CAR shows similar antigen detection threshold as the other CD20 CARs in vitro. (B) CARs containing hybrid scFv sequence and/or alanine insertion remain cluster-free on the cell surface. Jurkat cells transduced with CAR-HaloTag fusion proteins were stained with the TMR red fluorescent dye and imaged by confocal microscopy. CAR molecules are uniformly distributed on cell surface in the absence of antigen stimulation.

FIG. 41A-C. (A) Activation and exhaustion maker expression by CAR-$T_{N/M}$ cells in the absence of CD20 antigen stimulation was evaluated 11 days post Dynabead removal. Data bars indicate the means of technical triplicates±1 S.D. *p<0.05, p<0.01, *p<0.001, n.s. not statistically significant. (B) Proliferation of CAR+ TN/M cells stained with CTV dye was assayed after a 4-day culture in the absence of target cells or exogenous cytokines. Data shown in the histogram correspond to donor 1 in the bar graph. *p<0.05, p<0.01, *p<0.001, n.s. not statistically significant. (C) IFN-γ, TNF-α, IL-2 production by CAR+ TN/M cells in the absence of antigen stimulation. Cytokine concentration in the supernatant of cells cultured in the absence of exogenous cytokines for 48 hours was measured by ELISA. Data bars indicate the means of technical triplicates±1 S.D. *p<0.05, p<0.01, *p<0.001, n.s. not statistically significant. Each set of seven bars represents, in order of left to right, data for EGFRt, CD19, Leu16, Rituximab, Rituximab.AA, RFR-LCDR, and RFR-LCDR.AA, respectively. The data in (B) represents, from top to bottom, EGFRt, CD19, Leu16, Rituximab, Rituximab.AA, RFR-LCDR, and RFR-LCDR.AA.

Figure 42:
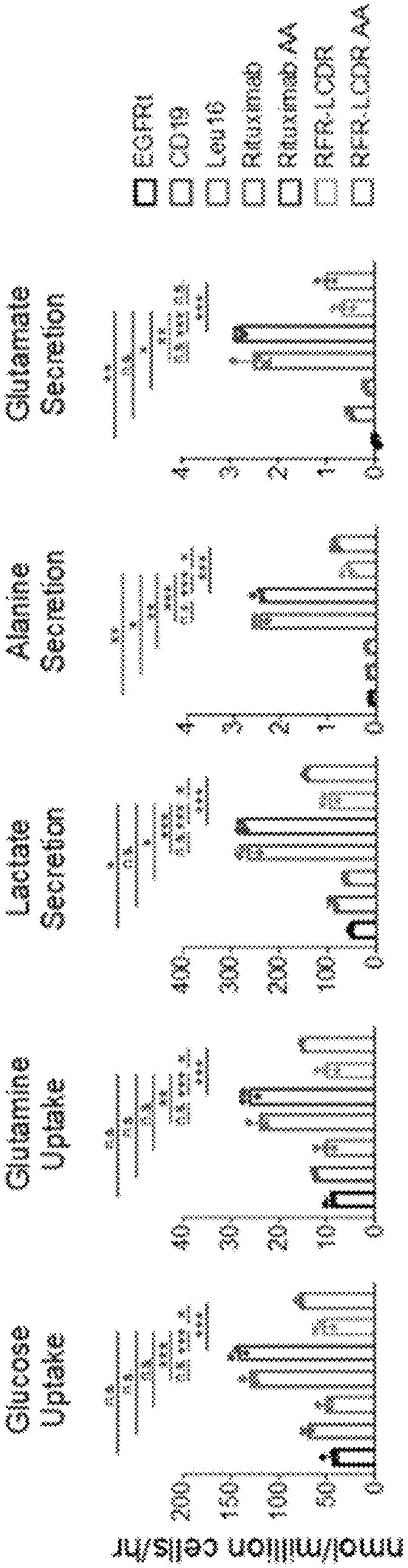

FIG. 42. Tonic signaling of CARs. Each set of seven bars represents, in order of left to right, data for EGFRt, CD19, Leu16, Rituximab, Rituximab.AA, RFR-LCDR, and RFR-LCDR.AA, respectively.

FIG. 43A-H. Tonically signaling CARs show distinct transcriptional profiles indicating (A) increased mitochondrial protein translation, (B) increased antigen presentation, (C) increased MYC signaling, (D) increased MTORC signaling, (E) increased TNF-α signaling, (F) divergent interferon responses, (G) enriched signature of genes associated with effector (as opposed to memory) T-cell subtypes, and (H) increased cell-cycle activity. For heat maps containing genes in excess of the space available for display, the names of genes shown in the heat map are listed in order to the side of each map.

FIG. 44A-D. The RFR-LCDR hybrid CD20 CAR shows superior tumor clearance in vivo. (A) Schematic of animal study. NSG mice were engrafted with 0.5 million firefly luciferase-expressing Raji lymphoma cells and treated with two doses of T cells. Animals were re-challenged with a second dose of tumor cells 55 days after the first T-cell treatment. (B) Tumor progression was monitored through bioluminescence imaging. (C) Survival curve is shown as Kaplan-Meier curve. Results indicate the hybrid CAR is superior to both parental CD20 CARs as well as the CD19 CAR in tumor clearance and long-term relapse prevention. (D) Frequency of CAR-expressing human T cells in peripheral blood 23 days post initial T-cell injection was measured by flow cytometry. The addition of two alanine residues into the CAR improved the rituximab-based receptor, corroborating previous data shown in FIG. 5. Combining the hybrid CAR with two alanine insertion further accelerated the rate of initial tumor clearance and led to significantly increased T-cell persistence compared to the hybrid CAR without alanine insertion, indicating that the scFv alteration and alanine insertion strategies can be combined to result in synergistic improvements in CAR function.

Figure 45A:
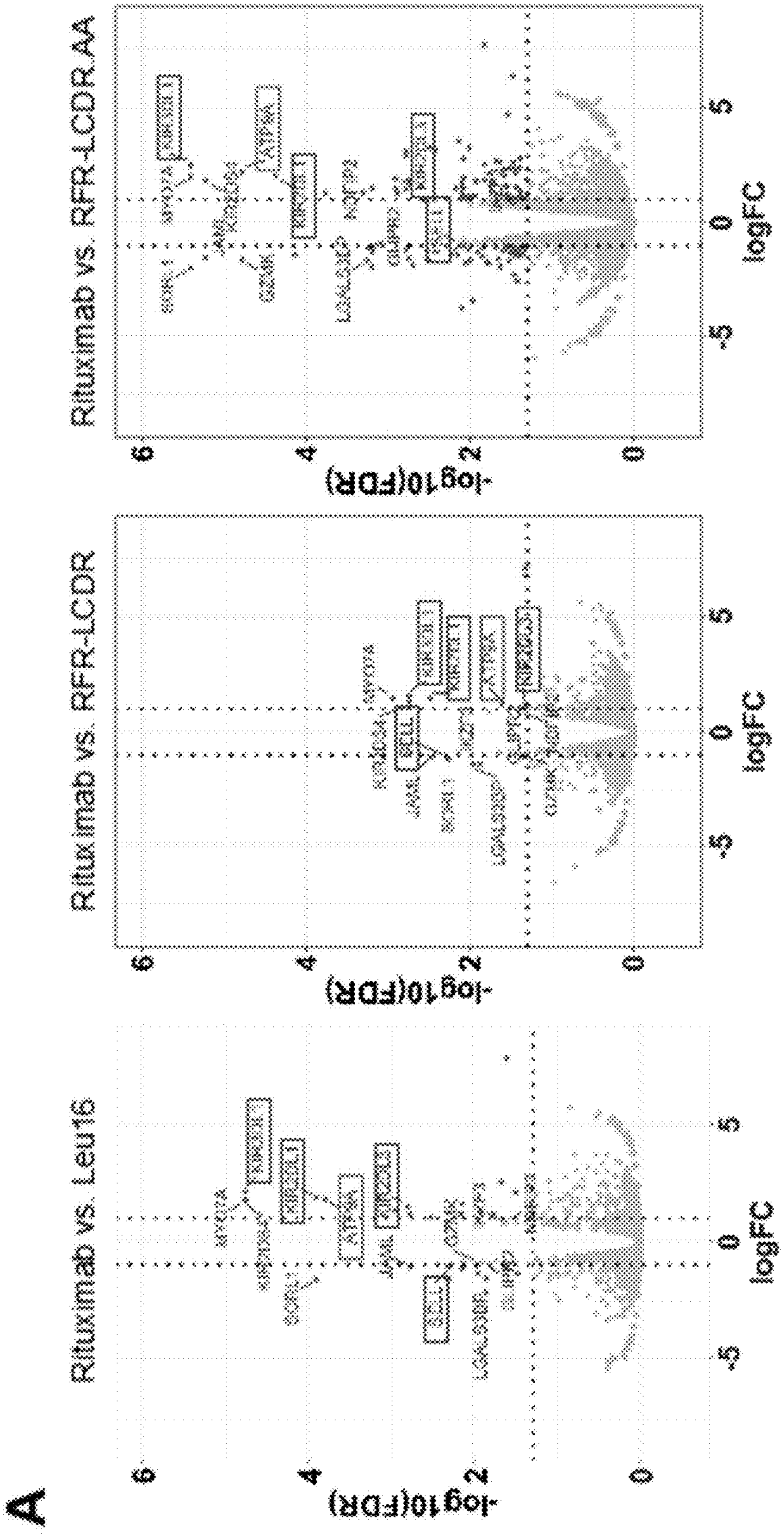
Figure 45B:
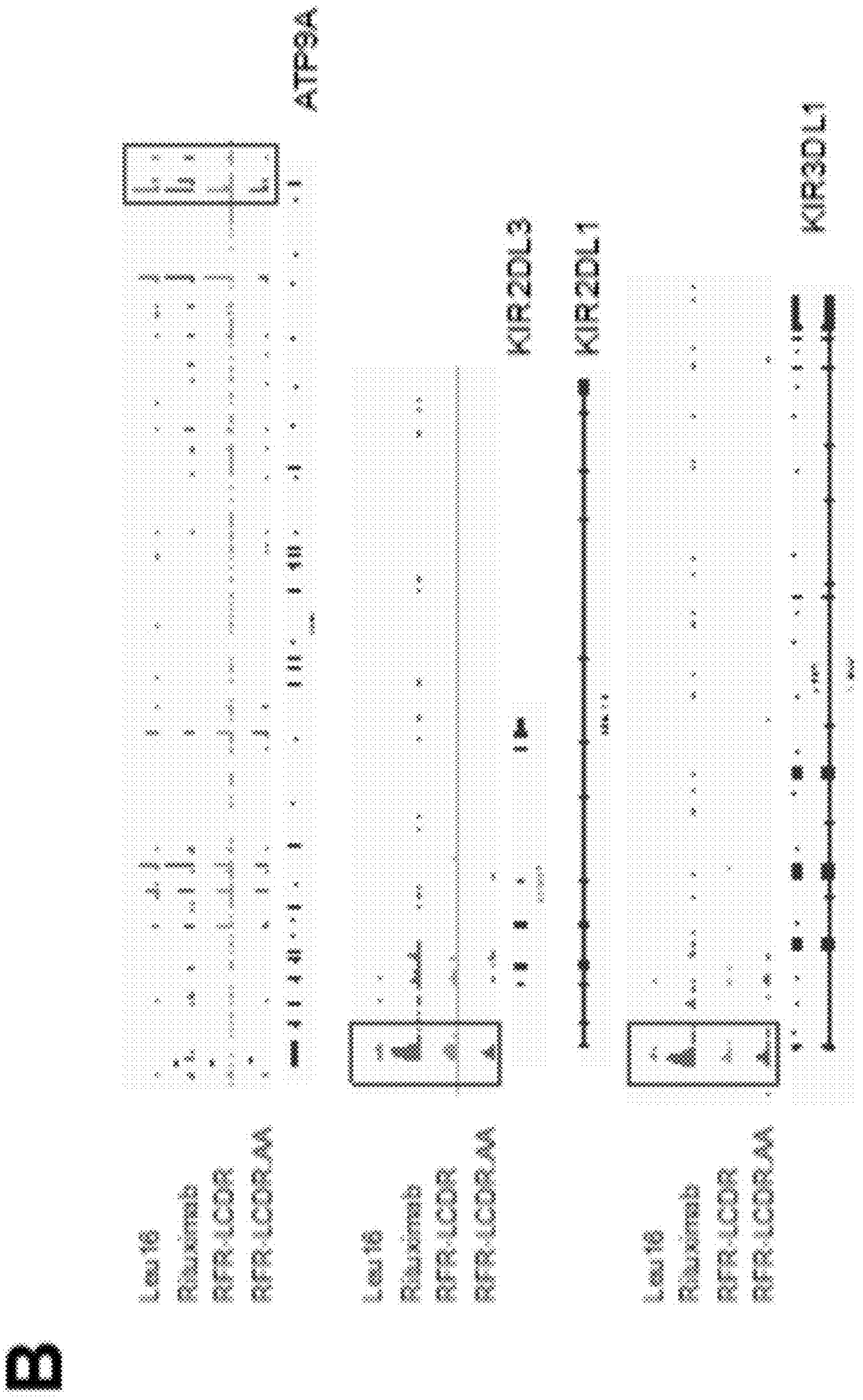
Figure 45C:
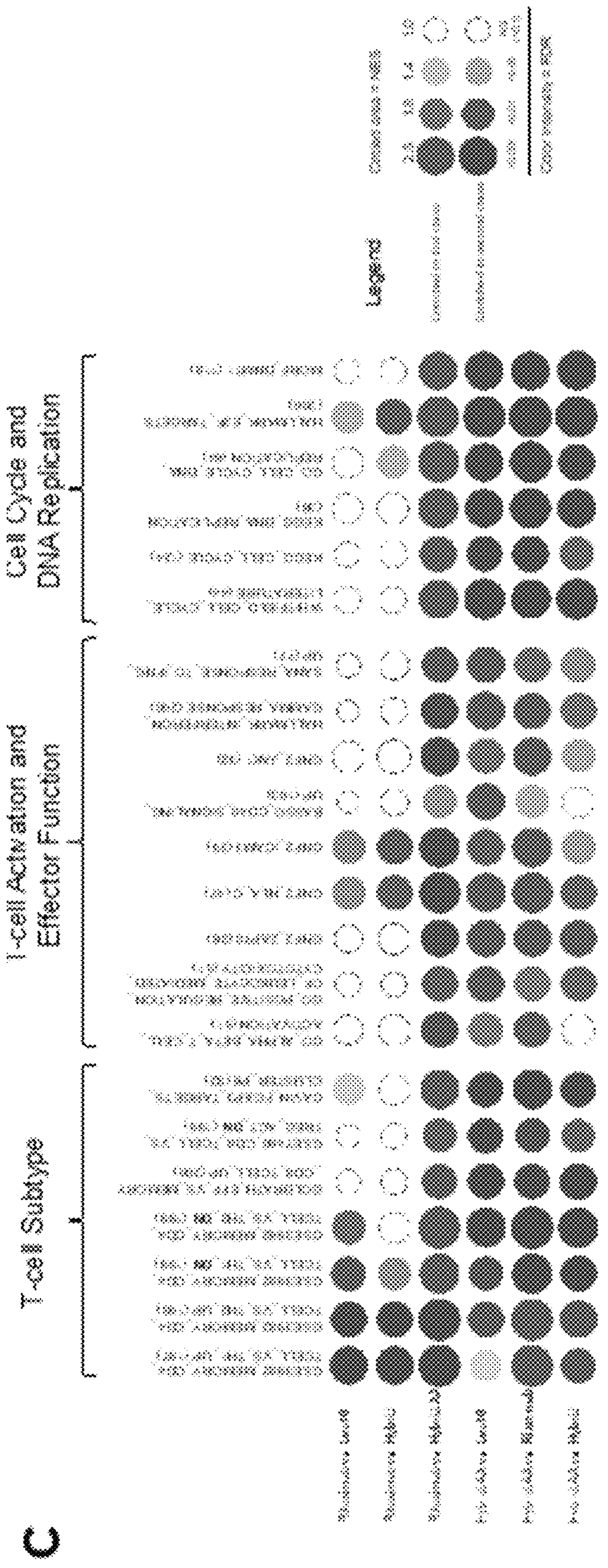

FIG. 45A-C. (A) Volcano plots of differentially expressed genes of Rituximab CAR-T cells versus Leu16 (left), RFR-LCDR (middle), or RFR-LCDR.AA (right) CAR-T cells based on RNAseq. All differentially expressed genes are plotted in grey. Genes that have at least 2-fold upregulation or downregulation ($\log_2$FC>1 or $\log_2$FC<−1) with FDR<0.05 are shown as red dots. The names of genes that appear in all three sets of pair-wise comparisons with $\log_2$FC>1 and FDR<0.05 or $\log_2$FC<−1 and FDR<0.05 are labeled. (B) Genome browser files of differentially accessible regions based on ATACseq in Leu16, Rituximab, RFR-LCDR, RFR-LCDR.AA CAR-T cells at the ATP9A, KIR2DL3, KIR2DL1, KIR3DL1 loci. (C) Gene Set Enrichment Analysis (GSEA) was performed on RNA-seq data obtained as described in FIG. 5A. A summary of results in pathways related to T-cell phenotype and function are shown in BubbleGUM map format.

DESCRIPTION OF ILLUSTRATIVE EMBODIMENTS

Chimeric antigen receptors comprise a single chain variable fragment (scFv) having a heavy chain (VH) and a light chain (VL) that each contains framework regions (FRs) flanking the complementarity determining regions (CDRs). The framework region is believed to be a major determinant of the structure of the scFv. It has been proposed that specific FR sequences, when incorporated as part of the scFv portion of the CAR, can cause tonic signaling, likely due to their effect on inducing CAR clustering. Previous work has shown that, the FR sequences of a tonically signaling CAR (GD2) were combined with the CDR sequences of a non-tonically signaling CD19 CAR, and the resulting hybrid CAR was shown to tonically signal. From this result, it was hypothesized that it would generally be undesirable to incorporate the FR sequences of a tonically signaling CAR in the development of new CAR molecules (Long et al. Nature Medicine, 2015. 21(6):581-590). Surprisingly, the inventors found that incorporation of FR from a tonically signaling CAR resulted in a CAR with superior properties. Accordingly, the compositions and methods of the disclosure provide a redesigned CAR, including a CD20 CAR, with increased in vivo efficacy.

I. Definitions

The peptides of the disclosure relate to peptides comprising chimeric antigen receptors, or CARs. CARs are engineered receptors, which are capable of grafting an arbitrary specificity onto an immune effector cell. In some cases, these receptors are used to graft the specificity of a monoclonal antibody onto a T cell. The receptors are called chimeric because they are composed of parts from different sources.

The terms "protein," "polypeptide," and "peptide" are used interchangeably herein when referring to a gene product.

"Homology," or "identity" refers to sequence similarity between two peptides or between two nucleic acid molecules. Identity can be determined by comparing a position in each sequence which may be aligned for purposes of comparison. When a position in the compared sequence is occupied by the same base or amino acid, then the molecules share sequence identity at that position. A degree of identity between sequences is a function of the number of matching or homologous positions shared by the sequences. An "unrelated" or "non-homologous" sequence shares less than 60% identity, less than 50% identity, less than 40% identity, less than 30% identity, or less than 25% identity, with one of the sequences of the current disclosure.

The terms "amino portion," "N-terminus," "amino terminus," and the like as used herein are used to refer to order of the regions of the polypeptide. Furthermore, when something is N-terminal to a region it is not necessarily at the terminus (or end) of the entire polypeptide, but just at the N-terminus of the region or domain. Similarly, the terms "carboxy portion," "C-terminus," "carboxy terminus," and the like as used herein is used to refer to order of the regions of the polypeptide, and when something is C-terminal to a region it is not necessarily at the terminus (or end) of the entire polypeptide, but just at the C-terminus of the region or domain.

The terms "polynucleotide," "nucleic acid," and "oligonucleotide" are used interchangeably and refer to a polymeric form of nucleotides of any length, either deoxyribonucleotides or ribonucleotides or analogs thereof. Polynucleotides can have any three-dimensional structure and may perform any function, known or unknown. The following are non-limiting examples of polynucleotides: a gene or gene fragment (for example, a probe, primer, EST or SAGE tag), exons, introns, messenger RNA (mRNA), transfer RNA, ribosomal RNA, ribozymes, cDNA, dsRNA, siRNA, miRNA, recombinant polynucleotides, branched polynucleotides, plasmids, vectors, isolated DNA of any sequence, isolated RNA of any sequence, nucleic acid probes and primers. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this invention that is a polynucleotide encompasses both the double-stranded form and each of two complementary single-stranded forms known or predicted to make up the double-stranded form.

A "gene," "polynucleotide," "coding region," "sequence," "segment," "fragment," or "transgene" which "encodes" a particular protein, is a nucleic acid molecule which is transcribed and optionally also translated into a gene product, e.g., a polypeptide, in vitro or in vivo when placed under the control of appropriate regulatory sequences. The coding region may be present in either a cDNA, genomic DNA, or RNA form. When present in a DNA form, the nucleic acid molecule may be single-stranded (i.e., the sense strand) or double-stranded. The boundaries of a coding region are determined by a start codon at the 5' (amino) terminus and a translation stop codon at the 3' (carboxy) terminus. A gene can include, but is not limited to, cDNA from prokaryotic or eukaryotic mRNA, genomic DNA sequences from prokaryotic or eukaryotic DNA, and synthetic DNA sequences. A transcription termination sequence will usually be located 3' to the gene sequence.

The term "antibody" includes monoclonal antibodies, polyclonal antibodies, dimers, multimers, multispecific antibodies and antibody fragments that may be human, mouse, humanized, chimeric, or derived from another species. A "monoclonal antibody" is an antibody obtained from a population of substantially homogeneous antibodies that is being directed against a specific antigenic site.

"Antibody or functional fragment thereof" means an immunoglobulin molecule that specifically binds to, or is immunologically reactive with a particular antigen or epitope, and includes both polyclonal and monoclonal antibodies. The term antibody includes genetically engineered or otherwise modified forms of immunoglobulins, such as intrabodies, peptibodies, chimeric antibodies, fully human antibodies, humanized antibodies, and heteroconjugate antibodies (e.g., bispecific antibodies, diabodies, triabodies, and tetrabodies). The term functional antibody fragment includes antigen binding fragments or regions of antibodies, including e.g., Fab', F(ab')2, Fab, Fv, rIgG, and scFv fragments. The term scFv refers to a single chain Fv antibody in which the variable domains of the heavy chain and of the light chain of a traditional two chain antibody have been joined to form one chain.

As used herein, the term "binding affinity" refers to the equilibrium constant for the reversible binding of two agents and is expressed as a dissociation constant (Kd). Binding affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more (or any derivable range therein), than the binding affinity of an antibody for unrelated amino acid sequences. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges.

"Individual, "subject," and "patient" are used interchangeably and can refer to a human or non-human.

The terms "lower," "reduced," "reduction," "decrease," or "inhibit" are all used herein generally to mean a decrease by a statistically significant amount. However, for avoidance of doubt, "lower," "reduced," "reduction, "decrease," or "inhibit" means a decrease by at least 10% as compared to a reference level, for example a decrease by at least about 20%, or at least about 30%, or at least about 40%, or at least about 50%, or at least about 60%, or at least about 70%, or at least about 80%, or at least about 90% or up to and including a 100% decrease (i.e. absent level as compared to a reference sample), or any decrease between 10-100% as compared to a reference level.

The terms "increased," "increase," "enhance," or "activate" are all used herein to generally mean an increase by a statically significant amount; for the avoidance of any doubt, the terms "increased," "increase," "enhance," or "activate" means an increase of at least 10% as compared to a reference level, for example an increase of at least about 20%, or at least about 30%, or at least about 40%, or at least about 50%, or at least about 60%, or at least about 70%, or at least about 80%, or at least about 90% or up to and including a 100% increase or any increase between 10-100% as compared to a reference level, or at least about a 2-fold, or at least about a 3-fold, or at least about a 4-fold, or at least about a 5-fold or at least about a 10-fold increase, or any increase between 2-fold and 10-fold or greater as compared to a reference level.

II. Polypeptides

A. Signal peptide

Polypeptides of the present disclosure may comprise a signal peptide. A "signal peptide" refers to a peptide sequence that directs the transport and localization of the protein within a cell, e.g., to a certain cell organelle (such as the endoplasmic reticulum) and/or the cell surface. In some embodiments, a signal peptide directs the nascent protein into the endoplasmic reticulum. This is essential if a receptor is to be glycosylated and anchored in the cell membrane. Generally, the signal peptide natively attached to the amino-terminal most component is used (e.g. in an scFv with orientation light chain-linker-heavy chain, the native signal of the light-chain is used).

In some embodiments, the signal peptide is cleaved after passage of the endoplasmic reticulum (ER), i.e., is a cleavable signal peptide. In some embodiments, a restriction site is at the carboxy end of the signal peptide to facilitate cleavage.

B. Antigen Binding Domain

Polypeptides of the present disclosure may comprise one or more antigen binding domains. An "antigen binding domain" describes a region of a polypeptide capable of binding to an antigen under appropriate conditions. In some embodiments, an antigen binding domain is a single-chain variable fragment (scFv) based on one or more antibodies (e.g., CD20 antibodies). In some embodiments, an antigen binding domain comprise a variable heavy (VH) region and a variable light (VL) region, with the VH and VL regions being on the same polypeptide. In some embodiments, the antigen binding domain comprises a linker between the VH and VL regions. A linker may enable the antigen binding domain to form a desired structure for antigen binding.

The variable regions of the antigen-binding domains of the polypeptides of the disclosure can be modified by mutating amino acid residues within the VH and/or VL CDR 1, CDR 2 and/or CDR 3 regions to improve one or more binding properties (e.g., affinity) of the antibody. The term "CDR" refers to a complementarity-determining region that is based on a part of the variable chains in immunoglobulins (antibodies) and T cell receptors, generated by B cells and T cells respectively, where these molecules bind to their specific antigen. Since most sequence variation associated with immunoglobulins and T cell receptors is found in the CDRs, these regions are sometimes referred to as hypervariable regions. Mutations may be introduced by site-directed mutagenesis or PCR-mediated mutagenesis and the effect on antibody binding, or other functional property of interest, can be evaluated in appropriate in vitro or in vivo assays. Preferably conservative modifications are introduced and typically no more than one, two, three, four or five residues within a CDR region are altered. The mutations may be amino acid substitutions, additions or deletions.

Framework modifications can be made to the antibodies to decrease immunogenicity, for example, by "backmutating" one or more framework residues to the corresponding germline sequence.

It is also contemplated that the antigen binding domain may be multi-specific or multivalent by multimerizing the antigen binding domain with VH and VL region pairs that bind either the same antigen (multi-valent) or a different antigen (multi-specific).

The binding affinity of the antigen binding region, such as the variable regions (heavy chain and/or light chain variable region), or of the CDRs may be at least 10-5M, 10-6M, 10-7M, 10-8M, 10-9M, 10-10M, 10-11M, 10-12M, or 10-13M. In some embodiments, the KD of the antigen binding region, such as the variable regions (heavy chain and/or light chain variable region), or of the CDRs may be at least 10-5M, 10-6M, 10-7M, 10-8M, 10-9M, 10-10M, 10-11M, 10-12M, or 10-13M (or any derivable range therein).

Binding affinity, KA, or KD can be determined by methods known in the art such as by surface plasmon resonance (SRP)-based biosensors, by kinetic exclusion assay (KinExA), by optical scanner for microarray detection based on polarization-modulated oblique-incidence reflectivity difference (OI-RD), or by ELISA.

In some embodiments, the polypeptide comprising the humanized binding region has equal, better, or at least 80, 81, 82, 83, 84, 85, 86, 87, 88, 89, 90, 91, 92, 93, 94, 95, 96, 97, 98, 99, 100, 101, 102, 103, 104, 104, 106, 106, 108, 109, 110, 115, or 120% binding affinity and/or expression level in host cells, compared to a polypeptide comprising a non-humanized binding region, such as a binding region from a mouse.

In some embodiments, the framework regions, such as FR1, FR2, FR3, and/or FR4 of a human framework can each or collectively have at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 (or any derivable range therein) amino acid substitutions, contiguous amino acid additions, or contiguous amino acid deletions with respect to a mouse framework.

In some embodiments, the framework regions, such as FR1, FR2, FR3, and/or FR4 of a mouse framework can each or collectively have at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, or 200 (or any derivable range therein) amino acid substitutions, contiguous amino acid additions, or contiguous amino acid deletions with respect to a human framework.

The substitution may be at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 of FR1, FR2, FR3, or FR4 of a heavy or light chain variable region.

C. Extracellular Spacer

An extracellular spacer may link an antigen-binding domain to a transmembrane domain. In some embodiments, a hinge is flexible enough to allow the antigen-binding domain to orient in different directions to facilitate antigen binding. In one embodiment, the spacer comprises the hinge region from IgG. In some embodiments, the spacer comprises or further comprises the CH2CH3 region of immunoglobulin and portions of CD3. In some embodiments, the CH2CH3 region may have L235E/N297Q or L235D/N297Q modifications, or at least 75%, at least 80%, at least 85%, at least 90%, at least 95%, at least 98%, or 100% amino acid sequence identity of the CH2CH3 region. In some embodiments, the spacer is from IgG4. An extracellular spacer may comprise a hinge region.

As used herein, the term "hinge" refers to a flexible polypeptide connector region (also referred to herein as "hinge region") providing structural flexibility and spacing to flanking polypeptide regions and can consist of natural or synthetic polypeptides. A "hinge" derived from an immunoglobulin (e.g., IgG1) is generally defined as stretching from Glu216 to Pro230 of human IgG1 (Burton (1985) Molec. Immunol., 22: 161-206). Hinge regions of other IgG isotypes may be aligned with the IgG1 sequence by placing the first and last cysteine residues forming inter-heavy chain disulfide (S—S) bonds in the same positions. The hinge region may be of natural occurrence or non-natural occurrence, including but not limited to an altered hinge region as described in U.S. Pat. No. 5,677,425, incorporated by reference herein. The hinge region can include a complete hinge region derived from an antibody of a different class or subclass from that of the CH1 domain. The term "hinge" can also include regions derived from CD8 and other receptors that provide a similar function in providing flexibility and spacing to flanking regions.

The extracellular spacer can have a length of at least, at most, or exactly 4, 5, 6, 7, 8, 9, 10, 12, 15, 16, 17, 18, 19, 20, 20, 25, 30, 35, 40, 45, 50, 75, 100, 110, 119, 120, 130, 140, 150, 160, 170, 180, 190, 200, 201, 202, 203, 204, 205, 206, 207, 208, 209, 210, 211, 212, 213, 214, 215, 216, 217, 218, 219, 220, 225, 226, 227, 228, 229, 230, 231, 232, 233, 234, 235, 236, 237, 238, 239, 240, 241, 242, 243, 244, 245, 246, 247, 248, 249, 250, 260, 270, 280, 290, 300, 325, 350, or 400 amino acids (or any derivable range therein). In some embodiments, the extracellular spacer consists of or comprises a hinge region from an immunoglobulin (e.g. IgG). Immunoglobulin hinge region amino acid sequences are known in the art; see, e.g., Tan et al. (1990) Proc. Natl. Acad. Sci. USA 87: 162; and Huck et al. (1986) Nucl. Acids Res.

The length of an extracellular spacer may have effects on the CAR's signaling activity and/or the CAR-T cells' expansion properties in response to antigen-stimulated CAR signaling. In some embodiments, a shorter spacer such as less than 50, 45, 40, 30, 35, 30, 25, 20, 15, 14, 13, 12, 11, or 10 amino acids is used. In some embodiments, a longer spacer, such as one that is at least 50, 60, 70, 80, 90, 100, 110, 120, 130, 140, 150, 200, 201, 202, 203, 204, 205, 206, 207, 208, 209, 210, 211, 212, 213, 214, 215, 216, 217, 218, 219, 220, 225, 226, 227, 228, 229, 230, 231, 232, 233, 234, 235, 236, 237, 238, 239, 240, 241, 242, 243, 244, 245, 246, 247, 248, 249, 250, 260, 270, 280, or 290 amino acids may have the advantage of increased expansion in vivo or in vitro.

As non-limiting examples, an immunoglobulin hinge region can include one of the following amino acid sequences:

TABLE

Exemplary Hinge Regions

| SEQUENCE | SEQ ID NO: |
|---|---|
| DKTHT | 42 |
| CPPC | 42 |
| CPEPKSCDTPPPCPR | 44 |

TABLE-continued

Exemplary Hinge Regions

| SEQUENCE | SEQ ID NO: |
|---|---|
| ELKTPLGDTTHT | 45 |
| KSCDKTHTCP | 46 |
| KCCVDCP | 47 |
| KYGPPCP | 48 |
| EPKSCDKTHTCPPCP | 49 |
| ELKTPLGDTTHTCPRCP | 50 |
| SPNMVPHAHHAQ | 51 |
| ESKYGPPCPPCP | 52 |
| EPKSCDKTYTCPPCP | 53 |

The extracellular spacer can comprise an amino acid sequence of a human IgG1, IgG2, IgG3, or IgG4, hinge region. The extracellular spacer may also include one or more amino acid substitutions and/or insertions and/or deletions compared to a wild-type (naturally-occurring) hinge region. For example, His229 of human IgG1 hinge can be substituted with Tyr, so that the hinge region comprises the sequence EPKSCDKTYTCPPCP (SEQ ID NO:53).

The extracellular spacer can comprise an amino acid sequence derived from human CD8; e.g., the hinge region can comprise the amino acid sequence: TTTPAPRPPTPAPTIASQPLSLRPEACRPAAGGAVHTRGLDFACD (SEQ ID NO:54), or a variant thereof.

The extracellular spacer may comprise or further comprise a CH2 region. An exemplary CH2 region is APEFEGGPSVFLFPPKPKDTLMISRTPEVTCVVVDVSQEDPEVQFNWYVDGVEVHNAKTKPREEQFQSTYRVVSVLTVLHQDWLNGKEYKCKVSNKGLPSSIEKTISKAK (SEQ ID NO:55). The extracellular spacer may comprise or further comprise a CH3 region. An exemplary CH3 region is (SEQ ID NO: 56)
GQPREPQVYTLPPSQEEMTKNQVSLTCLVKGFYPSDIAVEWESNGQPENN
YKTTPPVLDSDGSFFLYSRLTVDKSRWQEGNVFSCSVMHEALHNHYTQKS
LSLSLGK.

When the extracellular spacer comprises multiple parts, there may be anywhere from 0-50 amino acids in between the various parts. For example, there may be at least, at most, or exactly 0, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50 amino acids (or any derivable range therein) between the hinge and the CH2 or CH3 region or between the CH2 and CH3 region when both are present. In some embodiments, the extracellular spacer consists essentially of a hinge, CH2, and/or CH3 region, meaning that the hinge, CH2, and/or CH3 region is the only identifiable region present and all other domains or regions are excluded, but further amino acids not part of an identifiable region may be present.

D. Transmembrane Domain

Polypeptides of the present disclosure may comprise a transmembrane domain. In some embodiments, a transmembrane domain is a hydrophobic alpha helix that spans the membrane. Different transmembrane domains may result in different receptor stability.

In some embodiments, the transmembrane domain is interposed between the extracellular spacer and the cytoplasmic region. In some embodiments, the transmembrane domain is interposed between the extracellular spacer and one or more costimulatory regions. In some embodiments, a linker is between the transmembrane domain and the one or more costimulatory regions.

Any transmembrane domain that provides for insertion of a polypeptide into the cell membrane of a eukaryotic (e.g., mammalian) cell may be suitable for use. In some embodiments, the transmembrane domain is derived from CD28, CD8, CD4, CD3-zeta, CD134, or CD7.

Exemplary transmembrane domains useful in any of the embodiments of the disclosure include those in the table below:

TABLE

Exemplary transmembrane domain sequences

| Description | Sequence | SEQ ID NO: |
|---|---|---|
| CD28-derived | FWVLVVVGGVLACYSLLVTVAFIIFWV | 57 |
| CD8 beta derived | LGLLVAGVLVLLVSLGVAIHLCC | 58 |
| CD4 derived | ALIVLGGVAGLLLFIGLGIFFCVRC | 59 |
| CD3 zeta derived | LCYLLDGILFIYGVILTALFLRV | 60 |
| CD28 derived | WVLVVVGGVLACYSLLVTVAFIIFWV | 61 |
| CD134 (OX40) derived | VAAILGLGLVLGLLGPLAILLALYLL | 62 |
| CD7 derived | ALPAALAVISFLLGLGLGVACVLA | 63 |

E. Cytoplasmic Region

After antigen recognition, receptors of the present disclosure may cluster and a signal transmitted to the cell through the cytoplasmic region. In some embodiments, the costimulatory domains described herein are part of the cytoplasmic region. In some embodiments, the cytoplasmic region comprises an intracellular signaling domain. An intracellular signaling domain may comprise a primary signaling domain and one or more costimulatory domains.

Cytoplasmic regions and/or costimulatory regions suitable for use in the polypeptides of the disclosure include any desired signaling domain that provides a distinct and detectable signal (e.g., increased production of one or more cytokines by the cell; change in transcription of a target gene; change in activity of a protein; change in cell behavior, e.g., cell death; cellular proliferation; cellular differentiation; cell survival; modulation of cellular signaling responses; etc.) in response to activation by way of binding of the antigen to the antigen binding domain. In some embodiments, the cytoplasmic region includes at least one (e.g., one, two, three, four, five, six, etc.) ITAM motif as described herein. In some embodiments, the cytoplasmic region includes DAP10/CD28 type signaling chains.

Cytoplasmic regions suitable for use in the polypeptides of the disclosure include immunoreceptor tyrosine-based activation motif (ITAM)-containing intracellular signaling polypeptides. An ITAM motif is YX1X2(L/I), where X1 and X2 are independently any amino acid. In some cases, the cytoplasmic region comprises 1, 2, 3, 4, or 5 ITAM motifs. In some cases, an ITAM motif is repeated twice in an endodomain, where the first and second instances of the ITAM motif are separated from one another by 6 to 8 amino acids, e.g., (YX1X2(L/I))(X3)n(YX1X2(L/I)), where n is an integer from 6 to 8, and each of the 6-8 X3 can be any amino acid.

A suitable cytoplasmic region may be an ITAM motif-containing portion that is derived from a polypeptide that contains an ITAM motif. For example, a suitable cytoplasmic region can be an ITAM motif-containing domain from any ITAM motif-containing protein. Thus, a suitable endodomain need not contain the entire sequence of the entire protein from which it is derived. Examples of suitable ITAM motif-containing polypeptides include, but are not limited to: DAP12, DAP10, FCER1G (Fc epsilon receptor I gamma chain); CD3D (CD3 delta); CD3E (CD3 epsilon); CD3G (CD3 gamma); CD3-zeta; and CD79A (antigen receptor complex-associated protein alpha chain).

Exemplary cytoplasmic regions are known in the art. The cytoplasmic regions shown below also provide examples of regions that may be incorporated in a CAR of the disclosure:

In some embodiments, a suitable cytoplasmic region can comprise an ITAM motif-containing portion of the full length DAP12 amino acid sequence. In some embodiments, the cytoplasmic region is derived from FCER1G (also known as FCRG; Fc epsilon receptor I gamma chain; Fc receptor gamma-chain; fc-epsilon R1-gamma; fcRgamma; fceRI gamma; high affinity immunoglobulin epsilon receptor subunit gamma; immunoglobulin E receptor, high affinity, gamma chain; etc.). In some embodiments, a suitable cytoplasmic region can comprise an ITAM motif-containing portion of the full length FCER1G amino acid sequence.

In some embodiments, the cytoplasmic region is derived from T cell surface glycoprotein CD3 delta chain (also known as CD3D; CD3-DELTA; T3D; CD3 antigen, delta subunit; CD3 delta; CD36; CD3d antigen, delta polypeptide (TiT3 complex); OKT3, delta chain; T cell receptor T3 delta chain; T cell surface glycoprotein CD3 delta chain; etc.). In some embodiments, a suitable cytoplasmic region can comprise an ITAM motif-containing portion of the full length CD3 delta amino acid sequence. In some embodiments, the cytoplasmic region is derived from T cell surface glycoprotein CD3 epsilon chain (also known as CD3e, CD3ε; T cell surface antigen T3/Leu-4 epsilon chain, T cell surface glycoprotein CD3 epsilon chain, AI504783, CD3, CD3-epsilon, T3e, etc.). In some embodiments, a suitable cytoplasmic region can comprise an ITAM motif-containing portion of the full length CD3 epsilon amino acid sequence. In some embodiments, the cytoplasmic region is derived from T cell surface glycoprotein CD3 gamma chain (also known as CD3G, CD3γ, T cell receptor T3 gamma chain, CD3-GAMMA, T3G, gamma polypeptide (TiT3 complex), etc.). In some embodiments, a suitable cytoplasmic region can comprise an ITAM motif-containing portion of the full length CD3 gamma amino acid sequence. In some embodiments, the cytoplasmic region is derived from T cell surface glycoprotein CD3 zeta chain (also known as CD3Z, CD3c, T cell receptor T3 zeta chain, CD247, CD3-ZETA, CD3H, CD3Q, T3Z, TCRZ, etc.). In some embodiments, a suitable cytoplasmic region can comprise an ITAM motif-containing portion of the full length CD3 zeta amino acid sequence.

In some embodiments, the cytoplasmic region is derived from CD79A (also known as B-cell antigen receptor complex-associated protein alpha chain; CD79a antigen (immunoglobulin-associated alpha); MB-1 membrane glycoprotein; ig-alpha; membrane-bound immunoglobulin-associated protein; surface IgM-associated protein; etc.). In some embodiments, a suitable cytoplasmic region can comprise an ITAM motif-containing portion of the full length CD79A amino acid sequence.

Specific exemplary cytoplasmic regions are known in the art and further shown in the table below.

TABLE

Cytoplasmic Regions

| SEQUENCE | SEQ ID NO: |
|---|---|
| MGGLEPCSRLLLLPLLLAVSGLRPVQAQAQSDCSCSTVSPGVLAGIVMGDLV LTVLIALAVYFLGRLVPRGRGAAEAATRKQRITETESPYQELQGQRSDVYSD LNTQRPYYK | 64 |
| MGGLEPCSRLLLLPLLLAVSGLRPVQAQAQSDCSCSTVSPGVLAGIVMGDLV LTVLIALAVYFLGRLVPRGRGAAEATRKQRITETESPYQELQGQRSDVYSDL NTQRPYYK | 65 |
| MGGLEPCSRLLLLPLLLAVSDCSCSTVSPGVLAGIVMGDLVLTVLIALAVYFL GRLVPRGRGAAEAATRKQRITETESPYQELQGQRSDVYSDLNTQRPYYK | 66 |
| MGGLEPCSRLLLLPLLLAVSDCSCSTVSPGVLAGIVMGDLVLTVLIALAVYFL GRLVPRGRGAAEATRKQRITETESPYQELQGQRSDVYSDLNTQRPYYK | 67 |
| MIPAVVLLLLLLVEQAAALGEPQLCYILDAILFLYGIVLTLLYCRLKIQVRKA AITSYEKSDGVYTGLSTRNQETYETLKHEKPPQ | 68 |
| DGVYTGLSTRNQETYETLKHE | 69 |
| MEHSTFLSGLVLATLLSQVSPFKIPIEELEDRVFVNCNTSITWVEGTVGTLLSD ITRLDLGKRILDPRGIYRCNGTDIYKDKESTVQVHYRMCQSCVELDPATVAGI IVTDVIATLLLALGVFCFAGHETGRLSGAADTQALLRNDQVYQPLRDRDDA QYSHLGGNWARNK | 70 |

TABLE-continued

Cytoplasmic Regions

| SEQUENCE | SEQ ID NO: |
|---|---|
| MEHSTFLSGLVLATLLSQVSPFKIPIEELEDRVFVNCNTSITWVEGTVGTLLSD ITRLDLGKRILDPRGIYRCNGTDIYKDKESTVQVHYRTADTQALLRNDQVYQ PLRDRDDAQYSHLGGNWARNK | 71 |
| DQVYQPLRDRDDAQYSHLGGN | 72 |
| MQSGTHWRVLGLCLLSVGVWGQDGNEEMGGITQTPYKVSISGTTVILTCPQ YPGSEILWQHNDKNIGGDEDDKNIGSDEDHLSLKEFSELEQSGYYVCYPRGS KPEDANFYLYLRARVCENCMEMDVMSVATIVIVDICITGGLLLLVYYWSKN RKAKAKPVTRGAGAGGRQRGQNKERPPPVPNPDYEPIRKGQRDLYSGLNQR RI | 73 |
| NPDYEPIRKGQRDLYSGLNQR | 74 |
| MEQGKGLAVLILAIILLQGTLAQSIKGNHLVKVYDYQEDGSVLLTCDAEAKN ITWFKDGKMIGFLTEDKKKWNLGSNAKDPRGMYQCKGSQNKSKPLQVYYR MCQNCIELNAATISGFLFAEIVSIFVLAVGVYFIAGQDGVRQSRASDKQTLLP NDQLYQPLKDREDDQYSHLQGNQLRRN | 75 |
| DQLYQPLKDREDDQYSHLQGN | 76 |
| MKWKALFTAAILQAQLPITEAQSFGLLDPKLCYLLDGILFIYGVILTALFLRV KFSRSADAPAYQQGQNQLYNELNLGRREEYDVLDKRRGRDPEMGGKPRRK NPQEGLYNELQKDKMAEAYSEIGMKGERRRGKGHDGLYQGLSTATKDTYD ALHMQALPPR | 77 |
| MKWKALFTAAILQAQLPITEAQSFGLLDPKLCYLLDGILFIYGVILTALFLRV KFSRSADAPAYQQGQNQLYNELNLGRREEYDVLDKRRGRDPEMGGKPQRR KNPQEGLYNELQKDKMAEAYSEIGMKGERRRGKGHDGLYQGLSTATKDTY DALHMQALPPR | 78 |
| RVKFSRSADAPAYQQGQNQLYNELNLGRREEYDVLDKRRGRDPEMGGKPR RKNPQEGLYNELQKDKMAEAYSEIGMKGERRRGKGHDGLYQGLSTATKDT YDALHMQALPPR | 39 |
| NQLYNELNLGRREEYDVLDKR | 79 |
| EGLYNELQKDKMAEAYSEIGMK | 80 |
| DGLYQGLSTATKDTYDALHMQ | 81 |
| MPGGPGVLQALPATIFLLFLLSAVYLGPGCQALWMHKVPASLMVSLGEDAH FQCPHNSSNNANVTWWRVLHGNYTWPPEFLGPGEDPNGTLIIQNVNKSHGG IYVCRVQEGNESYQQSCGTYLRVRQPPPRPFLDMGEGTKNRIITAEGIILLFCA VVPGTLLLFRKRWQNEKLGLDAGDEYEDENLYEGLNLDDCSMYEDISRGLQ GTYQDVGSLNIGDVQLEKP | 82 |
| MPGGPGVLQALPATIFLLFLLSAVYLGPGCQALWMHKVPASLMVSLGEDAH FQCPHNSSNNANVTWWRVLHGNYTWPPEFLGPGEDPNEPPPRPFLDMGEGT KNRIITAEGIILLFCAVVPGTLLLFRKRWQNEKLGLDAGDEYEDENLYEGLNL DDCSMYEDISRGLQGTYQDVGSLNIGDVQLEKP | 83 |
| ENLYEGLNLDDCSMYEDISRG | 84 |
| FWVLVVVGGVLACYSLLVTVAFIIFWVRSKRSRLLHSDYMNMTPRRPGPTR KHYQPYAPPRDFAAYRS | 85 |
| FWVLVVVGGVLACYSLLVTVAFIIFWVRSKRSRLLHSDYMNMTPRRPGPTR KHYQPYAPPRDFAAYRS | 86 |

F. Costimulatory Region

Non-limiting examples of suitable costimulatory regions, such as those included in the cytoplasmic region, include, but are not limited to, polypeptides from 4-1BB (CD137), CD28, ICOS, OX-40, BTLA, CD27, CD30, GITR, and HVEM.

A costimulatory region may have a length of at least, at most, or exactly 20, 25, 30, 35, 40, 50, 60, 70, 80, 90, 100, 150, 200, or 300 amino acids or any range derivable therein. In some embodiments, the costimulatory region is derived from an intracellular portion of the transmembrane protein 4-1BB (also known as TNFRSF9; CD137; CDw137; ILA; etc.). In some embodiments, the costimulatory region is derived from an intracellular portion of the transmembrane protein CD28 (also known as Tp44). In some embodiments, the costimulatory region is derived from an intracellular portion of the transmembrane protein ICOS (also known as AILIM, CD278, and CVID1). In some embodiments, the costimulatory region is derived from an intracellular portion of the transmembrane protein OX-40 (also known as TNFRSF4, RP5-902P8.3, ACT35, CD134, OX40, TXGP1L). In some embodiments, the costimulatory region is derived from an intracellular portion of the transmembrane protein BTLA (also known as BTLA1 and CD272). In some embodiments, the costimulatory region is derived from an intracellular portion of the transmembrane protein CD27 (also known as S 152, T14, TNFRSF7, and Tp55). In some embodiments, the costimulatory region is derived from an intracellular portion of the transmembrane protein CD30 (also known as TNFRSF8, D1S166E, and Ki-1). In some embodiments, the costimulatory region is derived from an intracellular portion of the transmembrane protein GITR (also known as TNFRSF18, RP5-902P8.2, AITR, CD357, and GITR-D). In some embodiments, the costimulatory region derived from an intracellular portion of the transmembrane protein HVEM (also known as TNFRSF14, RP3-395M20.6, ATAR, CD270, HVEA, HVEM, LIGHTR, and TR2).

Specific exemplary co-stimulatory domains are represented by the amino acid sequences below:

TABLE

Co-stimulatory domains

| SEQUENCE | SEQ ID NO: |
|---|---|
| KRGRKKLLYIFKQPFMRPVQTTQEEDGCSCRFPEEEEGGCEL | 87 |
| FWVRSKRSRLLHSDYMNMTPRRPGPTRKHYQPYAPPRDFAAYRS | 88 |
| TKKKYSSSVHDPNGEYMFMRAVNTAKKSRLTDVTL | 89 |
| RRDQRLPPDAHKPPGGGSFRTPIQEEQADAHSTLAKI | 90 |
| CCLRRHQGKQNELSDTAGREINLVDAHLKSEQTEASTRQNSQVLLSETGIYD NDPDLCFRMQEGSEVYSNPCLEENKPGIVYASLNHSVIGPNSRLARNVKEAP TEYASICVRS | 91 |
| HQRRKYRSNKGESPVEPAEPCRYSCPREEEGSTIPIQEDYRKPEPACSP | 92 |
| RRACRKRIRQKLHLCYPVQTSQPKLELVDSRPRRSSTQLRSGASVTEPVAEER GLMSQPLMETCHSVGAAYLESLPLQDASPAGGPSSPRDLPEPRVSTEHTNNKI EKIYIMKADTVIVGTVKAELPEGRGLAGPAEPELEEELEADHTPHYPEQETEP PLGSCSDVMLSVEEEGKEDPLPTAASGK | 93 |
| HIWQLRSQCMWPRETQLLLEVPPSTEDARSCQFPEEERGERSAEEKGRLGDL WV | 94 |
| CVKRRKPRGDVVKVIVSVQRKRQEAEGEATVIEALQAPPDVTTVAVEETIPS FTGRSPNH | 95 |
| RSKRSRGGHSDYMNMTPRRPGPTRKHYQPYAPPRDFAAYRS | 38 |

G. Detection Peptides

In some embodiments, the polypeptides described herein may further comprise a detection peptide. Suitable detection peptides include hemagglutinin (HA; e.g., YPYDVPDYA (SEQ ID NO:96); FLAG (e.g., DYKDDDDK (SEQ ID NO:97); c-myc (e.g., EQKLISEEDL; SEQ ID NO:98), and the like. Other suitable detection peptides are known in the art.

H. Peptide Linkers

In some embodiments, the polypeptides of the disclosure include peptide linkers (sometimes referred to as a linker). A peptide linker may be used to separate any of the peptide domain/regions described herein. As an example, a linker may be between the signal peptide and the antigen binding domain, between the VH and VL of the antigen binding domain, between the antigen binding domain and the peptide spacer, between the peptide spacer and the transmembrane domain, flanking the costimulatory region or on the N- or C-region of the costimulatory region, and/or between the transmembrane domain and the endodomain. The peptide linker may have any of a variety of amino acid sequences. Domains and regions can be joined by a peptide linker that is generally of a flexible nature, although other chemical linkages are not excluded. A linker can be a peptide of between about 6 and about 40 amino acids in length, or between about 6 and about 25 amino acids in length. These linkers can be produced by using synthetic, linker-encoding oligonucleotides to couple the proteins.

Peptide linkers with a degree of flexibility can be used. The peptide linkers may have virtually any amino acid sequence, bearing in mind that suitable peptide linkers will have a sequence that results in a generally flexible peptide. The use of small amino acids, such as glycine and alanine, are of use in creating a flexible peptide. The creation of such sequences is routine to those of skill in the art.

Suitable linkers can be readily selected and can be of any suitable length, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Example flexible linkers include glycine polymers (G)n, glycine-serine polymers (including, for example, (GS)n, (GSGGS)n (SEQ ID NO:99), (G4S)n and (GGGS)n (SEQ ID NO:100), where n is an integer of at least one. In some embodiments, n is at least, at most, or exactly 1, 2, 3, 4, 5, 6, 7, 8, 9, or 10 (or any derivable range therein). Glycine-alanine polymers, alanine-serine polymers, and other flexible linkers known in the art. Glycine and glycine-serine polymers can be used; both Gly and Ser are relatively unstructured, and therefore can serve as a neutral tether between components. Glycine polymers can be used; glycine accesses significantly more phi-psi space than even alanine, and is much less restricted than residues with longer side chains. Exemplary spacers can comprise amino acid sequences including, but not limited to, GGSG (SEQ ID NO:101), GGSGG (SEQ ID NO:102), GSGSG (SEQ ID NO:103), GSGGG (SEQ ID NO:104), GGGSG (SEQ ID NO:105), GSSSG (SEQ ID NO:106), and the like.

In further embodiments, the linker comprises (EAAAK)n (SEQ ID NO:107), wherein n is an integer of at least one. In some embodiments, n is at least, at most, or exactly 1, 2, 3, 4, 5, 6, 7, 8, 9, or 10 (or any derivable range therein).

I. Additional Modifications and Polypeptide Enhancements

Additionally, the polypeptides of the disclosure may be chemically modified. Glycosylation of the polypeptides can be altered, for example, by modifying one or more sites of glycosylation within the polypeptide sequence to increase the affinity of the polypeptide for antigen (U.S. Pat. Nos. 5,714,350 and 6,350,861).

It is contemplated that a region or fragment of a polypeptide of the disclosure may have an amino acid sequence that has, has at least or has at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200 or more amino acid substitutions, contiguous amino acid additions, or contiguous amino acid deletions with respect to any of SEQ ID NOS:1-144. Alternatively, a region or fragment of a polypeptide of the disclosure may have an amino acid sequence that comprises or consists of an amino acid sequence that is, is at least, or is at most 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100% (or any range derivable therein) identical to any of SEQ ID NOs: 1-144. Moreover, in some embodiments, a region or fragment comprises an amino acid region of 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500 or more contiguous amino acids starting at position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500 in any of SEQ ID NOs:1-144 (where position 1 is at the N-terminus of the SEQ ID NO). The polypeptides of the disclosure may include 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 or more variant amino acids or be at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% similar, identical, or homologous with at least, or at most 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 600, or more contiguous amino acids, or any range derivable therein, of any of SEQ ID NOs:1-144.

The polypeptides of the disclosure may include at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300,301, 302, 303, 304, 305, 306,307, 308, 309, 310, 311, 312, 313, 314, 315, 316, 317, 318, 319, 320, 321, 322, 323, 324, 325, 326, 327, 328, 329, 330, 331, 332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391,392, 393, 394, 395,396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 615 substitutions (or any range derivable therein).

The substitution may be at amino acid position 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 251, 252, 253, 254, 255, 256, 257, 258, 259, 260, 261, 262, 263, 264, 265, 266, 267, 268, 269, 270, 271, 272, 273, 274, 275, 276, 277, 278, 279, 280, 281, 282, 283, 284, 285, 286, 287, 288, 289, 290, 291, 292, 293, 294, 295, 296, 297, 298, 299, 300, 301, 302, 303, 304, 305, 306, 307, 308, 309, 310, 311, 312, 313, 314, 315, 316, 317, 318, 319, 320, 321,322, 323, 324, 325,326, 327, 328, 329, 330, 331,332, 333, 334, 335, 336, 337, 338, 339, 340, 341, 342, 343, 344, 345, 346, 347, 348, 349, 350, 351, 352, 353, 354, 355, 356, 357, 358, 359, 360, 361, 362, 363, 364, 365, 366, 367, 368, 369, 370, 371, 372, 373, 374, 375, 376, 377, 378, 379, 380, 381, 382, 383, 384, 385, 386, 387, 388, 389, 390, 391, 392, 393, 394, 395, 396, 397, 398, 399, 400, 401, 402, 403, 404, 405, 406, 407, 408, 409, 410, 411, 412, 413, 414, 415, 416, 417, 418, 419, 420, 421, 422, 423, 424, 425, 426, 427, 428, 429, 430, 431, 432, 433, 434, 435, 436, 437, 438, 439, 440, 441, 442, 443, 444, 445, 446, 447, 448, 449, 450, 451, 452, 453, 454, 455, 456, 457, 458, 459, 460, 461, 462, 463, 464, 465, 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511,512, 513, 514, 515,516, 517, 518, 519, 520, 521,522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, or 650 of any of SEQ ID NOs:1-144 (or any derivable range therein).

The polypeptides described herein may be of a fixed length of at least, at most, or exactly 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 121, 122, 123, 124, 125, 126, 127, 128, 129, 130, 131, 132, 133, 134, 135, 136, 137, 138, 139, 140, 141, 142, 143, 144, 145, 146, 147, 148, 149, 150, 151, 152, 153, 154, 155, 156, 157, 158, 159, 160, 161, 162, 163, 164, 165, 166, 167, 168, 169, 170, 171, 172, 173, 174, 175, 176, 177, 178, 179, 180, 181, 182, 183, 184, 185, 186, 187, 188, 189, 190, 191, 192, 193, 194, 195, 196, 197, 198, 199, 200, 201, 202, 203, 204, 205, 206, 207, 208, 209, 210, 211, 212, 213, 214, 215, 216, 217, 218, 219, 220, 221, 222, 223, 224, 225, 226, 227, 228, 229, 230, 231, 232, 233, 234, 235, 236, 237, 238, 239, 240, 241, 242, 243, 244, 245, 246, 247, 248, 249, 250, 300, 400, 500, 550, 1000 or more amino acids (or any derivable range therein).

Substitutional variants typically contain the exchange of one amino acid for another at one or more sites within the protein, and may be designed to modulate one or more properties of the polypeptide, with or without the loss of other functions or properties. Substitutions may be conservative, that is, one amino acid is replaced with one of similar shape and charge. Conservative substitutions are well known in the art and include, for example, the changes of: alanine to serine; arginine to lysine; asparagine to glutamine or histidine; aspartate to glutamate; cysteine to serine; glutamine to asparagine; glutamate to aspartate; glycine to proline; histidine to asparagine or glutamine; isoleucine to leucine or valine; leucine to valine or isoleucine; lysine to arginine; methionine to leucine or isoleucine; phenylalanine to tyrosine, leucine or methionine; serine to threonine; threonine to serine; tryptophan to tyrosine; tyrosine to tryptophan or phenylalanine; and valine to isoleucine or leucine. Alternatively, substitutions may be non-conservative such that a function or activity of the polypeptide is affected. Non-conservative changes typically involve substituting a residue with one that is chemically dissimilar, such as a polar or charged amino acid for a nonpolar or uncharged amino acid, and vice versa.

Proteins may be recombinant, or synthesized in vitro. Alternatively, a non-recombinant or recombinant protein may be isolated from bacteria. It is also contemplated that bacteria containing such a variant may be implemented in compositions and methods. Consequently, a protein need not be isolated.

The term "functionally equivalent codon" is used herein to refer to codons that encode the same amino acid, such as the six codons for arginine or serine, and also refers to codons that encode biologically equivalent amino acids.

It also will be understood that amino acid and nucleic acid sequences may include additional residues, such as additional N- or C-terminal amino acids, or 5' or 3' sequences, respectively, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region.

The following is a discussion based upon changing of the amino acids of a protein to create an equivalent, or even an improved, second-generation molecule. For example, certain amino acids may be substituted for other amino acids in a protein structure without appreciable loss of interactive binding capacity. Structures such as, for example, an enzymatic catalytic domain or interaction components may have amino acid substituted to maintain such function. Since it is the interactive capacity and nature of a protein that defines that protein's biological functional activity, certain amino acid substitutions can be made in a protein sequence, and in its underlying DNA coding sequence, and nevertheless produce a protein with like properties. It is thus contemplated by the inventors that various changes may be made in the DNA sequences of genes without appreciable loss of their biological utility or activity.

In other embodiments, alteration of the function of a polypeptide is intended by introducing one or more substitutions. For example, certain amino acids may be substituted for other amino acids in a protein structure with the intent to modify the interactive binding capacity of interaction components. Structures such as, for example, protein interaction domains, nucleic acid interaction domains, and catalytic sites may have amino acids substituted to alter such function. Since it is the interactive capacity and nature of a protein that defines that protein's biological functional activity, certain amino acid substitutions can be made in a protein sequence, and in its underlying DNA coding sequence, and nevertheless produce a protein with different properties. It is thus contemplated by the inventors that various changes may be made in the DNA sequences of genes with appreciable alteration of their biological utility or activity.

In making such changes, the hydropathic index of amino acids may be considered. The importance of the hydropathic amino acid index in conferring interactive biologic function on a protein is generally understood in the art (Kyte and Doolittle, 1982). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

It also is understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein. It is understood that an amino acid can be substituted for another having a similar hydrophilicity value and still produce a biologically equivalent and immunologically equivalent protein.

As outlined above, amino acid substitutions generally are based on the relative similarity of the amino acid side-chain substituents, for example, their hydrophobicity, hydrophilicity, charge, size, and the like. Exemplary substitutions that take into consideration the various foregoing characteristics are well known and include: arginine and lysine; glutamate and aspartate; serine and threonine; glutamine and asparagine; and valine, leucine and isoleucine.

In specific embodiments, all or part of proteins described herein can also be synthesized in solution or on a solid support in accordance with conventional techniques. Various automatic synthesizers are commercially available and can be used in accordance with known protocols. See, for example, Stewart and Young, (1984); Tam et al., (1983); Merrifield, (1986); and Barany and Merrifield (1979), each incorporated herein by reference. Alternatively, recombinant DNA technology may be employed wherein a nucleotide sequence that encodes a peptide or polypeptide is inserted into an expression vector, transformed or transfected into an appropriate host cell and cultivated under conditions suitable for expression.

One embodiment includes the use of gene transfer to cells, including microorganisms, for the production and/or presentation of proteins. The gene for the protein of interest may be transferred into appropriate host cells followed by culture of cells under the appropriate conditions. A nucleic acid encoding virtually any polypeptide may be employed. The generation of recombinant expression vectors, and the elements included therein, are discussed herein. Alternatively, the protein to be produced may be an endogenous protein normally synthesized by the cell used for protein production.

III. Cells

Certain embodiments relate to cells comprising polypeptides or nucleic acids of the disclosure. In some embodiments the cell is an immune cell or a T cell. "T cell" includes all types of immune cells expressing CD3 including T-helper cells, invariant natural killer T (iNKT) cells, cytotoxic T cells, T-regulatory cells (Treg) gamma-delta T cells, natural-killer (NK) cells, and neutrophils. The T cell may refer to a CD4+ or CD8+ T cell.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), human embryonic kidney (HEK) 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RATI cells, mouse L cells (ATCC No. CCLI.3), HLHepG2 cells, Hut-78, Jurkat, HL-60, NK cell lines (e.g., NKL, NK92, and YTS), and the like.

In some instances, the cell is not an immortalized cell line, but is instead a cell (e.g., a primary cell) obtained from an individual. For example, in some cases, the cell is an immune cell obtained from an individual. As an example, the cell is a T lymphocyte obtained from an individual. As another example, the cell is a cytotoxic cell obtained from an individual. As another example, the cell is a stem cell (e.g., peripheral blood stem cell) or progenitor cell obtained from an individual.

IV. Methods for Modifying Genomic DNA

In certain embodiments, the genomic DNA is modified either to include additional mutations, insertions, or deletions, or to integrate certain molecular constructs of the disclosure so that the constructs are expressed from the genomic DNA. In some embodiments, a nucleic acid encoding a polypeptide of the disclosure is integrated into the genomic DNA of a cell. In some embodiments, a nucleic acid is integrated into a cell via viral transduction, such as gene transfer by lentiviral or retroviral transduction. In some embodiments, genomic DNA is modified by integration of nucleic acid encoding a polypeptide of the present disclosure (e.g., a CAR) into the genome of a host cell via a retroviral vector, a lentiviral vector, or an adeno-associated viral vector.

In some embodiments, the integration is targeted integration. In some embodiments, targeted integration is achieved through the use of a DNA digesting agent/polynucleotide modification enzyme, such as a site-specific recombinase and/or a targeting endonuclease. The term "DNA digesting agent" refers to an agent that is capable of cleaving bonds (i.e. phosphodiester bonds) between the nucleotide subunits of nucleic acids. One specific target is the TRAC (T cell receptor alpha constant) locus. For instance, cells would first be electroporated with a ribonucleoprotein (RNP) complex consisting of Cas9 protein complexed with a single-guide RNA (sgRNA) targeting the TRAC (T cell receptor alpha constant) locus. Fifteen minutes post electroporation, the cells would be treated with AAV6 carrying the HDR template that encodes for the CAR. In another example, double stranded or single stranded DNA comprises the HDR template and is introduced into the cell via electroporation together with the RNP complex.

Therefore, one aspect, the current disclosure includes targeted integration. One way of achieving this is through the use of an exogenous nucleic acid sequence (i.e., a landing pad) comprising at least one recognition sequence for at least one polynucleotide modification enzyme, such as a site-specific recombinase and/or a targeting endonuclease. Site-specific recombinases are well known in the art, and may be generally referred to as invertases, resolvases, or integrases. Non-limiting examples of site-specific recombinases may include lambda integrase, Cre recombinase, FLP recombinase, gamma-delta resolvase, Tn3 resolvase, ΦC31 integrase, Bxb1-integrase, and R4 integrase. Site-specific recombinases recognize specific recognition sequences (or recognition sites) or variants thereof, all of which are well known in the art. For example, Cre recombinases recognize LoxP sites and FLP recombinases recognize FRT sites.

Contemplated targeting endonucleases include zinc finger nucleases (ZFNs), meganucleases, transcription activator-like effector nucleases (TALENs), CRISPR/Cas-like endonucleases, I-Tev1 nucleases or related monomeric hybrids, or artificial targeted DNA double strand break inducing agents. Exemplary targeting endonucleases is further described below. For example, typically, a zinc finger nuclease comprises a DNA binding domain (i.e., zinc finger) and a cleavage domain (i.e., nuclease), both of which are described below. Also included in the definition of polynucleotide modification enzymes are any other useful fusion proteins known to those of skill in the art, such as may comprise a DNA binding domain and a nuclease.

A landing pad sequence is a nucleotide sequence comprising at least one recognition sequence that is selectively bound and modified by a specific polynucleotide modification enzyme such as a site-specific recombinase and/or a targeting endonuclease. In general, the recognition sequence (s) in the landing pad sequence does not exist endogenously in the genome of the cell to be modified. For example, where the cell to be modified is a CHO cell, the recognition sequence in the landing pad sequence is not present in the endogenous CHO genome. The rate of targeted integration may be improved by selecting a recognition sequence for a high efficiency nucleotide modifying enzyme that does not exist endogenously within the genome of the targeted cell. Selection of a recognition sequence that does not exist endogenously also reduces potential off-target integration. In other aspects, use of a recognition sequence that is native in the cell to be modified may be desirable. For example, where multiple recognition sequences are employed in the landing pad sequence, one or more may be exogenous, and one or more may be native.

One of ordinary skill in the art can readily determine sequences bound and cut by site-specific recombinases and/or targeting endonucleases.

Another example of a targeting endonuclease that can be used is an RNA-guided endonuclease comprising at least one nuclear localization signal, which permits entry of the endonuclease into the nuclei of eukaryotic cells. The RNA-guided endonuclease also comprises at least one nuclease domain and at least one domain that interacts with a guiding RNA. An RNA-guided endonuclease is directed to a specific chromosomal sequence by a guiding RNA such that the RNA-guided endonuclease cleaves the specific chromosomal sequence. Since the guiding RNA provides the specificity for the targeted cleavage, the endonuclease of the RNA-guided endonuclease is universal and may be used with different guiding RNAs to cleave different target chromosomal sequences. Discussed in further detail below are exemplary RNA-guided endonuclease proteins. For example, the RNA-guided endonuclease can be a CRISPR/Cas protein or a CRISPR/Cas-like fusion protein, an RNA-guided endonuclease derived from a clustered regularly interspersed short palindromic repeats (CRISPR)/CRISPR-associated (Cas) system.

The targeting endonuclease can also be a meganuclease. Meganucleases are endodeoxyribonucleases characterized by a large recognition site, i.e., the recognition site generally ranges from about 12 base pairs to about 40 base pairs. As a consequence of this requirement, the recognition site generally occurs only once in any given genome. Among meganucleases, the family of homing endonucleases named "LAGLIDADG" has become a valuable tool for the study of genomes and genome engineering. Meganucleases may be targeted to specific chromosomal sequence by modifying their recognition sequence using techniques well known to those skilled in the art. See, for example, Epinat et al., 2003, Nuc. Acid Res., 31(11):2952-62 and Stoddard, 2005, Quarterly Review of Biophysics, pp. 1-47.

Yet another example of a targeting endonuclease that can be used is a transcription activator-like effector (TALE) nuclease. TALEs are transcription factors from the plant pathogen *Xanthomonas* that may be readily engineered to bind new DNA targets. TALEs or truncated versions thereof may be linked to the catalytic domain of endonucleases such as FokI to create targeting endonuclease called TALE nucleases or TALENs. See, e.g., Sanjana et al., 2012, Nature Protocols 7(1):171-192; Bogdanove A J, Voytas D F., 2011, Science, 333(6051):1843-6; Bradley P, Bogdanove A J, Stoddard B L., 2013, Curr Opin Struct Biol., 23(1):93-9.

V. Methods

Aspects of the current disclosure relate to methods for treating cancer, such as melanoma. In further embodiments, the therapeutic receptors (e.g., CARs) described herein may be used for stimulating an immune response. The immune response stimulation may be done in vitro, in vivo, or ex vivo. In some embodiments, the therapeutic receptors described herein are for preventing relapse. The method generally involves genetically modifying a mammalian cell with an expression vector, or a DNA, an RNA (e.g., in vitro transcribed RNA), or an adeno-associated virus (AAV) comprising nucleotide sequences encoding a polypeptide of the disclosure or directly transferring the polypeptide to the cell. The cell can be an immune cell (e.g., a T lymphocyte or NK cell), a stem cell, a progenitor cell, etc. In some embodiments, the cell is a cell described herein.

In some embodiments, the genetic modification is carried out ex vivo. For example, a T lymphocyte, a stem cell, or an NK cell (or cell described herein) is obtained from an individual; and the cell obtained from the individual is genetically modified to express a polypeptide of the disclosure. In some cases, the genetically modified cell is activated ex vivo. In other cases, the genetically modified cell is introduced into an individual (e.g., the individual from whom the cell was obtained); and the genetically modified cell is activated in vivo.

In some embodiments, the methods relate to administration of the cells or peptides described herein for the treatment of a cancer or administration to a person with a cancer. In some embodiments, the cancer is a CD20+ cancer. In some embodiments, the cancer is melanoma.

VI. Additional Therapies

A. Immunotherapy

In some embodiments, the methods comprise administration of a cancer immunotherapy. Cancer immunotherapy (sometimes called immuno-oncology, abbreviated IO) is the use of the immune system to treat cancer. Immunotherapies can be categorized as active, passive or hybrid (active and passive). These approaches exploit the fact that cancer cells often have molecules on their surface that can be detected by the immune system, known as tumor-associated antigens (TAAs); they are often proteins or other macromolecules (e.g. carbohydrates). Active immunotherapy directs the immune system to attack tumor cells by targeting TAAs. Passive immunotherapies enhance existing anti-tumor responses and include the use of monoclonal antibodies, lymphocytes and cytokines. Immunotherapies useful in the methods of the disclosure are described below.

1. Checkpoint Inhibitors and Combination Treatment

Embodiments of the disclosure may include administration of immune checkpoint inhibitors (also referred to as checkpoint inhibitor therapy), which are further described below. The checkpoint inhibitor therapy may be a monotherapy, targeting only one cellular checkpoint proteins or may be combination therapy that targets at least two cellular checkpoint proteins. For example, the checkpoint inhibitor monotherapy may comprise one of: a PD-1, PD-L1, or PD-L2 inhibitor or may comprise one of a CTLA-4, B7-1, or B7-2 inhibitor. The checkpoint inhibitor combination therapy may comprise one of: a PD-1, PD-L1, or PD-L2 inhibitor and, in combination, may further comprise one of a CTLA-4, B7-1, or B7-2 inhibitor. The combination of inhibitors in combination therapy need not be in the same composition, but can be administered either at the same time, at substantially the same time, or in a dosing regimen that includes periodic administration of both of the inhibitors, wherein the period may be a time period described herein.

a. PD-1, PD-L 1, and PD-L2 Inhibitors

PD-1 can act in the tumor microenvironment where T cells encounter an infection or tumor. Activated T cells upregulate PD-1 and continue to express it in the peripheral tissues. Cytokines such as IFN-gamma induce the expression of PD-L1 on epithelial cells and tumor cells. PD-L2 is expressed on macrophages and dendritic cells. The main role of PD-1 is to limit the activity of effector T cells in the periphery and prevent excessive damage to the tissues during an immune response. Inhibitors of the disclosure may block one or more functions of PD-1 and/or PD-L1 activity.

Alternative names for "PD-1" include CD279 and SLEB2. Alternative names for "PD-L1" include B7-H1, B7-4, CD274, and B7-H. Alternative names for "PD-L2" include B7-DC, Btdc, and CD273. In some embodiments, PD-1, PD-L1, and PD-L2 are human PD-1, PD-L1 and PD-L2.

In some embodiments, the PD-1 inhibitor is a molecule that inhibits the binding of PD-1 to its ligand binding partners. In a specific aspect, the PD-1 ligand binding partners are PD-L1 and/or PD-L2. In another embodiment, a PD-L1 inhibitor is a molecule that inhibits the binding of PD-L1 to its binding partners. In a specific aspect, PD-L1 binding partners are PD-1 and/or B7-1. In another embodiment, the PD-L2 inhibitor is a molecule that inhibits the binding of PD-L2 to its binding partners. In a specific aspect, a PD-L2 binding partner is PD-1. The inhibitor may be an antibody, an antigen binding fragment/region thereof, an immunoadhesin, a fusion protein, or oligopeptide. Exemplary antibodies are described in U.S. Pat. Nos. 8,735,553, 8,354,509, and 8,008,449, all incorporated herein by reference. Other PD-1 inhibitors for use in the methods and compositions provided herein are known in the art such as described in U.S. Patent Application Nos. US2014/0294898, US2014/022021, and US2011/0008369, all incorporated herein by reference.

In some embodiments, the PD-1 inhibitor is an anti-PD-1 antibody (e.g., a human antibody, a humanized antibody, or a chimeric antibody). In some embodiments, the anti-PD-1 antibody is selected from the group consisting of nivolumab, pembrolizumab, and pidilizumab. In some embodiments, the PD-1 inhibitor is an immunoadhesin (e.g., an immunoadhesin comprising an extracellular or PD-1 binding portion of PD-L1 or PD-L2 fused to a constant region (e.g., an Fc region of an immunoglobulin sequence). In some embodiments, the PD-L1 inhibitor comprises AMP-224. Nivolumab, also known as MDX-1106-04, MDX-1106, ONO-4538, BMS-936558, and OPDIVO®, is an anti-PD-1 antibody described in WO2006/121168. Pembrolizumab, also known as MK-3475, Merck 3475, lambrolizumab, KEYTRUDA®, and SCH-900475, is an anti-PD-1 antibody described in WO2009/114335. Pidilizumab, also known as CT-011, hBAT, or hBAT-1, is an anti-PD-1 antibody described in WO2009/101611. AMP-224, also known as B7-DCIg, is a PD-L2-Fc fusion soluble receptor described in WO2010/027827 and WO2011/066342. Additional PD-1 inhibitors include MEDI0680, also known as AMP-514, and REGN2810.

In some embodiments, the immune checkpoint inhibitor is a PD-L1 inhibitor such as Durvalumab, also known as MEDI4736, atezolizumab, also known as MPDL3280A, avelumab, also known as MSB00010118C, MDX-1105, BMS-936559, or combinations thereof. In certain aspects, the immune checkpoint inhibitor is a PD-L2 inhibitor such as rHIgM12B7.

In some embodiments, the inhibitor comprises the heavy and light chain CDRs or VRs of nivolumab, pembrolizumab, or pidilizumab. Accordingly, in one embodiment, the inhibitor comprises the CDR1, CDR2, and CDR3 domains of the VH region of nivolumab, pembrolizumab, or pidilizumab, and the CDR1, CDR2 and CDR3 domains of the VL region of nivolumab, pembrolizumab, or pidilizumab. In another embodiment, the antibody competes for binding with and/or binds to the same epitope on PD-1, PD-L1, or PD-L2 as the above-mentioned antibodies. In another embodiment, the antibody has at least about 70, 75, 80, 85, 90, 95, 97, or 99% (or any derivable range therein) variable region amino acid sequence identity with the above-mentioned antibodies.

b. CTLA-4, B7-1, and B7-2 Inhibitors

Another immune checkpoint that can be targeted in the methods provided herein is the cytotoxic T-lymphocyte-associated protein 4 (CTLA-4), also known as CD152. The complete cDNA sequence of human CTLA-4 has the Genbank accession number L15006. CTLA-4 is found on the surface of T cells and acts as an "off" switch when bound to B7-1 (CD80) or B7-2 (CD86) on the surface of antigen-presenting cells. CTLA-4 is a member of the immunoglobulin superfamily that is expressed on the surface of Helper T cells and transmits an inhibitory signal to T cells. CTLA-4 is similar to the T-cell co-stimulatory protein, CD28, and both molecules bind to B7-1 and B7-2 on antigen-presenting cells. CTLA-4 transmits an inhibitory signal to T cells, whereas CD28 transmits a stimulatory signal. Intracellular CTLA-4 is also found in regulatory T cells and may be important to their function. T cell activation through the T cell receptor and CD28 leads to increased expression of CTLA-4, an inhibitory receptor for B7 molecules. Inhibitors of the disclosure may block one or more functions of CTLA-4, B7-1, and/or B7-2 activity. In some embodiments, the inhibitor blocks the CTLA-4 and B7-1 interaction. In some embodiments, the inhibitor blocks the CTLA-4 and B7-2 interaction.

In some embodiments, the immune checkpoint inhibitor is an anti-CTLA-4 antibody (e.g., a human antibody, a humanized antibody, or a chimeric antibody), an antigen binding fragment thereof, an immunoadhesin, a fusion protein, or oligopeptide.

Anti-human-CTLA-4 antibodies (or VH and/or VL domains derived therefrom) suitable for use in the present methods can be generated using methods well known in the art. Alternatively, art recognized anti-CTLA-4 antibodies can be used. For example, the anti-CTLA-4 antibodies disclosed in: U.S. Pat. No. 8,119,129, WO 01/14424, WO 98/42752; WO 00/37504 (CP675,206, also known as tremelimumab; formerly ticilimumab), U.S. Pat. No. 6,207,156; Hurwitz et al., 1998; can be used in the methods disclosed herein. The teachings of each of the aforementioned publications are hereby incorporated by reference. Antibodies that compete with any of these art-recognized antibodies for binding to CTLA-4 also can be used. For example, a humanized CTLA-4 antibody is described in International Patent Application No. WO2001/014424, WO2000/037504, and U.S. Pat. No. 8,017,114; all incorporated herein by reference.

A further anti-CTLA-4 antibody useful as a checkpoint inhibitor in the methods and compositions of the disclosure is ipilimumab (also known as 10OD1, MDX-010, MDX-101, and Yervoy®) or antigen binding fragments and variants thereof (see, e.g., WO0 1/14424).

In some embodiments, the inhibitor comprises the heavy and light chain CDRs or VRs of tremelimumab or ipilimumab. Accordingly, in one embodiment, the inhibitor comprises the CDR1, CDR2, and CDR3 domains of the VH region of tremelimumab or ipilimumab, and the CDR1, CDR2 and CDR3 domains of the VL region of tremelimumab or ipilimumab. In another embodiment, the antibody competes for binding with and/or binds to the same epitope on PD-1, B7-1, or B7-2 as the above-mentioned antibodies. In another embodiment, the antibody has at least about 70, 75, 80, 85, 90, 95, 97, or 99% (or any derivable range therein) variable region amino acid sequence identity with the above-mentioned antibodies.

2. Inhibition of Co-Stimulatory Molecules

In some embodiments, the immunotherapy comprises an inhibitor of a co-stimulatory molecule. In some embodiments, the inhibitor comprises an inhibitor of B7-1 (CD80), B7-2 (CD86), CD28, ICOS, OX40 (TNFRSF4), 4-1BB (CD137; TNFRSF9), CD40L (CD40LG), GITR (TNFRSF18), and combinations thereof. Inhibitors include inhibitory antibodies, polypeptides, compounds, and nucleic acids.

3. Dendritic Cell Therapy

Dendritic cell therapy provokes anti-tumor responses by causing dendritic cells to present tumor antigens to lymphocytes, which activates them, priming them to kill other cells that present the antigen. Dendritic cells are antigen presenting cells (APCs) in the mammalian immune system. In cancer treatment, they aid cancer antigen targeting. One example of cellular cancer therapy based on dendritic cells is sipuleucel-T.

One method of inducing dendritic cells to present tumor antigens is by vaccination with autologous tumor lysates or short peptides (small parts of protein that correspond to the protein antigens on cancer cells). These peptides are often given in combination with adjuvants (highly immunogenic substances) to increase the immune and anti-tumor responses. Other adjuvants include proteins or other chemicals that attract and/or activate dendritic cells, such as granulocyte macrophage colony-stimulating factor (GM-CSF).

Dendritic cells can also be activated in vivo by making tumor cells express GM-CSF. This can be achieved by either genetically engineering tumor cells to produce GM-CSF or by infecting tumor cells with an oncolytic virus that expresses GM-CSF.

Another strategy is to remove dendritic cells from the blood of a patient and activate them outside the body. The dendritic cells are activated in the presence of tumor antigens, which may be a single tumor-specific peptide/protein or a tumor cell lysate (a solution of broken down tumor cells). These cells (with optional adjuvants) are infused and provoke an immune response.

Dendritic cell therapies include the use of antibodies that bind to receptors on the surface of dendritic cells. Antigens can be added to the antibody and can induce the dendritic cells to mature and provide immunity to the tumor.

4. Cytokine Therapy

Cytokines are proteins produced by many types of cells present within a tumor. They can modulate immune responses. The tumor often employs them to allow it to grow and reduce the immune response. These immune-modulating effects allow them to be used as drugs to provoke an immune response. Two commonly used cytokines are interferons and interleukins.

Interferons are produced by the immune system. They are usually involved in anti-viral response, but also have use for cancer. They fall in three groups: type I (IFN$\alpha$ and IFN$\beta$), type II (IFN$\gamma$) and type III (IFN$\lambda$).

Interleukins have an array of immune system effects. IL-2 is an exemplary interleukin cytokine therapy.

5. Adoptive T-Cell Therapy

Adoptive T cell therapy is a form of passive immunization by the transfusion of T-cells (adoptive cell transfer). They are found in blood and tissue and usually activate when they find foreign pathogens. Specifically, they activate when the T-cell's surface receptors encounter cells that display parts of foreign proteins on their surface antigens. These can be either infected cells, or antigen presenting cells (APCs). They are found in normal tissue and in tumor tissue, where they are known as tumor infiltrating lymphocytes (TILs). They are activated by the presence of APCs such as dendritic cells that present tumor antigens. Although these cells can attack the tumor, the environment within the tumor is highly immunosuppressive, preventing immune-mediated tumor death.

Multiple ways of producing and obtaining tumor targeted T-cells have been developed. T-cells specific to a tumor antigen can be removed from a tumor sample (TILs) or filtered from blood. Subsequent activation and culturing is performed ex vivo, with the results reinfused. Tumor targeted T cells can be generated through gene therapy. Tumor targeted T cells can be expanded by exposing the T cells to tumor antigens.

In some embodiments, therapeutic cells used in adoptive cell therapies express chimeric antigen receptors (CARs). CARs are fusion proteins that are commonly composed of an extracellular antigen-binding domain (which may be an scFv), an extracellular spacer, a transmembrane domain, costimulatory signaling regions (the number of which varies depending on the specific CAR design), and a CD3-zeta signaling domain/endodomain.

In some embodiments, therapeutic cells used in adoptive cell therapies express engineered T-cell receptors (TCRs), which are heterologous TCR molecules that target tumor antigens. Immune cells, including T cells and natural killer (NK) cells, can be engineered to express CARs or TCRs by a variety of methods known in the art, including viral transduction, DNA nucleofection, and RNA nucleofection. Binding of the CAR or TCR to the antigen target can activate human T cells expressing the CAR or TCR, which may result in killing of the cell bearing the antigen or some other immunological response.

In some embodiments, the cells comprise a cancer-specific CAR or TCR. The term "cancer-specific" in the context of CAR or TCR polypeptides refers to a polypeptide that has an antigen binding specificity for a cancer-specific molecule, such as a cancer-specific antigen. In some embodiments, the cancer-specific CAR and another CAR are on separate polypeptides.

B. Oncolytic Virus

In some embodiments, the additional therapy comprises an oncolytic virus. An oncolytic virus is a virus that preferentially infects and kills cancer cells. As the infected cancer cells are destroyed by oncolysis, they release new infectious virus particles or virions to help destroy the remaining tumor. Oncolytic viruses are thought not only to cause direct destruction of the tumor cells, but also to stimulate host anti-tumor immune responses for long-term immunotherapy.

C. Polysaccharides

In some embodiments, the additional therapy comprises polysaccharides. Certain compounds found in mushrooms, primarily polysaccharides, can up-regulate the immune system and may have anti-cancer properties. For example, beta-glucans such as lentinan have been shown in laboratory studies to stimulate macrophage, NK cells, T cells and immune system cytokines and have been investigated in clinical trials as immunologic adjuvants.

D. Neoantigens

In some embodiments, the additional therapy comprises targeting of neoantigen mutations. Many tumors express mutations. These mutations potentially create new targetable antigens (neoantigens) for use in T cell immunotherapy. The presence of CD8+ T cells in cancer lesions, as identified using RNA sequencing data, is higher in tumors with a high mutational burden. The level of transcripts associated with cytolytic activity of natural killer cells and T cells positively correlates with mutational load in many human tumors.

E. Chemotherapies

In some embodiments, the additional therapy comprises a chemotherapy. Suitable classes of chemotherapeutic agents include (a) Alkylating Agents, such as nitrogen mustards (e.g., mechlorethamine, cylophosphamide, ifosfamide, melphalan, chlorambucil), ethylenimines and methylmelamines (e.g., hexamethylmelamine, thiotepa), alkyl sulfonates (e.g., busulfan), nitrosoureas (e.g., carmustine, lomustine, chlorozoticin, streptozocin) and triazines (e.g., dicarbazine), (b) Antimetabolites, such as folic acid analogs (e.g., methotrexate), pyrimidine analogs (e.g., 5-fluorouracil, floxuridine, cytarabine, azauridine) and purine analogs and related materials (e.g., 6-mercaptopurine, 6-thioguanine, pentostatin), (c) Natural Products, such as vinca alkaloids (e.g., vinblastine, vincristine), epipodophylotoxins (e.g., etoposide, teniposide), antibiotics (e.g., dactinomycin, daunorubicin, doxorubicin, bleomycin, plicamycin and mitoxanthrone), enzymes (e.g., L-asparaginase), and biological response modifiers (e.g., Interferon-a), and (d) Miscellaneous Agents, such as platinum coordination complexes (e.g., cisplatin, carboplatin), substituted ureas (e.g., hydroxyurea), methylhydiazine derivatives (e.g., procarbazine), and adreocortical suppressants (e.g., taxol and mitotane). In some embodiments, cisplatin is a particularly suitable chemotherapeutic agent.

Cisplatin has been widely used to treat cancers such as, for example, metastatic testicular or ovarian carcinoma, advanced bladder cancer, head or neck cancer, cervical cancer, lung cancer or other tumors. Cisplatin is not absorbed orally and must therefore be delivered via other routes such as, for example, intravenous, subcutaneous, intratumoral or intraperitoneal injection. Cisplatin can be used alone or in combination with other agents, with efficacious doses used in clinical applications including about 15 mg/m2 to about 20 mg/m2 for 5 days every three weeks for a total of three courses being contemplated in certain embodiments. In some embodiments, the amount of cisplatin delivered to the cell and/or subject in conjunction with the construct comprising an Egr-1 promoter operatively linked to a polynucleotide encoding the therapeutic polypeptide is less than the amount that would be delivered when using cisplatin alone.

Other suitable chemotherapeutic agents include antimicrotubule agents, e.g., Paclitaxel ("Taxol") and doxorubicin hydrochloride ("doxorubicin"). The combination of an Egr-1 promoter/TNFα construct delivered via an adenoviral vector and doxorubicin was determined to be effective in overcoming resistance to chemotherapy and/or TNF-α, which suggests that combination treatment with the construct and doxorubicin overcomes resistance to both doxorubicin and TNF-α.

Doxorubicin is absorbed poorly and is preferably administered intravenously. In certain embodiments, appropriate intravenous doses for an adult include about 60 mg/m2 to about 75 mg/m2 at about 21-day intervals or about 25 mg/m2 to about 30 mg/m2 on each of 2 or 3 successive days repeated at about 3 week to about 4 week intervals or about 20 mg/m2 once a week. The lowest dose should be used in elderly patients, when there is prior bone-marrow depression caused by prior chemotherapy or neoplastic marrow invasion, or when the drug is combined with other myelopoietic suppressant drugs.

Nitrogen mustards are another suitable chemotherapeutic agent useful in the methods of the disclosure. A nitrogen mustard may include, but is not limited to, mechlorethamine (HN2), cyclophosphamide and/or ifosfamide, melphalan (L-sarcolysin), and chlorambucil. Cyclophosphamide (CYTOXAN®) is available from Mead Johnson and NEOSTAR® is available from Adria), is another suitable chemotherapeutic agent. Suitable oral doses for adults include, for example, about 1 mg/kg/day to about 5 mg/kg/day, intravenous doses include, for example, initially about 40 mg/kg to about 50 mg/kg in divided doses over a period of about 2 days to about 5 days or about 10 mg/kg to about 15 mg/kg about every 7 days to about 10 days or about 3 mg/kg to about 5 mg/kg twice a week or about 1.5 mg/kg/day to about 3 mg/kg/day. Because of adverse gastrointestinal effects, the intravenous route is preferred. The drug also sometimes is administered intramuscularly, by infiltration or into body cavities.

Additional suitable chemotherapeutic agents include pyrimidine analogs, such as cytarabine (cytosine arabinoside), 5-fluorouracil (fluouracil; 5-FU) and floxuridine (fluorode-oxyuridine; FudR). 5-FU may be administered to a subject in a dosage of anywhere between about 7.5 to about 1000 mg/m2. Further, 5-FU dosing schedules may be for a variety of time periods, for example up to six weeks, or as determined by one of ordinary skill in the art to which this disclosure pertains.

Gemcitabine diphosphate (GEMZAR®, Eli Lilly & Co., "gemcitabine"), another suitable chemotherapeutic agent, is recommended for treatment of advanced and metastatic pancreatic cancer, and will therefore be useful in the present disclosure for these cancers as well.

The amount of the chemotherapeutic agent delivered to the patient may be variable. In one suitable embodiment, the chemotherapeutic agent may be administered in an amount effective to cause arrest or regression of the cancer in a host, when the chemotherapy is administered with the construct. In other embodiments, the chemotherapeutic agent may be administered in an amount that is anywhere between 2 to 10,000 fold less than the chemotherapeutic effective dose of the chemotherapeutic agent. For example, the chemotherapeutic agent may be administered in an amount that is about 20 fold less, about 500 fold less or even about 5000 fold less than the chemotherapeutic effective dose of the chemotherapeutic agent. The chemotherapeutics of the disclosure can be tested in vivo for the desired therapeutic activity in combination with the construct, as well as for determination of effective dosages. For example, such compounds can be tested in suitable animal model systems prior to testing in humans, including, but not limited to, rats, mice, chicken, cows, monkeys, rabbits, etc. In vitro testing may also be used to determine suitable combinations and dosages, as described in the examples.

F. Radiotherapy

In some embodiments, the additional therapy or prior therapy comprises radiation, such as ionizing radiation. As used herein, "ionizing radiation" means radiation comprising particles or photons that have sufficient energy or can produce sufficient energy via nuclear interactions to produce ionization (gain or loss of electrons). An exemplary and preferred ionizing radiation is an x-radiation. Means for delivering x-radiation to a target tissue or cell are well known in the art.

In some embodiments, the amount of ionizing radiation is greater than 20 Gy and is administered in one dose. In some embodiments, the amount of ionizing radiation is 18 Gy and is administered in three doses. In some embodiments, the amount of ionizing radiation is at least, at most, or exactly 2, 4, 6, 8, 10, 15, 16, 17, 18, 19, 20, 21, 22, 23, 24, 25, 26, 27, 18, 19, 30, 31, 32, 33, 34, 35, 36, 37, 38, 39, 40, 41, 42, 43, 44, 45, 46, 47, 48, 49, or 40 Gy (or any derivable range therein). In some embodiments, the ionizing radiation is administered in at least, at most, or exactly 1, 2, 3, 4, 5, 6, 7, 8, 9, or 10 does (or any derivable range therein). When more than one dose is administered, the does may be about 1, 4, 8, 12, or 24 hours or 1, 2, 3, 4, 5, 6, 7, or 8 days or 1, 2, 3, 4, 5, 6, 7, 8, 9, 10, 12, 14, or 16 weeks apart, or any derivable range therein.

In some embodiments, the amount of IR may be presented as a total dose of IR, which is then administered in fractionated doses. For example, in some embodiments, the total dose is 50 Gy administered in 10 fractionated doses of 5 Gy each. In some embodiments, the total dose is 50-90 Gy, administered in 20-60 fractionated doses of 2-3 Gy each. In some embodiments, the total dose of IR is at least, at most, or about 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 101, 102, 103, 104, 105, 106, 107, 108, 109, 110, 111, 112, 113, 114, 115, 116, 117, 118, 119, 120, 125, 130, 135, 140, or 150 (or any derivable range therein). In some embodiments, the total dose is administered in fractionated doses of at least, at most, or exactly 1, 2, 3, 4, 5, 6, 7, 8, 9, 10, 12, 14, 15, 20, 25, 30, 35, 40, 45, or 50 Gy (or any derivable range therein. In some embodiments, at least, at most, or exactly 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 fractionated doses are administered (or any derivable range therein). In some embodiments, at least, at most, or exactly 1, 2, 3, 4, 5, 6, 7, 8, 9, 10, 11, or 12 (or any derivable range therein) fractionated doses are administered per day. In some embodiments, at least, at most, or exactly 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 (or any derivable range therein) fractionated doses are administered per week.

G. Surgery

Approximately 60% of persons with cancer will undergo surgery of some type, which includes preventative, diagnostic or staging, curative, and palliative surgery. Curative surgery includes resection in which all or part of cancerous tissue is physically removed, excised, and/or destroyed and may be used in conjunction with other therapies, such as the treatment of the present embodiments, chemotherapy, radiotherapy, hormonal therapy, gene therapy, immunotherapy, and/or alternative therapies. Tumor resection refers to physical removal of at least part of a tumor. In addition to tumor resection, treatment by surgery includes laser surgery, cryosurgery, electrosurgery, and microscopically-controlled surgery (Mohs' surgery).

Upon excision of part or all of cancerous cells, tissue, or tumor, a cavity may be formed in the body. Treatment may be accomplished by perfusion, direct injection, or local application of the area with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

H. Other Agents

It is contemplated that other agents may be used in combination with certain aspects of the present embodiments to improve the therapeutic efficacy of treatment. These additional agents include agents that affect the upregulation of cell surface receptors and GAP junctions, cytostatic and differentiation agents, inhibitors of cell adhesion, agents that increase the sensitivity of the hyperproliferative cells to apoptotic inducers, or other biological agents. Increases in intercellular signaling by elevating the number of GAP junctions would increase the anti-hyperproliferative effects on the neighboring hyperproliferative cell population. In other embodiments, cytostatic or differentiation agents can be used in combination with certain aspects of the present embodiments to improve the anti-hyperproliferative efficacy of the treatments. Inhibitors of cell adhesion are contemplated to improve the efficacy of the present embodiments. Examples of cell adhesion inhibitors are focal adhesion kinase (FAKs) inhibitors and Lovastatin. It is further contemplated that other agents that increase the sensitivity of a hyperproliferative cell to apoptosis, such as the antibody c225, could be used in combination with certain aspects of the present embodiments to improve the treatment efficacy.

It is contemplated that a cancer treatment may exclude any of the cancer treatments described herein. Furthermore, embodiments of the disclosure include patients that have been previously treated for a therapy described herein, are currently being treated for a therapy described herein, or have not been treated for a therapy described herein. In some embodiments, the patient is one that has been determined to be resistant to a therapy described herein. In some embodiments, the patient is one that has been determined to be sensitive to a therapy described herein.

VII. Pharmaceutical Compositions

The present disclosure includes methods for treating disease and modulating immune responses in a subject in need thereof. The disclosure includes cells that may be in the form of a pharmaceutical composition that can be used to induce or modify an immune response.

Administration of the compositions according to the current disclosure will typically be via any common route. This includes, but is not limited to parenteral, orthotopic, intradermal, subcutaneous, orally, transdermally, intramuscular, intraperitoneal, intraperitoneally, intraorbitally, by implantation, by inhalation, intraventricularly, intranasally or intravenous injection. In some embodiments, compositions of the present disclosure (e.g., compositions comprising cells expressing a therapeutic receptor).

Typically, compositions and therapies of the disclosure are administered in a manner compatible with the dosage formulation, and in such amount as will be therapeutically effective and immune modifying. The quantity to be administered depends on the subject to be treated. Precise amounts of active ingredient required to be administered depend on the judgment of the practitioner.

The manner of application may be varied widely. Any of the conventional methods for administration of pharmaceutical compositions comprising cellular components are applicable. The dosage of the pharmaceutical composition will depend on the route of administration and will vary according to the size and health of the subject.

In many instances, it will be desirable to have multiple administrations of at most about or at least about 3, 4, 5, 6, 7, 8, 9, 10 or more. The administrations may range from 2-day to 12-week intervals, more usually from one to two week intervals. The course of the administrations may be followed by assays for alloreactive immune responses and T cell activity.

The phrases “pharmaceutically acceptable” or “pharmacologically acceptable” refer to molecular entities and compositions that do not produce an adverse, allergic, or other untoward reaction when administered to an animal, or human. As used herein, “pharmaceutically acceptable carrier” includes any and all solvents, dispersion media, coatings, antibacterial and antifungal agents, isotonic and absorption delaying agents, and the like. The use of such media and agents for pharmaceutical active substances is well known in the art. Except insofar as any conventional media or agent is incompatible with the active ingredients, its use in immunogenic and therapeutic compositions is contemplated. The pharmaceutical compositions of the current disclosure are pharmaceutically acceptable compositions.

The compositions of the disclosure can be formulated for parenteral administration, e.g., formulated for injection via the intravenous, intramuscular, sub-cutaneous, or even intraperitoneal routes. Typically, such compositions can be prepared as injectables, either as liquid solutions or suspensions and the preparations can also be emulsified.

The pharmaceutical forms suitable for injectable use include sterile aqueous solutions or dispersions; formulations including sesame oil, peanut oil, or aqueous propylene glycol. It also should be stable under the conditions of manufacture and storage and must be preserved against the contaminating action of microorganisms, such as bacteria and fungi.

Sterile injectable solutions are prepared by incorporating the active ingredients (i.e. cells of the disclosure) in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above.

An effective amount of a composition is determined based on the intended goal. The term “unit dose” or “dosage” refers to physically discrete units suitable for use in a subject, each unit containing a predetermined quantity of the composition calculated to produce the desired responses discussed herein in association with its administration, i.e., the appropriate route and regimen. The quantity to be administered, both according to number of treatments and unit dose, depends on the result and/or protection desired. Precise amounts of the composition also depend on the judgment of the practitioner and are peculiar to each individual. Factors affecting dose include physical and clinical state of the subject, route of administration, intended goal of treatment (alleviation of symptoms versus cure), and potency, stability, and toxicity of the particular composition. Upon formulation, solutions will be administered in a manner compatible with the dosage formulation and in such amount as is therapeutically or prophylactically effective. The formulations are easily administered in a variety of dosage forms, such as the type of injectable solutions described above.

The compositions and related methods of the present disclosure, particularly administration of a composition of the disclosure may also be used in combination with the administration of additional therapies such as the additional therapeutics described herein or in combination with other traditional therapeutics known in the art.

The therapeutic compositions and treatments disclosed herein may precede, be co-current with and/or follow another treatment or agent by intervals ranging from minutes to weeks. In embodiments where agents are applied separately to a cell, tissue or organism, one would generally ensure that a significant period of time did not expire between the time of each delivery, such that the therapeutic agents would still be able to exert an advantageously combined effect on the cell, tissue or organism. For example, in such instances, it is contemplated that one may contact the cell, tissue or organism with two, three, four or more agents or treatments substantially simultaneously (i.e., within less than about a minute). In other aspects, one or more therapeutic agents or treatments may be administered or provided within 1 minute, 5 minutes, 10 minutes, 20 minutes, 30 minutes, 45 minutes, 60 minutes, 2 hours, 3 hours, 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 22 hours, 23 hours, 24 hours, 25 hours, 26 hours, 27 hours, 28 hours, 29 hours, 30 hours, 31 hours, 32 hours, 33 hours, 34 hours, 35 hours, 36 hours, 37 hours, 38 hours, 39 hours, 40 hours, 41 hours, 42 hours, 43 hours, 44 hours, 45 hours, 46 hours, 47 hours, 48 hours, 1 day, 2 days, 3 days, 4 days, 5 days, 6 days, 7 days, 8 days, 9 days, 10 days, 11 days, 12 days, 13 days, 14 days, 15 days, 16 days, 17 days, 18 days, 19 days, 20 days, 21 days, 1 week, 2 weeks, 3 weeks, 4 weeks, 5 weeks, 6 weeks, 7 weeks, or 8 weeks or more, and any range derivable therein, prior to and/or after administering another therapeutic agent or treatment.

The treatments may include various “unit doses.” Unit dose is defined as containing a predetermined-quantity of the therapeutic composition. The quantity to be administered, and the particular route and formulation, is within the skill of determination of those in the clinical arts. A unit dose need not be administered as a single injection but may comprise continuous infusion over a set period of time. In some embodiments, a unit dose comprises a single administrable dose.

The quantity to be administered, both according to number of treatments and unit dose, depends on the treatment effect desired. An effective dose is understood to refer to an amount necessary to achieve a particular effect. In the practice in certain embodiments, it is contemplated that doses in the range from 10 mg/kg to 200 mg/kg can affect the protective capability of these agents. Thus, it is contemplated that doses include doses of about 0.1, 0.5, 1, 5, 10, 15, 20, 25, 30, 35, 40, 45, 50, 55, 60, 65, 70, 75, 80, 85, 90, 100, 105, 110, 115, 120, 125, 130, 135, 140, 145, 150, 155, 160, 165, 170, 175, 180, 185, 190, 195, and 200, 300, 400, 500, 1000 μg/kg, mg/kg, μg/day, or mg/day or any range derivable therein. Furthermore, such doses can be administered at multiple times during a day, and/or on multiple days, weeks, or months.

In some embodiments, the therapeutically effective or sufficient amount of the immune checkpoint inhibitor, such as an antibody and/or microbial modulator, that is administered to a human will be in the range of about 0.01 to about 50 mg/kg of patient body weight whether by one or more administrations. In some embodiments, the therapy used is about 0.01 to about 45 mg/kg, about 0.01 to about 40 mg/kg, about 0.01 to about 35 mg/kg, about 0.01 to about 30 mg/kg, about 0.01 to about 25 mg/kg, about 0.01 to about 20 mg/kg, about 0.01 to about 15 mg/kg, about 0.01 to about 10 mg/kg, about 0.01 to about 5 mg/kg, or about 0.01 to about 1 mg/kg administered daily, for example. In one embodiment, a therapy described herein is administered to a subject at a dose of about 100 mg, about 200 mg, about 300 mg, about 400 mg, about 500 mg, about 600 mg, about 700 mg, about 800 mg, about 900 mg, about 1000 mg, about 1100 mg, about 1200 mg, about 1300 mg or about 1400 mg on day 1 of 21-day cycles. The dose may be administered as a single dose or as multiple doses (e.g., 2 or 3 doses), such as infusions. The progress of this therapy is easily monitored by conventional techniques.

In certain embodiments, the effective dose of the pharmaceutical composition is one which can provide a blood level of about 1 μM to 150 μM. In another embodiment, the effective dose provides a blood level of about 4 μM to 100 μM.; or about 1 μM to 100 μM; or about 1 μM to 50 μM; or about 1 μM to 40 μM; or about 1 μM to 30 μM; or about 1 μM to 20 μM; or about 1 μM to 10 μM; or about 10 μM to 150 μM; or about 10 μM to 100 μM; or about 10 μM to 50 μM; or about 25 μM to 150 μM; or about 25 μM to 100 μM; or about 25 μM to 50 μM; or about 50 μM to 150 μM; or about 50 μM to 100 μM (or any range derivable therein). In other embodiments, the dose can provide the following blood level of the agent that results from a therapeutic agent being administered to a subject: about, at least about, or at most about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100 M or any range derivable therein. In certain embodiments, the therapeutic agent that is administered to a subject is metabolized in the body to a metabolized therapeutic agent, in which case the blood levels may refer to the amount of that agent. Alternatively, to the extent the therapeutic agent is not metabolized by a subject, the blood levels discussed herein may refer to the unmetabolized therapeutic agent.

Precise amounts of the therapeutic composition also depend on the judgment of the practitioner and are peculiar to each individual. Factors affecting dose include physical and clinical state of the patient, the route of administration, the intended goal of treatment (alleviation of symptoms versus cure) and the potency, stability and toxicity of the particular therapeutic substance or other therapies a subject may be undergoing.

It will be understood by those skilled in the art and made aware that dosage units of μg/kg or mg/kg of body weight can be converted and expressed in comparable concentration units of μg/ml or mM (blood levels), such as 4 μM to 100 μM. It is also understood that uptake is species and organ/tissue dependent. The applicable conversion factors and physiological assumptions to be made concerning uptake and concentration measurement are well-known and would permit those of skill in the art to convert one concentration measurement to another and make reasonable comparisons and conclusions regarding the doses, efficacies and results described herein.

VIII. Therapeutic Methods

The compositions of the disclosure may be used for in vivo, in vitro, or ex vivo administration. The route of administration of the composition may be, for example, intracutaneous, subcutaneous, intravenous, local, topical, and intraperitoneal administrations.

In some embodiments, the disclosed methods are directed to methods for treating cancer. The cancer may be a solid tumor, metastatic cancer, or non-metastatic cancer. In certain embodiments, the cancer may originate in the bladder, blood, bone, bone marrow, brain, breast, urinary, cervix, esophagus, duodenum, small intestine, large intestine, colon, rectum, anus, gum, head, kidney, liver, lung, nasopharynx, neck, ovary, prostate, skin, stomach, testis, tongue, or uterus.

The cancer may specifically be of one or more of the following histological types, though it is not limited to these: undifferentiated carcinoma, bladder, blood, bone, brain, breast, urinary, esophageal, thymomas, duodenum, colon, rectal, anal, gum, head, kidney, soft tissue, liver, lung, nasopharynx, neck, ovary, prostate, skin, stomach, testicular, tongue, uterine, thymic, cutaneous squamous-cell, noncolorectal gastrointestinal, colorectal, melanoma, Merkel-cell, renal-cell, cervical, hepatocellular, urothelial, non-small cell lung, head and neck, endometrial, esophagogastric, small-cell lung mesothelioma, ovarian, esophogogastric, glioblastoma, adrencorical, vueal, pancreatic, germ-cell, giant and spindle cell carcinoma; small cell carcinoma; papillary carcinoma; squamous cell carcinoma; lymphoepithelial carcinoma; basal cell carcinoma; pilomatrix carcinoma; transitional cell carcinoma; papillary transitional cell carcinoma; adenocarcinoma; cholangiocarcinoma; hepatocellular carcinoma; combined hepatocellular carcinoma and cholangiocarcinoma; trabecular adenocarcinoma; adenoid cystic carcinoma; adenocarcinoma in adenomatous polyp; adenocarcinoma, familial polyposis coli; solid carcinoma; branchiolo-alveolar adenocarcinoma; papillary adenocarcinoma; chromophobe carcinoma; acidophil carcinoma; oxyphilic adenocarcinoma; basophil carcinoma; clear cell adenocarcinoma; granular cell carcinoma; follicular adenocarcinoma; papillary and follicular adenocarcinoma; nonencapsulating sclerosing carcinoma; adrenal cortical carcinoma; endometroid carcinoma; skin appendage carcinoma; apocrine adenocarcinoma; sebaceous adenocarcinoma; ceruminous adenocarcinoma; mucoepidermoid carcinoma; cystadenocarcinoma; papillary cystadenocarcinoma; papillary serous cystadenocarcinoma; mucinous cystadenocarcinoma; mucinous adenocarcinoma; signet ring cell carcinoma; infiltrating duct carcinoma; medullary carcinoma; lobular carcinoma; inflammatory carcinoma; Paget's disease, mammary; acinar cell carcinoma; adenosquamous carcinoma; thymoma; thecoma; androblastoma; sertoli cell carcinoma; malignant melanoma; amelanotic melanoma; superficial spreading melanoma; epithelioid cell melanoma; sarcoma; mesenchymal (e.g., fibrosarcoma; fibrous histiocytoma; myxosarcoma; liposarcoma; leiomyosarcoma; rhabdomyosarcoma; embryonal rhabdomyosarcoma; alveolar rhabdomyosarcoma; stromal sarcoma; mullerian mixed tumor; nephroblastoma; hepatoblastoma; carcinosarcoma; dysgerminoma; embryonal carcinoma; choriocarcinoma; mesonephroma; hemangiosarcoma; Kaposi's sarcoma; lymphangiosarcoma; osteosarcoma; juxtacortical osteosarcoma; chondrosarcoma; mesenchymal chondrosarcoma; giant cell tumor of bone; Ewing's sarcoma; ameloblastic odontosarcoma; ameloblastic fibrosarcoma; chordoma; ependymoma; astrocytoma; protoplasmic astrocytoma; fibrillary astrocytoma; astroblastoma; oligodendroglioma; oligodendroblastoma; primitive neuroectodermal; cerebellar sarcoma; ganglioneuroblastoma; neuroblastoma; retinoblastoma; olfactory neurogenic tumor; neurofibrosarcoma; paragranuloma); or hematopoietic (e.g., multiple myeloma; mast cell sarcoma; immunoproliferative small intestinal disease; leukemia; lymphoid leukemia; plasma cell leukemia; erythroleukemia; lymphosarcoma cell leukemia; myeloid leukemia; basophilic leukemia; eosinophilic leukemia; monocytic leukemia; mast cell leukemia; megakaryoblastic leukemia; myeloid sarcoma; hairy cell leukemia).

IX. Sequences

The amino acid sequence of example chimeric polypeptides and CAR molecules useful in the methods and compositions of the present disclosure are provided in Table 1 below.

| Description | Sequence | SEQ ID NO: |
|---|---|---|
| Leu16 VL | DIVLTQSPAILSASPGEKVTMTCRASSSVNYMDWYQKKPG SSPKPWIYATSNLASGVPARFSGSGSGTSYSLTISRVEAEDA ATYYCQQWSFNPPTFGGGTKLEIK | 1 |
| Leu16 VH | EVQLQQSGAELVKPGASVKMSCKASGYTFTSYNMHWVKQ TPGQGLEWIGAIYPGNGDTSYNQKFKGKATLTADKSSSTA YMQLSSLTSEDSADYYCARSNYYGSSYWFFDVWGAGTTV TVSS | 2 |
| Rituximab VL | QIVLSQSPAILSASPGEKVTMTCRASSSVSYIHWFQQKPGSS PKPWIYATSNLASGVPVRFSGSGSGTSYSLTISRVEAEDAAT YYCQQWTSNPPTFGGGTKLEIK | 3 |
| Rituximab VH | QVQLQQPGAELVKPGASVKMSCKASGYTFTSYNMHWVK QTPGRGLEWIGAIYPGNGDTSYNQKFKGKATLTADKSSST AYMQLSSLTSEDSAVYYCARSTYYGGDWYFNVWGAGTT VTVSS | 4 |
| RFR-LCDR VL | QIVLSQSPAILSASPGEKVTMTCRASSSVNYMDWFQQKPGS SPKPWIYATSNLASGVPVRFSGSGSGTSYSLTISRVEAEDAA TYYCQQWSFNPPTFGGGTKLEIK | 5 |
| RFR-LCDR VH | QVQLQQPGAELVKPGASVKMSCKASGYTFTSYNMHWVK QTPGRGLEWIGAIYPGNGDTSYNQKFKGKATLTADKSSST AYMQLSSLTSEDSAVYYCARSNYYGSSYWFFDVWGAGTT VTVSS | 6 |
| LFR-RCDR VL | DIVLTQSPAILSASPGEKVTMTCRASSSVSYIHWYQKKPGSS PKPWIYATSNLASGVPARFSGSGSGTSYSLTISRVEAEDAAT YYCQQWTSNPPTFGGGTKLEIK | 7 |
| LFR-RCDR VH | EVQLQQSGAELVKPGASVKMSCKASGYTFTSYNMHWVKQ TPGQGLEWIGAIYPGNGDTSYNQKFKGKATLTADKSSSTA YMQLSSLTSEDSADYYCARSrYYGGDWYFNVWGAGTTVT VSS | 8 |
| Leu16 HCDR1 | SYNMH | 9 |
| Leu16 HCDR2 | AIYPGNGDTSYNQKFKG | 10 |
| Leu16 HCDR3 | SNYYGSSYWFFDV | 11 |
| Leu16 LCDR1 | RASSSVNYMD | 12 |
| Leu16 LCDR2 | ATSNLAS | 13 |
| Leu16 LCDR3 | QQWSFNPPT | 14 |
| Leu16 HFR1 | EVQLQQSGAELVKPGASVKMSCKASGYTFT | 15 |
| Leu16 HFR2 | WVKQTPGQGLEWIG | 16 |
| Leu16 HFR3 | KATLTADKSSSTAYMQLSSLTSEDSADYYCAR | 17 |
| Leu16 HFR4 | WGAGTTVTVSS | 18 |
| Leu16 LFR1 | DIVLTQSPAILSASPGEKVTMTC | 19 |
| Leu16 LFR2 | WYQKKPGSSPKPWIY | 20 |
| Leu16 LFR3 | GVPARFSGSGSGTSYSLTISRVEAEDAATYYC | 21 |
| Leu16 LFR4 | FGGGTKLEIK | 22 |
| Rituximab HCDR1 | SYNMH | 9 |
| Rituximab HCDR2 | AIYPGNGDTSYNQKFKG | 10 |

-continued

| Description | Sequence | SEQ ID NO: |
|---|---|---|
| Rituximab HCDR3 | STYYGGDWYFNV | 23 |
| Rituximab LCDR1 | RASSSVSYIH | 24 |
| Rituximab LCDR2 | ATSNLAS | 13 |
| Rituximab LCDR3 | QQWTSNPPT | 25 |
| Rituximab HFR1 | QVQLQQPGAELVKPGASVKMSCKASGYTFT | 26 |
| Rituximab HFR2 | WVKQTPGRGLEWIG | 27 |
| Rituximab HFR3 | KATLTADKSSSTAYMQLSSLTSEDSAVYYCAR | 28 |
| Rituximab HFR4 | WGAGTTVTVSS | 18 |
| Rituximab LFR1 | QIVLSQSPAILSASPGEKVTMTC | 29 |
| Rituximab LFR2 | WFQQKPGSSPKPWIY | 30 |
| Rituximab LFR3 | GVPVRFSGSGSGTSYSLTISRVEAEDAATYYC | 31 |
| Rituximab LFR4 | FGGGTKLEIK | 22 |
| RFR-LCDR HCDR1 | SYNMH | 9 |
| RFR-LCDR HCDR2 | AIYPGNGDTSYNQKFKG | 10 |
| RFR-LCDR HCDR3 | SNYYGSSYWFFDV | 11 |
| RFR-LCDR LCDR1 | RASSSVNYMD | 12 |
| RFR-LCDR LCDR2 | ATSNLAS | 13 |
| RFR-LCDR LCDR3 | QQWSFNPPT | 14 |
| RFR-LCDR HFR1 | QVQLQQPGAELVKPGASVKMSCKASGYTFT | 26 |
| RFR-LCDR HFR2 | WVKQTPGRGLEWIG | 27 |
| RFR-LCDR HFR3 | KATLTADKSSSTAYMQLSSLTSEDSAVYYCAR | 28 |
| RFR-LCDR HFR4 | WGAGTTVTVSS | 18 |
| RFR-LCDR LFR1 | QIVLSQSPAILSASPGEKVTMTC | 29 |
| RFR-LCDR LFR2 | WFQQKPGSSPKPWIY | 30 |

-continued

| Description | Sequence | SEQ ID NO: |
|---|---|---|
| RFR-LCDR LFR3 | GVPVRFSGSGSGTSYSLTISRVEAEDAATYYC | 31 |
| RFR-LCDR LFR4 | FGGGTKLEIK | 22 |
| LFR-RCDR HCDR1 | SYNMH | 9 |
| LFR-RCDR HCDR2 | AIYPGNGDTSYNQKFKG | 10 |
| LFR-RCDR HCDR3 | STYYGGDWYFNV | 23 |
| LFR-RCDR LCDR1 | RASSSVSYIH | 24 |
| LFR-RCDR LCDR2 | ATSNLAS | 13 |
| LFR-RCDR LCDR3 | QQWTSNPPT | 25 |
| LFR-RCDR HFR1 | EVQLQQSGAELVKPGASVKMSCKASGYTFT | 15 |
| LFR-RCDR HFR2 | WVKQTPGQGLEWIG | 16 |
| LFR-RCDR HFR3 | KATLTADKSSSTAYMQLSSLTSEDSADYYCAR | 17 |
| LFR-RCDR HFR4 | WGAGTTVTVSS | 18 |
| LFR-RCDR LFR1 | DIVLTQSPAILSASPGEKVTMTC | 19 |
| LFR-RCDR LFR2 | WYQKKPGSSPKPWIY | 20 |
| LFR-RCDR LFR3 | GVPARFSGSGSGTSYSLTISRVEAEDAATYYC | 21 |
| LFR-RCDR LFR4 | FGGGTKLEIK | 22 |
| RFR-LCDR (pYC1917)-Murine kappa chain signal sequence-RFR-LCDR VL-scFv linker-RFR-LCDR VH-IgG4 hinge/CH2/CH3 (L235E, N297Q)-CD28 transmembrane-CD28 cytoplasmic (gg)-GGG-CD3-zeta-cytoplasmic-T2A-EGFRt | METDTLLLWVLLLWVPGSTGQIVLSQSPAILSASPGEKVTM TCRASSSVNYMDWFQQKPGSSPKPWIYATSNLASGVPVRF SGSGSGTSYSLTISRVEAEDAATYYCQQWSFNPPTFGGGTK LEIKGSTSGGGSGGGSGGGGSSQVQLQQPGAELVKPGASV KMSCKASGYTFTSYNMHWVKQTPGRGLEWIGAIYPGNGD TSYNQKFKGKATLTADKSSSTAYMQLSSLTSEDSAVYYCA RSNYYGSSYWFFDVWGAGTTVTVSSESKYGPPCPPCPAPEF EGGPSVFLFPPKPKDTLMISRTPEVTCVVVDVSQEDPEVQF NWYVDGVEVHNAKTKPREEQFQSTYRVVSVLTVLHQDWL NGKEYKCKVSNKGLPSSIEKTISKAKGQPREPQVYTLPPSQ EEMTKNQVSLTCLVKGFYPSDIAVEWESNGQPENNYKTTP PVLDSDGSFFLYSRLTVDKSRWQEGNVFSCSVMHEALHNH YTQKSLSLSLGKMFWVLVVVGGVLACYSLLVTVAFIIFWV RSKRSRGGHSDYMNMTPRRPGPTRKHYQPYAPPRDFAAY RSGGGRVKFSRSADAPAYQQGQNQLYNELNLGRREEYDV LDKRRGRDPEMGGKPRRKNPQEGLYNELQKDKMAEAYSE IGMKGERRRGKGHDGLYQGLSTATKDTYDALHMQALPPR LEGGGEGRGSLLTCGDVEENPGPRMLLLVTSLLLCELPHPA FLLIPRKVCNGIGIGEFKDSLSINATNIKHFKNCTSISGDLHIL PVAFRGDSFTHTPPLDPQELDILKTVKEITGFLLIQAWPENR TDLHAFENLEIIRGRTKQHGQFSLAVVSLNITSLGLRSLKEIS DGDVIISGNKNLCYANTINWKKLFGTSGQKTKIISNRGENS CKATGQVCHALCSPEGCWGPEPRDCVSCRNVSRGRECVD KCNLLEGEPREFVENSECIQCHPECLPQAMNITCTGRGPDN CIQCAHYIDGPHCVKTCPAGVMGENNTLVWKYADAGHVC HLCHPNCTYGCTGPGLEGCPTNGPKIPSIATGMVGALLLLL VVALGIGLFM* | 33 |

-continued

| Description | Sequence | SEQ ID NO: |
|---|---|---|
| LFR-RCDR<br>(pYC1918);<br>Murine kappa<br>chain signal<br>sequence-<br>LFR-RCDR VL-<br>scFv linker-<br>LFR-RCDR<br>VH-IgG4<br>hinge/CH2/CH3<br>(L235E,<br>N297Q)-<br>CD28<br>transmembrane-<br>CD28<br>cytoplasmic<br>(gg)-GGG-<br>CD3-zeta-<br>cytoplasmic-<br>T2A-EGFRt | METDTLLLWVLLLWVPGSTGDIVLTQSPAILSASPGEKVTM<br>TCRASSSVSYIHWYQKKPGSSPKPWIYATSNLASGVPARFS<br>GSGSGTSYSLTISRVEAEDAATYYCQQWTSNPPTFGGGTKL<br>EIKGSTSGGGSGGGSGGGGSSEVQLQQSGAELVKPGASVK<br>MSCKASGYTFTSYNMHWVKQTPGQGLEWIGAIYPGNGDT<br>SYNQKFKGKATLTADKSSSTAYMQLSSLTSEDSADYYCAR<br>STYYGGDWYFNVWGAGTTVTVSSESKYGPPCPPCPAPEFE<br>GGPSVFLFPPKPKDTLMISRTPEVTCVVVDVSQEDPEVQFN<br>WYVDGVEVHNAKTKPREEQFQSTYRVVSVLTVLHQDWLN<br>GKEYKCKVSNKGLPSSIEKTISKAKGQPREPQVYTLPPSQEE<br>MTKNQVSLTCLVKGFYPSDIAVEWESNGQPENNYKTTPPV<br>LDSDGSFFLYSRLTVDKSRWQEGNVFSCSVMHEALHNHYT<br>QKSLSLSLGKMFWVLVVVGGVLACYSLLVTVAFIIFWVRS<br>KRSRGGHSDYMNMTPRRPGPTRKHYQPYAPPRDFAAYRS<br>GGGRVKFSRSADAPAYQQGQNQLYNELNLGRREEYDVLD<br>KRRGRDPEMGGKPRRKNPQEGLYNELQKDKMAEAYSEIG<br>MKGERRRGKGHDGLYQGLSTATKDTYDALHMQALPPRLE<br>GGGEGRGSLLTCGDVEENPGPRMLLLVTSLLLCELPHPAFL<br>LIPRKVCNGIGIGEFKDSLSINATNIKHFKNCTSISGDLHILPV<br>AFRGDSFTHTPPLDPQELDILKTVKEITGFLLIQAWPENRTD<br>LHAFENLEIIRGRTKQHGQFSLAVVSLNITSLGLRSLKEISDG<br>DVIISGNKNLCYANTINWKKLFGTSGQKTKIISNRGENSCK<br>ATGQVCHALCSPEGCWGPEPRDCVSCRNVSRGRECVDKC<br>NLLEGEPREFVENSECIQCHPECLPQAMNITCTGRGPDNCIQ<br>CAHYIDGPHCVKTCPAGVMGENNTLVWKYADAGHVCHL<br>CHPNCTYGCTGPGLEGCPTNGPKIPSIATGMVGALLLLLVV<br>ALGIGLFM* | 34 |
| RFR-LCDR<br>(RFR-LCDR<br>VL-scFv<br>linker-RFR-<br>LCDR VH-<br>IgG4<br>hinge/CH2/CH3<br>(L235E,<br>N297Q)-<br>CD28<br>transmembrane-<br>CD28<br>cytoplasmic<br>(gg)-GGG-<br>CD3-zeta-<br>cytoplasmic-<br>T2A-EGFRt) | QIVLSQSPAILSASPGEKVTMTCRASSSVNYMDWFQQKPGS<br>SPKPWIYATSNLASGVPVRFSGSGSGTSYSLTISRVEAEDAA<br>TYYCQQWSFNPPTFGGGTKLEIKGSTSGGGSGGGSGGGGS<br>SQVQLQQPGAELVKPGASVKMSCKASGYTFTSYNMHWVK<br>QTPGRGLEWIGAIYPGNGDTSYNQKFKGKATLTADKSSST<br>AYMQLSSLTSEDSAVYYCARSNYYGSSYWFFDVWGAGTT<br>VTVSSESKYGPPCPPCPAPEFEGGPSVFLFPPKPKDTLMISRT<br>PEVTCVVVDVSQEDPEVQFNWYVDGVEVHNAKTKPREEQ<br>FQSTYRVVSVLTVLHQDWLNGKEYKCKVSNKGLPSSIEKTI<br>SKAKGQPREPQVYTLPPSQEEMTKNQVSLTCLVKGFYPSDI<br>AVEWESNGQPENNYKTTPPVLDSDGSFFLYSRLTVDKSRW<br>QEGNVFSCSVMHEALHNHYTQKSLSLSLGKMFWVLVVVG<br>GVLACYSLLVTVAFIIFWVRSKRSRGGHSDYMNMTPRRPG<br>PTRKHYQPYAPPRDFAAYRSGGGRVKFSRSADAPAYQQGQ<br>NQLYNELNLGRREEYDVLDKRRGRDPEMGGKPRRKNPQE<br>GLYNELQKDKMAEAYSEIGMKGERRRGKGHDGLYQGLST<br>ATKDTYDALHMQALPPRLEGGGEGRGSLLTCGDVEENPGP<br>RMLLLVTSLLLCELPHPAFLLIPRKVCNGIGIGEFKDSLSINA<br>TNIKHFKNCTSISGDLHILPVAFRGDSFTHTPPLDPQELDILK<br>TVKEITGFLLIQAWPENRTDLHAFENLEIIRGRTKQHGQFSL<br>AVVSLNITSLGLRSLKEISDGDVIISGNKNLCYANTINWKKL<br>FGTSGQKTKIISNRGENSCKATGQVCHALCSPEGCWGPEPR<br>DCVSCRNVSRGRECVDKCNLLEGEPREFVENSECIQCHPEC<br>LPQAMNITCTGRGPDNCIQCAHYIDGPHCVKTCPAGVMGE<br>NNTLVWKYADAGHVCHLCHPNCTYGCTGPGLEGCPTNGP<br>KIPSIATGMVGALLLLLVVALGIGLFM* | 42 |
| LFR-RCDR<br>(LFR-RCDR<br>VL-scFv<br>linker-LFR-<br>RCDRVH-<br>IgG4<br>hinge/CH2/CH3<br>(L235E,<br>N297Q)-<br>CD28<br>transmembrane-<br>CD28<br>cytoplasmic<br>(gg)-GGG-<br>CD3-zeta-<br>cytoplasmic-<br>T2A-EGFRt) | DIVLTQSPAILSASPGEKVTMTCRASSSVSYIHWYQKKPGSS<br>PKPWIYATSNLASGVPARFSGSGSGTSYSLTISRVEAEDAAT<br>YYCQQWTSNPPTFGGGTKLEIKGSTSGGGSGGGSGGGGSS<br>EVQLQQSGAELVKPGASVKMSCKASGYTFTSYNMHWVKQ<br>TPGQGLEWIGAIYPGNGDTSYNQKFKGKATLTADKSSSTA<br>YMQLSSLTSEDSADYYCARSTYYGGDWYFNVWGAGTTVT<br>VSSESKYGPPCPPCPAPEFEGGPSVFLFPPKPKDTLMISRTPE<br>VTCVVVDVSQEDPEVQFNWYVDGVEVHNAKTKPREEQFQ<br>STYRVVSVLTVLHQDWLNGKEYKCKVSNKGLPSSIEKTISK<br>AKGQPREPQVYTLPPSQEEMTKNQVSLTCLVKGFYPSDIAV<br>EWESNGQPENNYKTTPPVLDSDGSFFLYSRLTVDKSRWQE<br>GNVFSCSVMHEALHNHYTQKSLSLSLGKMFWVLVVVGGV<br>LACYSLLVTVAFIIFWVRSKRSRGGHSDYMNMTPRRPGPTR<br>KHYQPYAPPRDFAAYRSGGGRVKFSRSADAPAYQQGQNQ<br>LYNELNLGRREEYDVLDKRRGRDPEMGGKPRRKNPQEGL<br>YNELQKDKMAEAYSEIGMKGERRRGKGHDGLYQGLSTAT<br>KDTYDALHMQALPPRLEGGGEGRGSLLTCGDVEENPGPR<br>MLLLVTSLLLCELPHPAFLLIPRKVCNGIGIGEFKDSLSINAT<br>NIKHFKNCTSISGDLHILPVAFRGDSFTHTPPLDPQELDILKT<br>VKEITGFLLIQAWPENRTDLHAFENLEIIRGRTKQHGQFSLA<br>VVSLNITSLGLRSLKEISDGDVIISGNKNLCYANTINWKKLF | 43 |

-continued

| Description | Sequence | SEQ ID NO: |
|---|---|---|
| | GTSGQKTKIISNRGENSCKATGQVCHALCSPEGCWGPEPRD CVSCRNVSRGRECVDKCNLLEGEPREFVENSECIQCHPECL PQAMNITCTGRGPDNCIQCAHYIDGPHCVKTCPAGVMGEN NTLVWKYADAGHVCHLCHPNCTYGCTGPGLEGCPTNGPK IPSIATGMVGALLLLLVVALGIGLFM* | |
| Murine kappa chain signal sequence | METDTLLLWVLLLWVPGSTG | 35 |
| scFv Linker | GSTSGGGSGGGSGGGGSS | 32 |
| IgG4 hinge/CH2/CH3 | ESKYGPPCPPCPAPEFEGGPSVFLFPPKPKDTLMISRTPEVTC VVVDVSQEDPEVQFNWYVDGVEVHNAKTKPREEQFQSTY RVVSVLTVLHQDWLNGKEYKCKVSNKGLPSSIEKTISKAK GQPREPQVYTLPPSQEEMTKNQVSLTCLVKGFYPSDIAVE WESNGQPENNYKTTPPVLDSDGSFFLYSRLTVDKSRWQEG NVFSCSVMHEALHNHYTQKSLSLSLGK | 36 |
| CD28 transmembrane | MFWVLVVVGGVLACYSLLVTVAFIIFWV | 37 |
| CD28 cytoplasmic (gg) | RSKRSRGGHSDYMNMTPRRPGPTRKHYQPYAPPRDFAAY RS | 38 |
| CD3-zeta cytoplasmic | RVKFSRSADAPAYQQGQNQLYNELNLGRREEYDVLDKRR GRDPEMGGKPRRKNPQEGLYNELQKDKMAEAYSEIGMKG ERRRGKGHDGLYQGLSTATKDTYDALHMQALPPR | 39 |
| T2A | LEGGGEGRGSLLTCGDVEENPGPR | 40 |
| EGFRt | MLLLVTSLLLCELPHPAFLLIPRKVCNGIGIGEFKDSLSINAT NIKHFKNCTSISGDLHILPVAFRGDSFTHTPPLDPQELDILKT VKEITGFLLIQAWPENRTDLHAFENLEIIRGRTKQHGQFSLA VVSLNITSLGLRSLKEISDGDVIISGNKNLCYANTINWKKLF GTSGQKTKIISNRGENSCKATGQVCHALCSPEGCWGPEPRD CVSCRNVSRGRECVDKCNLLEGEPREFVENSECIQCHPECL PQAMNITCTGRGPDNCIQCAHYIDGPHCVKTCPAGVMGEN NTLVWKYADAGHVCHLCHPNCTYGCTGPGLEGCPTNGPK IPSIATGMVGALLLLLVVALGIGLFM | 41 |
| KM8138 (huKM666L) VH | QVQLQESGPGLVKPSQTLSITCTVSGFSLASYNIHWVRQPP GKGLEWLGVIWAGGSTNYNSALMSRLTISKDNSKNQVFLK MSSLTAADTAVYYCAKRSDDYSWFAYWGQGTLVTVSS | 108 |
| KM8138 (huKM666L) VL | ENQMTQSPSSLSASVGDRVTMTCRASSSVSSSYLHWYQQK SGKAPKVWIYSTSNLASGVPSRFSGSGSGTDYTLTISSLQPE DFATYYCQQYSGYPITFGQGTKVEIK | 109 |
| KM8138 (huKM666L) HCDR1 | SYNIH | 110 |
| KM8138 (huKM666L) HCDR2 | VIWAGGSTNYNSALMS | 111 |
| KM8138 (huKM666L) HCDR3 | RSDDYSWFAY | 112 |
| KM8138 (huKM666L) LCDR1 | RASSSVSSSYLH | 113 |
| KM8138 (huKM666L) LCDR2 | STSNLAS | 114 |
| KM8138 (huKM666L) LCDR3 | QQYSGYPIT | 115 |

-continued

| Description | Sequence | SEQ ID NO: |
|---|---|---|
| KM8138 (huKM666L) HFR1 | QVQLQESGPGLVKPSQTLSITCTVSGFSLA | 116 |
| KM8138 (huKM666L) HFR2 | WVRQPPGKGLEWLG | 117 |
| KM8138 (huKM666L) HFR3 | RLTISKDNSKNQVFLKMSSLTAADTAVYYCAK | 118 |
| KM8138 (huKM666L) HFR4 | WGQGTLVTVSS | 119 |
| KM8138 (huKM666L) LFR1 | ENQMTQSPSSLSASVGDRVTMTC | 120 |
| KM8138 (huKM666L) LFR2 | WYQQKSGKAPKVWIY | 121 |
| KM8138 (huKM666L) LFR3 | GVPSRFSGSGSGTDYTLTISSLQPEDFATYYC | 122 |
| KM8138 (huKM666L) LFR4 | FGQGTKVEIK | 123 |
| 14g2a VH | EVQLLQSGPELEKPGASVMISCKASGSSFTGYNMNWVRQN IGKSLEWIGAIDPYYGGTSYNQKFKGRATLTVDKSSSTAYM HLKSLTSEDSAVYYCVSGMEYWGQGTSVTVSS | 124 |
| 14g2a VL | DVVMTQTPLSLPVSLGDQASISCRSSQSLVHRNGNTYLHW YLQKPGQSPKLLIHKVSNRFSGVPDRFSGSGSGTDFTLKISR VEAEDLGVYFCSQSTHVPPLTFGAGTKLELKRA | 125 |
| 14g2a HCDR1 | GYNMN | 126 |
| 14g2a HCDR2 | AIDPYYGGTSYNQKFKG | 127 |
| 14g2a HCDR3 | GMEY | 128 |
| 14g2a LCDR1 | RSSQSLVHRNGNTYLH | 129 |
| 14g2a LCDR2 | KVSNRFS | 130 |
| 14g2a LCDR3 | SQSTHVPPLT | 131 |
| 14g2a HFR1 | EVQLLQSGPELEKPGASVMISCKASGSSFT | 132 |
| 14g2a HFR2 | WVRQNIGKSLEWIG | 133 |
| 14g2a HFR3 | RATLTVDKSSSTAYMHLKSLTSEDSAVYYCVS | 134 |
| 14g2a HFR4 | WGQGTSVTVSS | 135 |
| 14g2a LFR1 | DVVMTQTPLSLPVSLGDQASISC | 136 |
| 14g2a LFR2 | WYLQKPGQSPKLLIH | 137 |
| 14g2a LFR3 | GVPDRFSGSGSGTDFTLKISRVEAEDLGVYFC | 138 |
| 14g2a LFR4 | FGAGTKLELKRA | 139 |
| 14g2a FR + KM8138 CDR VH | EVQLLQSGPELEKPGASVMISCKASGSSFTSYNIHWVRQNI GKSLEWIGVIWAGGSTNYNSALMSRATLTVDKSSSTAYMH LKSLTSEDSAVYYCVSRSDDYSWFAYWGQGTSVTVSS | 140 |
| 14g2a FR + KM8138 CDR VL | DVVMTQTPLSLPVSLGDQASISCRASSSVSSSYLHWYLQKP GQSPKLLIHSTSNLASGVPDRFSGSGSGTDFTLKISRVEAED LGVYFCQQYSGYPITFGAGTKLELKRA | 141 |

-continued

| Description | Sequence | SEQ ID NO: |
|---|---|---|
| KM8138 FR + 14g2a CDR VH | QVQLQESGPGLVKPSQTLSITCTVSGFSLAGYNMNWVRQP PGKGLEWLGAIDPYYGGTSYNQKFKGRLTISKDNSKNQVF LKMSSLTAADTAVYYCAKGMEYWGQGTLVTVSS | 143 |
| KM8138 FR + 14g2a CDR VL | ENQMTQSPSSLSASVGDRVTMTCRSSQSLVHRNGNTYLHW YQQKSGKAPKVWIYKVSNRFSGVPSRFSGSGSGTDYTLTIS SLQPEDFATYYCSQSTHVPPLTFGQGTKVEIK | 144 |

X. Examples

The following examples are included to demonstrate preferred embodiments of the disclosure. It should be appreciated by those of skill in the art that the techniques disclosed in the examples which follow represent techniques discovered by the inventor to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure. The Examples should not be construed as limiting in any way. The contents of all cited references (including literature references, issued patents, published patent applications, and GenBank Accession numbers as cited throughout this application) are hereby expressly incorporated by reference. When definitions of terms in documents that are incorporated by reference herein conflict with those used herein, the definitions used herein govern.

Example 1: Torsionally Modified CARs

Figure 2:
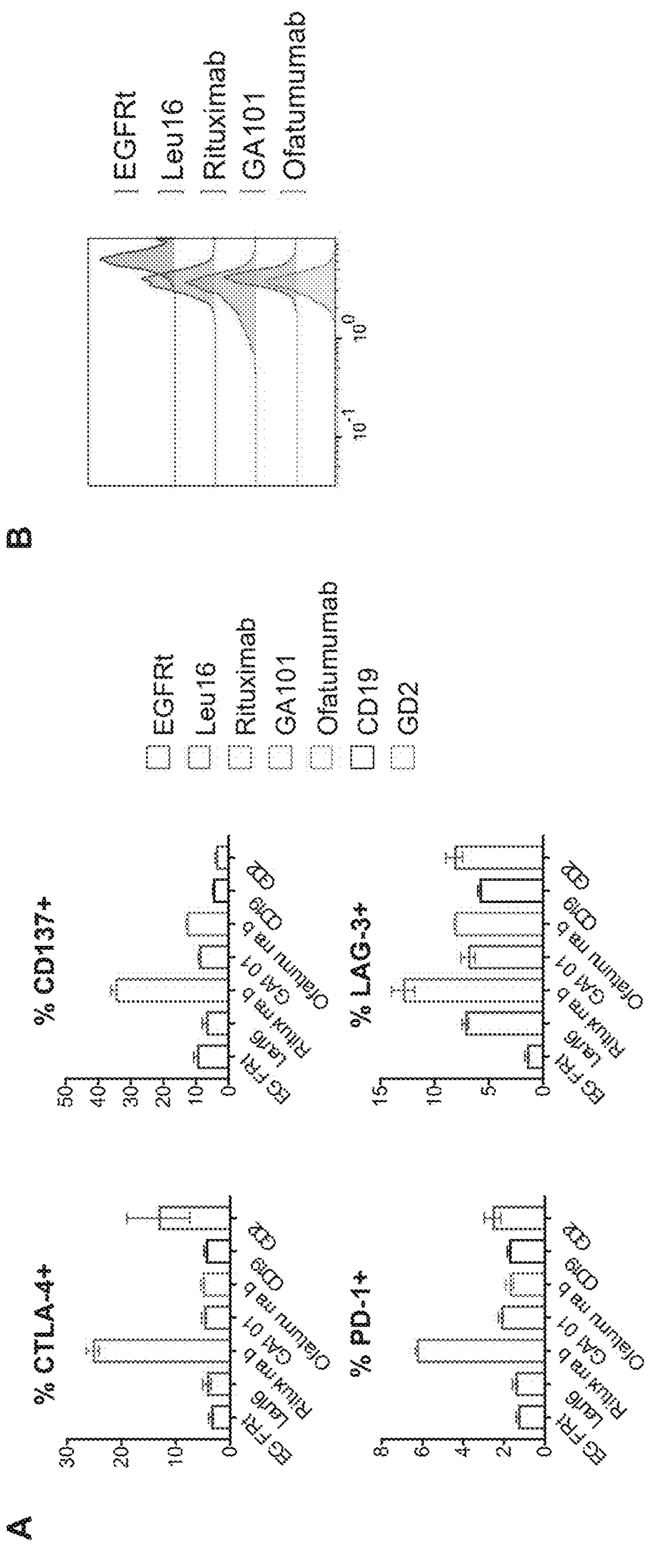
FIG. 2A-B. Rituximab-derived CD20 CAR shows antigen-independent CAR signaling, resulting in (A) upregulation of activation and exhaustion markers and (B) T-cell proliferation in the absence of antigen stimulation. The CD19 CAR and GD2 CAR were included as a negative and positive control, respectively, for tonic signaling.

The observation that some CARs can signal in the absence of antigen stimulation suggests the possibility that these receptors may adopt a native protein conformation that is conducive to signal transduction. A corollary of this hypothesis is that altering the conformation of the CAR protein may influence tonic signaling propensity, and potentially also the intensity of antigen-dependent CAR signaling. Here, the inventors report the finding that the anti-tumor activity of CAR-T cells can be tuned by inserting alanines between the transmembrane and cytoplasmic signaling domains of CARs (FIG. 1). The insertion of each alanine is expected to cause about a 1090 turn. It was hypothesized that one could significantly improve the in vivo antitumor efficacy of a second-generation CD20 CAR containing CD28 co-stimulatory domain by inserting alanines between the transmembrane and cytoplasmic domains of the CAR (FIG. 2; results confirmed in follow-up study shown in FIG. 8). In addition to CD20, it is contemplated that this design can be incorporated into other CARs. In some embodiments, the alanine insertions are incorporated into GD2 CARs that are useful for treating neuroblastoma.

Example 2: Hybrid CARs with Increased Efficacy

Figure 3:
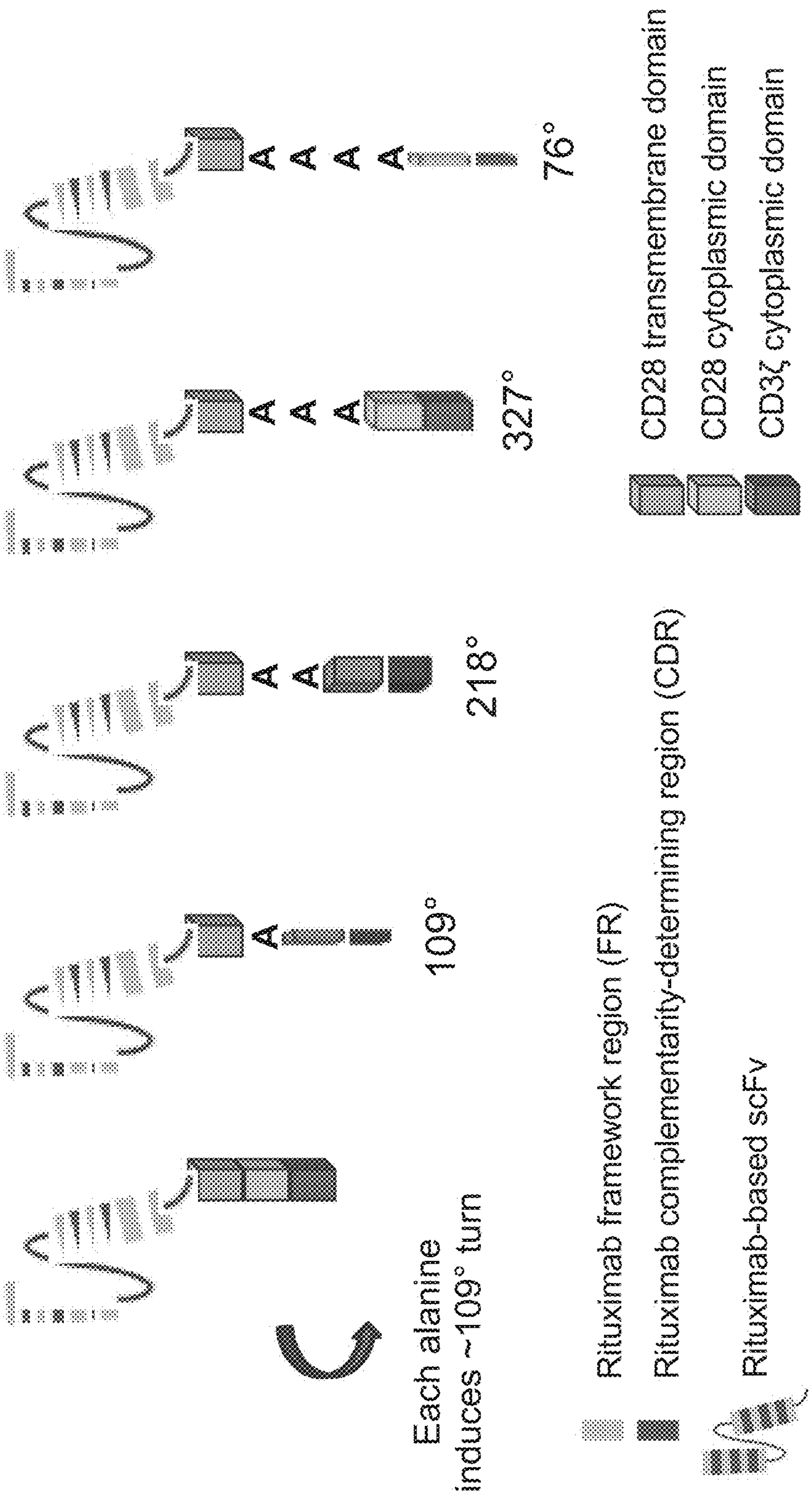
FIG. 3. Schematic of alanine insertion to cause structural turning of CAR molecules.
Figure 4:
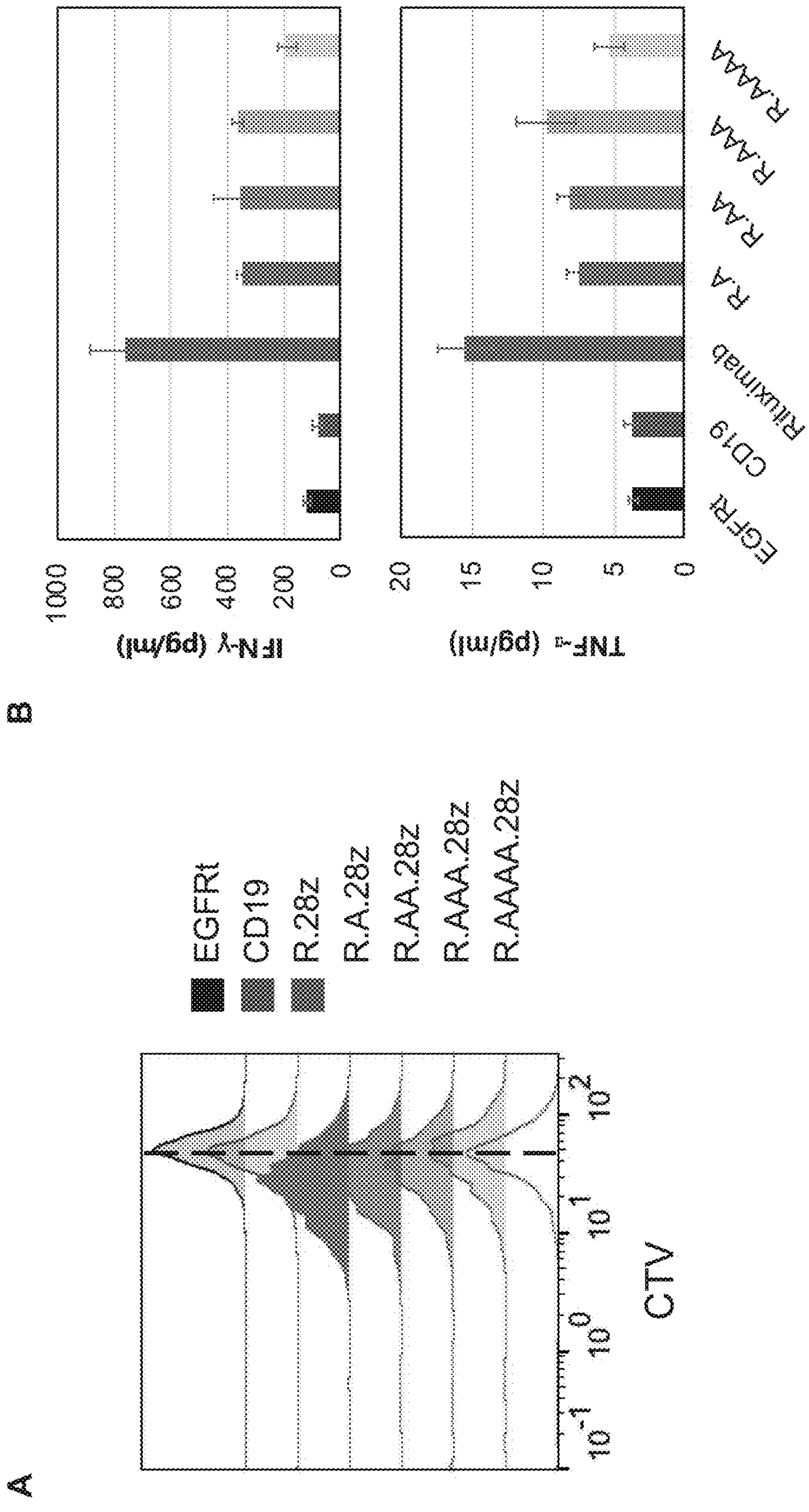
FIG. 4. Alanine insertion calibrates CAR tonic signaling intensity. (A) T-cell proliferation as quantified by CellTrace Violoet dye dilution and (B) cytokine production as quantified by ELISA in the absence of antigen stimulation show varying degrees of antigen-independent activation in T cells expressing rituximab-derived CD20 CARs containing various numbers of alanine residues inserted between the transmembrane and cytoplasmic CD28 domains.
Figure 5:
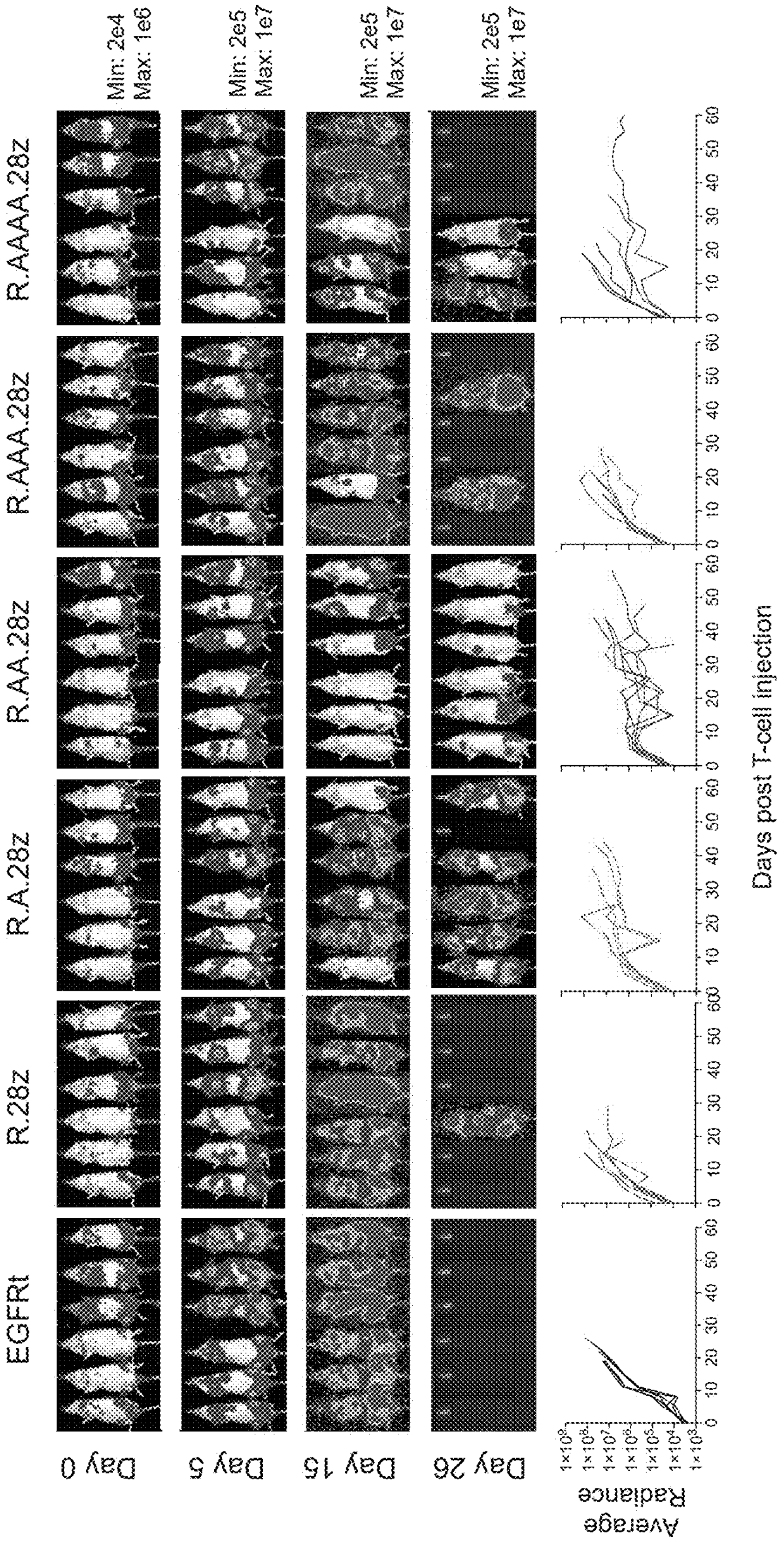
FIG. 5. Rituximab-derived CD20 CAR containing two alanine residues inserted between the transmembrane and cytoplasmic CD28 domains result in superior in vivo antitumor function. NOD/scid/γ−/− (NSG) mice were engrafted with 0.5 million firefly luciferase-expressing Raji lymphoma cells and treated with 1.35 million T cells expressing either a CD20 CAR or a transduction marker (EGFRt) 7 days post tumor injection. Animals were re-dosed with 1.5 million T cells 7 days later. All CARs tested in this study contained a rituximab-derived scFv, IgG4 hinge-CH2-CH3 extracellular spacer, CD28 transmembrane and cytoplasmic domains, and CD3 zeta signaling domain. Zero to four alanines were inserted between the CD28 transmembrane and CD28 cytoplasmic domains. Tumor progression was monitored through bioluminescence imaging, and radiance signal as a function of time since tumor injection is shown. The two-alanine insertion variant showed superior tumor control and extended median survival compared to the parental (no alanine insertion) construct as well as the other variants.
Figure 6:
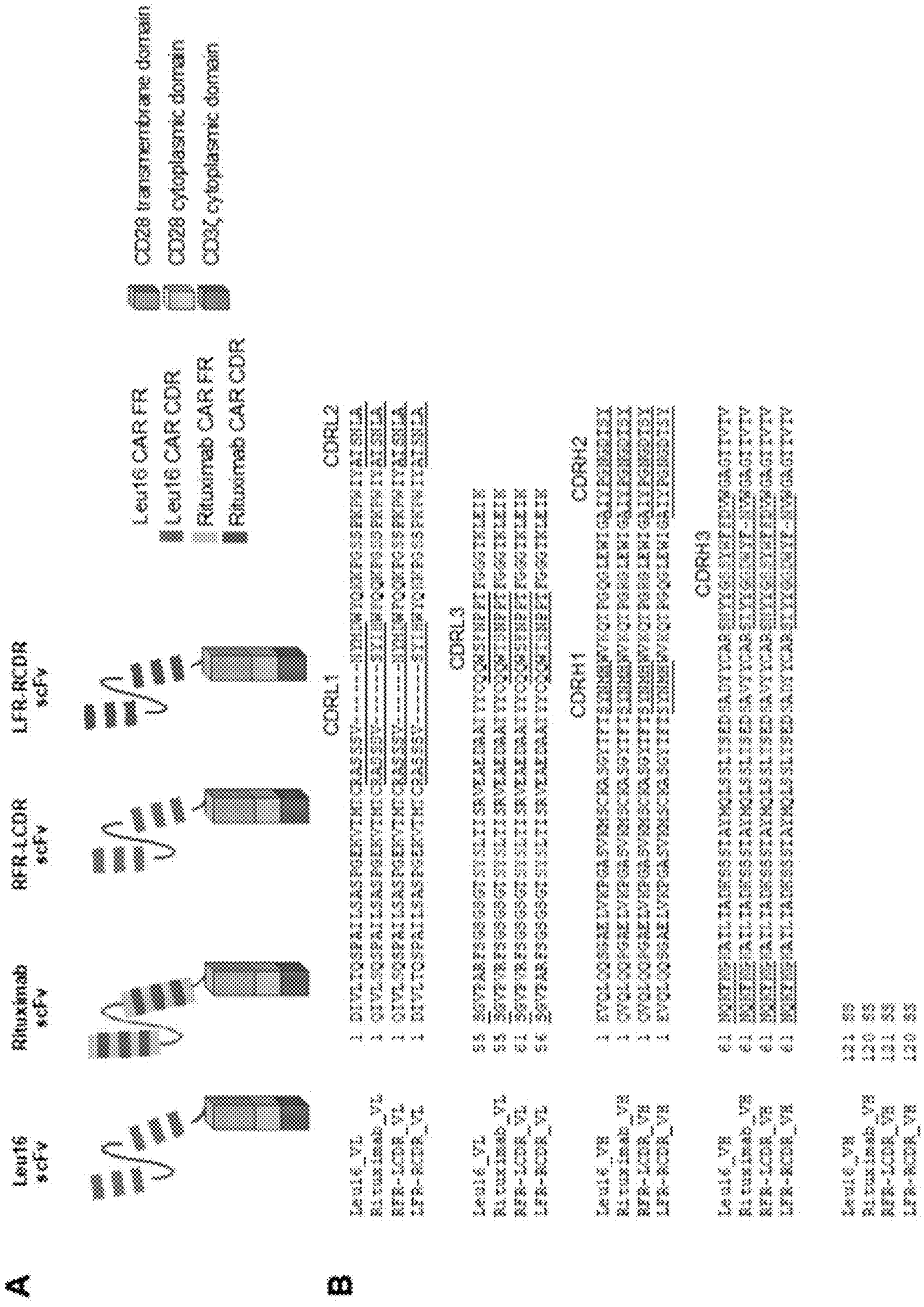
FIG. 6A-B. (A) Schematic of CD20 CARs containing Leu16-derived, Rituximab-derived, or hybrid scFv domains. Two hybrids were constructed. Only the RFR-LCDR hybrid was functional (see FIG. 7). All CARs were second-generation receptors containing the CD28 co-stimulatory domain as shown in FIG. 3. (B) Sequence of scFv domains used in CD20 CAR construction. Leu16 VL (SEQ ID NO:1), Rituximab VL (SEQ ID NO:3), RFR-LCDR VL (SEQ ID NO:5), LFR-RCDR VL (SEQ ID NO:7), Leu16 VH (SEQ ID NO:2), Rituximab VH (SEQ ID NO:4), RFR-LCDR VH (SEQ ID NO:6), LFR-RCDR VH (SEQ ID NO: 8).
Figure 7:
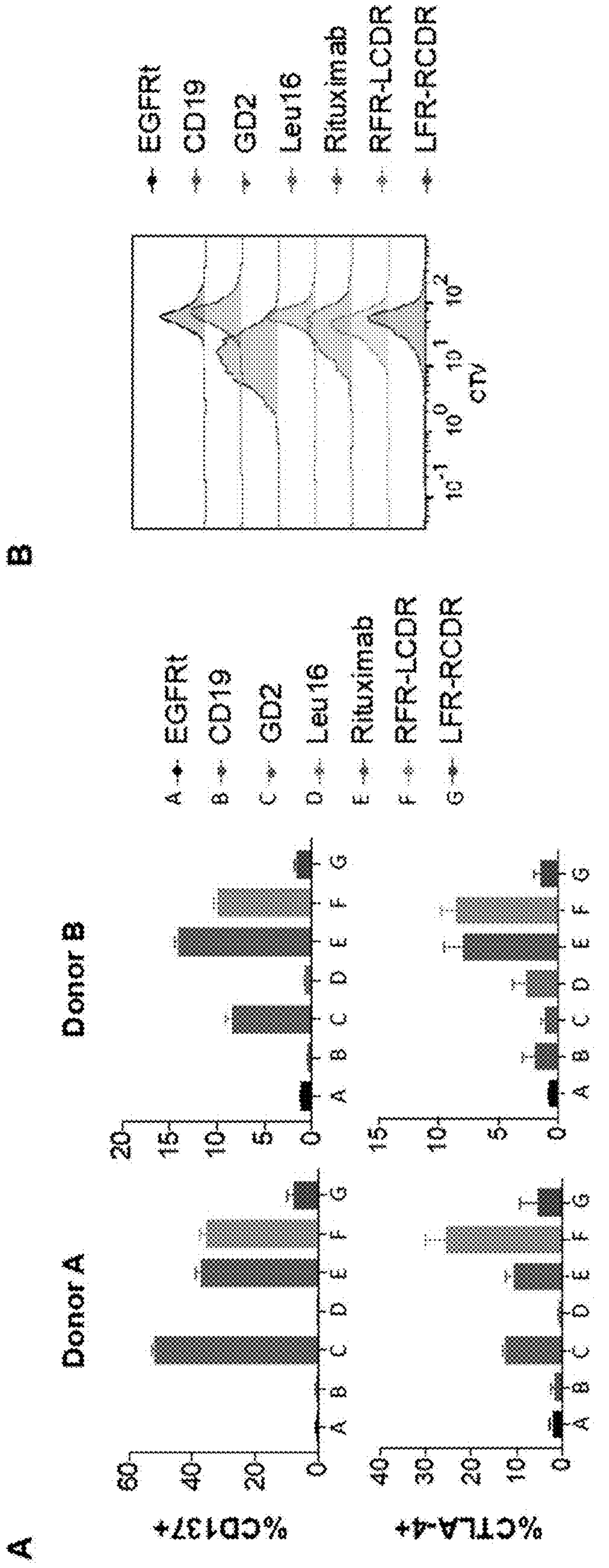
FIG. 7A-B. The RFR-LCDR hybrid CD20 CAR shows antigen-independent CAR signaling, resulting in (A) upregulation of activation and exhaustion markers and (B) T-cell proliferation in the absence of antigen stimulation. The CD19 CAR and GD2 CAR were included as a negative and positive control, respectively, for tonic signaling.
Figure 8:
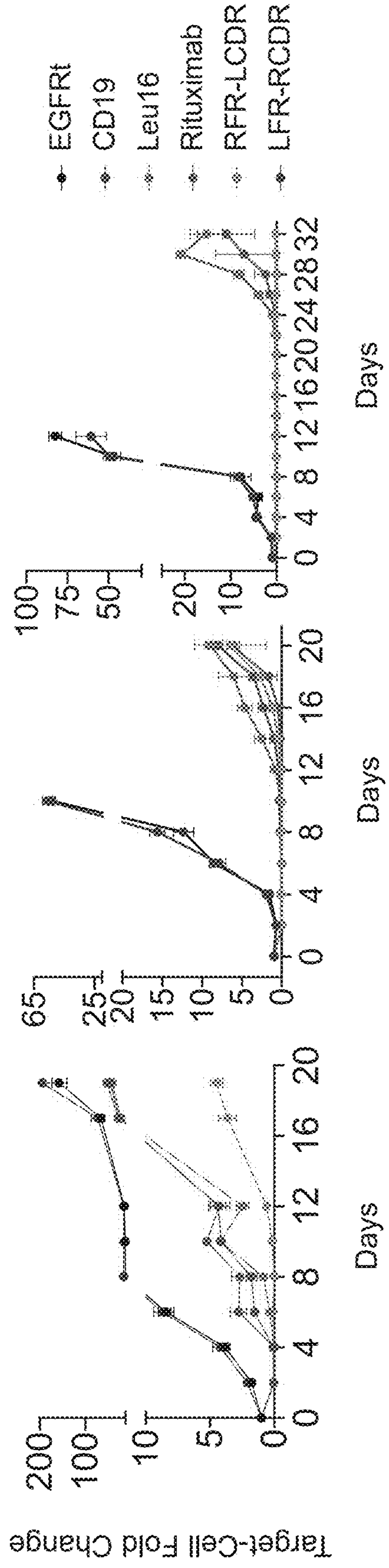
FIG. 8. The RFR-LCDR hybrid CD20 CAR shows superior tumor-cell killing upon repeated antigen challenge in vitro. T cells expressing various CARs or a transduction marker (EGFRt) were challenged with fresh Raji lymphoma cells every 48 hours. Viable target-cell count was quantified by flow cytometry before each re-challenge. Results from multiple donors indicate superior tumor-cell killing by the RFR-LCDR hybrid CAR compared to either of its parental constructs (Leu16 and Rituximab).
Figure 9A:
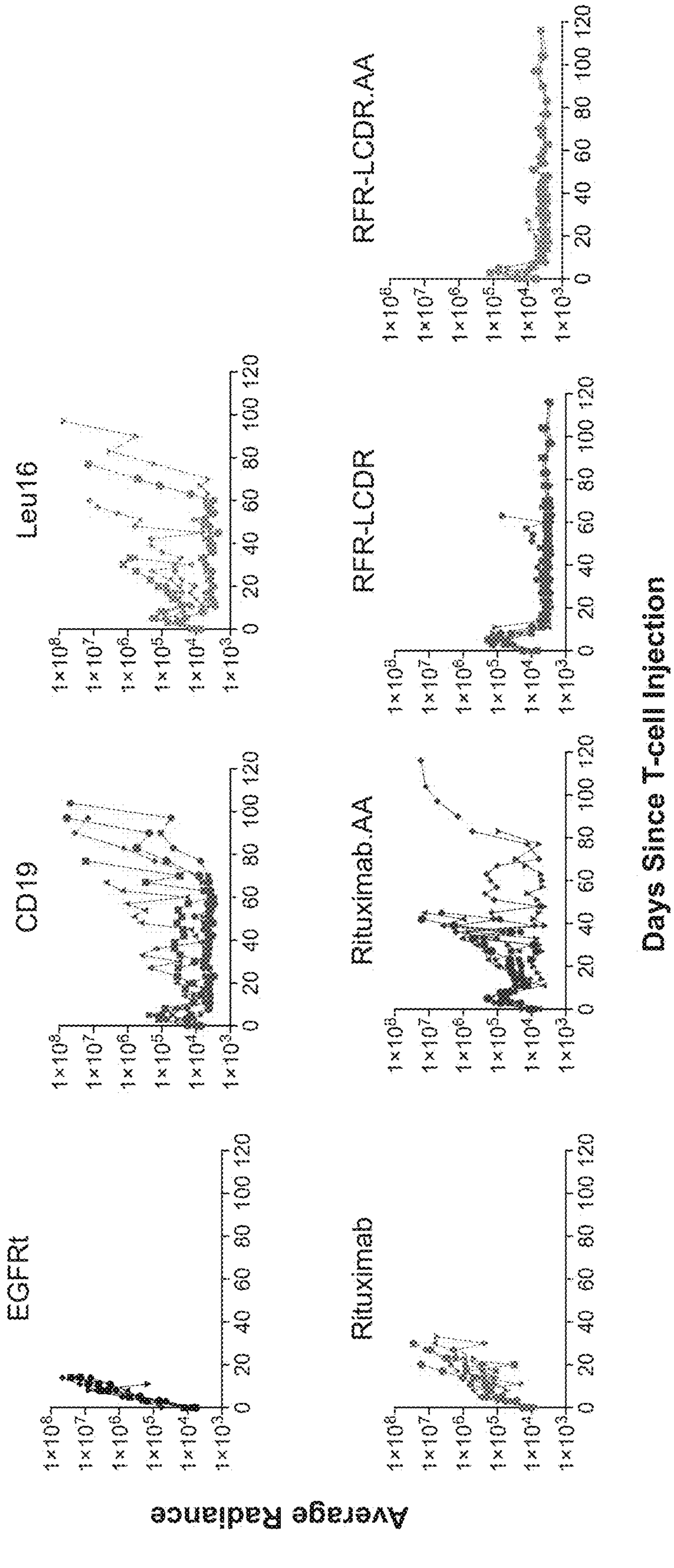

The inventors report the finding that contrary to previously proposed hypothesis (5), one could construct a functionally superior CAR by combining the FR sequences of a tonically signaling CAR with the CDR sequences of a non-tonically signaling CAR. Leu16 and rituximab are both monoclonal antibodies that target CD20. scFvs were made from the Vh and Vh of each antibody (FIG. 3). CARs incorporating the Leu16-derived scFv does not tonically signal, whereas CARs incorporating the rituximab-derived scFv does tonically signal (FIG. 4). The inventors constructed a "hybrid" CD20 CAR whose scFv comprises the FR sequences of the rituximab-derived scFv coupled to the CDR sequences of the Leu16-derived scFv (FIG. 5). This hybrid CAR, referred to as "RFR-LCDR", also tonically signals (FIG. 6). However, T cells expressing the RFR-LCDR hybrid CAR was shown to be functionally superior compared to T cells expressing either of the parental (i.e., Leu16- or rituximab-based) CARs, both in vitro (FIG. 7) and in vivo (FIG. 8). Importantly, the RFR-LCDR hybrid CAR outperformed the CD19 CAR in the tumor xenograft model, achieving complete and durable tumor clearance and prevention of tumor relapse even upon a second dose of tumor challenge 55 days after initial T-cell treatment (FIG. 8).

Example 3: Rational Tuning of CAR Tonic Signaling Yields Superior T-Cell Therapy for Cancer Chimeric antigen receptors (CARs) are modular proteins capable of redirecting immune cells toward a wide variety of disease-associated antigens. However, CAR-directed immunotherapies to date have achieved limited clinical efficacy outside B-cell malignancies. Here, the inventors systematically explore the effects of CAR protein sequence and structure on CAR-T cell function. The inventors report that tonic signaling significantly impacts the metabolism and anti-tumor efficacy of CAR-T cells. Specifically, the inventors found that low but non-zero levels of tonic signaling can promote robust effector function upon antigen stimulation while avoiding premature functional exhaustion by CAR-T cells. Furthermore, the inventors demonstrate the intensity of tonic signaling can be tuned through rational alterations of the CAR's ligand-binding domain and overall protein conformation, yielding CD20 CAR variants that outperform the CD19 CAR in tumor xenograft models. These findings point to tonic signaling and basal T-cell activation as informative parameters to guide the rational design of next-generation CARs for cancer therapy.

The adoptive transfer of chimeric antigen receptor (CAR)-T cells has shown remarkable efficacy for advanced B-cell malignancies, and CAR-T cell candidates against a wide variety of cancer types have entered clinical testing. However, few have shown comparable anti-tumor efficacy to CD19 CAR-T cells to date (Grigor et al., 2019; Guedan et al., 2018; Majzner and Mackall, 2019; Yamamoto et al., 2019). Standard approaches to CAR construction rely on recombining a limited set of extracellular spacer, transmembrane, and cytoplasmic signaling domains with ligand-binding moieties specific to the antigen of interest. While this empirically driven process can reliably yield CAR molecules with tumor reactivity, the resulting CAR-T cells often fail to achieve robust clinical efficacy. For example, although CD20 CAR-T cells showed promising activity in preclinical models, clinical trial results demonstrated markedly lower efficacy compared to CD19 CAR-T cell therapy against the same disease types (Till et al., 2012; Zhang et al., 2016). Similarly, a second-generation GD2 CAR incorporating the CD28 co-stimulatory domain has been shown to exhibit inferior in vivo anti-tumor function compared to a CD19 CAR containing the same signaling domains (Long et al., 2015). The inability to consistently generate robustly functional CARs against antigens of interest highlights the need to further understand the molecular and mechanistic relationship between CAR design and CAR-T cell function.

CAR engineering efforts thus far have revealed several design parameters that influence CAR-T cell function (Chang and Chen, 2017; Hong et al., 2020). These include co-stimulatory domains that booster T-cell activation upon antigen stimulation (Omer et al., 2018; Wijewarnasuriya et al., 2020; Zhao et al., 2015), extracellular domains that provide structural support for optimal T-cell/target-cell conjugation (Hudecek et al., 2013; Srivastava and Riddell, 2015), binding affinity between the CAR and the targeted antigen (Drent et al., 2019; Liu et al., 2015), as well as CAR-independent parameters such as antigen expression level on target cells (Majzner et al., 2020; Watanabe et al., 2015). However, these parameters cannot fully explain the difference between the CD19 CAR and other constructs such as CD20 CARs, which have similarly high binding affinities, contain the same co-stimulatory domains, and bind an antigen that is also highly expressed on the same type of tumor cells as targeted by the CD19 CAR.

More recently, several studies highlighted the phenomenon of CAR tonic signaling—i.e., CAR signaling in the absence of antigen stimulation—and its potential role in triggering premature T-cell dysfunction (Frigault et al., 2015; Gomes-Silva et al., 2017; Long et al., 2015; Watanabe et al., 2016). It has been suggested that the robust functionality of CD19 CAR-T cells can be attributed to a lack of tonic signaling by the CD19 CAR (Frigault et al., 2015; Long et al., 2015). However, phenotypic descriptions of tonically signaling T cells have been varied, and hypotheses on what specific CAR components could cause or prevent tonic signaling are at times contradictory (Frigault et al., 2015; Gomes-Silva et al., 2017; Long et al., 2015). Furthermore, given that most studies on tonic signaling compare the CD19 CAR against CARs targeting other antigens, it remains unclear whether the functional differences observed were strictly attributable to tonic signaling, and whether the abolishment of tonic signaling would predictably lead to improvements in anti-tumor efficacy of CAR-T cells.

Here, the inventors report that CAR sequence and architecture have significant and tunable impacts on tonic signaling, and that CAR-T cell metabolism and anti-tumor function can be altered through the tuning of tonic-signaling intensity and associated basal T-cell activation. The inventors show that a low but non-zero level of tonic signaling can increase CAR-T cell function by potentiating rapid anti-tumor response while avoiding premature T-cell exhaustion, and the level of basal T-cell activation can be tuned through the insertion of torsional linkers and the sequence hybridization of different ligand-binding domains. By applying these protein-engineering strategies, the inventors generated novel CD20 CARs that outperform the CD19 CAR in mouse models of B-cell lymphoma, and found memory phenotype enrichment and minimization of CAR-driven metabolic disturbance as properties associated with improved CAR-T cell function. These results point to the rational tuning of tonic signaling and basal T-cell activation as a useful and potentially broadly generalizable approach to engineering robust CAR-T cell therapies for cancer.

a. Results 1. scFv Sequence Alters Tonic Signaling and CAR-T Cell Metabolism

To date, studies on tonic signaling have primarily relied on comparing CARs targeting different antigens, thus complicating the interpretation of results due to concurrent changes in multiple parameters, including CAR sequence, antigen identity and expression level, and the biophysical characteristics of the CAR-antigen binding interaction (Frigault et al., 2015; Gomes-Silva et al., 2017; Long et al., 2015). Here, the inventors began by examining the hypothesis that the amino-acid sequence of the ligand-binding domain of a CAR can significantly impact receptor activity, independent of the target-antigen identity or binding affinity. The inventors chose to focus on CD20 CARs as the test platform because CD20 is a clinically validated antigen and enables direct benchmarking against the CD19 CAR in the treatment of B-cell lymphoma. A panel of CD20 CARs was constructed with single-chain variable fragments (scFvs) derived from four different monoclonal antibodies with similar KDl values (Mossner et al., 2010; Reff et al., 1994; Uchiyama et al., 2010) and similar complementarity determining region (CDR) structures predicted by abYsis (Martin and Thornton, 1996; Swindells et al., 2017). Three of the scFvs (Leu16, rituximab, and GA101) bind overlapping epitopes on the major extracellular loop of CD20, while ofatumumab binds both the minor and major loops of CD20 (Klein et al., 2013; Niederfellner et al., 2011; Rufener et al., 2016; Teeling et al., 2006) (FIG. 10A; FIG. S16A). All four CARs have identical extracellular spacer, transmembrane, and cytoplasmic signaling domains. This panel enables attribution of functional differences specifically to the scFv sequence while eliminating confounding factors such as differences in binding affinity and binding-epitope location. To better explore the potential relationship between scFv sequence and CAR tonic signaling, the inventors chose to incorporate CD28 as the co-stimulatory domain, as CD28-containing CARs had previously been reported to be more prone to tonic signaling than 4-1BB-containing CARs (Frigault et al., 2015; Long et al., 2015).

Figure 17A:
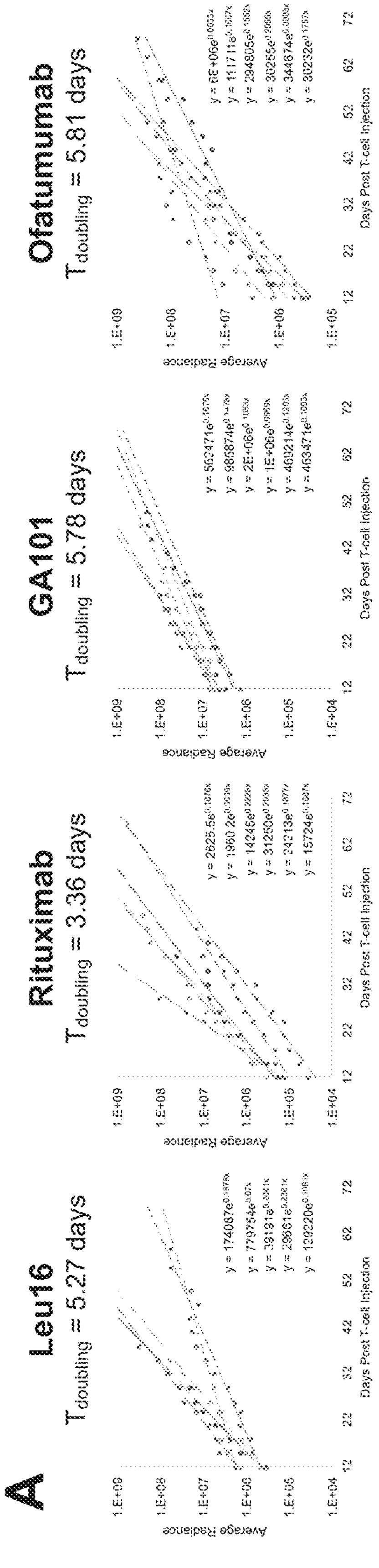

All four CD20 CAR variants were efficiently expressed on the surface of primary human T cells (FIG. 16B), and T cells expressing each CAR grew at comparable rates during ex vivo expansion with cytokine support (FIG. 16C). In response to repeated antigen stimulation, all CAR-T cell variants demonstrated the ability to lyse target cells and proliferate (FIG. 16D). However, despite similar performances during in vitro functional assays, T cells expressing the four CD20 CAR variants showed distinct in vivo tumor-killing dynamics in the Raji xenograft model (FIG. 10B). In particular, rituximab-based CAR-T cells exerted substantially stronger tumor control at early time points compared to all other CD20 CAR-T cells tested (FIG. 10B). And yet, starting approximately two weeks post T-cell injection, animals treated with rituximab CAR-T cells began exhibiting accelerated tumor growth-faster than any other test group (FIG. 10C; FIG. 17A) suggesting rapid onset of functional exhaustion among the rituximab CAR-T cells.

Animals in all test groups carried detectable populations of CAR-T cells at the time of sacrifice, particularly in the liver, spleen, and tumor metastases recovered from the brain (FIG. 17B,C). However, nearly all T cells were PD-1+ and many showed elevated LAG-3 expression (FIG. 17D,E).

Combined with the failure to eradicate tumor, these results suggest all four groups of CAR-T cells were dysfunctional by the end of the study, despite their persistence in vivo.

The inventors next sought to elucidate what biological differences among the four CD20 CAR-T cell variants could explain the different temporal dynamics of their in vivo tumor response, and whether the underlying biology could shed light on improved CAR designs capable of sustained tumor control. In particular, the inventors wished to understand why the rituximab CAR led to initially robust but ultimately short-lived anti-tumor response, and whether the inventors could prolong anti-tumor efficacy through rational CAR protein engineering.

In the absence of antigen stimulation, T cells expressing the rituximab CAR showed clear activation-marker expression (FIG. 10D) and cell proliferation (FIG. 10E), to a similar or stronger degree than T cells expressing the 14g2a-based GD2 CAR that is known to tonically signal (Long et al., 2015). These observations indicated clear basal activation of rituximab CAR-T cells that was directly attributable to the CAR construct, and led us to hypothesize that rituximab CAR-T cells could rapidly initiate anti-tumor response in part due to this pre-inclination toward T-cell activation. It has been shown that initiation of robust T-cell effector function requires support from aerobic glycolysis (Chang et al., 2013). Therefore, to examine the hypothesis that rituximab CAR-T cells are potentiated toward rapid effector function, the inventors set out to characterize its basal metabolic state by measuring the rates of nutrient uptake and byproduct secretion. In the absence of antigen stimulation, rituximab CAR-T cells exhibited significantly faster glucose, glutamine, and amino acid uptake compared to mock-transduced T cells and T cells expressing either the CD19 CAR or the Leu16-based CD20 CAR (FIG. 10F, FIG. 18). Furthermore, rituximab CAR-T cells showed 2-7-fold increases in lactate and alanine secretion, as well as >3-fold increase in glutamate secretion compared to the other CAR-T cells, indicating dramatically increased glycolytic flux and glutaminolysis, respectively. As glucose and glutamine are responsible for the majority of ATP production, faster glycolysis and glutaminolysis imply greater energy expenditure, consistent with the behavior of activated T cells (Chang et al., 2013).

Taken together, these observations indicate that, in the absence of antigen stimulation, rituximab CAR-T cells are basally activated and metabolically equipped to initiate T-cell effector function. This heighted metabolism at rest may explain rituximab CAR-T cells' rapid anti-tumor activity at early time points in vivo, but chronic, low-level T-cell activation in the absence of antigen stimulation may also have contributed to rituximab CAR-T cells' accelerated loss of tumor control compared to the other CAR-T cell variants, as observed in the animal study. To evaluate this possibility and its implication on CAR design, the inventors next investigated whether tuning the level of basal activation could yield CAR-T cells that are capable of both rapid and sustained anti-tumor response.

2. Torsional Reorientation of Signaling Domain Tunes CAR-T Cell Activity

Receptor dimerization at the cell surface can trigger CAR signaling (Chang et al., 2018), and an earlier study suggested that tonic signaling may be a consequence of antigen-independent CAR clustering caused by certain scFv sequences (Long et al., 2015). The inventors verified that all four CD20 CAR variants shown in FIG. 10A are uniformly distributed on the T-cell surface in the absence of antigen stimulation (FIG. 19), thus ruling out macro-scale CAR clustering as the cause of tonic signaling by the rituximab-based CAR. Nevertheless, the signaling cascade downstream of CD3ζ involves adaptor proteins and kinases whose interactions with the receptor chain are directly impacted by the physical proximity and conformation of receptor chains (Hartman and Groves, 2011). The inventors thus hypothesized that tonically signaling CARs may adopt a conformation that enables basal receptor signaling, and that altering the conformation of the CAR molecule could enable the tuning of CAR signaling intensity both in the absence and in the presence of antigen stimulation, thereby impacting downstream CAR-T cell behavior.

To systematically investigate the effect of CAR-conformation change, the inventors inserted one to four alanines between the transmembrane and cytoplasmic domains of CD28 in the rituximab-based CAR, with each alanine expected to cause a ~109° turn in the protein structure through the formation of an alpha helix (Constantinescu et al., 2001; Liu et al., 2008; Scheller et al., 2018) (FIG. 11A; FIG. 20A). This "twisting" process is designed to alter the alignment between the CAR's extracellular ligand-binding domain and its cytoplasmic signaling domains, potentially impacting the packing behavior of receptors in high-density areas (e.g., within microclusters upon antigen-ligation), as well as the accessibility of docking and phosphorylation residues involved in downstream signaling.

All alanine-insertion variants as well as the original rituximab CAR expressed well on the T-cell surface (FIG. 20B), demonstrated similar ability to lyse target cells and proliferate in response to repeated antigen challenge (FIG. 20C), and showed similar levels of activation and exhaustion marker expression in the absence of antigen stimulation (FIG. 20D). However, alanine insertion resulted in a clear reduction of antigen-independent T-cell proliferation and TNF-α production compared to the original rituximab-based CAR (FIG. 11B,C), indicating the insertion of torsional linkers significantly reduced basal CAR-T cell activity. The impact of CAR structural alteration was evident in vivo, with T cells expressing rituximab-based CARs containing one, two, or four alanines showing significantly improved control of Raji xenografts compared to the original rituximab CAR (FIG. 11D). In particular, the two-alanine CAR increased median survival period by 2.1-fold compared to the original rituximab CAR (55 days vs. 26 days; FIG. 11E).

In principle, the insertion of alanine-based torsional linkers can be performed on any CAR protein, irrespective of the particular ligand-binding or signaling domains incorporated in the CAR. To probe the generalizability of this CAR-tuning method, the inventors evaluated the effects of alanine insertion in the 14g2a-based GD2 CAR. All five GD2 CAR variants (with zero to four alanines inserted between the transmembrane and cytoplasmic domains) expressed well on the T-cell surface, and exhibited similar anti-tumor responses upon repeated antigen challenge in vitro (FIG. 21A-C). Consistent with results from the CD20 CAR panel (FIG. 11D), T cells expressing GD2 CARs containing one, two, or four alanines outperformed GD2 CARs with zero or three alanine inserted (FIG. 21D). Furthermore, analysis of liver and spleen recovered at the time of sacrifice revealed a significantly higher level of T cells expressing the two-alanine CAR construct, underscoring the utility of two-alanine insertion in CARs containing CD28 transmembrane and cytoplasmic domains (FIG. 21E).

Taken together, these results indicate that alanine insertion into CAR molecules is a generalizable method to tune CAR-T cell activation and strengthen anti-tumor efficacy in vivo. However, despite the improvements seen with alanine insertion, the CD20 CAR-T cells remained unable to eradicate Raji xenografts in the mouse model (FIG. 11D,E). The inventors thus set out to explore additional design parameters that could further enhance CAR-T cell function.

3. scFv Sequence Hybridization Yields Superior CAR Variant

The observation that the rituximab CAR's behavior was distinct among the original panel of four CD20 CARs was striking given that all CARs had identical components aside from the scFv (FIG. 10A). Furthermore, the rituximab scFv has 91% sequence identity compared to the Leu16 scFv (FIG. 16A), yet Leu16 and rituximab CAR-T cells had dramatically different behaviors in terms of both basal T-cell activation and in vivo tumor-killing dynamics (FIG. 10B-E). These results indicate that limited variations in scFv sequence can exert a significant impact on CAR signaling activities.

Each scFv comprises a light chain and a heavy chain, and each chain can be further subdivided into four framework regions (FRs) flanking three complementarity-determining regions (CDRs) (FIG. 11A). It has previously been suggested that the FRs of certain scFvs such as 14g2a may be the cause of tonic signaling and CAR-T cell exhaustion, and it was demonstrated that incorporation of the 14g2a scFv's FRs into the CD19 CAR resulted in a hybrid receptor that triggered T-cell exhaustion (Long et al., 2015). Thus it was possible to impair a CAR through scFv alterations, but it remained unclear whether a CAR can be improved through scFv sequence hybridization. The inventors' results thus far indicated that lowering the intensity of CAR tonic signaling via alanine insertion can improve CAR-T cell function. The inventors next explored whether changes in scFv through sequence hybridization could provide a second "knob" by which CAR signaling activities could be rationally tuned.

Figure 12A:
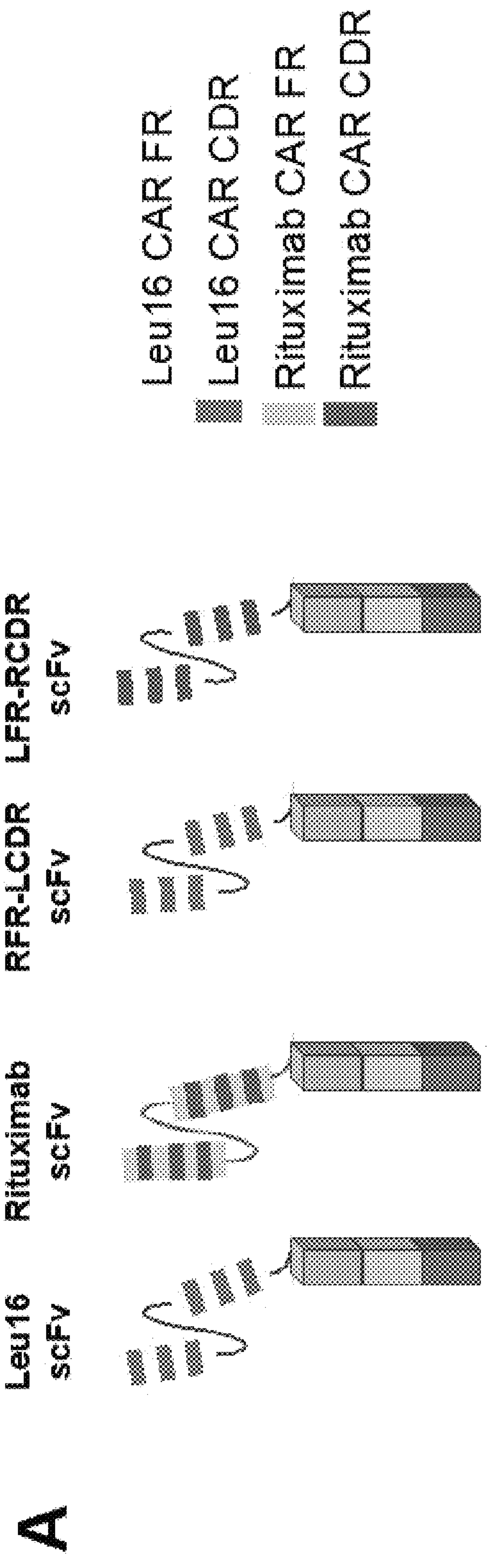
Figures 1, 22A:
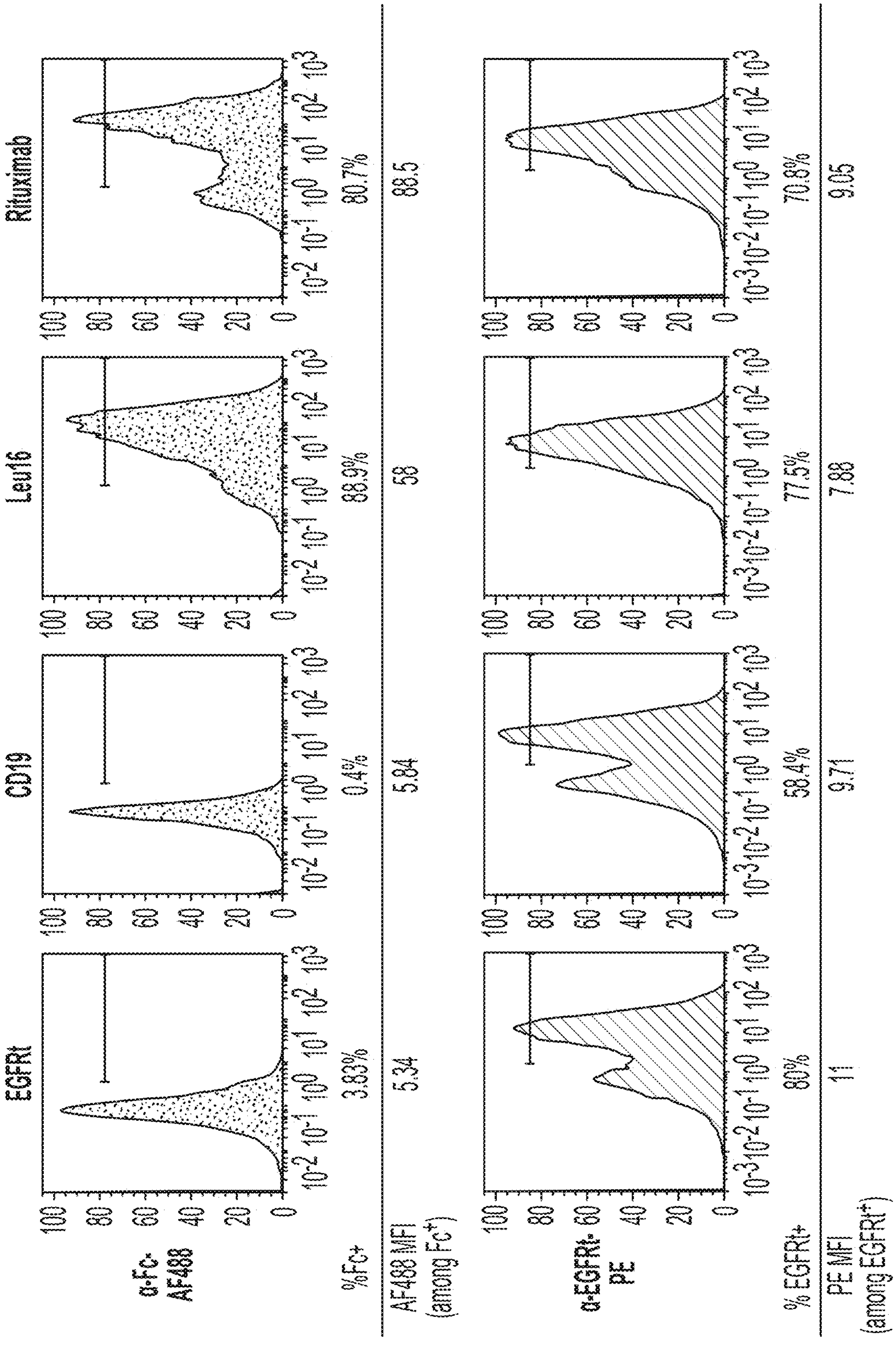
Figures 2, 22A:
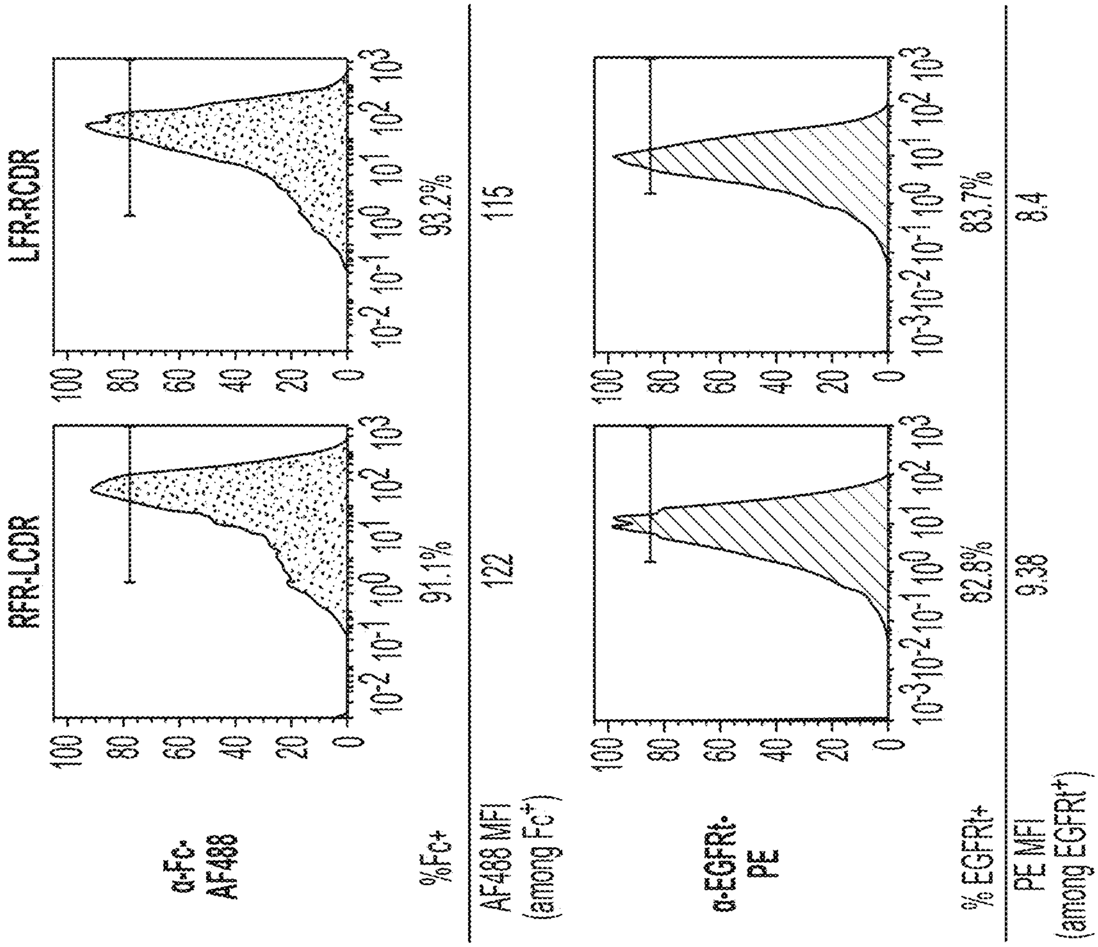
Figure 22B:
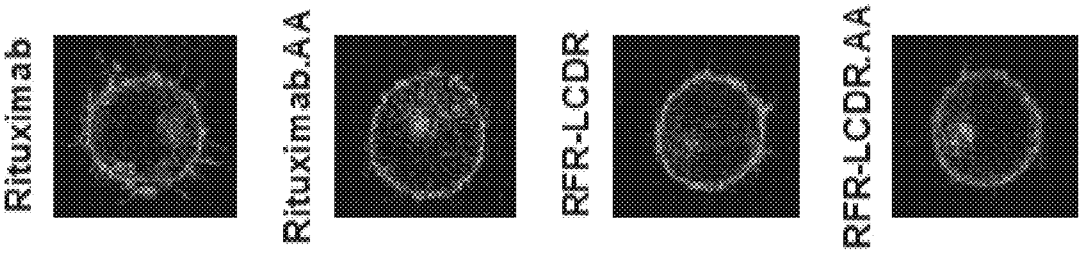

Leu16 and rituximab were chosen as the starting point for hybridization due to their similar sequences yet disparate activity profiles. The inventors constructed hybrid CARs whose scFv comprised the FRs of rituximab and CDRs of Leu16 (RFR-LCDR), or vice versa (LFR-RCDR) (FIG. 12A). The RFR-LCDR hybrid CAR triggered robust tumor-cell lysis and T-cell proliferation upon repeated antigen challenge, providing the first example of a CD20 CAR whose functionality is comparable to that of the CD19 CAR in the in vitro assays (FIG. 12B). RFR-LCDR hybrid CAR-T cells showed clear activation marker expression in the absence of antigen stimulation, indicating a non-zero level of T-cell activation at rest (FIG. 12C). In contrast, the LFR-RCDR hybrid was completely non-functional despite being efficiently expressed on the T-cell surface (FIG. 12B; FIG. 22A), thus it was excluded from further characterization. Henceforth, the term "hybrid CAR" refers to the RFR-LCDR variant.

Figure 12D:
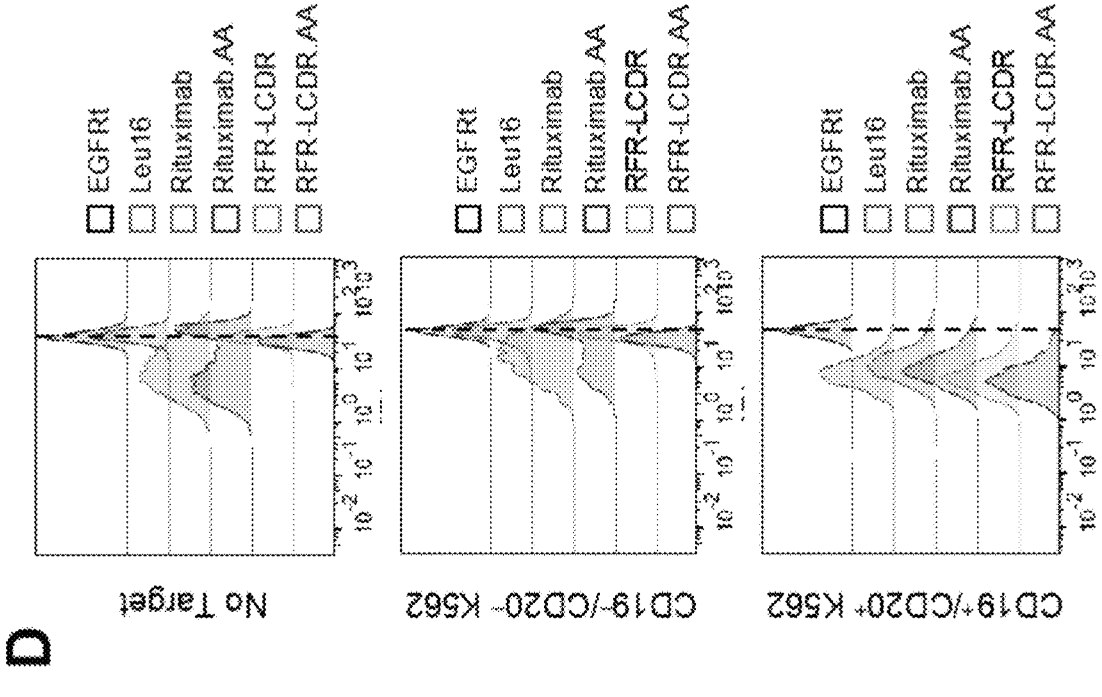
Figure 12E:
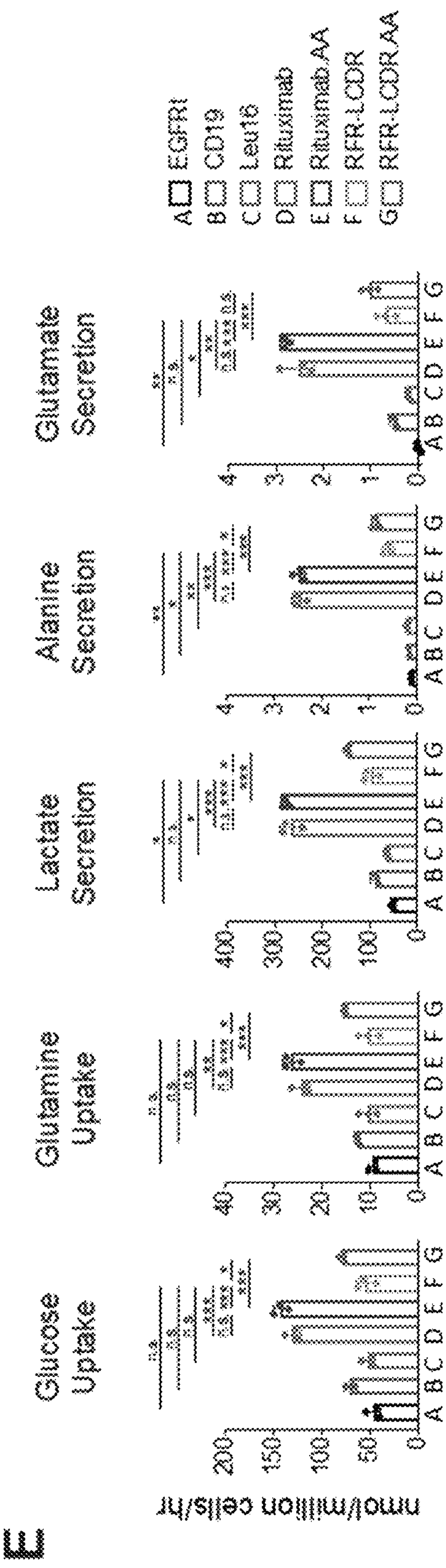

A modified hybrid CAR with two alanines inserted between the transmembrane and cytoplasmic CD28 signaling domains (RFR-LCDR.AA) was included in subsequent studies to determine whether sequence hybridization and alanine insertion would synergize to further improve CAR-T cell function. Both hybrid CARs showed similar surface distribution as rituximab-based CARs with and without alanine (FIG. 22B), and all CAR-T cells produced Th1 cytokines in response to antigen stimulation (FIG. 22C), confirming tumor reactivity. However, hybrid CAR-T cells showed no sign of antigen-independent T-cell proliferation (FIG. 12D), and scFv sequence hybridization significantly reduced TNF-α production and increased IL-2 production in the absence of antigen stimulation compared to rituximab-based CAR-T cells (FIG. 22D). Furthermore, metabolic analysis on CAR-T cell culture supernatant revealed that scFv hybridization significantly reduced glucose and glutamine uptake as well as glutamate, alanine, and lactate secretion in the absence of antigen stimulation (FIG. 12E; FIG. 23). Consequently, the metabolic rates for hybrid CAR-T cells at rest were at an intermediate level, between those of T cells expressing either of the two parental constructs (i.e., rituximab or Leu16 CARs). Taken together, these results indicate scFv hybridization can significantly reduce the intensity of tonic signaling without completely abolishing basal T-cell activation.

The inventors next performed head-to-head comparisons of the hybrid CAR against each of its parent constructs and the CD19 CAR in vivo (FIG. 13A). Results indicate that RFR-LCDR CAR-T cells efficiently rejected both the original tumor as well as tumor re-challenge (FIG. 13B,C). In fact, this marked the first example to the knowledge of the inventors of a CD20 CAR that outperforms the CD19 CAR in eradicating B-cell lymphoma xenografts.

Consistent with prior results, alanine insertion substantially improved the rituximab CAR (FIG. 13B,C). Since RFR-LCDR and RFR-LCDR.AA CAR-T cells both conferred nearly perfect protection against tumor and re-challenge, the inventors could not assess whether alanine insertion in the hybrid CAR context provided further benefits in tumor killing. However, RO blood analysis indicated that RFR-LCDR.AA CAR-T cells had superior in vivo survival and expansion compared to RFR-LCDR CAR-T cells (FIG. 13D). These results were further validated in a second in vivo study where animals were treated with a single (instead of split) dose of CAR-T cells and re-challenged with tumor cells twice, with escalating tumor dosage levels (FIG. 13E, F). Rituximab.AA, RFR-LCDR, and RFR-LCDR.AA CAR-T cells all persisted and rebounded after each tumor re-challenge, with RFR-LCDR.AA CAR-T cells showing the highest level of CAR-T cells in peripheral blood both before and after the first tumor re-challenge (FIG. 13G). Both hybrid CAR variants conferred complete protection to the animals through the study.

Taken together, these results indicate that the functionality of a CAR can be improved by changing its scFv sequence and that tuning-rather that complete elimination of basal T-cell activation could result in CAR designs with significantly improved anti-tumor functions.

Figure 14A:
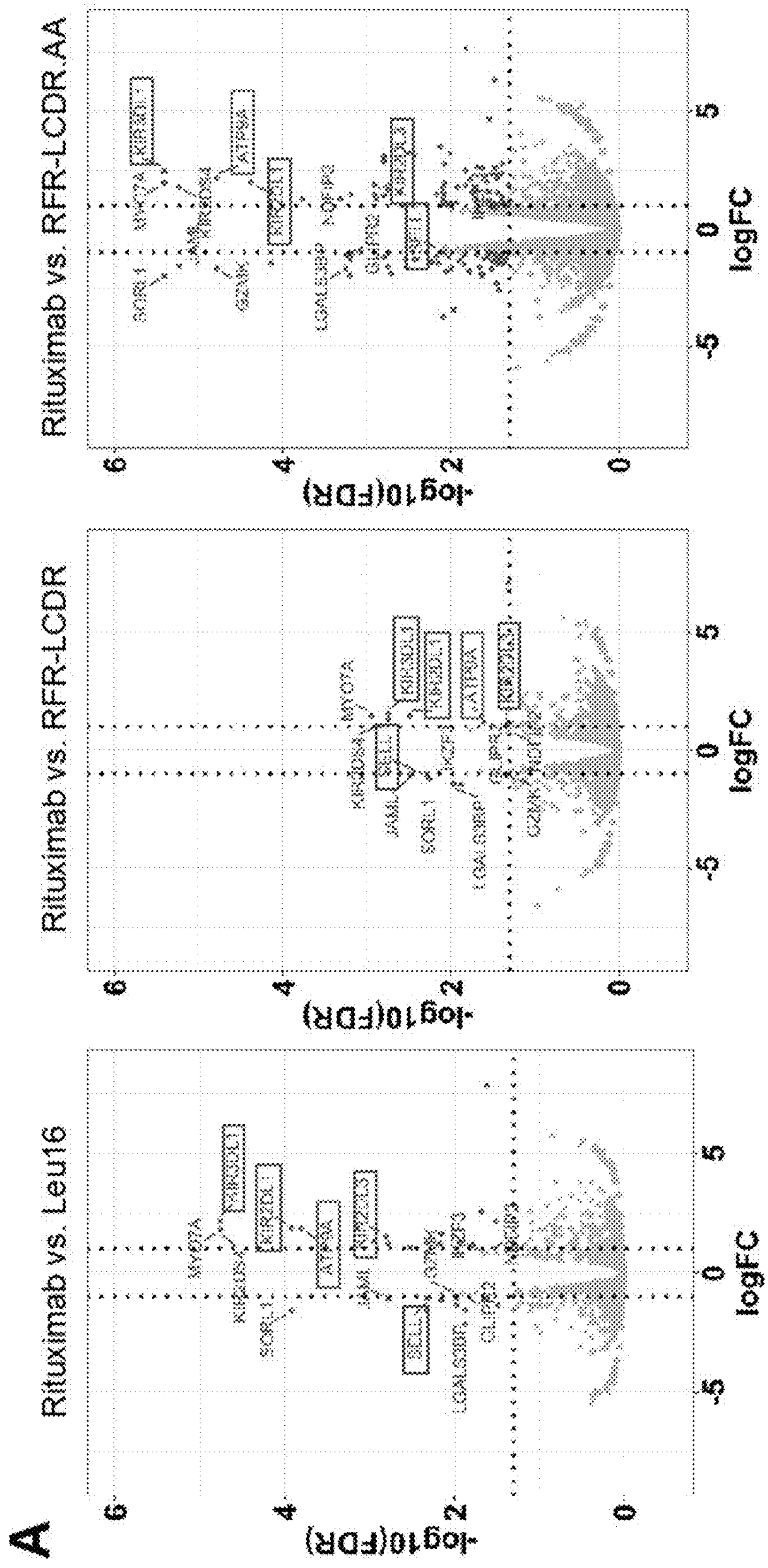

4. Memory Phenotype Enrichment and Minimization of CAR-Driven Metabolic Disturbance Enhance CAR-T Cell Function To better understand the biology that underpins the functional differences observed in vivo, the inventors performed RNA-seq and ATAC-seq analyses on rituximab, Leu16, RFR-LCDR, and RFR-LCDR.AA CAR-T cells recovered from tumor-bearing animals 9 days post T-cell injection (FIG. 249). Results revealed stark differences in the transcriptomic and epigenetic profiles of rituximab CAR-T cells compared to the others, with the RFR-LCDR.AA CAR being the most distant from the rituximab CAR (FIG. 14A,B; FIG. 25). Compared to each of the other CAR variants, rituximab CAR-T cells showed significantly increased expression of ATP9A, which encodes for a phospholipid flippase that positively regulates GLUT1 recycling (Tanaka et al., 2016) (FIG. 14B,C). GLUT1 recycling from endosomes to the plasma membrane is essential for cellular glucose uptake in support of glycolysis, and different GLUT1 expression levels have been shown to correlate with distinct effector functions in human T cells (Cretenet et al., 2016; Macintyre et al., 2014). These results echoed previous observation that rituximab and rituximab.AA CAR-T cells exhibit elevated glucose uptake at rest (FIG. 12E), and prompted us to analyze the glucose level in blood-serum samples that had been collected from the in vivo study shown in FIGS. 13E-G. The results revealed significantly lower glucose levels in the serum of mice treated with rituximab.AA CAR-T cells (FIG. 14D), further supporting the notion that rituximab-based CAR-T cells are substantially more glycolytically active than hybrid CAR-T cells.

In addition to increased glycolysis, rituximab CAR-T cells recovered from mice showed significantly lower CD62L expression (encoded by the SELL gene) and higher transcript levels for the inhibitory receptors KIR2DL1, KIR2DL3, and KIR3DL1 (Bjorkstrom et al., 2012) compared to each of the other three CAR-T cell types (FIG. 14B). Upregulation of the inhibitory KIRs was further confirmed by ATAC-seq (FIG. 14C). Taken together, rituximab CAR-T cells exhibit a phenotype consistent with effector T cells trending toward functional exhaustion.

Figure 15A:
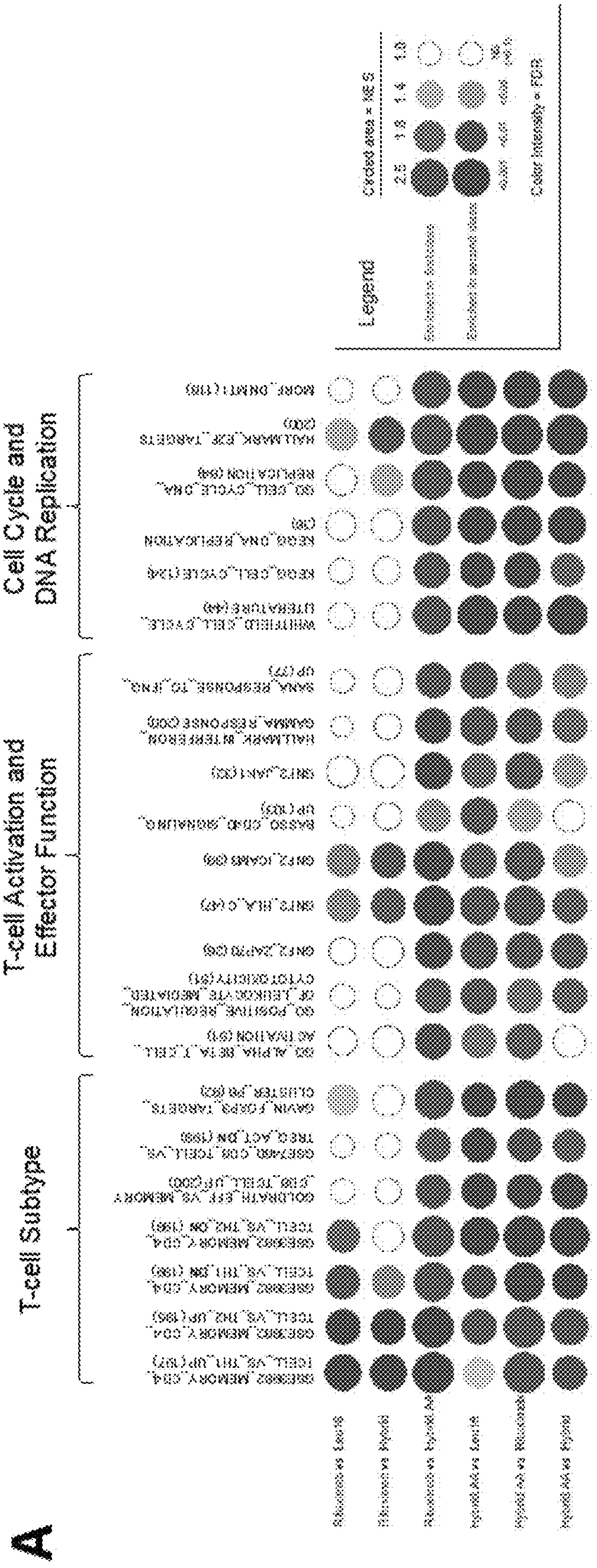
Figures 1, 15B:
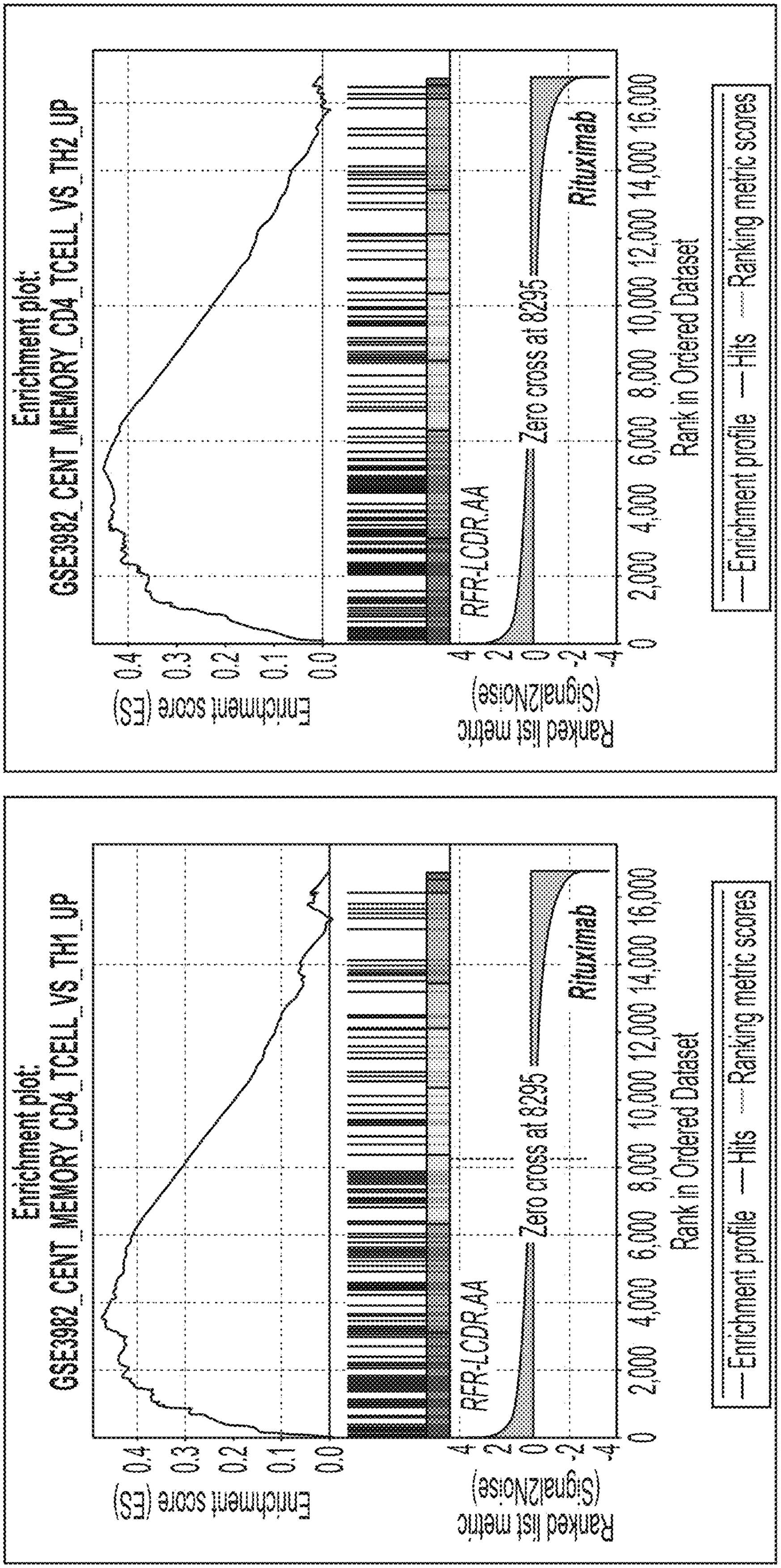
Figure 15B:
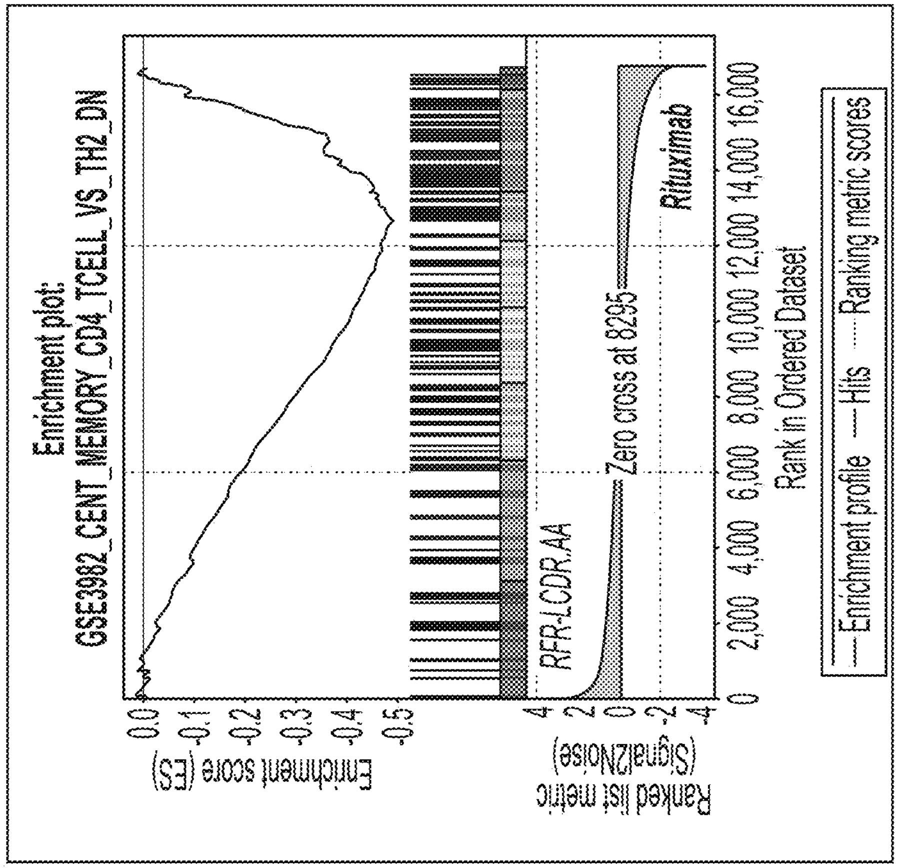
Figure 2:
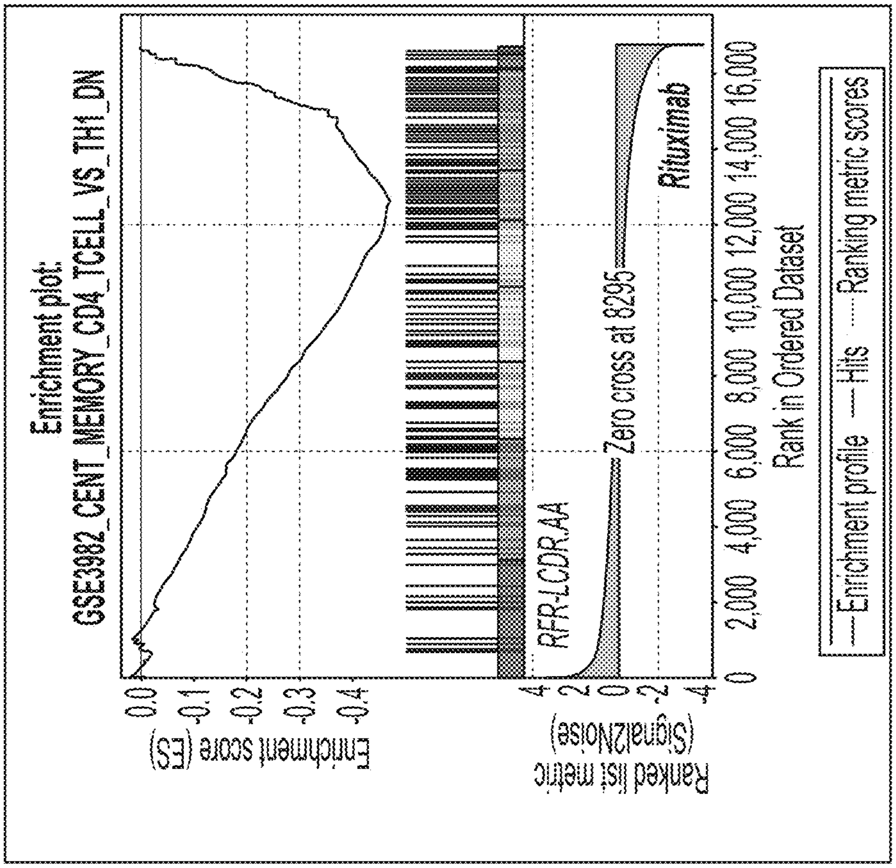
Figures 1, 15C:
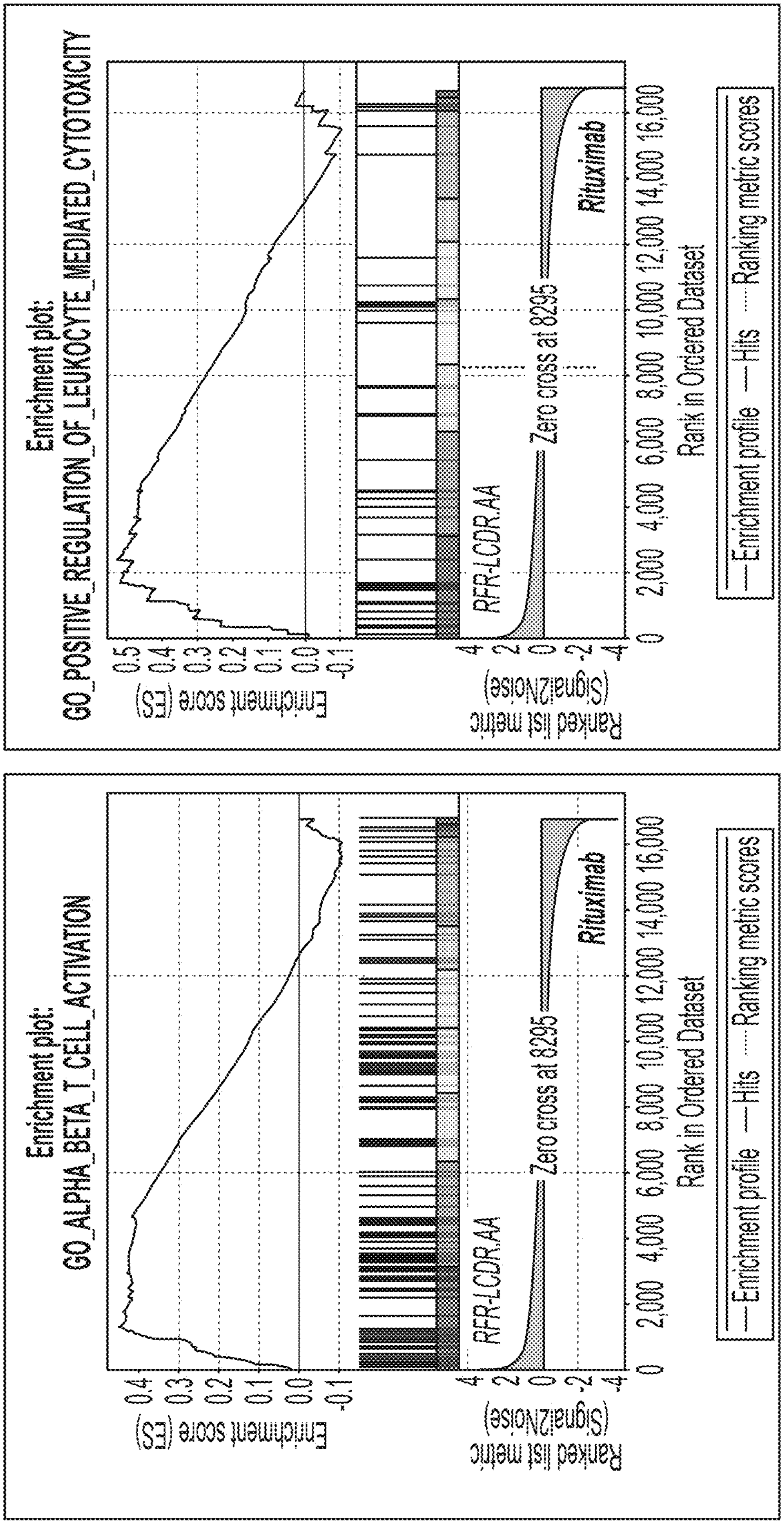
Figure 15C:
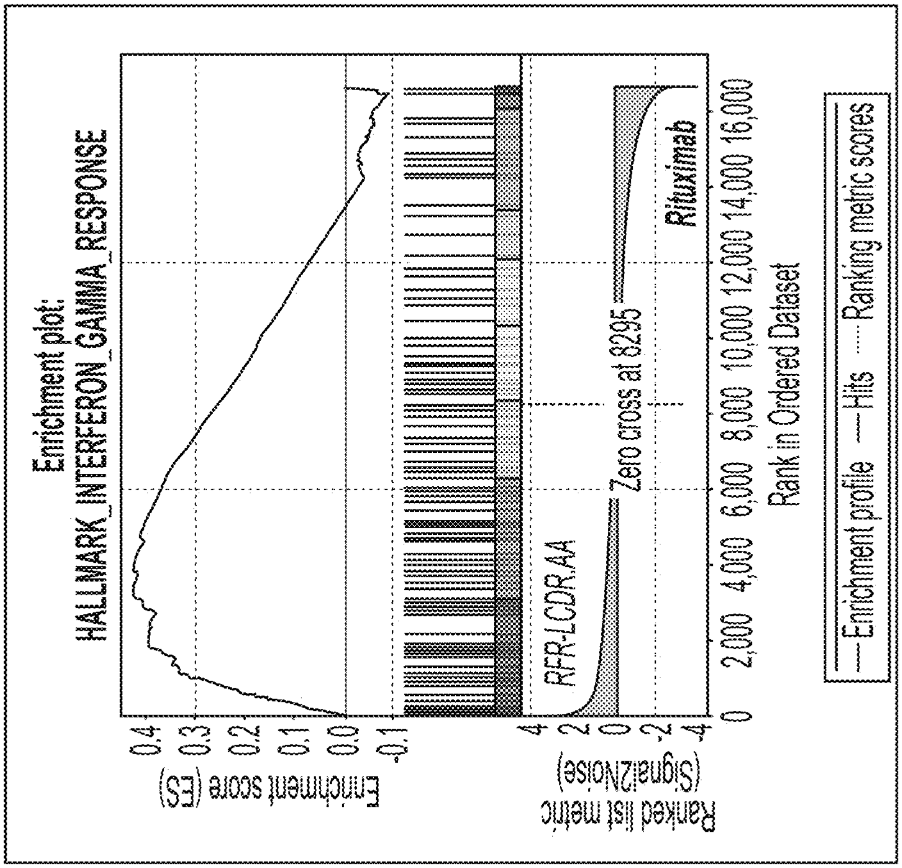
Figure 2:
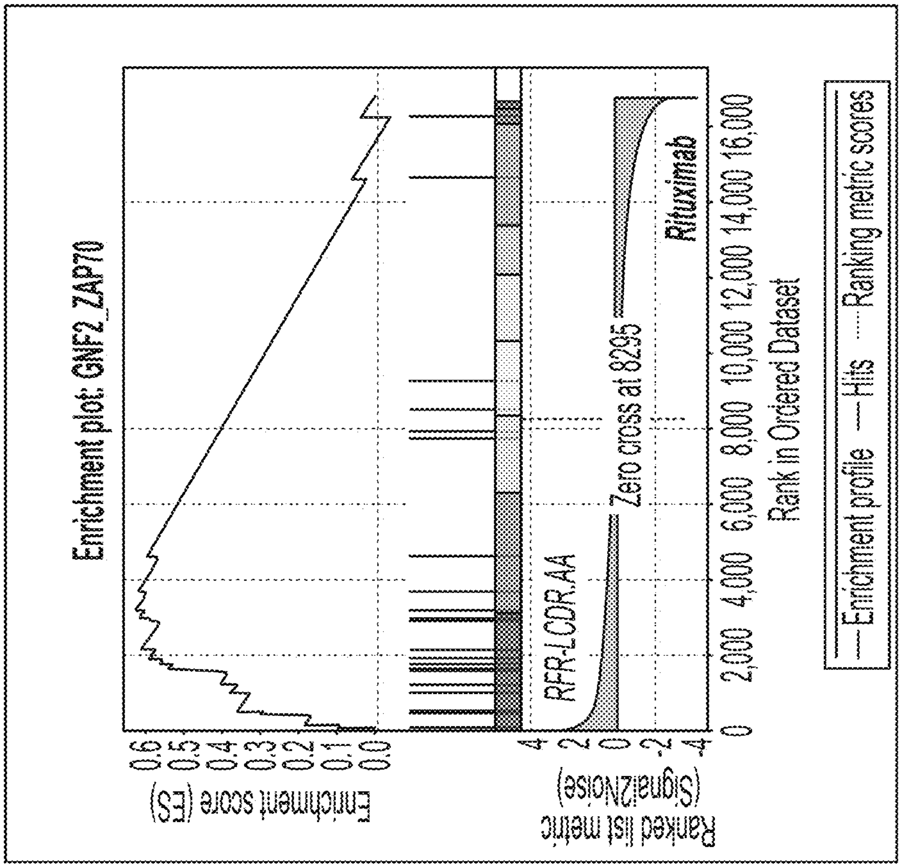
Figures 1, 15D:
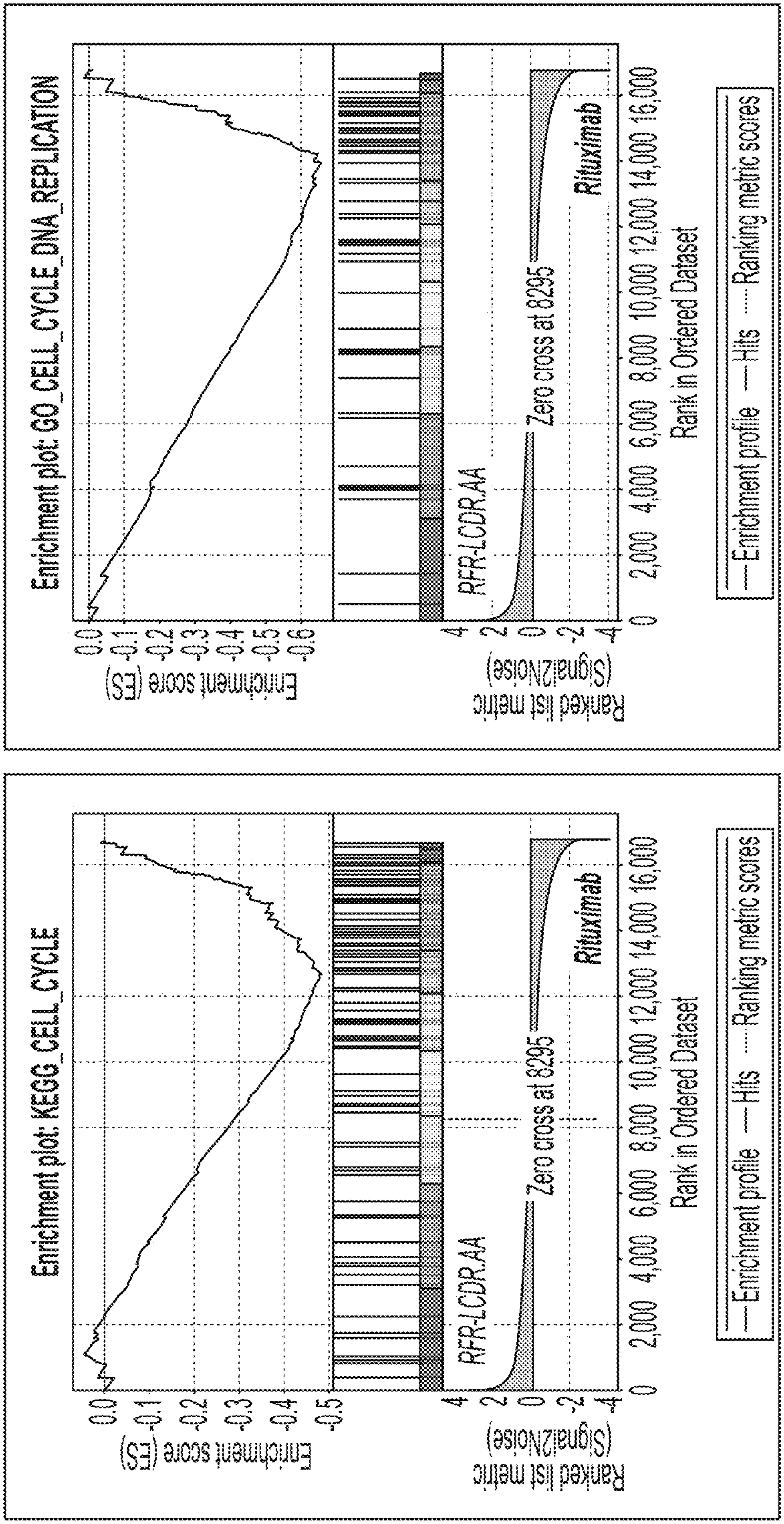
Figures 2, 15D:
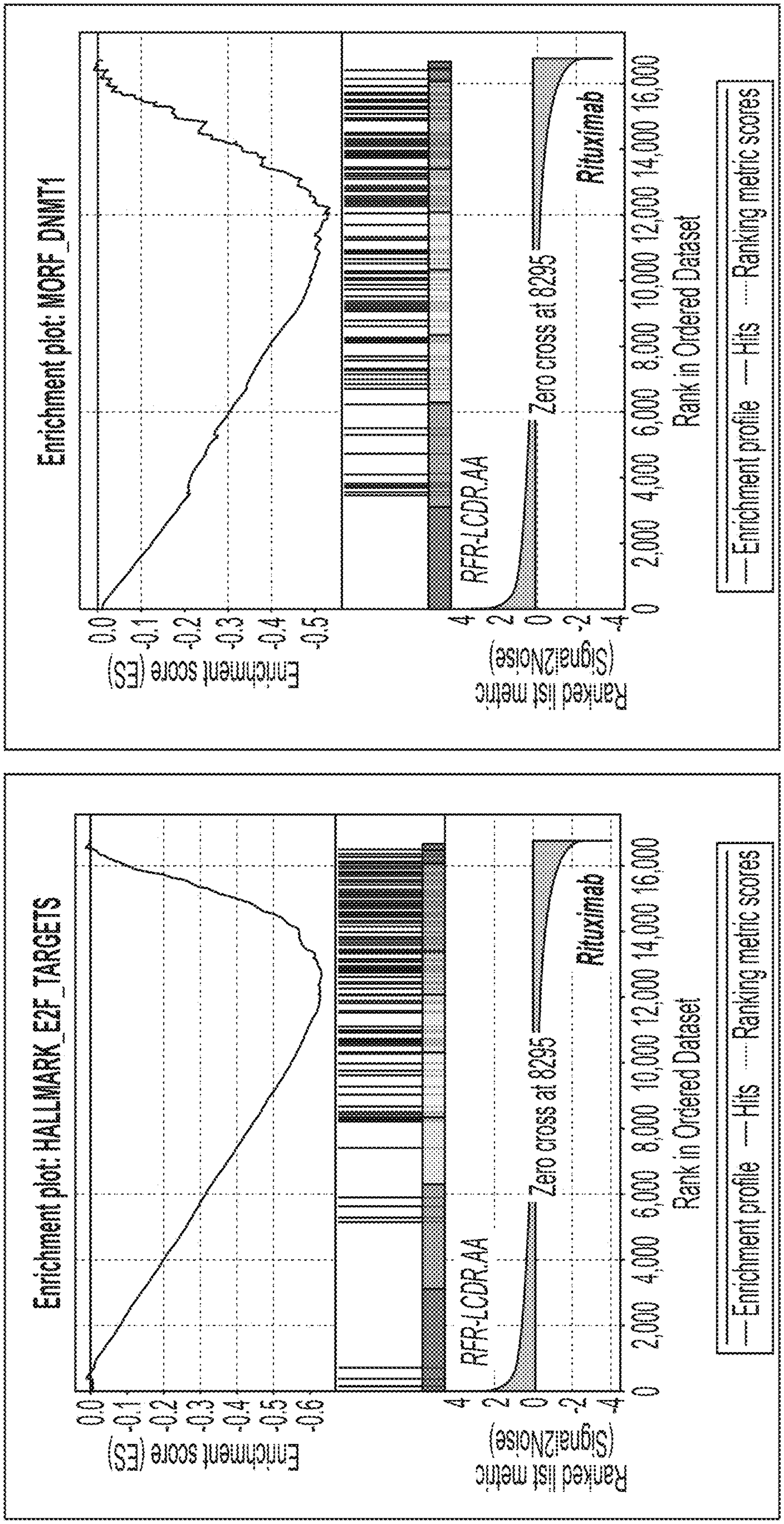
Figure 16A:
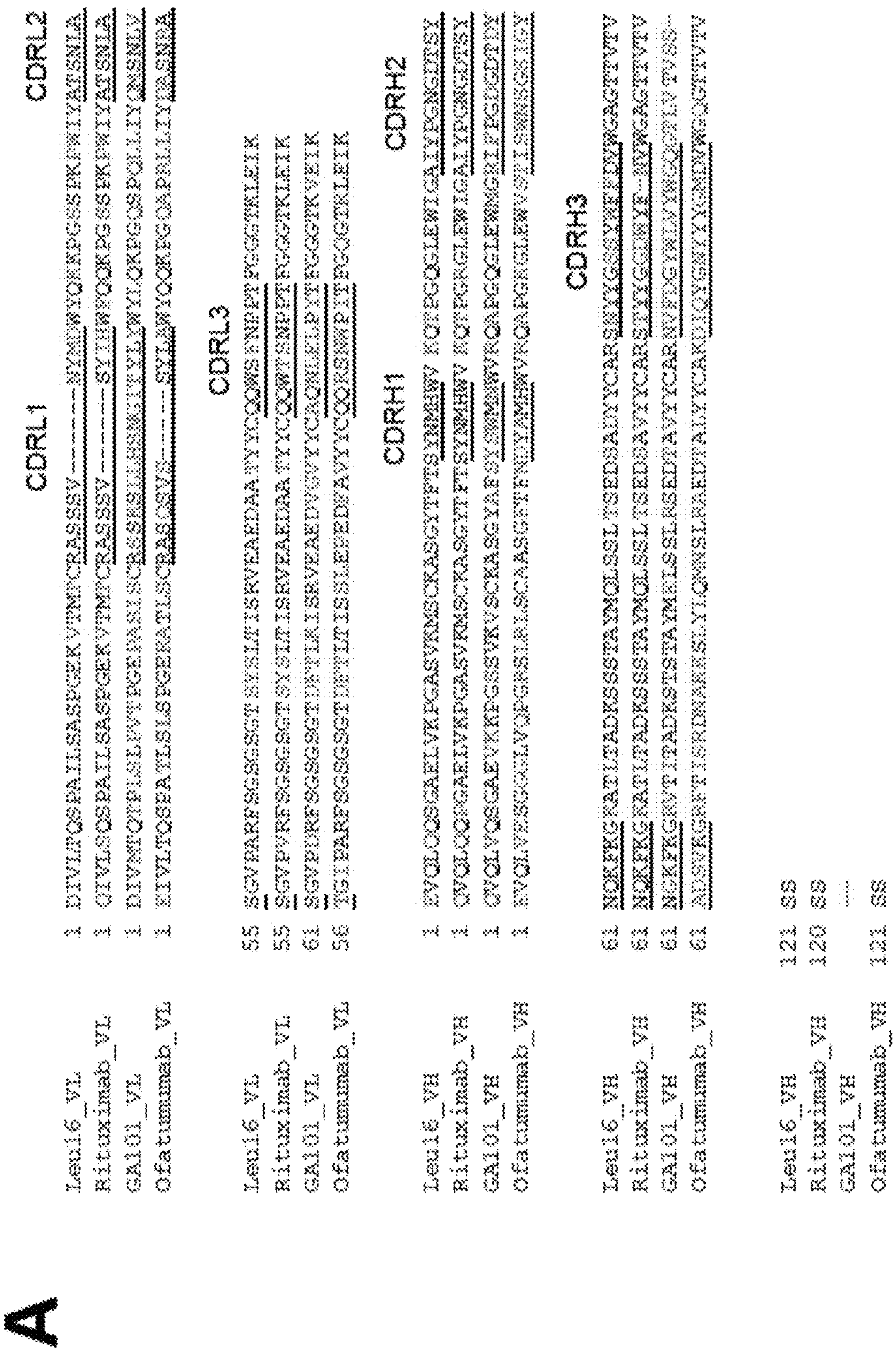

In contrast, hybrid CAR-T cells, particularly RFR-LCDR.AA CAR-T cells, are significantly enriched in the memory phenotype based on Gene Set Enrichment Analysis (GSEA) (FIG. 15A,B). GSEA also revealed that both hybrid CAR-T cell populations recovered from mice exhibit significantly stronger T-cell activation, cytotoxicity, receptor-signaling, and interferon gamma signatures compared to rituximab and Leu16 CAR-T cells (FIG. 15A,C). For RFR-LCDR.AA CAR-T cells in particular, this strong T-cell activation signature coexists with low cell-cycle and DNA-replication activity, consistent with the memory phenotype and in stark contrast with rituximab CAR-T cells (FIG. 15A,D). Of note, the enrichment of memory subtype among RFR-LCDR.AA CAR-T cells was not evident prior to injection into tumor-bearing mice (FIG. 2611), indicating the change occurred upon encountering antigen stimulation and/or the in vivo environment.

Taken together, these data indicate that rituximab CAR-T cells exhibit elevated glycolysis both at rest and upon antigen exposure in vivo. In contrast, RFR-LCDR.AA, a novel CAR obtained through scFv sequence hybridization combined synergistically with alanine insertion, promotes the formation of memory T cells that can mount robust effector functions while maintaining relatively low metabolic activity levels as well as long-term persistence in vivo.

B. Discussion

In this study, the inventors explored the effect of rational CAR sequence and structural modifications on the behavior of CAR-T cells, and observed that even modest alterations—as small as the insertion of two alanine residues—can induce dramatic changes in the anti-tumor efficacy of the resulting CAR-T cells. The inventors found tonic signaling—and the associated basal T-cell activation—to be a useful measure by which to quantify and tune CAR behavior. These results suggest that the effects of tonic signaling operate on a gradient, and a sweet spot exists in which low-level tonic signaling could potentiate rapid T-cell response to antigen stimulation while enabling sustained anti-tumor activity. Methods such as the insertion of torsional linkers comprised of alanines and the hybridization of FR and CDR sequences from different scFvs enable the generation of CAR variants that fall along the spectrum of tonic-signaling intensities, and some of these variants could outperform even the gold-standard CD19 CAR in in vivo tumor control.

Alanine insertion is a generalizable method for tuning CAR tonic signaling as well as antigen-stimulated CAR-T cell function. In this study, the inventors found the insertion of two alanines between the transmembrane and cytoplasmic domains of CD28 to improve the in vivo function of both CD20 and GD2 CARs. Given that the intended effect of alanine insertion is to alter or "twist" the CAR conformation, and the starting protein conformation is likely dependent on the specific components incorporated in the CAR, the optimal number of alanine may vary with the specific transmembrane and cytoplasmic domains used in the CAR. Detailed biochemical analysis of the downstream signal-transduction pathway could further elucidate the molecular mechanism that underpins the functional improvements in the study, and inform on whether the alanine-insertion strategy could be adapted to CARs with a variety of transmembrane and cytoplasmic domains.

In addition to alanine insertion, scFv hybridization proved to be a fruitful method by which to generate improved CAR variants. In the case of the RFR-LCDR hybrid characterized in this study, a CAR built with FRs from a tonically signaling CAR (rituximab) and CDRs from a non-tonically signaling CAR (Leu16) led to a chimera with intermediate tonic-signaling intensity, and far-superior anti-tumor efficacy compared to either parent. This result highlights the unpredictability of the effect of scFv sequence on CAR-T cell function. In-depth analysis of protein structure and site-specific mutations may allow for precise identification of the truly critical residues and enable a fully rational approach to scFv design in the future.

A phenotype found to be strongly associated with tonic signaling—and tunable by the protein-engineering methods discussed above—is elevated metabolic activity at rest, particularly glycolysis and glutaminolysis. A significant body of literature has shown that increased glycolytic activity is characteristic of effector T cells, and that heightened glycolysis is essential to robust T-cell effector function (Bantug et al., 2018). The fact that rituximab CAR-T cells exhibit strong glycolysis both at rest and upon antigen stimulation is consistent with the hypothesis that tonic signaling and basal T-cell activation could potentiate T cells for rapid effector function. At the same time, sustained aerobic glycolytic activity is also associated with the acquisition of senescent phenotypes and a lack of potential for long-term persistence and memory formation (Kishton et al., 2017), consistent with the inability of rituximab-based CAR-T cells to achieve sustained control of tumor xenografts. This stands in stark contrast to the hybrid CAR-T cells that exhibit relatively low glycolytic flux but robust and sustained anti-tumor activity. A major challenge faced by CAR-T cells with intrinsically high metabolic rates is metabolic competition with tumor cells, which could further constrain the CAR-T cells' ability to sustain their function (Chang et al., 2015). The Warburg effect, characterized by high rates of glucose uptake and lactate secretion despite the presence of oxygen, is a hallmark of tumor cells (Liberti and Locasale, 2016). In the tumor microenvironment, CAR-T cells and tumor cells must compete for the same limited supply of nutrients and contribute to the same potentially toxic acidification of the tumor microenvironment via lactate secretion (Fischer et al., 2007). This competition could have a disproportionately strong impact on the anti-tumor efficacy of rituximab-based CAR-T cells compared to other CAR-T cell variants with lower metabolic burdens.

Given that high metabolic rates are necessary to support robust effector T-cell function while memory phenotypes are conducive to long-term tumor control, an intriguing question is whether combining different CAR-T cells that target the same antigen—e.g., by co-administering rituximab CAR-T cells with RFR-LCDR.AA CAR-T cells either simultaneously or sequentially—would achieve greater therapeutic efficacy than administering either cell population alone. The use of multiple cell products could incur significant costs and technical complications compared to single-product administration. Nevertheless, such combinations may prove useful in conditions that have thus far resisted response to CAR-T cell therapy.

The structural modularity of CAR molecules supports the development of CAR-T cell therapies for a wide range of disorders, but the ability to rationally design CARs that yield predictably robust function in vivo remains elusive. The protein-engineering strategies and CAR-T cell characterization methods explored in this study offer a systematic approach to tune CAR signaling and quantitatively evaluate CAR-T cell phenotype and metabolism, supporting the engineering of next-generation CAR-T cells for refractory diseases that currently lack effective options.

C. Materials and Methods

1. Construction of Anti-CD20 scFvs and CARs

Plasmids encoding scFv sequences of rituximab and GA101 were generous gifts from Dr. Anna M. Wu (Zettlitz et al., 2017) (UCLA and City of Hope). DNA sequence encoding the ofatumumab scFv was codon optimized and synthesized by Integrated DNA Technologies (IDT; Coralville, IA). Plasmid encoding scFv derived from the leu16 monoclonal antibody (mAb) was a generous gift from Dr. Michael C. Jensen (Seattle Children's Research Institute) (Jensen et al., 1998). $V_L$ and $V_H$ sequences of anti-GD2 scFv were identified from the 14g2a mAb (PDB code 4TUJ) using abYsis (Swindells et al., 2017). Anti-CD20 CARs were constructed by assembling an scFv (in $V_L$-$V_H$ orientation), an extracellular IgG4 hinge-CH2-CH3 spacer containing the L235E N297Q mutation (Hudecek et al., 2015), CD28 transmembrane and cytoplasmic domain, CD3C cytoplasmic domain, and a T2A "self-cleaving" sequence followed by a truncated epidermal growth factor receptor (EGFRt) with the MSCV backbone. EGFRt was used as a transduction and sorting marker. The abovementioned anti-CD20 CAR constructs were used as templates to generate CAR-HaloTag fusion proteins for microscopy imaging of CAR clustering.

Cell Line Generation and Maintenance

HEK 293T and Raji cells were obtained from ATCC. K562 cells were a gift from Dr. Michael C. Jensen (Seattle Children's Research Institute). $CD19^+CD20^+$ K562 cells were generated as previously described (Zah et al., 2016). Luciferase-expressing CHLA-255 cell line (CHLA-255-Luc) was a gift from Dr. Shahab Asgharzadeh (Children's Hospital of Los Angeles). CHLA-255-Luc-EGFP cells were generated by retroviral transduction of CHLA-255-Luc to express EGFP, and EGFP+ cells were enriched by fluorescence-activated cell sorting (FACS) on FACSAria (II) (BD Bioscience) at the UCLA Flow Cytometry Core Facility. HEK 293T cells were cultured in DMEM (HyClone) supplemented with 10% heat-inactivated FBS (HI-FBS; ThermoFisher). CHLA-255-Luc-EGFP cells were cultured in IMDM (ThermoFisher) with 10% HI-FBS. Primary human T cells, Raji, and K562 cells were cultured in RPMI-1640 (Lonza) with 10% HI-FBS. For CAR-T cells used in metabolomics studies, T cells were cultured in RPMI-1640 containing 2 g/L of 1,2-$^{13}$C-glucose with 10% heat-inactivated dialyzed FBS (HI-dFBS).

2. Retrovirus Production and Generation of Human Primary CAR-T Cells

Retroviral supernatants were produced by transient co-transfection of HEK 293T cells with plasmids encoding anti-CD20 CAR or control constructs, and pRD114/pHIT60 virus-packaging plasmids (gifts from Dr. Steven Feldman), using linear polyethylenimine (PEI, 25 kDa; Polysciences). Supernatants were collected 48 and 72 hours later and pooled after removal of cell debris by a 0.45 m membrane filter. Healthy donor blood was obtained from the UCLA Blood and Platelet Center. $CD8^+$ T cells were isolated using RosetteSep Human $CD8^+$ T Cell Enrichment Cocktail (StemCell Technologies) following manufacturer's protocol. Peripheral blood mononuclear cells (PBMCs) were isolated from a Ficoll-Paque PLUS (GE Healthcare) density gradient. $CD14^-/CD25^-/CD62L^+$ naïve/memory T cells ($T_{N/M}$) were enriched from PBMCs using magnetic-activated cell sorting (Miltenyi). T cells were stimulated with CD3/CD28 Dynabeads (ThermoFisher) at a 3:1 cell-to-bead ratio on Day 0 (day of isolation) and transduced with retroviral supernatant on Day 2 and Day 3. Dynabeads were removed on Day 7. T cells were cultured in RPMI-1640 supplemented with 10% HI-FBS and fed with recombinant human IL-2 (ThermoFisher) and IL-15 (Miltenyi) every 2 days to final concentrations of 50 U/mL and 1 ng/mL, respectively. For CAR-T cells used in RNA-seq, ATAC-seq and metabolomic study, T cells were enriched for $CAR^+$ expression by magnetic cell sorting via staining of EGFRt with biotinylated cetuximab (Eli Lilly; biotinylated in-house) followed by anti-biotin microbeads (Miltenyi). For RNA-seq and ATAC-seq, dead cells were depleted with a dead cell removal kit (Miltenyi) prior to enrichment of $EGFRt^+$ population.

3. Cytokine Production Quantification

Fifty thousand $CAR^+$ T cells on Day 13 or 14 were incubated with 25,000 EGFP-expressing parental K562 ($CD19^-CD20^-$) or $CD19^+CD20^+$ K562 target cells at a 2:1 effector-to-target (E:T) ratio in 96-well U-bottom plate. To control for cell density while accounting for differences in transduction efficiency, untransduced T cells were added as necessary to reach the same number of total T cells per well. After a 48-hour co-incubation, cells were spun down at 300×g for 2 min. Supernatant was harvested and cytokine levels were quantified by ELISA (BioLegend).

4. Proliferation Assay

T cells were stained with 1.25 M CellTrace Violet (ThermoFisher) and 40,000 $CAR^+$ T cells were seeded in each well in 96-well U-bottom plates with parental K562 or $CD19^+CD20^+$K562 cells at a 2:1 E:T ratio. Untransduced T cells were added to wells as needed to normalize for differing transduction efficiencies and ensure the total number of T cells per well was consistent throughout. Cultures were passaged as needed, and CTV dilution was analyzed on a magnetic-activated cell sorting flow cytometer after a 4-day co-incubation.

5. Cytotoxicity Assay with Repeated Antigen Challenge $CAR^+$ T cells were seeded at $4\times10^5$ cells/well in 24-well plate and coincubated with target cells at a 2:1 E:T ratio. Untransduced T cells were added to wells as needed to normalize for differing transduction efficiencies and ensure the total number of T cells per well was consistent throughout. Cell counts were quantified by a magnetic-activated cell sorting flow cytometer every 2 days prior to addition of fresh target cells ($2\times10^5$ cells/well).

6. Antibody Staining for Flow-Cytometry Analysis

EGFRt expression was measured with biotinylated cetuximab (Eli Lilly; biotinylated in-house), followed by PE-conjugated streptavidin (Jackson ImmunoResearch #016-110-084). CAR expression was quantified by surface epitope staining using Flag tag (DYKDDDDK tag, APC, clone L5, BioLegend #637308), HA (FITC, clone GG8-1F3.3.1, Miltenyi #130-120-722), or with anti-Fc (fluorescent dye ALEXA FLUOR 488, Jackson ImmunoResearch #709-546-098). Antigen-independent activation-marker expression of CAR-T cells was evaluated by antibody staining for CD137

(PE/Cy7, clone 4B4-1, BioLegend #309818) and CTLA-4 (PE/Cy7, clone BNI3, BioLegend #369614) on Days 18 (i.e., 18 days after Dynabead addition and 11 days after Dynabead removal). Antibodies for CD45RA (VioGreen, clone T6D11, Miltenyi #130-113-361), CD62L (APC, clone DREG-56, ThermoFisher #17-0629-42), PD-1 (APC, clone EH12.2H7, BioLegend #329908), and LAG-3 (APC, clone 3DS223H, ThermoFisher #17-2239-42) were used to evaluate T-cell subtype and exhaustion status. T-cell and tumor-cell persistence in vivo were monitored by antibody staining of retro-orbital blood samples. Samples were treated with red blood cell lysis solution (10×, Miltenyi) following manufacturer's protocol. The remaining cellular content was stained with anti-human CD45 (PacBlue or PECy7, clone H130, BioLegend #304029 or #304016) and biotinylated cetuximab, followed by PE-conjugated streptavidin. All samples were analyzed on a magnetic-activated cell sorting flow cytometer (Miltenyi), and the resulting data were analyzed using the FlowJo software (TreeStar).

7. Confocal Microscopy

Jurkat cells transduced with CAR-HaloTag fusion protein were seeded at 10,000 cells per well in 50 μL RPMI-1640+10% HI-FBS in one well of a 48-well flat-bottom glass plate (MatTek). Scanning confocal imaging was acquired with a Zeiss LSM 880 laser scanning confocal microscope with AiryScan and a 63×1.4 NA oil objective.

8. In Vivo Studies

Six- to 8-week old NOD/SCID/IL-2Rγ$^{null}$ (NSG) mice were obtained from UCLA Department of Radiation and Oncology. The protocol was approved by UCLA Institutional Animal Care and Used Committee. For evaluation of CD19 and CD20 CAR-T cells, each mouse was administered $0.5\times10^5$ EGFP$^+$ firefly luciferase (ffLuc)-expressing Raji cells by tail-vein injection. Six to nine days later, $1.5\times10^6$-$5\times10^6$ CAR$^+$ T cells or cells expressing EGFRt only (negative control) were injected via tail vein to tumor-bearing mice after confirming tumor engraftment. A second dose at $0.5\times10^6$ and a third dose at $2\times10^6$ of tumor cells were administered in a subset of studies as noted in the text and figures. In the study of GD2 CAR-T cells, each mouse was administered with $3.5\times10^6$ CHLA-255-Luc-EGFP cells by tail-vein injection. Upon confirmation of CHLA-255 tumor engraftment (17 days post tumor injection), $2\times10^6$ CAR$^+$ T cells were injected via tail vein to tumor-bearing mice. Details of tumor dose, T-cell dose, tumor re-challenge were indicated in the text and figures. Tumor progression/regression was monitored with an IVIS Illumina III LT Imaging System (PerkinElmer). Blood samples were harvested via retro-orbital bleeding 3 days post T-cell injection and every 10 days thereafter. Mice were euthanized at the humane endpoint. Bone marrow, spleen and liver were collected after euthanasia. Tissues were ground and passed through a 100-μm filter followed by red-blood-cell lysis prior to flow-cytometry analysis. For ATAC-seq and RNA-seq experiments, NSG mice were engrafted with $0.5\times10^6$ Raji cells 6 days prior to treatment with $2.85\times10^6$ CAR-T cells. Nine days after T-cell injection, CAR-T cells were recovered from animal tissues (liver, spleen, cardiac blood, and bone marrow) and enriched for huCD45$^+$ and EGFRt$^+$ subpopulation by magnetic-activating cell sorting prior to ATAC-seq/RNA-seq library construction.

9. ATAC-seq Library Construction and Data Analysis

ATAC-seq libraries were constructed as previously described (Buenrostro et al., 2013; Corces et al., 2017). In brief, 30,000-50,000 viable T cells per mouse from magnetic-activated cell sorting were washed once with PBS and lysed in 50 μL Resuspension Buffer (RSB) buffer (10 mM Tris-HCL, pH 7.4, 10 mM NaCl, 3 mM $MgCl_2$) with 0.1% IGEPAL CA-630, 0.1% Tween-20, and 0.01% digitonin. Samples were washed with 1 mL RSB buffer containing 0.1% Tween-20 and centrifuged at 500×g for 10 minutes at 4° C. Pelleted nuclei were resuspended in 25 μL Tn5 transposition mix (12.5 μL 2×Tagment DNA buffer, 1.25 L Tn5 transposase, and 11.25 μL sterile water; Illumina) and stored in a shaking incubator at 37° C. and 500 RPM for one hour. Transposition reaction was purified with DNA Clean & Concentrator kit (Zymo Research). DNA fragments were PCR-amplified using NEB Q5 MasterMix and custom primers as previously described (Buenrostro et al., 2013). Libraries were size selected by AmPure beads (Beckman Coulter) and quantified by TapeStation. Libraries were sequenced on the Illumina NovaSeq S1 platform at the High Throughput Sequencing core at UCLA Broad Stem Cell Research Center with 50-bp paired-end reads. Fastq files from ATAC-seq were quality examined by FastQC (Linux, v0.11.8). Reads were processed by cutadapt (Linux, v1.18) to remove reads with low quality (quality score <33) and to trim adapters. Trimmed reads were aligned to mm10 reference genome using Bowtie2 (Linux, v2.2.9) to eliminate contaminating reads from mouse cells. Non-murine reads were subsequently mapped to hg38 genome by Bowtie2, and sam files were converted to bam files by samtools (Linux, v1.9). Peaks were called independently for each replicate using magnetic-activated cell sorting (Linux, v2.1.2) on the aligned reads, and subsequently merged by bedtools (v2.26.0). Reads assigned to each peak were counted by featureCounts function in subread (Linux, v1.6.3). To visualize chromatin accessible sites, peaks called from magnetic-activated cell sorting were visualized in IGV (v2.8.0). Fold enrichments (calculated by magnetic-activated cell sorting) of peaks within −1 kb to 1 kb of the transcription start site (TSS) indicate accessibility of promoter regions.

10. Bulk RNA-seq and Gene Set Enrichment Analysis (GSEA)

Total RNA was extracted from 200,000-700,000 magnetic-activated cell sorting-sorted CAR-T cells using Qiagen RNeasy Plus Mini kit. mRNAs were isolated using NEBNext Poly(A) mRNA Magnetic Isolation Module (New England BioLabs). RNA-seq libraries were generated using NEBNext Ultra II Directional RNA Library Prep Kit (New England BioLabs) following manufacturer's protocol. Fastq files from RNA-seq were quality-examined by FastQC (Linux, v0.11.8). Reads were processed by cutadapt (Linux, v1.18) to remove reads with low quality (quality score <33) and to trim adapters. Trimmed reads were aligned to mm10 reference genome using Tophat2 (Linux, v2.1.0) to remove the contaminated reads from mouse cells. Non-murine reads were mapped to hg38 genome by Tophat2. Reads assigned to each gene were counted by featureCounts function in subread package (Linux, v1.6.3) with ensembl 38 gene sets as references. Genes without at least 8 reads mapped in at least one sample were considered below reliable detection limit and eliminated. Read counts were normalized by Trimmed Mean of M-values method (TMM normalization method in edgeR running on R v3.6.3) to yield RPKM (reads per millions per kilobases) values, and differential expression was calculated using the package edgeR. Gene ontology analysis was performed using GSEA software (v4.1.0, Broad Institute) and BubbleGUM (v1.3.19) (Spinelli et al., 2015). Expression values of differentially expressed genes were input to the program and using a curated list of 2493 T-cell-relevant gene sets selected from current MSigDB gene sets. Heatmaps for differentially expressed genes were generated using pheamap and ggplot2 packages in R (version 3.6.3). Volcano plots were generated using ggplot2 in R (version 3.6.3).

11. Metabolite Extraction and Analysis

Cells were initially cultured in RPMI-1640 supplemented with 10% HI-FBS. At 24 to 72 hours before metabolite extraction, culture media were changed to RPMI containing 10% FBS or dialyzed FBS (dFBS) with 2 g/L 1,2-$^{13}$C-glucose. Cell culture media were collected from each cell line every 24 hours to evaluate nutrient uptake and consumption. Four volumes of 100% HPLC-grade methanol were added to one volume of media and centrifuged at 17,000×g and 4° C. for 5 minutes to precipitate cell debris. Clear supernatants were harvested and analyzed by liquid chromatography followed by mass spectrometry (LC-MS). To provide accurate estimation of nutrient uptake and consumption, partial media change was performed every 24 hours to avoid nutrient depletion. Twenty-four or 72 hours after switching to labeled-glucose media, intracellular metabolite extraction was performed as previously described (Bennett et al., 2008; Park et al., 2019). In brief, cells were transferred onto nylon membrane filters (0.45 m; Millipore) and vacuumed to remove media. Each filter was quickly soaked in 400 μL cold extraction solvent (HPLC-grade acetonitrile:methanol:water 40:40:20, v/v) in one well of a 6-well plate. The plates were incubated at −20° C. for 20 minutes. Cell extracts were subsequently transferred to 1.7 mL microcentrifuge tubes and centrifuged at 17,000×g in 4° C. for 5 minutes. Supernatants were lyophilized and reconstituted in HPLC-grade water normalized to total cell count (50 μL per 1 million cells). Both methanol-treated media samples and intracellular metabolite extracts were analyzed by reversed-phase ion-pairing liquid chromatography (Vanquish UPLC; Thermo Fisher Scientific) coupled to a high-resolution orbitrap mass spectrometer (Q-Exactive plus Orbitrap; Thermo Fisher Scientific) at the Molecular Instrumentation Center (MIC) in UCLA. Metabolites were identified by comparing mass-to-charge (m/z) ratio and retention time to previously validated standards. Samples were detected in both negative-ion mode and positive-ion mode. Negative-ion mode was separated into two subgroups—nlo and nhi—to obtain data with m/z ratio from 60 to 200 and 200 to 2000, respectively. LC-MS data were processed using Metabolomic Analysis and Visualization Engine (MAVEN) (Clasquin et al., 2012). Labeling fractions were corrected for the naturally occurring abundance of $^{13}$C. Concentration of metabolites in culture media was quantified at 24 and 72 hr by normalizing ion counts from LC-MS measurement to controls with known concentrations. Uptake and secretion rates were calculated by subtracting sample concentration from fresh media and normalizing to viable cell count (positive values indicated secretion and negative values indicated uptake). A mole balance was performed to account for media change from cell cultures. Calculation accounted for 10-20% of media evaporation every 24 hours.

12. Statistical Analysis

Statistical tests including two-tailed, unpaired, two-sample Student's t test and log-rank Mentel-Cox test were performed using GraphPad Prism V8. One-way ANOVA test for differential gene analysis in RNA-seq was performed with glmQLFTest function in edgeR.

Example 4.: CAR Engineering

This Example provides data to supplement the Examples above. In some instances, the data may be a duplicate of that in the above examples, just presented in a different way. Shown in FIG. 1 is a schematic of CD20 CARs constructed with scFv derived from various antibodies. All CARs were second generation receptors containing the CD28 co-stimulatory domain (FIG. 1A) and the sequence of scFv domains used in CD20 CAR construction.

CARs based on Leu16, rituximab, GA101, and ofatumumab are all efficiently expressed on the surface of primary human T cells, with no significant difference in their impact on T-cell expansion during ex vivo culture. (FIG. 27A-C). CARs based on Leu16, rituximab, GA101, and ofatumumab show similar antigen detection thresholds (FIG. 28A-C). Rituximab-derived CD20 CAR shows antigen-independent CAR signaling, resulting in (FIG. 29 A,B) upregulation of activation and exhaustion markers, and (FIG. 29 C,D) T-cell proliferation in the absence of antigen stimulation. FIGS. 29 A, C show tonic signaling in rituximab-based CAR-T cells that was observed in both CD8$^{+}$ and naïve/memory T (TN/M) cells, which was sorted for CD14−/CD25−/CD62L+ phenotype. Rituximab-derived CD20 CAR shows antigen-independent CAR signaling, resulting in upregulation of metabolic flux, as evidenced by increased glucose and glutamine uptake as well as increased lactate, alanine, and glutamate secretion. The CD19 CAR and GD2 CAR were included as a negative and positive control, respectively, for tonic signaling (FIG. 30). Confocal microcopy shows uniform surface expression of CARs based on Leu16, rituximab, GA101, and ofatumumab, indicating tonic signaling by rituximab CAR-T cells is not caused by CAR clustering (FIG. 31). Rituximab-based CAR-T cells show greater tumor control than Leu16-, GA101-, and Ofatumumab-based CARs at early time points but rapidly lose anti-tumor efficacy after 2 weeks (FIG. 32). Alanine-insertion variants (FIG. 17) of rituximab-based CARs express well on the surface of primary human T cells (FIG. 33). Alanine insertion results in reduced tonic signaling in rituximab-based CAR-T cells (FIG. 34). Alanine insertion did not alter in vitro anti-tumor activity of rituximab-based CAR-T cells (FIG. 35).

Rituximab-derived CD20 CAR containing two alanine residues inserted between the transmembrane and cytoplasmic CD28 domains result in superior in vivo anti-tumor function. NOD/scid/γ−/− (NSG) mice were engrafted with 0.5 million firefly luciferase-expressing Raji lymphoma cells and treated with 1.35 million T cells expressing either a CD20 CAR or a transduction marker (EGFRt) 7 days post tumor injection. Animals were re-dosed with 1.5 million T cells 7 days later. All CARs tested in this study contained a rituximab-derived scFv, IgG4 hinge-CH2-CH3 extracellular spacer, CD28 transmembrane and cytoplasmic domains, and CD3 zeta signaling domain. Zero to four alanines were inserted between the CD28 transmembrane and CD28 cytoplasmic domains. Tumor progression was monitored through bioluminescence imaging, and radiance signal as a function of time since tumor injection is shown. The end point of each radiance trace indicates the humane end point of each animal. The two-alanine insertion variant showed superior tumor control and extended median survival compared to the parental (no alanine insertion) construct as well as the other variants. This data is shown in FIG. 5. Alanine insertion is a generalizable method to improve CAR-T cell function (FIG. 36).

CD20 CARs with hybrid scFvs (FIG. 6) are efficiently expressed on the surface of primary human T cells (FIG. 37). The RFR-LCDR hybrid CD20 CAR shows antigen-independent CAR signaling, resulting in upregulation of activation and exhaustion markers (FIG. 38A) and T-cell proliferation in the absence of antigen stimulation (FIG. 38B). The CD19 CAR and GD2 CAR were included as a negative and positive control, respectively, for tonic signaling in FIG. 38. The RFR-LCDR hybrid CD20 CAR shows superior tumor-cell killing upon repeated antigen challenge in vitro. T cells expressing various CARs or a transduction marker (EGFRt) were challenged with fresh Raji lymphoma cells every 48 hours. Viable target-cell count was quantified by flow cytometry before each re-challenge. Results from multiple donors indicate superior tumor-cell killing by the RFR-LCDR hybrid CAR compared to either of its parental constructs (Leu16 and Rituximab) (FIG. 8). Binding kinetic parameters of Leu16, rituximab and RFR-LCDR scFvs were measured by bio-layer interferometry (FIG. 39).

Figure 40:
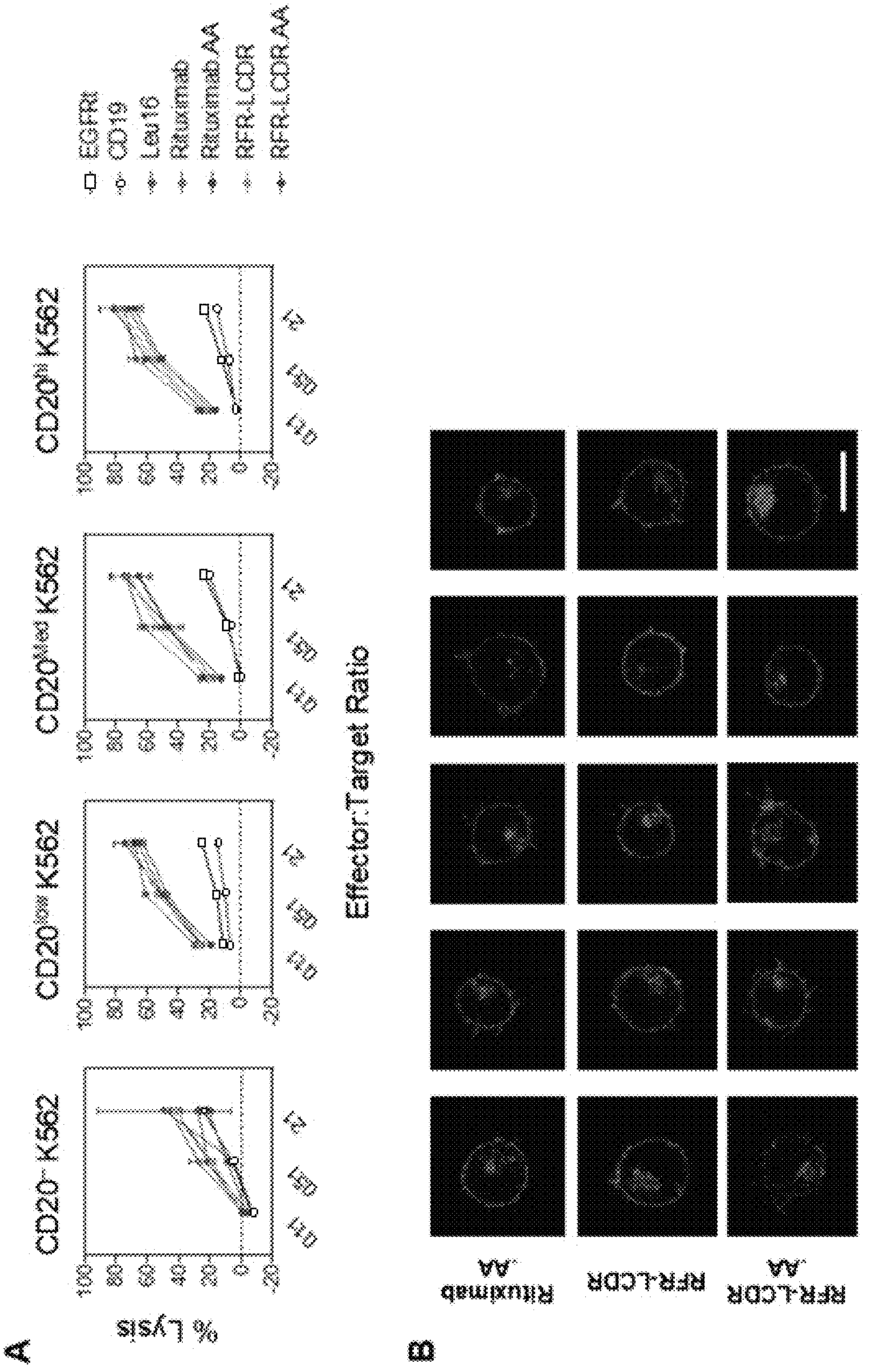
Figure 41:
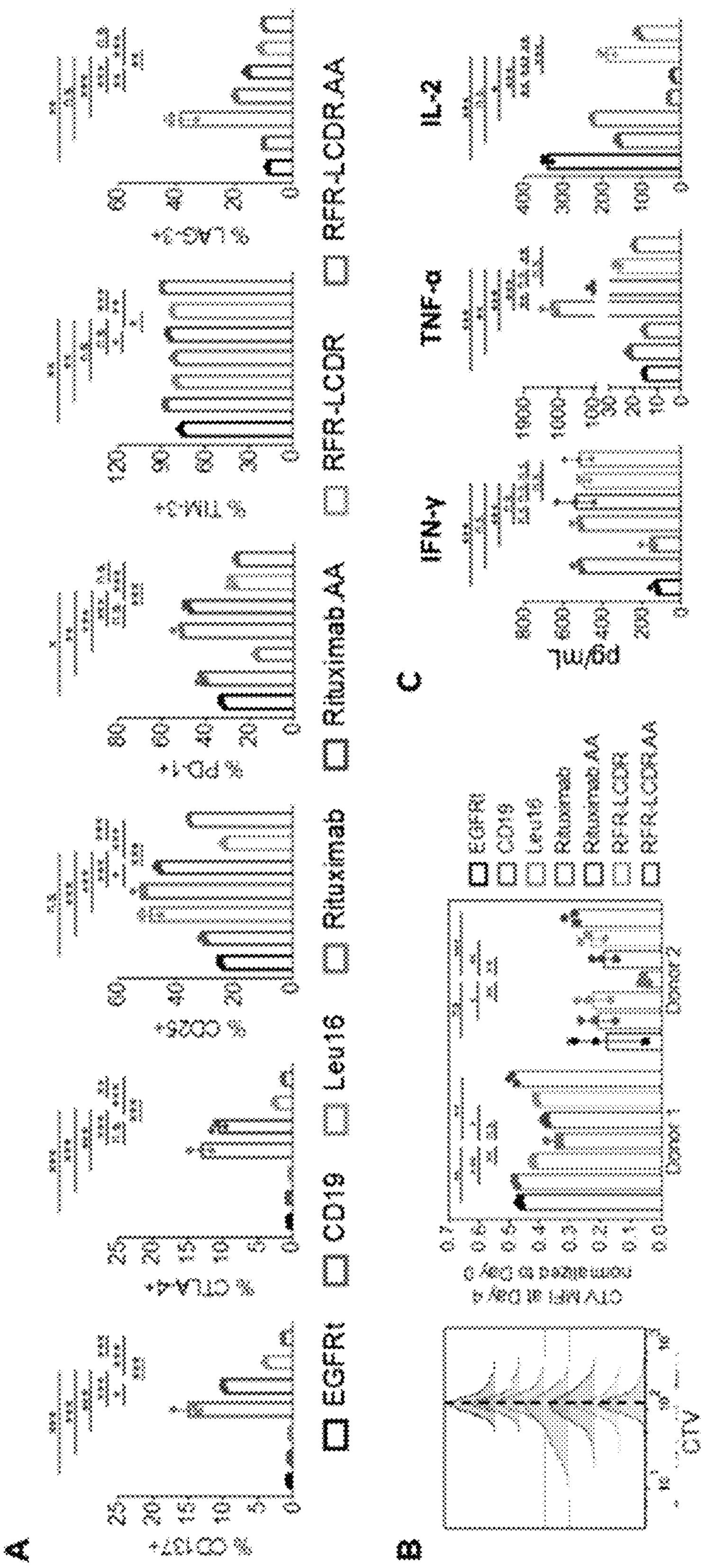
Figure 43G:
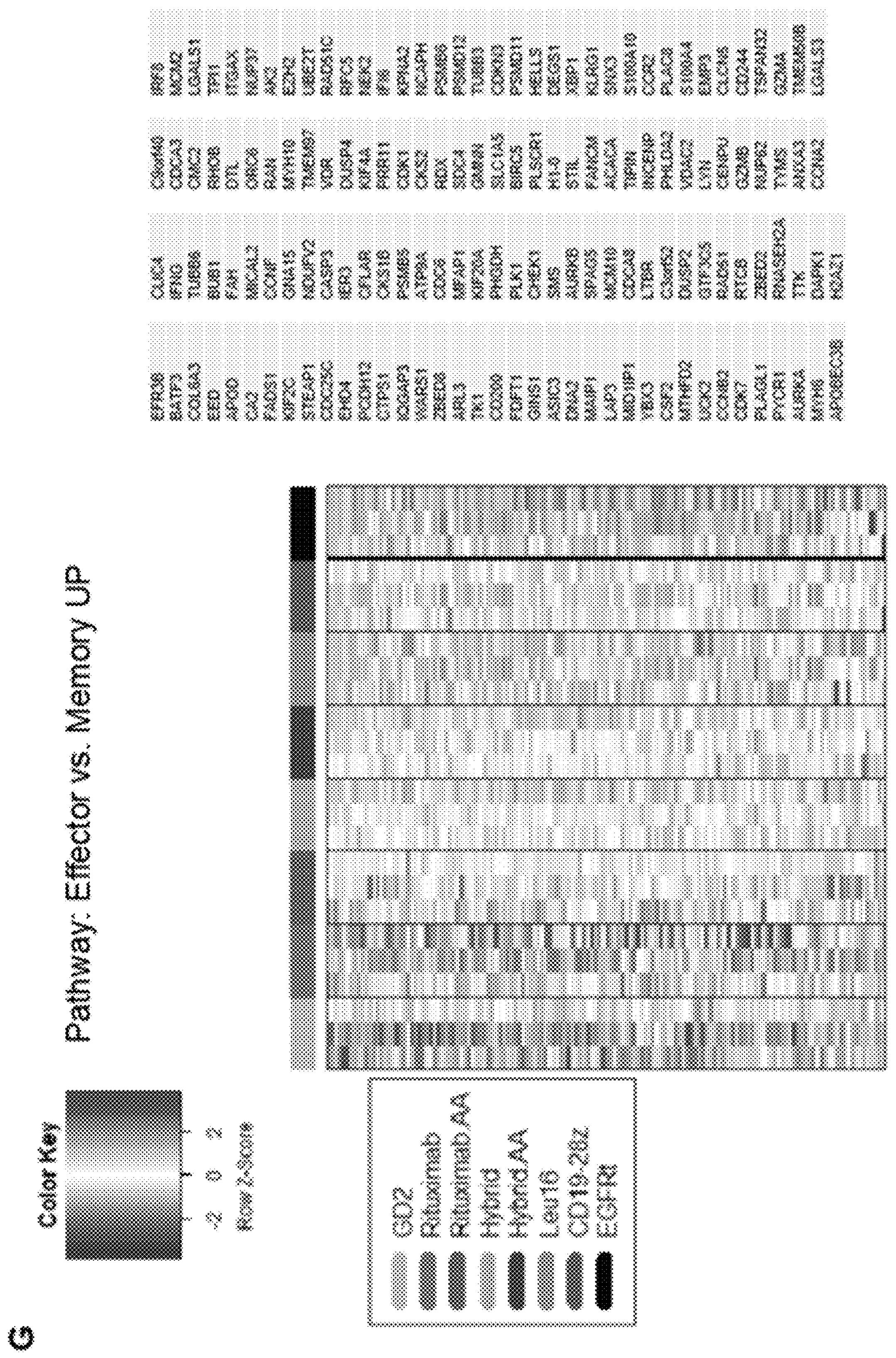
Figure 43H:
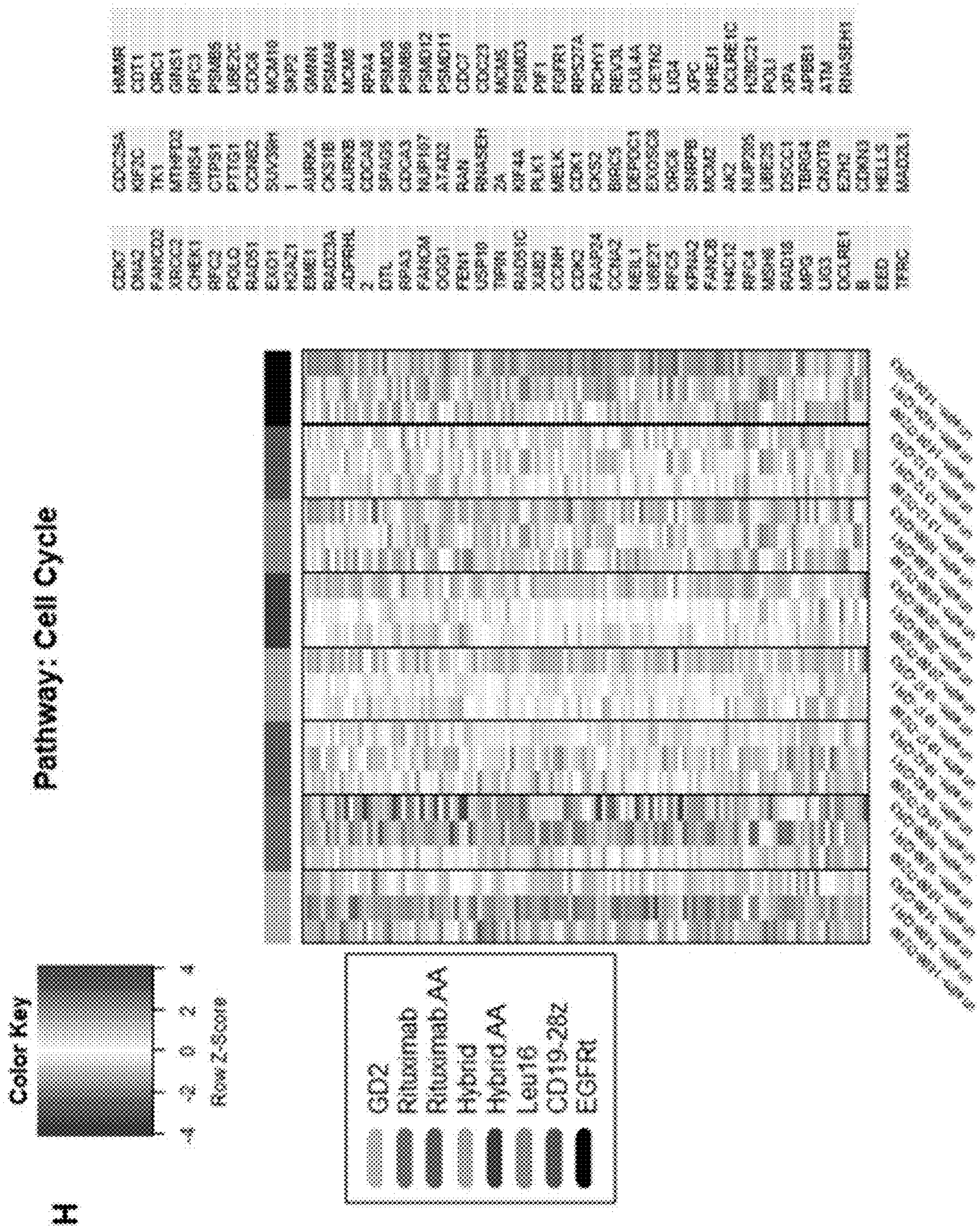

Alanine insertion and scFv hybridization can be combined to generate novel CAR constructs (FIG. 40). CARs containing the RFR-LCDR hybrid scFv, with and without alanine insertion, results in low but non-zero levels of tonic signaling (FIG. 41). CARs containing the RFR-LCDR hybrid scFv, with and without alanine insertion, results in low but non-zero levels of tonic signaling, as evidenced by glucose and glutamine uptake as well as lactate, alanine, and glutamate secretion (FIG. 42). Tonically signaling CARs show distinct transcriptional profiles indicating increased mitochondrial protein translation (FIG. 43A), increased antigen presentation (FIG. 43B), increased MYC signaling (FIG. 43C), increased MTORC signaling (FIG. 43D), increased TNF-α signaling (FIG. 43E), divergent interferon responses (FIG. 43F), enriched signature of genes associated with effector (as opposed to memory) T-cell subtypes (FIG. 43G), and increased cell-cycle activity (FIG. 43H). For heat maps containing genes in excess of the space available for display, the names of genes shown in the heat map are listed in order to the side of each map. The RFR-LCDR hybrid CD20 CAR shows superior tumor clearance in vivo (FIG. 44). Transcriptomic and epigenetic analyses reveal CAR-dependent variations in T-cell phenotypes (FIG. 45). NSG mice were injected i.v. with $0.5\times10^6$ firefly-luciferase-expressing Raji cells 6 days prior to treatment with $2.85\times10^6$ CAR T cells delivered i.v. Liver, spleen, cardiac blood, and bone marrow were collected from tumor-bearing mice 9 days after T-cell injection (n=2 mice per group). $CAR^+$ T cells were obtained by enriching for $huCD45^+$ $EGFRt^+$ populations, and subsequently analyzed by RNAseq and ATACseq (FIG. 45).

All of the methods disclosed and claimed herein can be made and executed without undue experimentation in light of the present disclosure. While the compositions and methods of this disclosure have been described in terms of preferred embodiments, it will be apparent to those of skill in the art that variations may be applied to the methods and in the steps or in the sequence of steps of the method described herein without departing from the concept, spirit and scope of the disclosure. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the disclosure as defined by the appended claims.

The references recited in the application, to the extent that they provide exemplary procedural or other details supplementary to those set forth herein, are specifically incorporated herein by reference.

The following references and the publications referred to throughout the specification, to the extent that they provide exemplary procedural or other details supplementary to those set forth herein, are specifically incorporated herein by reference.

REFERENCES

Till B. G. et al. Blood, 2008; 112(6):2261-2271.

Wang et al. Clinical Immunology, 2014; 155:160-175.

Constantiescu et al. Molecular Cell, 2001. 7:377-385.

Bantug, G. R., Galluzzi, L., Kroemer, G., and Hess, C. (2018). The spectrum of T cell metabolism in health and disease. Nat Rev Immunol 18, 19-34.

Bennett, B. D., Yuan, J., Kimball, E. H., and Rabinowitz, J. D. (2008). Absolute quantitation of intracellular metabolite concentrations by an isotope ratio-based approach. Nat Protoc 3, 1299-1311.

Bjorkstrom, N. K., Beziat, V., Cichocki, F., Liu, L. L., Levine, J., Larsson, S., Koup, R. A., Anderson, S. K., Ljunggren, H. G., and Malmberg, K. J. (2012). CD8 T cells express randomly selected KIRs with distinct specificities compared with NK cells. Blood 120, 3455-3465.

Buenrostro, J. D., Giresi, P. G., Zaba, L. C., Chang, H. Y., and Greenleaf, W. J. (2013). Transposition of native chromatin for fast and sensitive epigenomic profiling of open chromatin, DNA-binding proteins and nucleosome position. Nat Methods 10, 1213-1218.

Chang, C. H., Curtis, J. D., Maggi, L. B., Jr., Faubert, B., Villarino, A. V., O'Sullivan, D., Huang, S. C., van der Windt, G. J., Blagih, J., Qiu, J., et al. (2013). Posttranscriptional control of T cell effector function by aerobic glycolysis. Cell 153, 1239-1251.

Chang, C. H., Qiu, J., O'Sullivan, D., Buck, M. D., Noguchi, T., Curtis, J. D., Chen, Q., Gindin, M., Gubin, M. M., van der Windt, G. J., et al. (2015). Metabolic Competition in the Tumor Microenvironment Is a Driver of Cancer Progression. Cell 162, 1229-1241.

Chang, Z. L., and Chen, Y. Y. (2017). CARs: Synthetic Immunoreceptors for Cancer Therapy and Beyond. Trends Mol Med 23, 430-450.

Chang, Z. L., Lorenzini, M. H., Chen, X., Tran, U., Bangayan, N. J., and Chen, Y. Y. (2018). Rewiring T-cell responses to soluble factors with chimeric antigen receptors. Nat Chem Biol 14, 317-324.

Chothia, C., and Lesk, A. M. (1987). Canonical structures for the hypervariable regions of immunoglobulins. J Mol Biol 196, 901-917.

Chothia, C., Lesk, A. M., Tramontano, A., Levitt, M., Smith-Gill, S. J., Air, G., Sheriff, S., Padlan, E. A., Davies, D., Tulip, W. R., et al. (1989). Conformations of immunoglobulin hypervariable regions. Nature 342, 877-883.

Clasquin, M. F., Melamud, E., and Rabinowitz, J. D. (2012). LC-MS data processing with MAVEN: a metabolomic analysis and visualization engine. Curr Protoc Bioinformatics Chapter 14, Unit14 11.

Constantinescu, S. N., Keren, T., Socolovsky, M., Nam, H., Henis, Y. I., and Lodish, H. F. (2001). Ligand-independent oligomerization of cell-surface erythropoietin receptor is mediated by the transmembrane domain. Proc Natl Acad Sci USA 98, 4379-4384.

Corces, M. R., Trevino, A. E., Hamilton, E. G., Greenside, P. G., Sinnott-Armstrong, N. A., Vesuna, S., Satpathy, A. T., Rubin, A. J., Montine, K. S., Wu, B., et al. (2017). An improved ATAC-seq protocol reduces background and enables interrogation of frozen tissues. Nat Methods 14, 959-962.

Cretenet, G., Clerc, I., Matias, M., Loisel, S., Craveiro, M., Oburoglu, L., Kinet, S., Mongellaz, C., Dardalhon, V., and Taylor, N. (2016). Cell surface Glut1 levels distinguish human CD4 and CD8 T lymphocyte subsets with distinct effector functions. Sci Rep 6, 24129.
Drent, E., Poels, R., Ruiter, R., van de Donk, N., Zweegman, S., Yuan, H., de Bruijn, J., Sadelain, M., Lokhorst, H. M., Groen, R. W. J., et al. (2019). Combined CD28 and 4-1BB Costimulation Potentiates Affinity-tuned Chimeric Antigen Receptor-engineered T Cells. Clin Cancer Res 25, 4014-4025.
Fischer, K., Hoffmann, P., Voelkl, S., Meidenbauer, N., Ammer, J., Edinger, M., Gottfried, E., Schwarz, S., Rothe, G., Hoves, S., et al. (2007). Inhibitory effect of tumor cell-derived lactic acid on human T cells. Blood 109, 3812-3819.
Frigault, M. J., Lee, J., Basil, M. C., Carpenito, C., Motohashi, S., Scholler, J., Kawalekar, O. U., Guedan, S., McGettigan, S. E., Posey, A. D., Jr., et al. (2015). Identification of chimeric antigen receptors that mediate constitutive or inducible proliferation of T cells. Cancer Immunol Res 3, 356-367.
Gomes-Silva, D., Mukherjee, M., Srinivasan, M., Krenciute, G., Dakhova, O., Zheng, Y., Cabral, J. M. S., Rooney, C. M., Orange, J. S., Brenner, M. K., et al. (2017). Tonic 4-1BB Costimulation in Chimeric Antigen Receptors Impedes T Cell Survival and Is Vector-Dependent. Cell Rep 21, 17-26.
Grigor, E. J. M., Fergusson, D., Kekre, N., Montroy, J., Atkins, H., Seftel, M. D., Daugaard, M., Presseau, J., Thavorn, K., Hutton, B., et al. (2019). Risks and Benefits of Chimeric Antigen Receptor T-Cell (CAR-T) Therapy in Cancer: A Systematic Review and Meta-Analysis. Transfus Med Rev 33, 98-110.
Guedan, S., Ruella, M., and June, C. H. (2018). Emerging Cellular Therapies for Cancer. Annu Rev Immunol 37, 145-171.
Hartman, N. C., and Groves, J. T. (2011). Signaling clusters in the cell membrane. Curr Opin Cell Biol 23, 370-376.
Hong, M., Clubb, J. D., and Chen, Y. Y. (2020). Engineering CAR-T Cells for Next-Generation Cancer Therapy. Cancer Cell.
Hudecek, M., Lupo-Stanghellini, M. T., Kosasih, P. L., Sommermeyer, D., Jensen, M. C., Rader, C., and Riddell, S. R. (2013). Receptor affinity and extracellular domain modifications affect tumor recognition by ROR1-specific chimeric antigen receptor T cells. Clin Cancer Res 19, 3153-3164.
Hudecek, M., Sommermeyer, D., Kosasih, P. L., Silva-Benedict, A., Liu, L., Rader, C., Jensen, M. C., and Riddell, S. R. (2015). The nonsignaling extracellular spacer domain of chimeric antigen receptors is decisive for in vivo antitumor activity. Cancer Immunol Res 3, 125-135.
Jensen, M., Tan, G., Forman, S., Wu, A. M., and Raubitschek, A. (1998). CD20 is a molecular target for scFvFc:zeta receptor redirected T cells: implications for cellular immunotherapy of CD20+ malignancy. Biol Blood Marrow Transplant 4, 75-83.
Kabat, E. A., and Wu, T. T. (1971). Attempts to locate complementarity-determining residues in the variable positions of light and heavy chains. Ann N Y Acad Sci 190, 382-393.
Kishton, R. J., Sukumar, M., and Restifo, N. P. (2017). Metabolic Regulation of T Cell Longevity and Function in Tumor Immunotherapy. Cell Metab 26, 94-109.
Klein, C., Lammens, A., Schafer, W., Georges, G., Schwaiger, M., Mossner, E., Hopfner, K. P., Umana, P., and Niederfellner, G. (2013). Response to: monoclonal antibodies targeting CD20. MAbs 5, 337-338.
Liberti, M. V., and Locasale, J. W. (2016). The Warburg Effect: How Does it Benefit Cancer Cells? Trends Biochem Sci 41, 211-218.
Liu, W., Kawahara, M., Ueda, H., and Nagamune, T. (2008). Construction of a fluorescein-responsive chimeric receptor with strict ligand dependency. Biotechnol Bioeng 101, 975-984.
Liu, X., Jiang, S., Fang, C., Yang, S., Olalere, D., Pequignot, E. C., Cogdill, A. P., Li, N., Ramones, M., Granda, B., et al. (2015). Affinity-Tuned ErbB2 or EGFR Chimeric Antigen Receptor T Cells Exhibit an Increased Therapeutic Index against Tumors in Mice. Cancer Res 75, 3596-3607.
Long, A. H., Haso, W. M., Shern, J. F., Wanhainen, K. M., Murgai, M., Ingaramo, M., Smith, J. P., Walker, A. J., Kohler, M. E., Venkateshwara, V. R., et al. (2015). 4-1BB costimulation ameliorates T cell exhaustion induced by tonic signaling of chimeric antigen receptors. Nat Med 21, 581-590.
Macintyre, A. N., Gerriets, V. A., Nichols, A. G., Michalek, R. D., Rudolph, M. C., Deoliveira, D., Anderson, S. M., Abel, E. D., Chen, B. J., Hale, L. P., et al. (2014). The glucose transporter Glut1 is selectively essential for CD4 T cell activation and effector function. Cell Metab 20, 61-72.
Majzner, R. G., and Mackall, C. L. (2019). Clinical lessons learned from the first leg of the CAR T cell journey. Nat Med 25, 1341-1355.
Majzner, R. G., Rietberg, S. P., Sotillo, E., Dong, R., Vachharajani, V. T., Labanieh, L., Myklebust, J. H., Kadapakkam, M., Weber, E. W., Tousley, A. M., et al. (2020). Tuning the Antigen Density Requirement for CAR T-cell Activity. Cancer Discov 10, 702-723.
Martin, A. C., and Thornton, J. M. (1996). Structural families in loops of homologous proteins: automatic classification, modelling and application to antibodies. J Mol Biol 263, 800-815.
Mossner, E., Brunker, P., Moser, S., Puntener, U., Schmidt, C., Herter, S., Grau, R., Gerdes, C., Nopora, A., van Puijenbroek, E., et al. (2010). Increasing the efficacy of CD20 antibody therapy through the engineering of a new type II anti-CD20 antibody with enhanced direct and immune effector cell-mediated B-cell cytotoxicity. Blood 115, 4393-4402.
Niederfellner, G., Lammens, A., Mundigl, O., Georges, G. J., Schaefer, W., Schwaiger, M., Franke, A., Wiechmann, K., Jenewein, S., Slootstra, J. W., et al. (2011). Epitope characterization and crystal structure of GA101 provide insights into the molecular basis for type I/II distinction of CD20 antibodies. Blood 118, 358-367.
Notredame, C., Higgins, D. G., and Heringa, J. (2000). T-Coffee: A novel method for fast and accurate multiple sequence alignment. J Mol Biol 302, 205-217.
Omer, B., Castillo, P. A., Tashiro, H., Shum, T., Huynh, M. T. A., Cardenas, M., Tanaka, M., Lewis, A., Sauer, T., Parihar, R., et al. (2018). Chimeric Antigen Receptor Signaling Domains Differentially Regulate Proliferation and Native T Cell Receptor Function in Virus-Specific T Cells. Front Med (Lausanne) 5, 343.
Park, J. O., Tanner, L. B., Wei, M. H., Khana, D. B., Jacobson, T. B., Zhang, Z., Rubin, S. A., Li, S. H., Higgins, M. B., Stevenson, D. M., et al. (2019). Near-equilibrium glycolysis supports metabolic homeostasis and energy yield. Nat Chem Biol 15, 1001-1008.

Reff, M. E., Carner, K., Chambers, K. S., Chinn, P. C., Leonard, J. E., Raab, R., Newman, R. A., Hanna, N., and Anderson, D. R. (1994). Depletion of B cells in vivo by a chimeric mouse human monoclonal antibody to CD20. Blood 83, 435-445.

Rufener, G. A., Press, OW., Olsen, P., Lee, S. Y., Jensen, M. C., Gopal, A. K., Pender, B., Budde, L. E., Rossow, J. K., Green, D. J., et al. (2016). Preserved Activity of CD20-Specific Chimeric Antigen Receptor-Expressing T Cells in the Presence of Rituximab. Cancer Immunol Res 4, 509-519.

Scheller, L., Strittmatter, T., Fuchs, D., Bojar, D., and Fussenegger, M. (2018). Generalized extracellular molecule sensor platform for programming cellular behavior. Nat Chem Biol 14, 723-729.

Spinelli, L., Carpentier, S., Montanana Sanchis, F., Dalod, M., and Vu Manh, T. P. (2015). BubbleGUM: automatic extraction of phenotype molecular signatures and comprehensive visualization of multiple Gene Set Enrichment Analyses. BMC Genomics 16, 814.

Srivastava, S., and Riddell, S. R. (2015). Engineering CAR-T cells: Design concepts. Trends Immunol 36, 494-502.

Swindells, M. B., Porter, C. T., Couch, M., Hurst, J., Abhinandan, K. R., Nielsen, J. H., Macindoe, G., Hetherington, J., and Martin, A. C. (2017). abYsis: Integrated Antibody Sequence and Structure-Management, Analysis, and Prediction. J Mol Biol 429, 356-364.

Tanaka, Y., Ono, N., Shima, T., Tanaka, G., Katoh, Y., Nakayama, K., Takatsu, H., and Shin, H. W. (2016). The phospholipid flippase ATP9A is required for the recycling pathway from the endosomes to the plasma membrane. Mol Biol Cell 27, 3883-3893.

Teeling, J. L., Mackus, W. J., Wiegman, L. J., van den Brakel, J. H., Beers, S. A., French, R. R., van Meerten, T., Ebeling, S., Vink, T., Slootstra, J. W., et al. (2006). The biological activity of human CD20 monoclonal antibodies is linked to unique epitopes on CD20. J Immunol 177, 362-371.

Till, B. G., Jensen, M. C., Wang, J., Qian, X., Gopal, A. K., Maloney, D. G., Lindgren, C. G., Lin, Y., Pagel, J. M., Budde, L. E., et al. (2012). CD20-specific adoptive immunotherapy for lymphoma using a chimeric antigen receptor with both CD28 and 4-1BB domains: pilot clinical trial results. Blood 119, 3940-3950.

Uchiyama, S., Suzuki, Y., Otake, K., Yokoyama, M., Ohta, M., Aikawa, S., Komatsu, M., Sawada, T., Kagami, Y., Morishima, Y., et al. (2010). Development of novel humanized anti-CD20 antibodies based on affinity constant and epitope. Cancer Sci 101, 201-209.

Watanabe, K., Terakura, S., Martens, A. C., van Meerten, T., Uchiyama, S., Imai, M., Sakemura, R., Goto, T., Hanajiri, R., Imahashi, N., et al. (2015). Target antigen density governs the efficacy of anti-CD20-CD28-CD3 zeta chimeric antigen receptor-modified effector CD8+ T cells. J Immunol 194, 911-920.

Watanabe, N., Bajgain, P., Sukumaran, S., Ansari, S., Heslop, H. E., Rooney, C. M., Brenner, M. K., Leen, A. M., and Vera, J. F. (2016). Fine-tuning the CAR spacer improves T-cell potency. Oncoimmunology 5, e1253656.

Wijewarnasuriya, D., Bebernitz, C., Lopez, A. V., Rafiq, S., and Brentjens, R. J. (2020). Excessive Costimulation Leads to Dysfunction of Adoptively Transferred T Cells. Cancer Immunol Res 8, 732-742.

Yamamoto, T. N., Kishton, R. J., and Restifo, N. P. (2019). Developing neoantigen-targeted T cell-based treatments for solid tumors. Nat Med 25, 1488-1499.

Zah, E., Lin, M. Y., Silva-Benedict, A., Jensen, M. C., and Chen, Y. Y. (2016). T Cells Expressing CD19/CD20 Bispecific Chimeric Antigen Receptors Prevent Antigen Escape by Malignant B Cells. Cancer Immunol Res 4, 498-508.

Zettlitz, K. A., Tavare, R., Knowles, S. M., Steward, K. K., Timmerman, J. M., and Wu, A. M. (2017). ImmunoPET of Malignant and Normal B Cells with (89) Zr- and (124) I-Labeled Obinutuzumab Antibody Fragments Reveals Differential CD20 Internalization In Vivo. Clin Cancer Res 23, 7242-7252.

Zhang, W. Y., Wang, Y., Guo, Y. L., Dai, H. R., Yang, Q. M., Zhang, Y. J., Zhang, Y., Chen, M. X., Wang, C. M., Feng, K. C., et al. (2016). Treatment of CD20-directed Chimeric Antigen Receptor-modified T cells in patients with relapsed or refractory B-cell non-Hodgkin lymphoma: an early phase IIa trial report. Signal Transduct Target Ther 1, 16002.

Zhao, Z., Condomines, M., van der Stegen, S. J. C., Perna, F., Kloss, C. C., Gunset, G., Plotkin, J., and Sadelain, M. (2015). Structural Design of Engineered Costimulation Determines Tumor Rejection Kinetics and Persistence of CAR T Cells. Cancer Cell 28, 415-428.

What is claimed is:

1. A polypeptide comprising an anti-CD20 single chain variable fragment (scFv) comprising:

a light chain variable region (VL) comprising in order from amino-proximal to carboxy-proximal end of the light chain variable region: light chain framework region 1 (LFR1), light chain complementarity-determining region 1 (LCDR1), light chain framework region 2 (LFR2), light chain complementarity-determining region 2 (LCDR2), light chain framework region 3 (LFR3), light chain complementarity-determining region 3 (LCDR3), and light chain framework region 4 (LFR4); and a heavy chain variable region (VH) comprising in order from amino-proximal to carboxy-proximal end of the heavy chain variable region: heavy chain framework region 1 (HFR1), heavy chain complementarity-determining region 1 (HCDR1), heavy chain framework region 2 (HFR2), heavy chain complementarity-determining region 2 (HCDR2), heavy chain framework region 3 (HFR3), heavy chain complementarity-determining region 3 (HCDR3), and heavy chain framework region 4 (HFR4);

wherein LFR1, LFR2, LFR3, LFR4, LCDR1, LCDR2, and LCDR3 comprise the amino acid sequence of SEQ ID NOS: 29, 30, 31, 22, 12, 13, and 14, respectively; and wherein HFR1, HFR2, HFR3, HFR4, HCDR1, HCDR2, and HCDR3 comprise the amino acid sequence of SEQ ID NOS: 26, 27, 28, 18, 9, 10, and 11, respectively.

2. The polypeptide of claim 1, wherein the light chain variable region comprises an amino acid sequence with at least 90% sequence identity to SEQ ID NO:5 and a heavy chain variable region comprising an amino acid sequence with at least 90% sequence identity to SEQ ID NO: 6.

3. The polypeptide of claim 1, wherein the VH is amino proximal to the VL.

4. The polypeptide of claim 1, wherein the VH is carboxy proximal to the VL.

5. The polypeptide of claim 1, wherein the polypeptide comprises a chimeric antigen receptor (CAR) comprising the scFv, a transmembrane domain and a cytoplasmic region comprising a primary intracellular signaling domain.

6. The polypeptide of claim 5, wherein the CAR further comprises an extracellular spacer between the transmembrane domain and the scFv.

7. The polypeptide of claim 5, wherein the transmembrane domain is an alpha or beta chain of the T cell receptor, CD28, CD3ε (epsilon), CD45, CD4, CD5, CD8, CD9, CD16, CD22, CD33, CD37, CD64, CD80, CD86, CD123, CD134, CD137 or CD154 transmembrane domain.

8. The polypeptide of claim 5, wherein the cytoplasmic region further comprises one or more costimulatory domains.

9. The polypeptide of claim 8, wherein the one or more costimulatory domain(s) comprise a costimulatory domain from one or more of 4-1BB (CD137), CD28, IL-15Rα, OX40, CD2, CD27, CDS, ICAM-1, LFA-1 (CD11a/CD18), and/or ICOS (CD278).

10. The polypeptide of claim 1, wherein the polypeptide comprises SEQ ID NO:33 or 42.

11. The polypeptide of claim 5, wherein the polypeptide further comprises a torsional linker between the transmembrane domain and the cytoplasmic region.

12. The polypeptide of claim 11, wherein the torsional linker comprises 1, 2, 3, 4, 5, 6, 7, 8, 9, or 10 alanine residues.

13. A polypeptide comprising a CAR comprising, in order from amino proximal to carboxy proximal end, an anti-CD20 scFv, a CD28 transmembrane domain, a torsional linker, and a cytoplasmic region comprising a CD28 costimulatory domain and a CD3-zeta intracellular signaling domain, wherein the torsional linker comprises 1-12 alanine residues, wherein the anti-CD20 scFv comprises a light chain variable region (VL) comprising in order from amino-proximal to carboxy-proximal end of the light chain variable region: light chain framework region 1 (LFR1), light chain complementarity-determining region 1 (LCDR1), light chain framework region 2 (LFR2), light chain complementarity-determining region 2 (LCDR2), light chain framework region 3 (LFR3), light chain complementarity-determining region 3 (LCDR3), and light chain framework region 4 (LFR4); and a heavy chain variable region (VH) comprising in order from amino-proximal to carboxy-proximal end of the heavy chain variable region: heavy chain framework region 1 (HFR1), heavy chain complementarity-determining region 1 (HCDR1), heavy chain framework region 2 (HFR2), heavy chain complementarity-determining region 2 (HCDR2), heavy chain framework region 3 (HFR3), heavy chain complementarity-determining region 3 (HCDR3), and heavy chain framework region 4 (HFR4);

wherein LFR1, LFR2, LFR3, LFR4, LCDR1, LCDR2, and LCDR3 comprise the amino acid sequence of SEQ ID NOS: 29, 30, 31, 22, 12, 13, and 14, respectively; and wherein HFR1, HFR2, HFR3, HFR4, HCDR1, HCDR2, and HCDR3 comprise the amino acid sequence of SEQ ID NOS: 26, 27, 28, 18, 9, 10, and 11, respectively.

14. A nucleic acid comprising a sequence encoding the polypeptide of claim 1.

15. A cell or population of cells comprising the nucleic acid of claim 14.

16. The cell of claim 15, wherein the cell is a T cell, a natural killer (NK) cell, a naïve memory T cell, a natural killer T cell (NKT), an invariant natural killer T cell (INKT), stem cell, lymphoid progenitor cell, peripheral blood mononuclear cell (PBMC), bone marrow cell, fetal liver cell, embryonic stem cell, hematopoietic stem or progenitor cell (HSPC), cord blood cell, or induced pluripotent stem cell (IPS cell).

17. A method of treating a patient with cancer comprising administering to the patient an effective amount of the cell(s) of claim 15.

18. The method of claim 17, wherein the cancer comprises lymphoma or neuroblastoma.

* * * * *